(12) United States Patent
Bhandari et al.

(10) Patent No.: US 10,407,468 B2
(45) Date of Patent: Sep. 10, 2019

(54) METHODS FOR SYNTHESIZING α4β7 PEPTIDE ANTAGONISTS

(71) Applicant: Protagonist Therapeutics, Inc., Milpitas, CA (US)

(72) Inventors: Ashok Bhandari, Pleasanton, CA (US); Suresh Kumar Manthati, Sunnyvale, CA (US); Mukund M. Mehrotra, San Jose, CA (US); Sampath-Kumar Anandan, Fremont, CA (US); Dinesh V. Patel, Fremont, CA (US)

(73) Assignee: Protagonist Therapeutics, Inc., Newark, CA (US)

( * ) Notice: Subject to any disclaimer, the term of this patent is extended or adjusted under 35 U.S.C. 154(b) by 0 days.

(21) Appl. No.: 15/467,810

(22) Filed: Mar. 23, 2017

(65) Prior Publication Data

US 2017/0327541 A1 Nov. 16, 2017

Related U.S. Application Data

(60) Provisional application No. 62/403,527, filed on Oct. 3, 2016, provisional application No. 62/319,045, filed on Apr. 6, 2016, provisional application No. 62/312,345, filed on Mar. 23, 2016.

(51) Int. Cl.

| | |
|---|---|
| *C07K 7/06* | (2006.01) |
| *A61K 38/07* | (2006.01) |
| *C07K 7/64* | (2006.01) |
| *C07K 14/705* | (2006.01) |
| *C07K 1/02* | (2006.01) |
| *C07K 1/06* | (2006.01) |
| *C07K 1/10* | (2006.01) |
| *C07K 1/113* | (2006.01) |
| *C07K 1/20* | (2006.01) |
| *C07K 5/12* | (2006.01) |
| *C07K 7/02* | (2006.01) |
| *C07K 1/00* | (2006.01) |
| *A61K 38/00* | (2006.01) |

(52) U.S. Cl.
CPC ............ *C07K 7/64* (2013.01); *C07K 1/006* (2013.01); *C07K 1/026* (2013.01); *C07K 1/061* (2013.01); *C07K 1/10* (2013.01); *C07K 1/1133* (2013.01); *C07K 1/1136* (2013.01); *C07K 1/20* (2013.01); *C07K 5/126* (2013.01); *C07K 7/02* (2013.01); *C07K 7/06* (2013.01); *C07K 14/705* (2013.01); *C07K 14/70546* (2013.01); *A61K 38/00* (2013.01)

(58) Field of Classification Search
CPC ........ A61K 38/00; A61K 38/08; A61K 38/07; C07K 7/06
USPC .......................................................... 530/318
See application file for complete search history.

(56) References Cited

U.S. PATENT DOCUMENTS

| | | | |
|---|---|---|---|
| 4,684,620 A | 8/1987 | Hruby et al. | |
| 4,724,229 A | 2/1988 | Ali | |
| 5,990,084 A | 11/1999 | Richter et al. | |
| 6,235,711 B1 | 5/2001 | Dutta | |
| 6,818,617 B1 | 11/2004 | Niewiarowski | |
| 7,534,764 B2 | 5/2009 | Ganz et al. | |
| 8,435,941 B2 | 5/2013 | Ganz et al. | |
| 8,536,140 B2 | 9/2013 | Clandinin et al. | |
| 8,796,418 B2 | 8/2014 | Walensky et al. | |
| 8,946,150 B2 | 2/2015 | Gallagher et al. | |
| 8,999,935 B2 | 4/2015 | Huang | |
| 9,169,292 B2 | 10/2015 | Gallagher et al. | |
| 9,273,093 B2 | 3/2016 | Bhandari et al. | |
| 9,518,091 B2 | 12/2016 | Bhandari et al. | |
| 9,624,268 B2 | 4/2017 | Bourne et al. | |
| 9,714,270 B2 | 7/2017 | Bhandari et al. | |
| 9,809,623 B2 | 11/2017 | Bhandari et al. | |
| 10,059,744 B2 | 8/2018 | Bhandari et al. | |
| 2003/0166514 A1 | 9/2003 | Jones et al. | |
| 2004/0052785 A1 | 3/2004 | Goodman et al. | |
| 2004/0176293 A1 | 9/2004 | Peterson et al. | |
| 2006/0183884 A1 | 8/2006 | Blaschuk et al. | |
| 2007/0032417 A1 | 2/2007 | Baell | |
| 2007/0166308 A1 | 7/2007 | Pullen et al. | |
| 2007/0197430 A1 | 8/2007 | Baell et al. | |
| 2008/0260820 A1 | 10/2008 | Borrelly et al. | |
| 2008/0300180 A1 | 12/2008 | Schambye et al. | |
| 2009/0053819 A1 | 2/2009 | Seymour et al. | |
| 2009/0257952 A1 | 10/2009 | Cochran et al. | |
| 2010/0151487 A1 | 6/2010 | Rovin et al. | |
| 2010/0190710 A1 | 7/2010 | Chemtob et al. | |
| 2010/0196441 A1 | 8/2010 | Sondermeijer et al. | |
| 2010/0272731 A1 | 10/2010 | Presta et al. | |
| 2010/0280098 A1 | 11/2010 | Juliano et al. | |

(Continued)

FOREIGN PATENT DOCUMENTS

| | | |
|---|---|---|
| DE | 10107707 A1 | 8/2002 |
| WO | WO 1992/017492 A1 | 10/1992 |

(Continued)

OTHER PUBLICATIONS

U.S. Appl. No. 15/255,750, filed Sep. 2, 2016, Bhandari et al.

(Continued)

*Primary Examiner* — Kaipeen E Yang

(74) *Attorney, Agent, or Firm* — Cooley LLP

(57) ABSTRACT

The present invention provides methods of making α4β7 peptide monomer and dimer antagonists. Methods of the present invention include solid phase and solution phase methods, as well as synthesis via condensation of smaller peptide fragments. Methods of the present invention further include methods directed to the synthesis of peptides comprising one or more penicillamine residues.

24 Claims, 8 Drawing Sheets

Specification includes a Sequence Listing.

(56) References Cited

U.S. PATENT DOCUMENTS

| | | |
|---|---|---|
| 2011/0059087 A1 | 3/2011 | Lewis et al. |
| 2011/0086024 A1 | 4/2011 | Arthos et al. |
| 2011/0282029 A1 | 11/2011 | Holmes et al. |
| 2012/0021975 A1 | 1/2012 | Hoffman et al. |
| 2012/0071422 A1 | 3/2012 | Gallagher et al. |
| 2012/0115930 A1 | 5/2012 | Monia et al. |
| 2013/0029907 A1 | 1/2013 | Gallagher et al. |
| 2013/0172272 A1 | 7/2013 | Gallagher et al. |
| 2013/0183755 A1 | 7/2013 | Gallagher et al. |
| 2013/0310303 A1 | 11/2013 | Eldar-Finkelman et al. |
| 2014/0193465 A1 | 7/2014 | Bhandari et al. |
| 2014/0286953 A1 | 9/2014 | Sasu et al. |
| 2014/0294901 A1 | 10/2014 | Bhandari et al. |
| 2014/0294902 A1 | 10/2014 | Bhandari et al. |
| 2014/0336110 A1 | 11/2014 | Ganz et al. |
| 2015/0056301 A1 | 2/2015 | Kawabe et al. |
| 2015/0157692 A1 | 6/2015 | Fu |
| 2015/0284429 A1 | 10/2015 | Merutka |
| 2016/0031944 A1 | 2/2016 | Bhandari et al. |
| 2016/0145306 A1 | 5/2016 | Bourne et al. |
| 2016/0152664 A1 | 6/2016 | Bhandari et al. |
| 2016/0159862 A1 | 6/2016 | Bhandari et al. |
| 2016/0222076 A1 | 8/2016 | Smythe et al. |
| 2016/0368966 A1 | 12/2016 | Bhandari et al. |
| 2018/0099995 A1 | 4/2018 | Bhandari et al. |
| 2018/0105572 A1 | 4/2018 | Bhandari et al. |
| 2018/0148477 A1 | 5/2018 | Bhandari et al. |
| 2019/0002500 A1 | 1/2019 | Bhandari et al. |
| 2019/0016756 A1 | 1/2019 | Bhandari et al. |

FOREIGN PATENT DOCUMENTS

| | | | |
|---|---|---|---|
| WO | WO 1997/007129 A1 | 2/1997 | |
| WO | WO 1997/025351 A2 | 7/1997 | |
| WO | WO 1998/008871 A1 | 3/1998 | |
| WO | WO 2000/055184 A1 | 3/1998 | |
| WO | WO 1999/002194 A1 | 1/1999 | |
| WO | WO 1999/026615 A1 | 6/1999 | |
| WO | WO 2000/006243 A2 | 2/2000 | |
| WO | WO 2000/009560 A1 | 2/2000 | |
| WO | WO 2000/018789 A1 | 4/2000 | |
| WO | WO 2000/018790 A1 | 4/2000 | |
| WO | WO 2000/023474 A1 | 4/2000 | |
| WO | WO 2000/055119 A1 | 9/2000 | |
| WO | WO 2000/061580 A1 | 10/2000 | |
| WO | WO 2001/068586 A2 | 9/2001 | |
| WO | WO 2003/066678 A1 | 8/2003 | |
| WO | WO 2004/092405 A2 | 10/2004 | |
| WO | WO 2008/097461 A2 | 8/2008 | |
| WO | WO 2008/134659 A2 | 11/2008 | |
| WO | WO 2008/140602 A2 | 11/2008 | |
| WO | WO 2009/002947 A2 | 12/2008 | |
| WO | WO 2009/027752 A2 | 3/2009 | |
| WO | WO 2010/116752 A1 | 10/2010 | |
| WO | WO 2011/149942 A2 | 12/2011 | |
| WO | WO 2014/059213 A1 | 4/2014 | |
| WO | WO 2014/127316 A2 | 8/2014 | |
| WO | WO 2014/145561 A2 | 9/2014 | |
| WO | WO 2014/165448 A1 | 10/2014 | |
| WO | WO 2014/165449 A1 | 10/2014 | |
| WO | WO 2015/176035 A1 | 11/2015 | |
| WO | WO 2015/200916 A2 | 12/2015 | |
| WO | WO 2016/011208 A1 | 1/2016 | |
| WO | WO 2016/054411 A1 | 4/2016 | |
| WO | WO 2016/054445 A1 | 4/2016 | |
| WO | WO 2017/011820 A2 | 1/2017 | |
| WO | WO 2017/117411 A1 | 7/2017 | |

OTHER PUBLICATIONS

U.S. Appl. No. 15/258,540, filed Sep. 7, 2016, Bhandari et al.
U.S. Appl. No. 15/321,124, filed Dec. 21, 2016, Bourne et al.
U.S. Appl. No. 15/442,229, filed Feb. 24, 2017, Bourne et al.
U.S. Appl. No. 15/486,684, filed Apr. 13, 2017, Bhandari et al.
U.S. Appl. No. 15/493,471, filed Apr. 21, 2017, Bhandari et al.
U.S. Appl. No. 15/514,983, filed Mar. 28, 2017, Bhandari et al.
U.S. Appl. No. 15/614,047, filed Jun. 5, 2017, Bhandari et al.
Chatterjee, J. et al., "N-Methylation of Peptides: a New Perspective in Medicinal Chemistry", Accounts of Chemical Research, 41(10): 1331-1342 (2008).
Clark, Richard J., et al. "Design, synthesis, and characterization of cyclic analogues of the iron regulatory peptide hormone hepcidin." Peptide Science (2013); 100.5: 519-526.
Database EPO Proteins [Online] Dec. 3, 2010 (Dec. 3, 2010), "Sequence from Patent W02010124874." XP002761649, retrieved from EBI accession No. EPOP:HI656765 Database accession No. HI656765, 1 page.
Database USPTO Proteins [Online] Dec. 17, 2012 (Dec. 17, 2012), "Sequence from patent U.S. Pat. No. 8,313,950.", XP002761650, retrieved from EBI accession No. USPOP:AGA36544 Database accession No. AGA36544, 1 page.
Definition of Isostere, Medical Definition and More from Merriam-Webster Dictionary, 3 pages, www.merriam-webster.com/medical/isostere accessed on Feb. 5, 2015.
Desbenoit, N., et al. "Reversible metalation of a bis-disulfide analogue of the Cys*-X-Cys* hepcidin binding site: structural characterisation of the related copper complex]." Annales Pharmaceutiques Francaises (2010); 68(6): 388-396. (with English summary).
Dolain, Christel, et al. "Inducing α-Helices in Short Oligopeptides through Binding by an Artificial Hydrophobic Cavity." Journal of the American Chemical Society (2010); 132.16: 5564-5565.
Dubree, Nathan J.P. et al., "Selective α4β7 Integrin Antagonists and Their Potential as Antiinflammatory Agents", J. Med. Chem., 45: 3451-3457 (2002).
Dutta, Anand S., "Potent Cyclic Monomeric and Dimeric Peptide Inhibitors of VLA-4 (a4b1 Integrin)-Mediated Cell Adhesion Based on the Ile-Leu-Asp-Val Tetrapeptide", J. Peptide Sci. (2000); 6: 321-341.
European Application No. 13845982.1, Extended European Search Report dated May 13, 2016.
European Application No. 14763104.8, Extended European Search Report dated Sep. 23, 2016, 10 pages.
European Application No. 14779463.0, Extended European Search Report dated Nov. 9, 2016, 9 pages.
European Application No. 14780207.8, Partial Supplementary European Search Report dated Nov. 16, 2016, 6 pages.
European Application No. 14780207.8, Extended European Search Report dated Feb. 17, 2017, 9 pages.
Gee et al. "Cyclic Peptides as Non-carboxyl-terminal Ligands of Syntrophin PDZ Domains," The Journal of Biological Chemistry, 273(34): 21980-21987 (1998).
Girelli, Domenico, et al. "Hepcidin in the diagnosis of iron disorders." Blood (2016); 127.23 : 2809-2813.
Boer, J., et al., "Design and Synthesis of Potent and Selective $\alpha_4\beta_7$ Integrin Antagonists." J. Med. Chem. (2001); 44 (16): 2586-2592.
Ilyin, Gennady, et al. "Comparative analysis of mouse hepcidin 1 and 2 genes: evidence for different patterns of expression and co-inducibility during iron overload 1." FEBS Letters (2003); 542.1-3 : 22-26.
Jackson, D.Y., "Alpha 4 integrin antagonists." Current Pharmaceutical Design, (8)14: 1229-1253 (2002).
Janssen et al., "Comparison of a Monomeric and Dimeric Radiolabeled RGD-Peptide for Tumor Targeting", Cancer Biotherapy and Radiopharmaceuticals, 17(6): 641-646 (2002).
Haanstra, et al., "Antagonizing the a4B1 Integrin, but no a4B7, Inhibits Leukocytic Infiltration of the Central Nervous System in Rhesus Monkey Experimental Autoimmune Encephalomyelitis", Journal of Immunology, 90(5): 1961-1973 (2013).
Jordan, John B., et al. "Hepcidin revisited, disulfide connectivity, dynamics, and structure." Journal of Biological Chemistry (2009); 284.36: 24155-24167.
Kelleman, A. et al. "Incorporation of thioether building blocks into an $\alpha_v\beta_3$-specific RGD peptide: Synthesis and biological activity", Biopolymers (Peptide Science), 71(6): 686-695 (2003).

(56) References Cited

OTHER PUBLICATIONS

Kitazume and Yamazaki, Experimental Methods in Organic Fluorine Chemistry, Gordon and Breach Science Publishers, 1998, p. 9, 3 pages.
Kluskens, L.D. et al., "Angiotensin-(1-7) with Thioether Bridge: An Angiotensin-Converting Enzyme-Resistant, Potent Angiotensin-(1-7) Analog", The Journal of Pharmacology and Experimental Therapeutics, 328(3): 849-855 (2009).
Knudsen, Lotte B., et al. "Potent derivatives of glucagon-like peptide-1 with pharmacokinetic properties suitable for once daily administration." Journal of Medicinal Chemistry (2000); 43.9: 1664-1669.
Krause, Alexander, et al. "LEAP-1, a novel highly disulfide-bonded human peptide, exhibits antimicrobial activity." FEBS Letters (2000); 480.2-3 : 147-150.
Ley, Klaus, et al. "Integrin-based therapeutics: biological basis, clinical use and new drugs." Nature Reviews Drug Discovery (2016); 15.3: 173-183.
Liu, Shuang, "Radiolabeled Multimeric Cyclic RGD Peptides as Integrin avB3 Targeted Radiotracers for Tumor Imaging", School of Health Science, Purdue University, Molecular Pharmaceuticals, 3(5): 472-487 (2006).
Madsen, Kjeld, et al. "Structure-activity and protraction relationship of long-acting glucagon-like peptide-1 derivatives: importance of fatty acid length, polarity, and bulkiness." Journal of Medicinal Chemistry (2007); 50.24: 6126-6132.
Methods in Molecular Biology, vol. 35 Peptide Synthesis Protocols, Edited by M.W Pennington and B. M. Dunn Copyright, 1994 Humana Press Inc, Totowa, NJ, pp. 201-241.
Muñoz, Manuel, et al. "Disorders of iron metabolism. Part II: iron deficiency and iron overload." Journal of Clinical Pathology (2011); 64.4: 287-296.
Nemeth, Elizabeta, et al. "The N-terminus of hepcidin is essential for its interaction with ferroportin: structure-function study." Blood (2006); 107.1: 328-333.
Park, C.H., et al., "Hepcidin, a urinary antimicrobial peptide synthesized in the liver." J Biol Chem. (2001); 276(11): 7806-7810. Epub Dec. 11, 2000.
PCT/US2013/064439, International Search Report and Written Opinion, dated Jan. 24, 2014, 15 pages.
PCT/US2013/064439, International Preliminary Report on Patentability, dated Apr. 14, 2015, 8 pages.
PCT/US2014/030352, International Search Report and Written Opinion, dated Nov. 28, 2014, 12 pages.
PCT/US2014/030352, International Preliminary Report on Patentability, dated Sep. 15, 2015, 7 pages.
PCT/US2015/038370, International Search Report and Written Opinion, dated Sep. 14, 2015, 5 pages.
PCT/US2015/038370, International Preliminary Report on Patentability, dated Dec. 27, 2016, 4 pages.
PCT/US2014/032391, International Search Report, dated Aug. 7, 2014, 5 pages.
PCT/US2014/032391, Written Opinion, dated Aug. 7, 2014, 7 pages.
PCT/US2014/032391, International Preliminary Report on Patentability, dated Oct. 6, 2015, 8 pages.
PCT/US2014/032392, International Search Report and Written Opinion, dated Sep. 15, 2014, 15 pages.
PCT/US2014/032392, International Preliminary Report on Patentability, dated Oct. 6, 2015, 10 pages.
PCT/US2015/031243, International Search Report and Written Opinion, dated Aug. 5, 2015, 14 pages.
PCT/US2015/031243, International Preliminary Report on Patentability, dated Nov. 22, 2016, 8 pages.
PCT/US2015/040658, International Search Report and Written Opinion, dated Oct. 28, 2015, 12 pages.
PCT/US2015/040658, International Preliminary Report on Patentability, dated Jan. 17, 2017, 5 pages.
PCT/US2015/053558, International Search Report and Written Opinion, dated Feb. 19, 2016, 16 pages.
PCT/US2015/053558, International Preliminary Report on Patentability, dated Apr. 4, 2017, 9 pages.
PCT/US2015/053603, International Search Report and Written Opinion, dated Feb. 12, 2016, 13 pages.
PCT/US2015/053603, International Preliminary Report on Patentability, dated Apr. 4, 2017, 8 pages.
PCT/US2016/042680, International Search Report and Written Opinion, dated Jan. 13, 2017, 12 pages.
PCT/US2016/042680, (2nd) International Search Report and Written Opinion, dated Apr. 17, 2017, 13 pages.
PCT/US2016/069255, International Search Report and Written Opinion dated Jun. 1, 2017, 11 pages.
Pelton, J.T. et al., "Somatostatin Analogs with Affinity for Opiate Receptors in Rat Brain Binding Assay", Peptides, 6(Suppl 1): 159-163 (1985).
Rivera, Seth, et al. "Synthetic hepcidin causes rapid dose-dependent hypoferremia and is concentrated in ferroportin-containing organs." Blood (2005); 106.6: 2196-2199.
Shahidi, Neal, et al. "Vedolizumab for the treatment of ulcerative colitis." Expert Opinion on Biological Therapy (2016); 16.1 : 129-135.
SID 24885660, National Center for Biotechnology Information, PubChem Substance Database; SID=24885660, 5 pages. https://pubchem.ncbi.nlm.nih.gov/substance/24885660, available date: Jul. 16, 2007, accessed Jul. 21, 2016.
Soler-Ferran and Briskin, "Integrin $\alpha_4\beta_7$ Antagonists: Activities, Mechanisms of Action and Therapeutic Prospects", Current Immunology Reviews (2012), 8(2): 118-134.
Tandara, Leida, and Salamunic, Ilza . "Iron metabolism: current facts and future directions." Biochemia Medica (2012); 22.3: 311-328.
Temming, K. et al. "Rational Design of RGD-Albumin Conjugates for targeted Delivery of the VEGF-R Kinase Inhibitor PTK787 to Angiogenic Endothelium", ChemMedChem, 1: pp. 1200-1203 (2006).
Thermo Electron Corporation, Technical Information, "N-terminal and C-terminal Amidation of Peptides", 2 pages (2004).
Thumshirn, G. et al., "Multimeric Cyclic RGD Peptides as Potential Tools for Tumor Targeting: Solid Phase Peptide Synthesis and Chemoselective Oxime Ligation", Chem. Eur. J., 9: 2717-2725 (2003).
Waitemata District Health Board, "Crushing Guide for Oral Medication in Residential Aged Care", 2 pages (2011).
Xie, Youmei et al., "Nerve Growth Factor (NGF) Loop 4 Dimeric Mimetics Activate ERK and AKT and Promote NGF-like Neurotrophic Effects", The Journal of Biological Chemistry, 275(38): 29868-29874 (2000).
Yu and Gallagher, "A Naturally Occurring, Soluble Antagonist of Human IL-23 Inhibits the Development and In Vitro Function of Human Th17 Cells", The Journal of Immunology, 185: 7302-7308 (2010).
U.S. Appl. No. 14/050,349, Non-Final Office Action dated Feb. 27, 2015, 14 pages.
U.S. Appl. No. 14/229,799, Non-Final Office Action dated Jul. 24, 2015, 19 pages.
U.S. Appl. No. 14/229,784, Non-Final Office Action dated Aug. 13, 2015, 16 pages.
U.S. Appl. No. 14/050,349, Final Office Action dated Sep. 9, 2015, 17 pages.
U.S. Appl. No. 14/050,349, Notice of Allowance dated Jan. 12, 2016, 9 pages.
U.S. Appl. No. 14/229,799, Office Action dated Mar. 4, 2016, 18 pages.
U.S. Appl. No. 14/229,784, Office Action dated Mar. 8, 2016, 6 pages.
U.S. Appl. No. 15/046,325, Office Action dated Aug. 1, 2016, 13 pages.
U.S. Appl. No. 14/800,627, Office Action dated Aug. 25, 2016, 11 pages.
U.S. Appl. No. 14/714,198, Office Action dated Nov. 7, 2016, 6 pages.
U.S. Appl. No. 14/872,975, Office Action dated Dec. 27, 2016, 14 pages.

(56) References Cited

OTHER PUBLICATIONS

U.S. Appl. No. 14/800,627, Notice of Allowance dated Feb. 15, 2017, 9 pages.
U.S. Appl. No. 14/714,198, Notice of Allowance dated Mar. 7, 2017, 3 pages.
U.S. Appl. No. 14/775,469, Office Action dated Apr. 11, 2017, 22 pages.
U.S. Appl. No. 14/775,469, Notice of Allowance dated Aug. 10, 2017, 11 pages.
U.S. Appl. No. 15/514,983, filed Oct. 1, 2015, Bhandari, et al.
U.S. Appl. No. 15/831,099, filed Dec. 4, 2017, Bhandari, et al.
U.S. Appl. No. 15/836,648, filed Dec. 8, 2017, Bhandari, et al.
U.S. Appl. No. 16/035,060, filed Jul. 13, 2018, Bhandari, et al.
U.S. Appl. No. 16/039,813, filed Jul. 19, 2018, Bhandari, et al.
U.S. Appl. No. 16/113,072, filed Aug. 27, 2018, Bhandari, et al.
U.S. Appl. No. 16/282,908, filed Feb. 22, 2019, Bhandari, et al.
U.S. Appl. No. 16/282,920, filed Feb. 22, 2019, Bhandari, et al.
U.S. Appl. No. 15/698,407, filed Sep. 7, 2017, Bhandari, et al.
Cherry, et al., "Vedolizumab: an $\alpha 4\beta 7$ integrin antagonist for ulcerative colitis and Crohn's disease." Ther Adv Chronic Dis. (2015); 6(5): 224-233.
PCT/US2017/023859, Invitation to Pay Additional Fees, dated May 25, 2017, 9 pages.
PCT/US2017/023859, International Preliminary Report on Patentability, dated Sep. 25, 2018, 9 pages.
PCT/US2017/023859, International Search Report and Written Opinion, dated Jul. 26, 2017, 14 pages.

METHODS FOR SYNTHESIZING α4β7 PEPTIDE ANTAGONISTS

This application claims the benefit of U.S. Provisional Application No. 62/312,345 filed Mar. 23, 2016; U.S. Provisional Application No. 62/319,045, filed Apr. 6, 2016, and U.S. Provisional Application No. 62/403,527, filed Oct. 3, 2016, the disclosure of each of which are hereby incorporated by reference herein in its entirety.

BACKGROUND OF THE INVENTION

Integrins are noncovalently associated α/β heterodimeric cell surface receptors involved in numerous cellular processes ranging from cell adhesion and migration to gene regulation (Dubree, et al., Selective α4β7 Integrin Antagonist and Their Potential as Anti-inflammatory Agents, *J. Med. Chem.* 2002, 45, 3451-3457). Differential expression of integrins can regulate a cell's adhesive properties, allowing different leukocyte populations to be recruited to specific organs in response to different inflammatory signals. If left unchecked, integrins-mediated adhesion process can lead to chronic inflammation and autoimmune disease.

The α4 integrins, α4β1 and α4β7, play essential roles in lymphocyte migration throughout the gastrointestinal tract. They are expressed on most leukocytes, including B and T lymphocytes, where they mediate cell adhesion via binding to their respective primary ligands, vascular cell adhesion molecule (VCAM), and mucosal addressin cell adhesion molecule (MAdCAM), respectively. The proteins differ in binding specificity in that VCAM binds both α4β1 and to a lesser extent α4β7, while MAdCAM is highly specific for α4β7. In addition to pairing with the α4 subunit, the β7 subunit also forms a heterodimeric complex with αE subunit to form αEβ7, which is primarily expressed on intraepithelial lymphocytes (IEL) in the intestine, lung and genitourinary tract. αEβ7 is also expressed on dendritic cells in the gut. The αEβ7 heterodimer binds to E-cadherin on the epithelial cells. The IEL cells are thought to provide a mechanism for immune surveillance within the epithelial compartment. Therefore, blocking αEβ7 and α4β7 together may be a useful method for treating inflammatory conditions of the intestine Inhibitors of specific integrin-ligand interactions have been shown effective as anti-inflammatory agents for the treatment of various autoimmune diseases. For example, monoclonal antibodies displaying high binding affinity for α4β7 have displayed therapeutic benefits for gastrointestinal auto-inflammatory/autoimmune diseases, such as Crohn's disease, and ulcerative colitis. Id. However, one of these therapies interfered with α4β1 integrin-ligand interactions thereby resulting in dangerous side effects to the patient. Therapies utilizing a dual-specific small molecule antagonists have shown similar side effects in animal models.

Accordingly, there is a need in the art for integrin antagonist molecules having high affinity for the α4β7 integrin and high selectivity against the α4β1 integrin, as a therapy for various gastrointestinal autoimmune diseases.

Such integrin antagonist molecules and related compositions and methods have been described in the PCT Application titled "NOVEL α4β7 PEPTIDE MONOMER AND DIMER ANTAGONISTS," filed on Oct. 1, 2015. As a result, there is a need for improved methods of synthesizing such peptide dimers. Such improved solid phase and solution phase methods are described herein.

SUMMARY OF INVENTION

In certain aspects, the invention provides a method of preparing a peptide dimer compound comprising: (i) synthesizing a peptide having a sequence as described herein, and introducing an intramolecular disulfide bond between two residues of the peptide (or allowing the intramolecular bond to form), and conjugating a linker to the peptide; (ii) synthesizing a peptide having a sequence as described herein (e.g., the same sequence as for step (i)), and introducing an intramolecular disulfide bond between two residues of the peptide (or allowing the intramolecular disulfide bond to form); and (iii) conjugating the peptide of step (i) to the peptide of step (ii) via the linker attached to the peptide of step (i).

In other aspects, the methods of the present invention provide a method of preparing a peptide dimer compound comprising (i) synthesizing a peptide having a sequence comprising two penicillamine residues and introducing an intramolecular disulfide bridge between the two penicillamine residues of the peptide through oxidative cyclization of the peptide to provide a cyclic peptide, and (ii) conjugating two equivalents of the cyclized monomer peptide of step (i) via a linker.

In further embodiments of the invention, the peptides of the peptide dimers are synthesized by solid phase peptide synthesis. In still further embodiments of the invention, the peptides of the peptide dimers are synthesized by solution phase peptide synthesis.

In particular embodiments, methods of the present invention provide a process for the synthesis of a penicillamine containing peptide in commercial and/or industrial quantities by solution phase and/or solid phase chemistry methods using inexpensive starting materials and mild reagents to yield high purity peptide. In certain embodiments of the invention, the thiol group of penicillamine is protected by an acetamidomethyl (Acm) or triphenylmethyl (Trt) protecting group or as a pseudoproline ($^{\psi R,R}$Pro) derivative. In certain embodiments of the invention, penicillamine is incorporated into the peptide as a pseudoproline derivative.

In certain embodiments, the present invention provides methods of synthesizing Compound A (SEQ ID NO:1), zwitterion, hydrated, solveted forms and pharmaceutically acceptable salts, solvates, and hydrates thereof.

Compound A

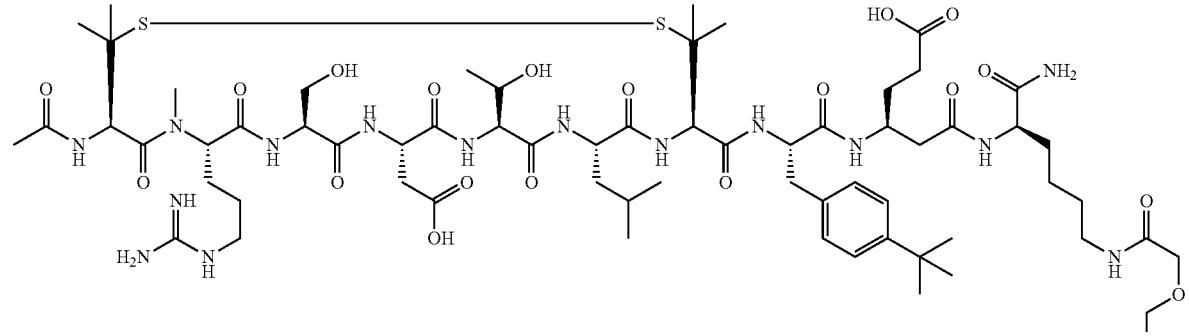

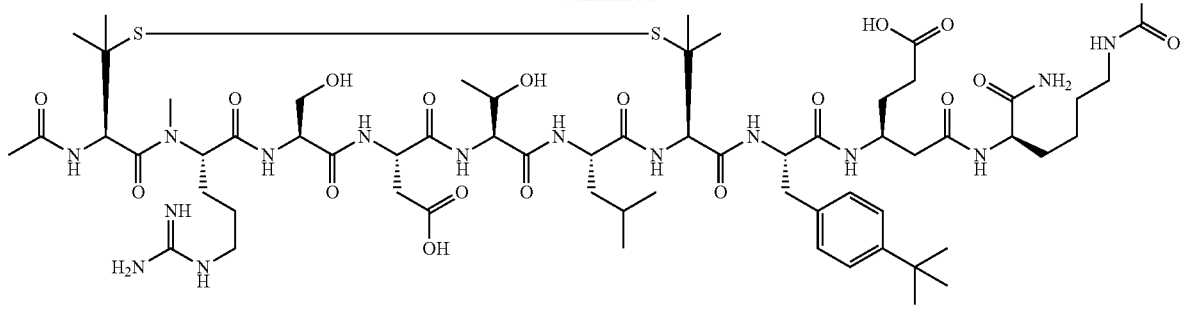

In particular embodiments, the present invention provides methods of synthesizing the cyclized peptide monomer of Compound B (SEQ ID NO:2).

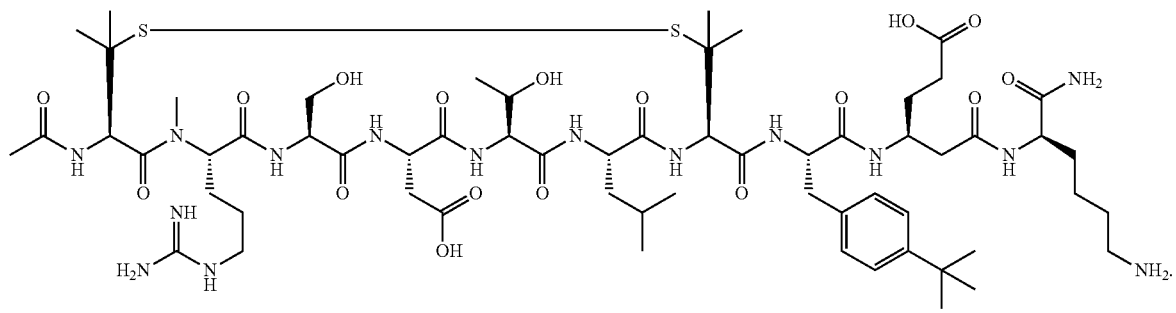

Compound B

In further embodiments of the invention, Compound B is prepared using solid phase peptide synthesis followed by oxidative cyclization of the Pen residues.

In still further embodiments of the invention, Compound B is prepared using Fmoc-chemistry, solid phase peptide synthesis. In particular embodiments of the invention, Compound B is synthesized on a suitable resin and with amino acids selected from the group consisting of Fmoc-L-D-Lys(Boc)-OH, Fmoc-β-homoGlu(O$^t$Bu)-OH, Fmoc-L-(4-$^t$Bu)Phe-OH, Fmoc-L-Pen(Acm)-OH, Fmoc-L-Pen(Trt)-OH, Fmoc-Pen($^{\psi Me,Me}$Pro)-OH, Bpoc-Pen($^{\psi Me,Me}$Pro)-OH, Cbz-Pen($^{\psi Me,Me}$Pro)-OH, Fmoc-Pen($^{\psi H,H}$ProPro)-OH, Bpoc-Pen($^{\psi H,H}$ProPro)-OH, Cbz-Pen($^{\psi H,H}$ProPro)-OH, Fmoc-Leu-Pen($^{\psi Me,Me}$Pro)-OH, Bpoc-Leu-Pen($^{\psi Me,Me}$Pro)-OH, Cbz-Leu-Pen($^{\psi Me,Me}$Pro)-OH, Fmoc-Leu-Pen($^{\psi H,H}$ProPro)-OH, Bpoc-Leu-Pen(Pro)-OH, or Cbz-Leu-Pen(Pro)-OH, Fmoc-L-Leu-OH, Fmoc-L-Thr($^t$Bu)OH, Fmoc-L-Asp(O$^t$Bu)-OH, Fmoc-L-Asp(O$^t$Bu)-Thr($^{\psi Me,Me}$Pro)-OH, Fmoc-L-Ser($^t$Bu)-OH, Fmoc-L-N(Me)-Arg(Pbf)-OH, Fmoc-L-Trp(Boc)-OH, Fmoc-β-homoGlu(O$^t$Bu)-OH, Fmoc-L-Glu(O$^t$Bu)-OH), Fmoc-D-Glu(O$^t$Bu)-OH, and Fmoc-N-D-Lys(Boc)-OH.

In yet further embodiments of the invention, Compound B is prepared on tricyclic amide linker resin (Ramage Resin). In still further embodiments of the invention, Compound B is prepared with the following protected amino acids: Fmoc-D-Lys(Boc)-OH, Fmoc-β-homoGlu(O$^t$Bu)-OH, Fmoc-L-(4-$^t$Bu)Phe-OH, Fmoc-L-Pen(Acm)-OH, Fmoc-L-Leu-OH, Fmoc-L-Thr($^t$Bu)OH, Fmoc-L-Asp(O$^t$Bu)-OH, Fmoc-L-Ser($^t$Bu)-OH, Fmoc-L-N(Me)-Arg(Pbf)-OH. In yet further embodiments of the invention, Compound B is prepared with the following protected amino acids: Fmoc-D-Lys(Boc)-OH, Fmoc-β-homoGlu(O$^t$Bu)-OH, Fmoc-L-(4-$^t$Bu)Phe-OH, Fmoc-L-Pen(Trt)-OH, Fmoc-L-Leu-OH, Fmoc-L-Asp(O$^t$Bu)-Thr($^{\psi Me,Me}$Pro)-OH, Fmoc-L-Ser($^t$Bu)-OH, Fmoc-N(Me)-Arg(Pbf)-OH.

In certain embodiments of the invention, the N-terminal Pen residue is acylated after coupling of the protected Pen residue, and prior to deprotection, cleavage, cyclization, and purification. In certain embodiments, deprotection and cleavage from the resin occur in the same step.

In yet other embodiments of the invention, a peptide having the sequence Ac-Pen-N(Me)Arg-Ser-Asp-Thr-Leu-Pen-Phe(4-$^t$Bu)-β-homoGlu-D-Lys-NH$_2$ (SEQ ID NO:25) is oxidatively cyclized by the introduction of an intramolecular disulfide bridge between the two Pen residues to form Compound B.

In still other embodiments of the invention, two equivalents of Compound B are dimerized with a diglycolic acid linker to provide Compound A.

In particular embodiments of the invention, the method provides synthesis of the linear decapeptide i.e: Ac-Pen-N(Me)Arg-Ser-Asp-Thr-Leu-Pen-Phe(4-$^t$Bu)-β-homoGlu-D-Lys-NH$_2$ (SEQ ID NO:25). In further embodiments of the invention, Ac-Pen-N(Me)Arg-Ser-Asp-Thr-Leu-Pen-Phe(4-$^t$Bu)-β-homoGlu-D-Lys-NH$_2$ (SEQ ID NO:25) is oxidized to form an intramolecularcyclic peptide through a disulfide bridge between the two Pen residues. In yet further embodiments, the cyclic decapeptide is dimerized with a suitable linker to yield a peptide dimer (Compound A).

In certain embodiments of the invention, the protected fragment Ac-Pen(R)-N(Me)Arg(pbf)-Ser($^t$Bu)-Asp(O$^t$Bu)-Thr($^t$Bu)-Leu-Pen(R)-Phe(4-$^t$Bu)-β-homoGlu(O$^t$Bu)-D-Lys(Boc)-NH$_2$ (SEQ ID NO:25) is prepared by condensation of the hexapeptide, Ac-Pen(R)-N(Me)Arg(pbf)-Ser($^t$Bu)-Asp(O$^t$Bu)-Thr($^t$Bu)-Leu-OH (SEQ ID NO:3), with the tetrapeptide, H-Pen(R)-Phe(4-$^t$Bu)-β-homoGlu(O$^t$Bu)-D-Lys(Boc)-NH$_2$ (SEQ ID NO:4), wherein each R is independently Acm or Trt.

In further embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-β-homoGlu(O$^t$Bu)-D-Lys(Boc)-NH$_2$ (SEQ ID NO:25) is prepared by condensation of the hexapeptide, Ac-Pen($^{\psi Me,Me}$Pro)-N(Me)Arg(pbf)-Ser($^t$Bu)-Asp(O$^t$Bu)-Thr($^t$Bu)-Leu-OH (SEQ ID NO:3), with the tetrapeptide, H-Pen($^{\psi Me,Me}$Pro)-Phe(4-$^t$Bu)-β-homoGlu(O$^t$Bu)-D-Lys(Boc)-NH$_2$ (SEQ ID NO:4).

In still further embodiments of the invention, the hexapeptide, Ac-Pen($^{\psi Me,Me}$Pro)-N(Me)Arg(pbf)-Ser($^t$Bu)-Asp(O$^t$Bu)-Thr($^t$Bu)-Leu-OH (SEQ ID NO:3), is prepared by condensation of Ac-Pen($^{\psi Me,Me}$Pro)-OH with the pentapeptide, HN(Me)Arg(pbf)-Ser($^t$Bu)-Asp(O$^t$Bu)-Thr($^t$Bu)-Leu-OMe (SEQ ID NO:5).

In still further embodiments of the invention, the hexapeptide, Ac-Pen(Acm)-N(Me)Arg(pbf)-Ser($^t$Bu)-Asp(O$^t$Bu)-Thr($^t$Bu)-Leu-OH (SEQ ID NO:3), is prepared by condensation of Ac-Pen(Acm)-OH with the pentapeptide, HN(Me)Arg(pbf)-Ser($^t$Bu)-Asp(O$^t$Bu)-Thr($^t$Bu)-Leu-OMe (SEQ ID NO:5).

In still further embodiments of the invention, the hexapeptide, Ac-Pen(Trt)-N(Me)Arg(pbf)-Ser($^t$Bu)-Asp(O$^t$Bu)-Thr($^t$Bu)-Leu-OH (SEQ ID NO:3), is prepared by condensation of Ac-Pen(Trt)-OH with the pentapeptide, HN(Me)Arg(pbf)-Ser($^t$Bu)-Asp(O$^t$Bu)-Thr($^t$Bu)-Leu-OMe (SEQ ID NO:5).

In yet further embodiments of the invention, the tetrapeptide, H-Pen($^{\psi Me,Me}$Pro)-Phe(4-$^t$Bu)-β-homoGlu(O$^t$Bu)-D-Lys(Boc)-NH$_2$ (SEQ ID NO:4), is prepared by condensation of Fmoc-Pen($^{\psi Me,Me}$Pro), Bpoc-Pen($^{\psi Me,Me}$Pro), or Cbz-Pen($^{\psi Me,Me}$Pro) with the tripeptide H-Phe(4-$^t$Bu)-β-homoGlu(O$^t$Bu)-D-Lys(Boc)-NH$_2$ (SEQ ID NO:4) followed by removal of the N-terminus protecting group.

In yet further embodiments of the invention, the pentapeptide, H-Leu-Pen($^{\psi Me,Me}$Pro)-Phe(4-$^t$Bu)-β-homoGlu(O$^t$Bu)-D-Lys(Boc)-NH$_2$ (SEQ ID NO:4), is prepared by condensation of dipeptide, Fmoc-Leu-Pen($^{\psi Me,Me}$Pro)-OH, with the tripeptide H-Phe(4-$^t$Bu)-β-homoGlu(O$^t$Bu)-D-Lys(Boc)-NH$_2$ followed by removal of the N-terminus protecting group.

In still further embodiments of the invention, the hexapeptide, Ac-Pen(R)-N(Me)Arg(pbf)-Ser($^t$Bu)-Asp(O$^t$Bu)-Thr($^{\psi Me,Me}$Pro)-Leu-OH (SEQ ID NO:3), is prepared by condensation of Ac-Pen(R)-OH with the pentapeptide, H N(Me)Arg(pbf)-Ser($^t$Bu)-Asp(O$^t$Bu)-Thr($^{\psi Me,Me}$Pro)-Leu-OMe (SEQ ID NO:5). Where R=Acm, Trt or ($^{\psi Me,Me}$Pro)

In yet further embodiments of the invention, the tetrapeptide, H-Pen(Acm)-Phe(4-$^t$Bu)-β-homoGlu(O$^t$Bu)-D-Lys(Boc)-NH$_2$ (SEQ ID NO:4), is prepared by condensation of Fmoc-Pen(Acm)-OH, with the tripeptide H-Phe(4-$^t$Bu)-β-homoGlu(O$^t$Bu)-D-Lys(Boc)-NH$_2$ (SEQ ID NO:4) followed by removal of the N-terminus protecting group.

In yet further embodiments of the invention, the tetrapeptide, H-Pen(Trt)-Phe(4-$^t$Bu)-β-homoGlu(O$^t$Bu)-D-Lys(Boc)-NH$_2$ (SEQ ID NO:4), is prepared by condensation of Fmoc-Pen(Trt)-OH, with the tripeptide H-Phe(4-$^t$Bu)-β-homoGlu(O$^t$Bu)-D-Lys(Boc)-NH$_2$ (SEQ ID NO:4) followed by removal of the N-terminus protecting group.

In yet further embodiments of the invention, the decapeptide, Ac-Pen(Trt)-N(Me)Arg(pbf)-Ser($^t$Bu)-Asp(O$^t$Bu)-Thr($^t$Bu)-Leu-Pen(Trt)-Phe(4-$^t$Bu)-β-homoGlu(O$^t$Bu)-D-Lys(Boc)-NH$_2$ (SEQ ID NO:25) is prepared by condensation of HN(Me)Arg(pbf)-Ser($^t$Bu)-Asp(O$^t$Bu)-Thr($^t$Bu)-Leu-Pen(Trt)-Phe(4-$^t$Bu)-β-homoGlu(O$^t$Bu)-D-Lys(Boc)-NH$_2$ (SEQ ID NO:87) and Fmoc-Pen(Trt)-OH followed by removal of the N-terminus protecting group and acetylation with actetic anhydride.

In yet further embodiments of the invention, the decapeptide, Ac-Pen(Acm)-N(Me)Arg(pbf)-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:25) is prepared by condensation of HN(Me)Arg(pbf)-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:87) and Fmoc-Pen(Acm)-OH followed by removal of the N-terminus protecting group and acetylation with actetic anhydride.

In yet further embodiments of the invention, the decapeptide, Ac-Pen(Trt)-N(Me)Arg(pbf)-Ser($^t$Bu)-Asp(O$^t$Bu)-Thr($^t$Bu)-Leu-Pen(Trt)-Phe(4-$^t$Bu)-β-homoGlu(O$^t$Bu)-D-Lys(Boc)-NH$_2$ (SEQ ID NO:25) is prepared by condensation of dipeptide Fmoc-Pen(Trt)-N(Me)Arg(pbf)-OH and octapeptide HSer($^t$Bu)-Asp(O$^t$Bu)-Thr($^t$Bu)-Leu-Pen(Trt)-Phe(4-$^t$Bu)-β-homoGlu(O$^t$Bu)-D-Lys(Boc)-NH$_2$ (SEQ ID NO:86), followed by removal of the N-terminus protecting group and acetylation with actetic anhydride.

In yet further embodiments of the invention, the decapeptide, Ac-Pen(Acm)-N(Me)Arg(pbf)-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:25) is prepared by condensation of dipeptide with Fmoc-Pen(Acm)-N(Me)Arg(pbf)-OH and octapeptide, HSer($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:86) followed by removal of the N-terminus protecting group and acetylation with actetic anhydride.

In yet further embodiments of the invention, the octapeptide, HSer($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:86) is prepared by condensation of tetrapeptide, Fmoc-Ser($^t$Bu)-Asp(O$^t$Bu)-Thr($^t$Bu)-Leu-OH (SEQ ID NO:5) and tetrapeptide, HPen(Acm)-Phe(4-$^t$Bu)-β-homoGlu(O$^t$Bu)-D-Lys(Boc)-NH$_2$ (SEQ ID NO:4) followed by removal of the N-terminus protecting group.

In yet further embodiments of the invention, the nanopeptide, HN(Me)Arg-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:87) is prepared by condensation of Pentapeptide HN(Me)Arg-Ser($^t$Bu)-Asp(O$^t$Bu)-Thr($^t$Bu)-Leu-OH (SEQ ID NO:5) and tetrapeptide HPen(Acm)-Phe(4-$^t$Bu)-β-homoGlu(O$^t$Bu)-D-Lys(Boc)-NH$_2$ (SEQ ID NO:4).

In further embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-β homoGlu(O$^t$Bu)-D-Lys(Boc)-NH$_2$ (SEQ ID NO:25) is prepared by condensation of the octapeptide, Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-OH (SEQ ID NO:80), with the dipeptide, Hβ-homoGlu(O$^t$Bu)-D-Lys(Boc)-NH$_2$.

In still further embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-β-homoGlu(O$^t$Bu)-D-Lys(Boc)-NH$_2$ (SEQ ID NO:25) is prepared by condensation of the heptapeptide, Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-OH (SEQ ID NO:81), with the tripeptide, HPhe(4-$^t$Bu)-β-homoGlu(O$^t$Bu)-D-Lys(Boc)-NH$_2$.

In yet further embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-β homoGlu(O$^t$Bu)-D-Lys(Boc)-NH$_2$ (SEQ ID NO:25) is prepared by condensation of the hexapeptide, Ac-Pen($^{\psi Me,Me}$Pro)-N (Me)Arg(pbf)-Ser($^t$Bu)-Asp(O$^t$Bu)-Thr($^t$Bu)-Leu-OH (SEQ ID NO:3), with the tetrapeptide, HPen($^{\psi Me,Me}$Pro)-Phe(4-$^t$Bu)-β-homoGlu(O$^t$Bu)-D-Lys(Boc)-NH$_2$ (SEQ ID NO:4).

In other embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-β homoGlu(O$^t$Bu)-D-Lys(Boc)-NH$_2$ (SEQ ID NO:25) is prepared by condensation of the pentapeptide, Ac-Pen($^{\psi Me,Me}$Pro)-N(Me)Arg(pbf)-Ser($^t$Bu)-Asp(O$^t$Bu)-Thr($^t$Bu)-OH (SEQ ID NO:73), with the pentapeptide, HLeu-Pen($^{\psi Me,Me}$Pro)-Phe(4-$^t$Bu)-β-homoGlu(O$^t$Bu)-D-Lys(Boc)-NH$_2$ (SEQ ID NO:83).

In certain embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-β homoGlu(O$^t$Bu)-D-Lys(Boc)-NH$_2$ (SEQ ID NO:25) is prepared by condensation of the tetrapeptide, Ac-Pen($^{\psi Me,Me}$Pro)-N(Me)Arg(pbf)-Ser($^t$Bu)-Asp(O$^t$Bu)-OH (SEQ ID NO:71), with the hexapeptide, HThr($^t$Bu)-Leu-Pen($^{\psi Me,Me}$Pro)-Phe(4-$^t$Bu)-β-homoGlu(O$^t$Bu)-D-Lys(Boc)-NH$_2$ (SEQ ID NO:84).

In particular embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-β homoGlu(O$^t$Bu)-D-Lys(Boc)-NH$_2$ (SEQ ID NO:25) is prepared by condensation of the tripeptide, Ac-Pen($^{\psi Me,Me}$Pro)-N(Me)Arg(pbf)-Ser($^t$Bu)-OH, with the heptapeptide, HAsp(O$^t$Bu)-Thr($^t$Bu)-Leu-Pen($^{\psi Me,Me}$Pro)-Phe(4-$^t$Bu)-β-homoGlu(O$^t$Bu)-D-Lys(Boc)-NH$_2$ (SEQ ID NO:85).

In further embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-β homoGlu(O$^t$Bu)-D-Lys(Boc)-NH$_2$ (SEQ ID NO:25) is prepared by condensation of the dipeptide, Ac-Pen($^{\psi Me,Me}$Pro)-N(Me)Arg(pbf)-OH, with the octapeptide, HSer($^t$Bu)-Asp(O$^t$Bu)-Thr($^t$Bu)-Leu-Pen($^{\psi Me,Me}$Pro)-Phe(4-$^t$Bu)-β-homoGlu(O$^t$Bu)-D-Lys(Boc)-NH$_2$ (SEQ ID NO:86).

In certain embodiments of the invention, Segment A, the protected hexapeptide Ac-Pen($^{\psi Me,Me}$Pro)-N(Me)Arg(pbf)-Ser($^t$Bu)-ASP(O$^t$Bu)-Thr($^t$Bu)-Leu-OH (SEQ ID NO:3) is prepared by condensation of the pentapeptide, HN(Me)Arg(pbf)-Ser($^t$Bu)-Asp(O$^t$Bu)-Thr($^t$Bu)-Leu-OMe (SEQ ID NO:5) with the Ac-Pen($^{\psi Me,Me}$Pro)-OH followed by saponification. In other embodiments of the invention, Segment B is prepared by the condensation of Cbz-Pen($^{\psi Me,Me}$Pro), Fmoc-Pen($^{\psi Me,Me}$Pro) or Bpoc-Pen($^{\psi Me,Me}$Pro) with HPhe(4-$^t$Bu)-β-homoGlu(O$^t$Bu)-D-Lys(Boc)-NH$_2$ followed by removal of the Cbz, Fmoc or Bpoc protecting group.

In a particular embodiment of the invention, the protected fragment Ac-Pen($^{\psi Me,Me}$Pro)-N(Me)Arg(pbf)-Ser($^t$Bu)-ASP(O$^t$Bu)-Thr($^t$Bu)-Leu-Pen($^{\psi Me,Me}$Pro)-Phe(4-$^t$Bu)-β-homoGlu(O$^t$Bu)-D-Lys(Boc)-NH$_2$ (SEQ ID NO:25) is prepared by condensation of hexapeptide Ac-Pen($^{\psi Me,Me}$Pro)-N(Me)Arg(pbf)-Ser($^t$Bu)-ASP(O$^t$Bu)-Thr($^t$Bu)-Leu-OH (SEQ ID NO:3) with the tetrapeptide, H-Pen($^{\psi Me,Me}$Pro)-Phe(4-$^t$Bu)-β-homoGlu(O$^t$Bu)-D-Lys(Boc)-NH$_2$ (SEQ ID NO:4). The protected decapeptide is treated with cocktail mixture TFA/water/TIS (9.0:0.5:0.25), in one step removes the pseudoproline ($^{\psi Me,Me}$Pro) group, $^t$Bu, O$^t$Bu, pbf and Boc groups to provide the unprotected decapeptide, followed by oxidation with hydrogen peroxide to form disulfide bonds to provide the cyclized decapeptide, Compound B, and dimerization with a diglycolate linker to provide Compound A.

In other embodiments of the invention, the protected fragment Ac-Pen(R)-N(Me)Arg(pbf)-Ser($^t$Bu)-Asp(O$^t$Bu)-Thr($^{\psi Me,Me}$Pro)-Leu-Pen(R)-Phe(4-$^t$Bu)-β-homoGlu(O$^t$Bu)-D-Lys(Boc)-NH$_2$ (SEQ ID NO:25) is prepared by condensation of the pentapeptide, Ac-Pen(R)-N(Me)Arg(pbf)-Ser($^t$Bu)-Asp(O$^t$Bu)-Thr($^{\psi Me,Me}$Pro)OH (SEQ ID NO:73), with the pentapeptide, HLeu-Pen(R)-Phe(4-$^t$Bu)-β-homoGlu(O$^t$Bu)-D-Lys(Boc)-NH$_2$ (SEQ ID NO:83). (R=Acm, Trt or $^{\psi Me,Me}$Pro)

In other embodiments of the invention, the protected fragment heptapeptide HAsp(O$^t$Bu)-Thr($^{\psi Me,Me}$Pro)-Leu-Pen(R)-Phe(4-$^t$Bu)-β-homoGlu(O$^t$Bu)-D-Lys(Boc)-NH$_2$ (SEQ ID NO:85) is prepared by condensation of the dipeptide, Cbz-Asp(O$^t$Bu)-Thr($^{\psi Me,Me}$Pro)-OH, with the pentapeptide, H-Leu-Pen(R)-Phe(4-$^t$Bu)-β-homoGlu(O$^t$Bu)-D-Lys(Boc)-NH$_2$ (SEQ ID NO:73). (R=Acm, Trt or $^{\psi Me,Me}$Pro).

DETAILED DESCRIPTION OF THE INVENTION

Definitions

Figure 1:
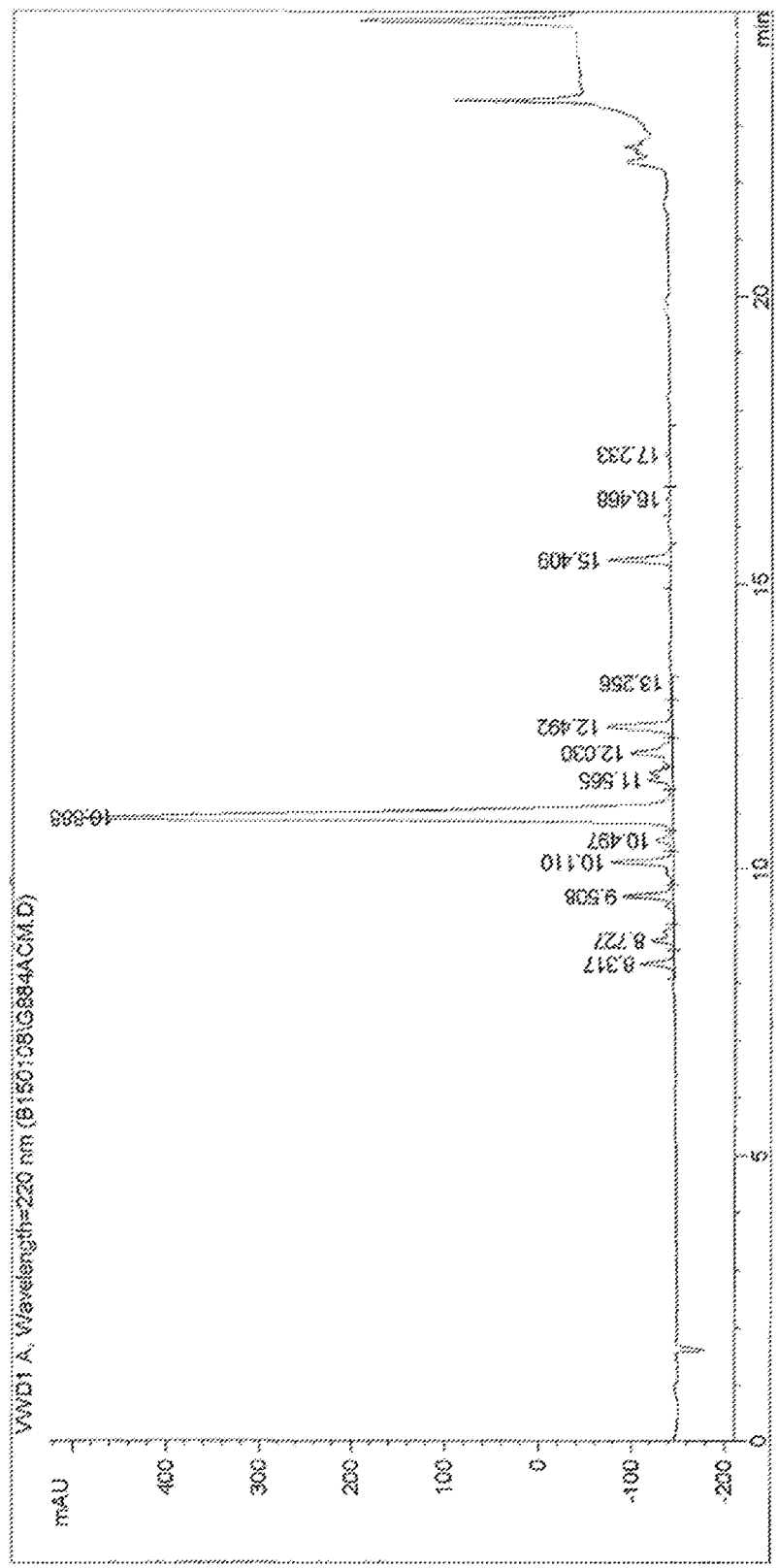
FIG. 1 represents the HPLC chromatogram of unpurified, unprotected, linear monomer. The monomer has a retention time of 10.888 min. Purity 67.05% (AUC). Peaks at 12.4 min and 15.4 min (~8% total) are the protected monomer.

As used herein, the singular forms "a," "and," and "the" include plural references unless the context clearly dictates otherwise.

As used in the present specification the following terms have the meanings indicated:

The term "peptide," as used herein, refers broadly to a sequence of two or more amino acids joined together by peptide bonds. It should be understood that this term does not connote a specific length of a polymer of amino acids, nor is it intended to imply or distinguish whether the polypeptide is produced using recombinant techniques, chemical or enzymatic synthesis, or is naturally occurring.

The term "dimer," as used herein, refers broadly to a peptide comprising two or more subunits, wherein the subunits are peptides linked at their C- or N-termini. Dimers also include peptides comprising two subunits that are linked via one or more internal amino acid residues or derivatives thereof. Each of the subunits may be linked to the other via its N-terminus, C-terminus, or through an internal amino acid or derivate thereof, which may be different for each of the two subunits. Dimers of the present invention may include homodimers and heterodimers and function as integrin antagonists. Peptide dimer compounds may be described herein using the following nomenclature: $[X_n]_2$, which indicates that the peptide dimer comprises two monomer subunits defined within the brackets (e.g., $X_n$, where X represents an amino acid and n indicates the number of amino acids in the peptide). A linker moiety linking the two peptide subunits may be shown as follows: $[X_n]_2$-λ, or λ-$[X_n]_2$, where λ is the linker. Other chemical moieties, such as detectable labels may be shown in a similar manner as for the linker.

The term "L-amino acid," as used herein, refers to the "L" isomeric form of an amino acid, and conversely the term "D-amino acid" refers to the "D" isomeric form of an amino acid. The amino acid residues described herein are in the "L" isomeric form unless otherwise indicated, however, residues in the "D" isomeric form can be substituted for any L-amino acid residue, as long as the desired function is retained by the peptide.

The term "$NH_2$," as used herein, refers to the free amino group present at the amino terminus of a polypeptide or the —$CONH_2$ group present at the C-terminus of a polypeptide. The term "OH," as used herein, refers to the free carboxy group present at the carboxy terminus of a peptide. Further, the term "Ac," as used herein, refers to Acetyl protection through acylation of the N-terminus of a polypeptide, or any amino acid in the peptide. The term "$NH_2$" may also be used herein to refer to a C-terminal amide group, e.g., in the context of a $CONH_2$.

The term "carboxy," as used herein, refers to —$CO_2H$.

The term "cyclized," as used herein, refers to a reaction in which one part of a polypeptide molecule becomes linked to another part of the polypeptide molecule to form a closed ring, such as by forming an intramolecular disulfide bridge or other similar bond, e.g. a lactam bond. In particular embodiments, peptide monomer compounds or monomer subunits of peptide dimer compounds described herein are cyclized via an intramolecular bond between two amino acid residues present in the peptide monomer or monomer subunit.

The term "subunit," as used herein, refers to one of a pair of polypeptide monomers that are joined at the C- or N-terminus to form a dimer peptide composition.

The term "linker," as used herein, refers broadly to a chemical structure that is capable of linking together a plurality of peptide monomer subunits to form a dimer.

The term "pharmaceutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by treatment of an amino group with a suitable acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalene sulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include, but are not limited to, inorganic acids such as hydrochloric, hydrobromic, sulfuric, and phosphoric, and organic acids such as oxalic, maleic, succinic, and citric. In certain embodiments, any of the peptide monomer compounds or peptide dimer compounds described herein are salt forms, e.g., acetate salts.

The term "N(alpha)Methylation", as used herein, describes the methylation of the alpha amine of an amino acid, also generally termed as an N-methylation.

All peptide sequences are written according to the generally accepted convention whereby the α-N-terminal amino acid residue is on the left and the α-C-terminal is on the right. As used herein, the term "α-N-terminal" refers to the free α-amino group of an amino acid in a peptide, and the term "α-C-terminal" refers to the free α-carboxylic acid terminus of an amino acid in a peptide. Unless otherwise specified, it is understood that the α-N-terminal residue on the left has a free α-amino group and the α-C-terminal residue on the right has a free α-carboxylic acid group. Peptide sequences may be shown in tables, which may further disclose additional moieties, such as N-terminal or C-terminal chemical modifications, linkers, conjugates, and/or labels, which are present in certain embodiments of the compounds of the invention.

It is noted that the term "comprising" is intended to be open and permits but does not require the inclusion of additional elements or steps. When the term "comprising" is used herein, the term "consisting of" is thus also encompassed and disclosed.

The term "amino acid" or "any amino acid" as used here refers to any and all amino acids, including naturally occurring amino acids (e.g., α-amino acids), unnatural amino acids, modified amino acids, and non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur in bacterial envelopes and some antibiotics. The "non-standard," natural amino acids are pyrrolysine (found in methanogenic organisms and other eukaryotes), selenocysteine (present in many noneukaryotes as well as most eukaryotes), and N-formylmethionine (encoded by the start codon AUG in bacteria, mitochondria and chloroplasts). "Unnatural" or "non-natural" amino acids are non-proteinogenic amino acids (i.e., those not naturally encoded or found in the genetic code) that either occur naturally or are chemically synthesized. Over 140 amino acids are known to occur naturally and thousands of more combinations are possible. Examples of "unnatural" amino acids include β-amino acids ($β^3$ and $β^2$), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, alpha-methyl amino acids and N-methyl amino acids. Unnatural or non-natural amino acids also include modified amino acids. "Modified" amino acids include amino acids (e.g., natural amino acids) that have been chemically modified to include a group, groups, or chemical moiety not naturally present on the amino acid.

For the most part, the names of naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

The term "isostere" or "isostere replacement," as used herein, refers to any amino acid or other analog moiety having physiochemical and/or structural properties similar to a specified amino acid. In particular embodiments, an "isostere" or "suitable isostere" of an amino acid is another amino acid of the same class, wherein amino acids belong to the following classes based on the propensity of the side chain to be in contact with polar solvent like water: hydrophobic (low propensity to be in contact with water), polar or charged (energetically favorable contact with water). Illustrative charged amino acid residues include lysine (+), arginine (+), aspartate (−) and glutamate (−). Illustrative polar amino acids include serine, threonine, asparagine, glutamine, histidine and tyrosine. Illustrative hydrophobic amino acids include alanine, valine, leucine, isoleucine, proline, phenylalanine, tryptophane, cysteine and methionine. The amino acid glycine does not have a side chain and is hard to assign to one of the above classes. However, glycine is often found at the surface of proteins, often within loops, providing high flexibility to these regions, and an isostere may have a similar feature. Proline has the opposite effect, providing rigidity to the protein structure by imposing certain torsion angles on the segment of the polypeptide chain. In certain embodiments, an isostere is a derivative of an amino acid, e.g., a derivative having one or more modified side chains as compared to the reference amino acid.

The term "Fmoc peptide synthesis" as used herein refers to the use of Fmoc α-amino (N-terminal) protected amino acids during peptide synthesis. The Fmoc protecting group can be cleaved under mild basic conditions. The side chains of these Fmoc protected amino acids are, as necessary, protected with an appropriate, orthogonal protecting groups that are stable under the mild basic conditions used to cleave the Fmoc protecting group from the N-terminus of the peptide.

The term "Cbz peptide synthesis" refers to the use of Cbz (Z) α-amino (N-terminal) protected amino acids during peptide synthesis. The Cbz protecting group can be cleaved under hydrogenolysis conditions using Pd/C and hydrogen. The side chains of these Cbz protected amino acids are, as necessary, protected with an appropriate, orthogonal protecting groups that are stable under the hydrogenolysis conditions used to cleave the Cbz protecting group from the N-terminus of the peptide.

TABLE 1

DEFINITIONS AND ABBREVIATIONS

| Abbreviation | Definition |
| --- | --- |
| 1,3-Phenylenediacetic acid | meta-Phenylenediacetic acid (Linker) |
| 1,4-Phenylenediacetic acid | para-Phenylenediacetic acid (Linker) |
| 1-1-Indane | 1-Aminoindane-1-carboxylic acid |
| 1-Nal | 1-Napthylalanine |
| 2-2-Indane | 2-Aminoindane-2-carboxylic acid |
| 2-Methly-trifluorobutyric acid | acylated with 2-Methy-4,4,4-Butyric acid |
| 2-Nal | 2-Napthylalanine |
| 3,3-DiphenylAla | 3,3-DiPhenylAlanine |
| 3,3-DiphenylGly | 3,3-DiPhenylGlycine |
| Ac- | Acetyl |
| Acm | Acetamidomethyl |
| Ahx | Aminohexanoic acid |
| Aic | aminoindan-2-carboxylic acid |
| Aoc | 2-Amino octonoic acid |
| AUC | Area Under Curve |
| Bip | Biphenylalanine |
| Boc | tert-Butyloxycarbonyl |
| Boc-Triazine | Boc-Triazine di-acid |
| Bpoc | (2-(4-Biphenyl)isopropoxycarbonyl) |
| Cav | Cavanine |
| Cba | Cyclobutyl alanine |
| Cbz<br>Z | Carbobenzyloxy |
| Cit | Citroline |
| CONH$_2$ | Amide |
| COOH | Acid |
| Cpa | Cyclopentyl Alanine |
| Cyclobutyl | Cyclobutylalanine |
| Dab | Diaminobutyric acid |
| Dap | Diaminopropionic acid |
| DIC | N,N'-Diisopropylcarbodiimide |
| DIG | DiGlycolic acid (Linker) |
| DTT | Dithiothreotol |
| Fmoc | 9-Fluorenylmethyloxycarbonyl |
| Gla | Gama-Carboxy-Glutamic acid |
| Glu(OMe) | L-glutamic acid g-methyl ester |
| HAsp or homoAsp | homoAspartic acid |

TABLE 1-continued

DEFINITIONS AND ABBREVIATIONS

| Abbreviation | Definition |
|---|---|
| HBTU | (2-(1H-benzotriazol-1-yl)-1,1,3,3-tetramethyluronium hexafluorophosphate |
| HCha | homocyclohexyl Alanine |
| HCys or homoCys | homoCysteine |
| HGlu or homoGlu | homoGlutamic acid |
| HLys or homoLys | homoLysine |
| HOBt | 1-hydroxy-benzotriazole |
| HomoLeu or homoLeu | homoLeucine |
| HPhe homoPhe | homo Phenylalanine |
| IDA | β-Ala-Iminodiacetic acid (Linker) |
| IDA-Palm | β-Ala (Palmityl)-Iminodiacetic acid |
| Me | Methyl |
| NH$_2$ | Free Amine |
| NHS | N-hydroxysuccinimide |
| Nle | Norleucine |
| N-Me-Arg; N(alpha)Methylation | N-Methyl-Arginine |
| N-Me-Lys | N-Methyl-Lysine |
| N-Me-Lys (Ac) | N-Methyl-Acetyl-D-lysine |
| O-Me-Tyr | Tyrosine (O-Methyl) |
| Orn | Ornithine |
| PEG13 | Bifunctional PEG linker with 13 PolyEthylene Glycol units |
| PEG1K | Bifunctional PEG linker with PolyEthylene Glycol Mol wt of 1000Da |
| PEG25 | Bifunctional PEG linker with 25 PolyEthylene Glycol units |
| PEG2K | Bifunctional PEG linker with PolyEthylene Glycol Mol wt of 2000Da |
| PEG3.4K | Bifunctional PEG linker with PolyEthylene Glycol Mol wt of 3400Da |
| PEG5K | Bifunctional PEG linker with PolyEthylene Glycol Mol wt of 5000Da |
| Pen | Penicillamine |
| Pen(=O) | Penicillamine sulfoxide |
| Phe(2,4-diCl) | (S)-Fmoc-2-amino-3-(2,4-dichlorophenyl)propionic acid |
| Phe(2-carbomyl) | L-2-carbamoylphenylalanine |
| Phe(3,4-diCl) | (S)-Fmoc-2-amino-3-(3,4-dichlorophenyl)propionic acid |
| Phe(3-carbomyl) | L-3-carbamoylphenylalanine |
| Phe(4-carbomyl) | L-4-carbomoylphenylalanine |
| Phe(4-CF3) | 4-Trifluoromethyl Phenylalanine |
| Phe(4-COOH) | (4-carboxy-tert-butyl)-L-phenylalanine |
| Phe(4-F) | 4-fluoro-L-phenylalanine |
| Phe(4-Guanidino) or 4-Guan | 4-Guanidine-Phenylalanine |
| Phe(4-OMe) | (S)-4-methoxyphenylalanine |
| Phe(4-$^t$Bu) | 2-amino-3-(4-tert-butyl-phenyl)propionic acid |
| Pseudoproline (di methyl) | ($^{\Psi Me,Me}$Pro) |
| Pseudoproline | ($^{\Psi H,H}$Pro) or (Pro) |
| Sar | Sarcosine |
| TFA | Trifluoroacetic Acid |
| Tic | (3S-)-1,2,3,4-tetrahydroisoquinoline-3-carboxylic acid |
| | 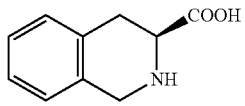 [SMILES: O=C(O)[C@@H]1Cc2ccccc2CN1] |
| TIS | Triisopropylsilane |
| Triazine | Amino propyl Triazine di-acid |
| Trifluorobutyric acid | Acylated with 4,4,4-Trifluorobutyric acid |
| Trifluorpentanoic acid | Acylated with 5,5,5-Trifluoropentanoic acid |
| Trt | Triphenylmethyl (Trityl) |
| β-Asp | β-Aspartic acid |

TABLE 1-continued

DEFINITIONS AND ABBREVIATIONS

| Abbreviation | Definition |
|---|---|
| β-HGlu<br>β-homoGlu<br>beta-homoGlu<br>Aad | β-homoglutamic acid |
| β-HPhe or<br>β-homoPhe | β-homophenylalanine |
| β-azido-Ala-OH | β-azido-Alanine |
| β-HTrp or<br>β-homoTrp | β-homoTrypophane |
| Ac-Pen($^{ΨMe,Me}$Pro)<br>(4R)-3-acetyl-2,2,5,5-<br>tetramethyl-thiazolidine-4-<br>carboxylic acid | |
| Ac-Pen(Pro)-OH<br>(4R)-3-acetyl-5,5-dimethyl-<br>thiazolidine-4-carboxylic acid | |
| Fmoc-Pen($^{ΨMe,Me}$Pro)-OH<br>(4R)-3-(9H-fluoren-9-<br>ylmethoxycarbonyl)-2,2,5,5-<br>tetramethyl-thiazolidine-4-<br>carboxylic acid | |
| Bpoc-Pen($^{ΨMe,Mee}$Pro)-OH<br>(R)-3-(((2-([1,1'-biphenyl]-4-<br>yl)propan-2-yl)oxy)carbonyl)-<br>2,2,5,5-<br>tetramethylthiazolidine-4-<br>carboxylic acid | |
| Cbz-Pen($^{ΨMe,Me}$Pro)-OH<br>(R)-3-((benzyloxy)carbonyl)-<br>2,2,5,5-<br>tetramethylthiazolidine-4-<br>carboxylic acid | |

TABLE 1-continued

DEFINITIONS AND ABBREVIATIONS

| Abbreviation | Definition |
| --- | --- |
| Fmoc-Pen(Pro)-OH<br>(R)-3-(((9H-fluoren-9-yl)methoxy)carbonyl)-5,5-dimethylthiazolidine-4-carboxylic acid | *(structure)* |
| Bpoc-Pen(Pro)-OH<br>(R)-3-(((2-([1,1'-biphenyl]-4-yl)propan-2-yl)oxy)carbonyl)-5,5-dimethylthiazolidine-4-carboxylic acid | *(structure)* |
| Cbz-Pen(Pro)-OH<br>(R)-3-((benzyloxy)carbonyl)-5,5-dimethylthiazolidine-4-carboxylic acid | *(structure)* |
| Fmoc-Leu-Pen($^{\Psi Me,Me}$Pro)-OH | *(structure)* |
| Bpoc-Leu-Pen($^{\Psi Me,MFe}$Pro)-OH | *(structure)* |
| Cbz-Leu-Pen($^{\Psi Me,Me}$Pro)-OH | *(structure)* |

TABLE 1-continued

DEFINITIONS AND ABBREVIATIONS

| Abbreviation | Definition |
| --- | --- |
| Fmoc-Leu-Pen(Pro)-OH | *(chemical structure)* |
| Bpoc-Leu-Pen(Pro)-OH | *(chemical structure)* |
| Cbz-Leu-Pen(Pro)-OH | *(chemical structure)* |

In certain embodiments, the invention provides a method of preparing a peptide dimer compound comprising: (i) synthesizing a peptide having a sequence as described herein, and introducing an intramolecular disulfide bond between two residues of the peptide (or allowing the intramolecular bond to form), and conjugating a linker to the peptide; (ii) synthesizing a peptide having a sequence as described herein (e.g., the same sequence as for step (i)), and introducing an intramolecular disulfide bond between two residues of the peptide (or allowing the intramolecular bond to form); and (iii) conjugating the peptide of step (i) to the peptide of step (ii) via the linker attached to the peptide of step (i).

In other embodiments, the methods of the present invention provide a method of preparing a peptide dimer compound comprising (i) synthesizing a peptide having a sequence comprising two thiol-containing residues, such as, but not limited to, penicillamine or cysteine, and introducing a disulfide bridge between the two thiol-containing residues of the peptide through oxidation of the peptide to provide a cyclized peptide, and (ii) conjugating two equivalents of the cyclized peptide of step (i) via a linker.

In other embodiments, the methods of the present invention provide a method of preparing a peptide dimer compound comprising (i) synthesizing a peptide having a sequence comprising two penicillamine residues and introducing an intramolecular disulfide bridge between the two penicillamine residues of the peptide through oxidation of the peptide to provide a cyclized peptide, and (ii) conjugating two equivalents of the cyclized peptide of step (i) via a linker.

In certain embodiments, the methods of the present invention provide a method of preparing the cyclized peptides of Compound B, Table 2, those disclosed in PCT Applications PCT/US2013/064439; PCT/US2014/032391; PCT/US2014/032392; PCT/US2015/053558; PCT/US2015/053603; and U.S. Pat. No. 9,518,091 B2, all of which are incorporated by reference herein in their entireties, the peptide monomers described herein, and pharmaceutically acceptable salts, hydrates, and solvates thereof.

Compound B (SEQ ID NO: 2)

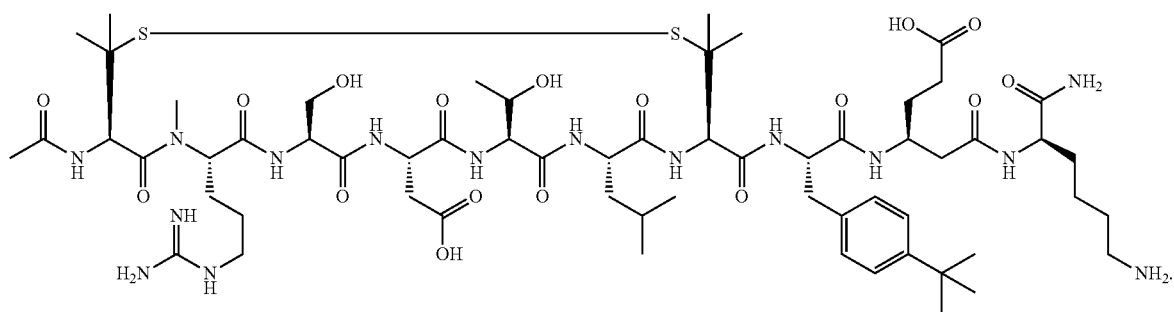

In certain embodiments of the invention, Compound B can be neutral. In further embodiments of the invention, Compound B can be in the form of an internal salt. In other embodiments of the invention, Compound B can be anhydrous.

In further embodiments of the invention, Compound B can form a salt with a pharmaceutically acceptable anion, such as, but not limited to, the anions in Table A. In particular embodiments, Compound B can form salt with a pharmaceutically acceptable anion selected from the group consisting of hydrochloride, sulfate, hydrobromide, citrate, mesylate, maleate and phosphate.

TABLE A

PHARMACETUICALLY ACCEPTABLE ANIONS

| | |
|---|---|
| chloride | $Cl^-$ |
| bromide | $Br^-$ |
| sulfate | $SO_4^-$ ($HSO_4^-$) |
| nitrate | $NO_3^-$ |
| phosphate | $H_2PO_4^-$ $HPO4^-$) |
| bicarbonate | $HCO_3^-$ |
| mesylate | $CH_3SO_3^-$ |
| esylate | $H_3C\diagdown\diagup SO_3^-$ |
| isethionate | $HO\diagdown\diagup SO_3^-$ |
| tosylate | $H_3C-C_6H_4-SO_3^-$ |
| napsylate | naphthyl-$SO_3^-$ |
| besylate | $C_6H_5-SO_3^-$ |
| acetate | $CH_3CO_2$ |
| propionate | $H_3C\diagdown\diagup CO_2^-$ |
| maleate | $HO_2C\diagdown\diagup CO_2^-$ |

TABLE A-continued

PHARMACETUICALLY ACCEPTABLE ANIONS

| | |
|---|---|
| benzoate | $C_6H_5-CO_2^-$ |
| salicylate | 2-HO-$C_6H_4$-$CO_2^-$ |
| fumarate | $HO_2C-CH=CH-CO_2^-$ |
| citrate | $HO_2C-CH_2-C(OH)(CO_2H)-CH_2-CO_2^-$ |
| lactate | $H_3C-CH(OH)-CO_2^-$ |
| malate | $HO_2C-CH_2-CH(OH)-CO_2^-$ |
| tartrate | $HO_2C-CH(OH)-CH(OH)-CO_2^-$ |
| pamoate | (methylenebis(hydroxynaphthoate)) |
| succinate | $HO_2C-CH_2-CH_2-CO_2^-$ |

TABLE A-continued

PHARMACETUICALLY ACCEPTABLE ANIONS

| | |
|---|---|
| glycolate | HOCH$_2$CO$_2^-$ |
| hexanoate | CH$_3$(CH$_2$)$_4$CO$_2^-$ |
| octanoate | CH$_2$(CH$_2$)$_6$CO$_2^-$ |
| decanoate | CH$_3$(CH$_2$)$_8$CO$_2^-$ |
| stearate | CH$_3$(CH$_2$)$_{16}$CO$_2^-$ |
| oleate | HO(H$_2$C)$_2$H$_3$C—CH=CH—CH(CH$_2$)$_3$CO$_2^-$ |
| aspartate | HO$_2$C-CH$_2$-CH(NH$_2$)-CO$_2^-$ |
| glutamate | HO$_2$C-CH$_2$-CH$_2$-CH(NH$_2$)-CO$_2^-$ |

In other embodiments of the invention, Compound B can form a salt with a pharmaceutically acceptable anion, such as, but not limited to, the anions in Table A. In still other embodiments of the invention, Compound B can form a salt with a pharmaceutically acceptable cation selected from the group consisting of sodium, calcium, potassium, magnesium, meglumine, aluminum, and zinc.

TABLE B

PHARMCETICALLY ACETABLE CATIONS

| | |
|---|---|
| sodium | Na$^+$ |
| potassium | K$^+$ |
| calcium | Ca$^{++}$ |
| magnesium | Mg$^{++}$ |
| lithium | Li$^+$ |
| zinc | Zn$^{++}$ |
| aluminum | Al$^{+++}$ |
| argenine | (structure: guanidinium-containing arginine cation) |
| lysine | (structure: protonated lysine) |
| histidine | (structure: protonated histidine) |
| triethylamine | (CH$_3$CH$_2$)$_3$NH$^+$ |
| ethanolamine | HOCH$_2$CH$_2$NH$_3^+$ |
| triethanolamine | (HOCH$_2$CH$_2$)$_3$NH$^+$ |
| ethylenediamine | H$_2$NCH$_2$CH$_2$NH$_3^+$ |
| choline | HOCH$_2$CH$_2$N(CH$_3$)$_3^+$ |
| meglumine | (structure: N-methylglucamine cation) |
| procaine | (structure: protonated procaine) |
| benzathine | (structure: protonated benzathine) |

TABLE 2

Peptides

Ac-Pen*-(N-Me-Arg)-Ser-Asp-Thr-Leu-Pen*-Trp-(D-Lys)-NH$_2$ (SEQ ID NO: 6)

Ac-Pen*-(N-Me-Arg)-Ser-Asp-Thr-Leu-Pen*-Trp-bHomoGlu-(D-Lys)-NH$_2$ (SEQ ID NO: 7)

Ac-Pen*-(N-Me-Arg)-Ser-Asp-Thr-Leu-Pen*-Trp-Glu-(N-Me-D-Lys)-NH$_2$ (SEQ ID NO: 8)

Ac-Pen*-(N-Me-Arg)-Ser-Asp-Thr-Leu-Pen*-Trp-Glu-(N-Me-Lys)-NH$_2$ (SEQ ID NO: 9)

Ac-Pen*-(N-Me-Arg)-Ser-Asp-Thr-Leu-Pen*-Trp-(D-Glu)-(D-Lys)-OH (SEQ ID NO: 10)

Ac-Pen*-(N-Me-Arg)-Ser-Asp-Thr-Leu-Pen*-Trp-Glu-(D-Lys)-NH$_2$ (SEQ ID NO: 11)

Ac-Pen* -(N-Me-Arg)-Ser-Asp-Thr-Leu-Pen*-Trp-(D-Glu)-(D-Lys)-NH$_2$ (SEQ ID NO: 10)

Ac-Pen*-(N-Me-Arg)-Ser-Asp-Thr-Leu-Pen*-Trp-Glu-(D-Lys)-OH (SEQ ID NO: 11)

*intramolecular disulfide bridge

In particular embodiments, the cyclized peptide is a pharmaceutically acceptable salt form. In one embodiment, it is an acetate salt. In a particular embodiment of the invention, Compound B is a pharmaceutically acceptable salt form. In one embodiment, Compound B is an acetate salt.

In certain embodiments, the methods of the present invention provide a method of preparing the peptide dimer compounds, including pharmaceutically acceptable salts, solvates, and hydrates thereof, of structure shown below (Compound A), the compounds of Table 3, the peptide dimers of disclosed in PCT Applications PCT/US2013/064439; PCT/US2014/032391; PCT/US2014/032392; PCT/US2015/053603, and U.S. Pat. No. 9,518,091 B2, the peptide dimers described herein, and pharmaceutically acceptable salts, solvates, and hydrates thereof.

Compound A (SEQ ID NO: 1)

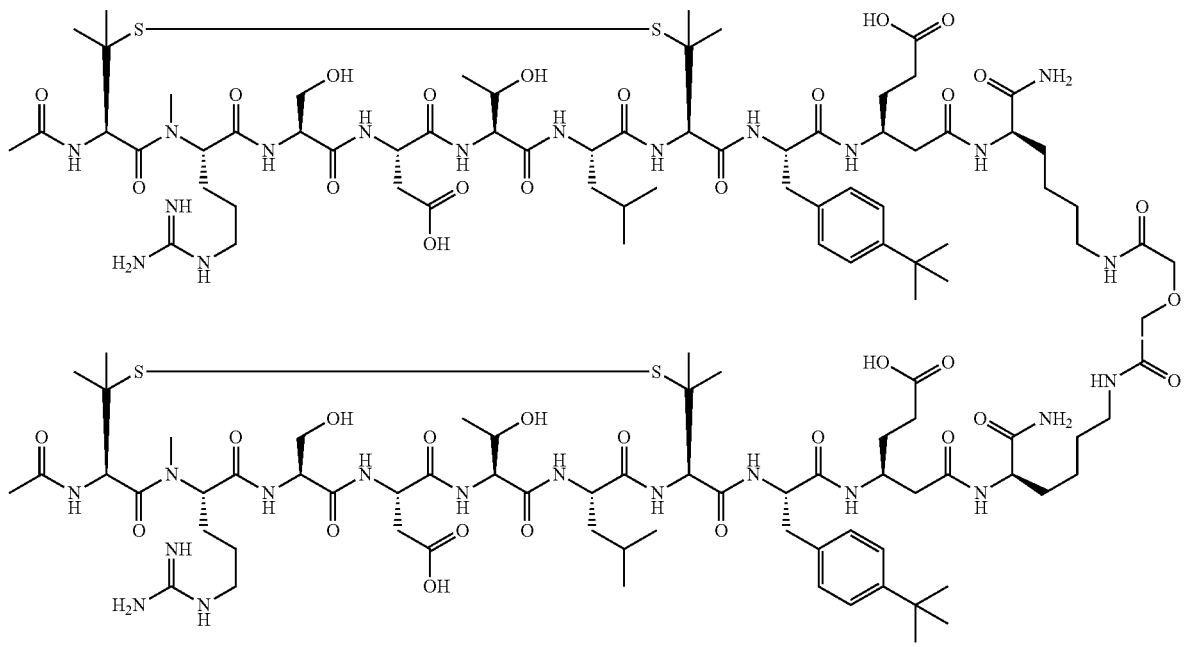

TABLE 3

Peptide Dimers

[Ac-Pen*-(N-Me-Arg)-Ser-Asp-Thr-Leu-Pen*-Trp-(D-Lys)-NH₂]₂-DIG (SEQ ID NO: 12)

[Ac-Pen*-(N-Me-Arg)-Ser-Asp-Thr-Leu-Pen*-Trp-bHomoGlu-(D-Lys)-NH₂]₂-DIG (SEQ ID NO: 13)

[Ac-Pen*-(N-Me-Arg)-Ser-Asp-Thr-Leu-Pen*-Trp-Glu-(N-Me-D-Lys)-NH₂]₂-DIG (SEQ ID NO: 14)

[Ac-Pen*-(N-Me-Arg)-Ser-Asp-Thr-Leu-Pen*-Trp-Glu-(N-Me-Lys)-NH₂]₂-DIG (SEQ ID NO: 15)

[Ac-Pen*-(N-Me-Arg)-Ser-Asp-Thr-Leu-Pen*-Trp-(D-Glu)-(D-Lys)-OH]₂-DIG (SEQ ID NO: 16)

[Ac-Pen*-(N-Me-Arg)-Ser-Asp-Thr-Leu-Pen*-Trp-Glu-(D-Lys)-NH₂]₂-DIG (SEQ ID NO: 17)

[Ac-Pen* -(N-Me-Arg)-Ser-Asp-Thr-Leu-Pen*-Trp-(D-Glu)-(D-Lys)-NH₂]₂-DIG (SEQ ID NO: 16)

[Ac-Pen*-(N-Me-Arg)-Ser-Asp-Thr-Leu-Pen*-Trp-Glu-(D-Lys)-OH]₂-DIG (SEQ ID NO: 17)

*intramolecular disulfide bridge

Embodiments of the invention include pharmaceutically acceptable salt forms of Compound A, the compounds of Table 3, and the peptide dimers disclosed in PCT Applications PCT/US2013/064439; PCT/US2014/032391; PCT/US2014/032392; PCT/US2015/053558; PCT/US2015/053603, and U.S. Pat. No. 9,518,091 B2, and the peptide dimers described herein, e.g., acetate salts of Compound A, as well as pharmaceutically acceptable salts, hydrates, and solvates thereof.

In certain embodiments of the invention, Compound A can be neutral. In further embodiments of the invention, Compound A can be in the form of an internal salt. In other embodiments of the invention, Compound A can be anhydrous.

In further embodiments of the invention, Compound A can form a salt with a pharmaceutically acceptable anion, such as, but not limited to, the anions in Table A. In particular embodiments, Compound A can form salt with a pharmaceutically acceptable anion selected from the group consisting of hydrochloride, sulfate, hydrobromide, citrate, mesylate, maleate and phosphate.

In other embodiments of the invention, Compound A can form a salt with a pharmaceutically acceptable anion, such as, but not limited to, the anions in Table A. In still other embodiments of the invention, Compound A can form a salt with a pharmaceutically acceptable cation selected from the group consisting of sodium, calcium, potassium, magnesium, meglumine, aluminum and zinc.

In particular embodiments, the invention is directed to the synthesis of a compound, wherein the compound is a peptide monomer or a peptide dimer as described below.

In certain embodiments of the invention, the two linked monomer subunits of the peptide dimer are linked together through their C-termini via a linking moiety. In other embodiments of the invention, the two linked monomer subunits of the peptide dimer are linked together through their N-termini via a linking moiety. In still other embodiments, the two linked monomer subunits of the peptide dimer are linked through one or more amino acid residues or derivatives thereof. Suitable linkers include, but are not limited to, those disclosed in PCT Applications PCT/US2013/064439; PCT/US2014/032391; PCT/US2014/032392; PCT/US2015/053558, PCT/US2015/053603; and U.S. Pat. No. 9,518,091 B2.

In certain embodiments, the compound is a peptide monomer comprising a monomer subunit of Formula (I) or a peptide dimer compound comprises two linked monomer subunits of Formula (I) (SEQ ID NO:18):

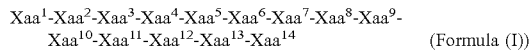

or a pharmaceutically acceptable salt, solvate, or hydrate thereof,
wherein:
Xaa$^1$ is absent, Ac, or any amino acid;
Xaa$^2$ is absent, Ac, or any amino acid;
Xaa$^3$ is absent, Ac, or any amino acid;
Xaa$^4$ is any amino acid capable of forming a bond with Xaa$^{10}$;
Xaa$^5$ is selected from the group consisting of: N-Me-Arg, Arg, N-Me-Lys, Phe(4-guanidino), Phe(4-carbomyl), Cit, Phe(4-NH$_2$), N-Me-homoArg, homoArg, Tyr, Dap, Dab, Arg-Me-sym, Arg-Me-asym, Cav, and His;
Xaa$^6$ is Ser, Gly, Thr or Ile;
Xaa$^7$ is Asp, Asp(OMe) or N-Me-Asp;
Xaa$^8$ is selected from the group consisting of: Thr, Val, Ile, Leu, homoLeu, Gln, Ser, Asp, Pro, Gly, His, Ala, Phe, Lys, Arg, Asn, Glu, Tyr, Trp, Met, Nle, and N-methyl amino acids, including N-Me-Thr;
Xaa$^9$ is selected from the group consisting of: Gln, Ser, Asp, Pro, Gly, Ala, Phe, Glu, Ile, Val, N-butyl Ala, N-pental Ala, N-hexyl Ala, cyclobutyl Ala, cyclopentylAla, Leu, Nle, Cba, homoLeu, Cpa, Aoc, and N-Me-Leu;
Xaa$^{10}$ is any amino acid capable of forming a bond with Xaa$^4$;
Xaa$^{11}$ is absent or selected from the group consisting of: aromatic amino acids, substituted aromatic amino acids, Tic, Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, HPhe, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3, 3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, Phe(2-carbomyl), Phe(3-carbomyl), Phe(4-COOH), Phe(4-OMe), and Phe(4-$^t$Bu), Phe(4-COOH), homoPhe and corresponding D-amino acids and suitable isosteres thereof,
Xaa$^{12}$ is absent or selected from the group consisting of: aromatic amino acids, substituted aromatic amino acids, Glu, D-Glu, homoGlu, Asp, D-Asp, D-homoGlu, Gla, β-homoGlu, Tic, Aic, Gln, Cit, Glu(OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, homo-Phe, D-1-Nal, D-2-Nal, Thr, and Val, and corresponding D-amino acids and isosteres;
Xaa$^{13}$ is absent or Pro or any amino acid; and
Xaa$^{14}$ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and homoSer, homoGlu, D-homoGlu, N-Me-Glu, N-Me-Asp, N-Me-D-Glu, and N-Me-D-Asp, wherein one or both monomer subunits of the peptide dimer compound comprises a bond between Xaa$^4$ and Xaa$^{10}$.

In one embodiment, Xaa$^4$ is Cys or Pen, Xaa$^{10}$ is Pen or Cys, and Xaa$^4$ and Xaa$^{10}$ are linked by a disulfide bond. In certain embodiments, both Xaa$^4$ and Xaa$^{10}$ are Pen. In other embodiments, both Xaa$^4$ and Xaa$^{10}$ are L-Pen. In yet other embodiments, both Xaa$^4$ and Xaa$^{10}$ are D-Pen.

In particular embodiments of Formula (I),
Xaa$^5$ is selected from the group consisting of Cit, Phe(4-carbomylamino), and N-Me-homoArg;
Xaa$^8$ is selected from the group consisting of Leu, homoLeu, Nle, and Val;
Xaa$^9$ is selected from the group consisting of Cba, homoLeu, and Cpa;
Xaa$^{11}$ is selected from the group consisting of Tic, Phe(2-carbomyl), Phe(3-carbomyl), Phe(4-COOH), Phe(4-OMe), and Phe(4-$^t$Bu);
Xaa$^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; and/or
Xaa$^{13}$ is Pro.

In further embodiments of Formula (I) Xaa$^{11}$ is absent or selected from the group consisting of: aromatic amino acids, substituted aromatic amino acids and Tic.

In other embodiments of Formula (I), Xaa$^1$ is Ac and three of Xaa$^2$, Xaa$^3$, Xaa$^{11}$, Xaa$^{12}$, Xaa$^{13}$ are absent.

In still other embodiments of Formula (I), four of Xaa$^1$, Xaa$^2$, Xaa$^3$, Xaa$^{11}$, Xaa$^{12}$, Xaa$^{13}$ are absent.

In yet other embodiments, Formula (I) is a ten amino acid peptide.

In particular embodiments of compounds comprising Formula (I), the compound further comprises a linker moiety linking the two monomer subunits, wherein the linker moiety is optionally selected from the group consisting of DIG, PEG13, PEG25, PEG1K, PEG2K, PEG34K, PEG4K, PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, cyclopropylacetic acid, 4-fluoorobenzoic acid, 4-fluorophenylacetic acid, 3-phenylpropionic acid, succinic acid, biotin, glutaric acid, Azelaic acid, Pimelic acid, Dodecanedioic acid, aliphatic amino acids, aromatic amino acids, heteroaromatics, polyethylene glycols having a molecular weight from approximately 400 Da to approximately 40,000 Da, bifunctional linkers, N-Hydroxy succinimide (NHS)-activated diesters, and bis-maleimides.

In certain embodiments of Formula (I), a peptide monomer compound or a both subunits of a peptide dimer compound comprise one of the following sequences:

```
                                          (SEQ ID NO: 19)
Pen-(N-Me-Arg)-Ser-Asp-Thr-Leu-Pen-Trp-(β- homoGlu)-(D-Lys);

(SEQ ID NO: 20)
Pen-(N-Me-Arg)-Ser-Asp-Thr-Leu-Pen-(Phe-(4-COOH)-

(β-homoGlu)-(D-Lys);

(SEQ ID NO: 21)
Pen-(N-Me-Arg)-Ser-Asp-Thr-Leu-Pen-Trp-Glu-(N-Me-

Lys);

(SEQ ID NO: 22)
Pen-(N-Me-Arg)-Ser-Asp-Thr-Leu-Pen-2-Nal-(β- homoGlu)-(D-Lys);
```

```
                                    (SEQ ID NO: 23)
Pen-(N-Me-Arg)-Ser-Asp-Thr-Leu-Pen-1-Nal-(β-
homoGlu)-(D-Lys);

(SEQ ID NO: 24)
Pen-(N-Me-Arg)-Ser-Asp-Thr-Leu-Pen-2-Nal-Glu-(N-
Me-Lys);

(SEQ ID NO: 25)
Pen-(N-Me-Arg)-Ser-Asp-Thr-Leu-Pen-Phe(4-'Bu)-(β-
homoGlu)-(D-Lys);

(SEQ ID NO: 26)
Pen-(N-Me-Arg)-Ser-Asp-Thr-Leu-Pen-Phe(4-'Bu)-(β-
homoGlu)-(N-Me-Lys);

(SEQ ID NO: 27)
Pen-(N-Me-Arg)-Ser-Asp-Thr-Leu-Pen-Trp-(β-
homoGlu)-(N-Me-Lys);

(SEQ ID NO: 28)
Pen-(N-Me-Arg)-Ser-Asp-Thr-Leu-Pen-2-Nal-(β-
homoGlu)-(N-Me-Lys);

(SEQ ID NO: 23)
Pen-(N-Me-Arg)-Ser-Asp-Thr-Leu-Pen-1-Nal-(β-
homoGlu)-(D-Lys);

(SEQ ID NO: 29)
Pen-(N-Me-Arg)-Ser-Asp-Thr-Leu-Pen-1-Nal-(β-
homoGlu)-(N-Me-Lys);

(SEQ ID NO: 19)
Pen-(N-Me-Arg)-Ser-Asp-Thr-Leu-Pen-Trp-(β-
homoGlu)-(D-Lys);
or
                                    (SEQ ID NO: 30)
Pen-(N-Me-Arg)-Ser-Asp-Thr-Leu-Pen-Trp-Glu-(N-
Me-D-Lys).
```

In certain embodiments of Formula (I), a peptide monomer compound or a both subunits of a peptide dimer compound comprise one of the following sequences:

```
                                    (SEQ ID NO: 19)
Ac-Pen-(N-Me-Arg)-Ser-Asp-Thr-Leu-Pen-Trp-(β-
homoGlu)-(D-Lys);

(SEQ ID NO: 20)
Ac-Pen-(N-Me-Arg)-Ser-Asp-Thr-Leu-Pen-(Phe-(4-
COOH)-(β-homoGlu)-(D-Lys);

(SEQ ID NO: 21)
Ac-Pen-(N-Me-Arg)-Ser-Asp-Thr-Leu-Pen-Trp-Glu-(N-
Me-Lys);

(SEQ ID NO: 22)
Ac-Pen-(N-Me-Arg)-Ser-Asp-Thr-Leu-Pen-2-Nal-(β-
homoGlu)-(D-Lys);

(SEQ ID NO: 23)
Ac-Pen-(N-Me-Arg)-Ser-Asp-Thr-Leu-Pen-1-Nal-(β-
homoGlu)-(D-Lys);

(SEQ ID NO: 24)
Ac-Pen-(N-Me-Arg)-Ser-Asp-Thr-Leu-Pen-2-Nal-Glu-
(N-Me-Lys);

(SEQ ID NO: 25)
Ac-Pen-(N-Me-Arg)-Ser-Asp-Thr-Leu-Pen-Phe(4-tBu)-
(β-homoGlu)-(D-Lys);

(SEQ ID NO: 26)
Ac-Pen-(N-Me-Arg)-Ser-Asp-Thr-Leu-Pen-Phe(4-tBu)-
(β-homoGlu)-(N-Me-Lys);

(SEQ ID NO: 27)
Ac-Pen-(N-Me-Arg)-Ser-Asp-Thr-Leu-Pen-Trp-(β-
homoGlu)-(N-Me-Lys);

(SEQ ID NO: 28)
Ac-Pen-(N-Me-Arg)-Ser-Asp-Thr-Leu-Pen-2-Nal-(β-
homoGlu)-(N-Me-Lys);

(SEQ ID NO: 23)
Ac-Pen-(N-Me-Arg)-Ser-Asp-Thr-Leu-Pen-1-Nal-(β-
homoGlu)-(D-Lys);

(SEQ ID NO: 29)
Ac-Pen-(N-Me-Arg)-Ser-Asp-Thr-Leu-Pen-1-Nal-(β-
homoGlu)-(N-Me-Lys);

(SEQ ID NO: 19)
Ac-Pen-(N-Me-Arg)-Ser-Asp-Thr-Leu-Pen-Trp-(P-
homoGlu)-(D-Lys);
and
                                    (SEQ ID NO: 30)
Ac-Pen-(N-Me-Arg)-Ser-Asp-Thr-Leu-Pen-Trp-Glu-
(N-Me-D-Lys).
```

In certain embodiments, both subunits comprise the same sequences. In particular embodiments of peptide dimer compounds, the subunits are linked via DIG at their C-termini.

In particular embodiments the peptide dimer compound has one of the following structures:

```
                                    (SEQ ID NO: 31)
[Ac-Pen-(N-Me-Arg)-Ser-Asp-Thr-Leu-Pen-Trp-(β-
homoGlu)-(D-Lys)-NH_2]_2-DIG;

(SEQ ID NO: 32)
[Ac-Pen-(N-Me-Arg)-Ser-Asp-Thr-Leu-Pen-(Phe-(4-
COOH)-(β-homoGlu)-(D-Lys)-NH_2]_2-DIG;

(SEQ ID NO: 33)
[Ac-Pen-(N-Me-Arg)-Ser-Asp-Thr-Leu-Pen-Trp-Glu-(N-
Me-Lys)-NH_2]_2-DIG;

(SEQ ID NO: 34)
[Ac-Pen-(N-Me-Arg)-Ser-Asp-Thr-Leu-Pen-2-Nal-(β-
homoGlu)-(D-Lys)-NH_2]_2-DIG;

(SEQ ID NO: 35)
[Ac-Pen-(N-Me-Arg)-Ser-Asp-Thr-Leu-Pen-1-Nal-(β-
homoGlu)-(D-Lys)-NH_2]_2-DIG;
```

-continued (SEQ ID NO: 36)
[Ac-Pen-(N-Me-Arg)-Ser-Asp-Thr-Leu-Pen-2-Nal-Glu-
(N-Me-Lys)-NH$_2$]$_2$-DIG;

(SEQ ID NO: 37)
[Ac-Pen-(N-Me-Arg)-Ser-Asp-Thr-Leu-Pen-Phe(4-$^t$Bu)-
(β-homoGlu)-(D-Lys)-NH$_2$]$_2$-DIG;

(SEQ ID NO: 38)
[Ac-Pen-(N-Me-Arg)-Ser-Asp-Thr-Leu-Pen-Phe(4-$^t$Bu)-
(β-homoGlu)-(N-Me-Lys)-NH$_2$]$_2$-DIG;

(SEQ ID NO: 39)
[Ac-Pen-(N-Me-Arg)-Ser-Asp-Thr-Leu-Pen-Trp-(β-
homoGlu)-(N-Me-Lys)-NH$_2$]$_2$-DIG;

(SEQ ID NO: 40)
[Ac-Pen-(N-Me-Arg)-Ser-Asp-Thr-Leu-Pen-2-Nal-(β-
homoGlu)-(N-Me-Lys)-NH$_2$]$_2$-DIG;

(SEQ ID NO: 35)
[Ac-Pen-(N-Me-Arg)-Ser-Asp-Thr-Leu-Pen-1-Nal-(β-
homoGlu)-(D-Lys)-NH$_2$]$_2$-DIG;

(SEQ ID NO: 41)
[Ac-Pen-(N-Me-Arg)-Ser-Asp-Thr-Leu-Pen-1-Nal-(β-
homoGlu)-(N-Me-Lys)-NH$_2$]$_2$-DIG;

(SEQ ID NO: 31)
[Ac-Pen-(N-Me-Arg)-Ser-Asp-Thr-Leu-Pen-Trp-(β-
homoGlu)-(D-Lys)-NH$_2$]$_2$-DIG;

(SEQ ID NO: 42)
[Ac-Pen-(N-Me-Arg)-Ser-Asp-Thr-Leu-Pen-Trp-Glu-(N-
Me-D-Lys)-NH$_2$]$_2$-DIG;

(SEQ ID NO: 31)
[Ac-Pen-(N-Me-Arg)-Ser-Asp-Thr-Leu-Pen-Trp-(β-
homoGlu)-(D-Lys)-OH]$_2$-DIG;

(SEQ ID NO: 32)
[Ac-Pen-(N-Me-Arg)-Ser-Asp-Thr-Leu-Pen-(Phe-(4-
COOH)-(β-homoGlu)-(D-Lys)-OH]$_2$-DIG;

(SEQ ID NO: 33)
[Ac-Pen-(N-Me-Arg)-Ser-Asp-Thr-Leu-Pen-Trp-Glu-(N-
Me-Lys)-OH]$_2$-DIG;

(SEQ ID NO: 34)
[Ac-Pen-(N-Me-Arg)-Ser-Asp-Thr-Leu-Pen-2-Nal-(β-
homoGlu)-(D-Lys)-OH]$_2$-DIG;

(SEQ ID NO: 35)
[Ac-Pen-(N-Me-Arg)-Ser-Asp-Thr-Leu-Pen-1-Nal-(β-
homoGlu)-(D-Lys)-OH]$_2$-DIG;

(SEQ ID NO: 36)
[Ac-Pen-(N-Me-Arg)-Ser-Asp-Thr-Leu-Pen-2-Nal-Glu-
(N-Me-Lys)-OH]$_2$-DIG;

(SEQ ID NO: 37)
[Ac-Pen-(N-Me-Arg)-Ser-Asp-Thr-Leu-Pen-Phe(4-$^t$Bu)-
(β-homoGlu)-(D-Lys)-OH]$_2$-DIG;

(SEQ ID NO: 38)
[Ac-Pen-(N-Me-Arg)-Ser-Asp-Thr-Leu-Pen-Phe(4-$^t$Bu)-
(β-homoGlu)-(N-Me-Lys)-OH]$_2$-DIG;

(SEQ ID NO: 39)
[Ac-Pen-(N-Me-Arg)-Ser-Asp-Thr-Leu-Pen-Trp-(β-
homoGlu)-(N-Me-Lys)-OH]$_2$-DIG;

(SEQ ID NO: 40)
[Ac-Pen-(N-Me-Arg)-Ser-Asp-Thr-Leu-Pen-2-Nal-(β-
homoGlu)-(N-Me-Lys)-OH2]$_2$-DIG;

(SEQ ID NO: 35)
[Ac-Pen-(N-Me-Arg)-Ser-Asp-Thr-Leu-Pen-1-Nal-(β-
homoGlu)-(D-Lys)-OH]$_2$-DIG;

(SEQ ID NO: 41)
[Ac-Pen-(N-Me-Arg)-Ser-Asp-Thr-Leu-Pen-1-Nal-(β-
homoGlu)-(N-Me-Lys)-OH]$_2$-DIG;

(SEQ ID NO: 31)
[Ac-Pen-(N-Me-Arg)-Ser-Asp-Thr-Leu-Pen-Trp-(β-
homoGlu)-(D-Lys)-OH]$_2$-DIG;
or (SEQ ID NO: 42)
[Ac-Pen-(N-Me-Arg)-Ser-Asp-Thr-Leu-Pen-Trp-Glu-(N-
Me-D-Lys)-OH]$_2$-DIG, wherein in certain embodiments, there is adisulfide bond between the two Pen residues in the monomer subunits.

In certain embodiments, a peptide monomer compound or a both subunits of a peptide dimer compound comprise one of the following sequences:

(SEQ ID NO: 43)
Pen-(N-Me-Arg)-Ser-Asp-Thr-Leu-Pen-(Phe(4-COOH))-
(Glu)-(D-Lys);

(SEQ ID NO: 20)
Pen-(N-Me-Arg)-Ser-Asp-Thr-Leu-Pen-(Phe(4-COOH))-
(β-homo-Glu)-(D-Lys);

(SEQ ID NO: 44)
Pen-(N-Me-Arg)-Ser-Asp-Thr-Leu-Pen-(Phe(4-$^t$Bu))-
Glu-(D-Lys);

(SEQ ID NO: 25)
Pen-(N-Me-Arg)-Ser-Asp-Thr-Leu-Pen-(Phe(4-$^t$Bu))-
(β-homo-Glu)-(D-Lys);

(SEQ ID NO: 45)
Pen-(N-Me-Arg)-Ser-Asp-Thr-Leu-Pen-(Phe(4-$^t$Bu))-
Glu-(N-Me-Lys);

(SEQ ID NO: 46)
Pen-(N-Me-Arg)-Ser-Asp-Thr-Leu-Pen-Bip-Glu-(D-
Lys);

(SEQ ID NO: 47)
Pen-(N-Me-Arg)-Ser-Asp-Thr-Leu-Pen-Bip-(β-homo-
Glu)-(D-Lys);

-continued (SEQ ID NO: 19)
Pen-(N-Me-Arg)-Ser-Asp-Thr-Leu-Pen-Trp-(β-homoGlu)-(D-Lys);

(SEQ ID NO: 20)
Pen-(N-Me-Arg)-Ser-Asp-Thr-Leu-Pen-(Phe-(4-COOH)-(β-homoGlu)-(D-Lys);

(SEQ ID NO: 21)
Pen-(N-Me-Arg)-Ser-Asp-Thr-Leu-Pen-Trp-Glu-(N-Me-Lys);

(SEQ ID NO: 22)
Pen-(N-Me-Arg)-Ser-Asp-Thr-Leu-Pen-2-Nal-(β-homoGlu)-(D-Lys);

(SEQ ID NO: 23)
Pen-(N-Me-Arg)-Ser-Asp-Thr-Leu-Pen-1-Nal-(β-homoGlu)-(D-Lys);

(SEQ ID NO: 24)
Pen-(N-Me-Arg)-Ser-Asp-Thr-Leu-Pen-2-Nal-Glu-(N-Me-Lys);

(SEQ ID NO: 25)
Pen-(N-Me-Arg)-Ser-Asp-Thr-Leu-Pen-Phe(4-ᵗBu)-(β-homoGlu)-(D-Lys);

(SEQ ID NO: 26)
Pen-(N-Me-Arg)-Ser-Asp-Thr-Leu-Pen-Phe(4-ᵗBu)-(β-homoGlu)-(N-Me-Lys);

(SEQ ID NO: 27)
Pen-(N-Me-Arg)-Ser-Asp-Thr-Leu-Pen-Trp-(β-homoGlu)-(N-Me-Lys);

(SEQ ID NO: 28)
Pen-(N-Me-Arg)-Ser-Asp-Thr-Leu-Pen-2-Nal-(β-homoGlu)-(N-Me-Lys);

(SEQ ID NO: 23)
Pen-(N-Me-Arg)-Ser-Asp-Thr-Leu-Pen-1-Nal-(β-homoGlu)-(D-Lys);

(SEQ ID NO: 29)
Pen-(N-Me-Arg)-Ser-Asp-Thr-Leu-Pen-1-Nal-(β-homoGlu)-(N-Me-Lys);

(SEQ ID NO: 19)
Pen-(N-Me-Arg)-Ser-Asp-Thr-Leu-Pen-Trp-(β-homoGlu)-(D-Lys);

(SEQ ID NO: 30)
Pen-(N-Me-Arg)-Ser-Asp-Thr-Leu-Pen-Trp-Glu-(N-Me-D-Lys);

(SEQ ID NO: 19)
Ac-Pen-(N-Me-Arg)-Ser-Asp-Thr-Leu-Pen-Trp-(β-homoGlu)-(D-Lys)-OH;

(SEQ ID NO: 20)
Ac-Pen-(N-Me-Arg)-Ser-Asp-Thr-Leu-Pen-(Phe-(4-COOH)-(β-homoGlu)-(D-Lys)-OH;

(SEQ ID NO: 21)
Ac-Pen-(N-Me-Arg)-Ser-Asp-Thr-Leu-Pen-Trp-Glu-(N-Me-Lys)-OH;

(SEQ ID NO: 22)
Ac-Pen-(N-Me-Arg)-Ser-Asp-Thr-Leu-Pen-2-Nal-(β-homoGlu)-(D-Lys)-OH;

(SEQ ID NO: 23)
Ac-Pen-(N-Me-Arg)-Ser-Asp-Thr-Leu-Pen-1-Nal-(β-homoGlu)-(D-Lys)-OH;

(SEQ ID NO: 24)
Ac-Pen-(N-Me-Arg)-Ser-Asp-Thr-Leu-Pen-2-Nal-Glu-(N-Me-Lys)-OH;

(SEQ ID NO: 25)
Ac-Pen-(N-Me-Arg)-Ser-Asp-Thr-Leu-Pen-Phe(4-ᵗBu)-(β-homoGlu)-(D-Lys)-OH;

(SEQ ID NO: 26)
Ac-Pen-(N-Me-Arg)-Ser-Asp-Thr-Leu-Pen-Phe(4-ᵗBu)-(β-homoGlu)-(N-Me-Lys)-OH;

(SEQ ID NO: 27)
Ac-Pen-(N-Me-Arg)-Ser-Asp-Thr-Leu-Pen-Trp-(β-homoGlu)-(N-Me-Lys)-OH;

(SEQ ID NO: 28)
Ac-Pen-(N-Me-Arg)-Ser-Asp-Thr-Leu-Pen-2-Nal-(β-homoGlu)-(N-Me-Lys)-OH;

(SEQ ID NO: 23)
Ac-Pen-(N-Me-Arg)-Ser-Asp-Thr-Leu-Pen-1-Nal-(β-homoGlu)-(D-Lys)-OH;

(SEQ ID NO: 29)
Ac-Pen-(N-Me-Arg)-Ser-Asp-Thr-Leu-Pen-1-Nal-(β-homoGlu)-(N-Me-Lys)-OH;

(SEQ ID NO: 19)
Ac-Pen-(N-Me-Arg)-Ser-Asp-Thr-Leu-Pen-Trp-(β-homoGlu)-(D-Lys)-OH;

(SEQ ID NO: 30)
Ac-Pen-(N-Me-Arg)-Ser-Asp-Thr-Leu-Pen-Trp-Glu-(N-Me-D-Lys)-OH;

(SEQ ID NO: 19)
Ac-Pen-(N-Me-Arg)-Ser-Asp-Thr-Leu-Pen-Trp-(β-homoGlu)-(D-Lys)-$NH_2$;

(SEQ ID NO: 20)
Ac-Pen-(N-Me-Arg)-Ser-Asp-Thr-Leu-Pen-(Phe-(4-COOH)-(β-homoGlu)-(D-Lys)-$NH_2$;

(SEQ ID NO: 21)
Ac-Pen-(N-Me-Arg)-Ser-Asp-Thr-Leu-Pen-Trp-Glu-(N-Me-Lys)-$NH_2$;

(SEQ ID NO: 22)
Ac-Pen-(N-Me-Arg)-Ser-Asp-Thr-Leu-Pen-2-Nal-(β-homoGlu)-(D-Lys)-$NH_2$;

(SEQ ID NO: 23)
Ac-Pen-(N-Me-Arg)-Ser-Asp-Thr-Leu-Pen-1-Nal-
(β-homoGlu)-(D-Lys)-NH₂;

(SEQ ID NO: 24)
Ac-Pen-(N-Me-Arg)-Ser-Asp-Thr-Leu-Pen-2-Nal-Glu-
(N-Me-Lys)-NH₂;

(SEQ ID NO: 25)
Ac-Pen-(N-Me-Arg)-Ser-Asp-Thr-Leu-Pen-Phe(4-ᵗBu)-
(β-homoGlu)-(D-Lys)-NH₂;

(SEQ ID NO: 26)
Ac-Pen-(N-Me-Arg)-Ser-Asp-Thr-Leu-Pen-Phe(4-ᵗBu)-
(β-homoGlu)-(N-Me-Lys)-NH₂;

(SEQ ID NO: 27)
Ac-Pen-(N-Me-Arg)-Ser-Asp-Thr-Leu-Pen-Trp-
(β-homoGlu)-(N-Me-Lys)-NH₂;

(SEQ ID NO: 28)
Ac-Pen-(N-Me-Arg)-Ser-Asp-Thr-Leu-Pen-2-Nal-
(β-homoGlu)-(N-Me-Lys)-NH₂;

(SEQ ID NO: 23)
Ac-Pen-(N-Me-Arg)-Ser-Asp-Thr-Leu-Pen-1-Nal-
(β-homoGlu)-(D-Lys)-NH₂;

(SEQ ID NO: 29)
Ac-Pen-(N-Me-Arg)-Ser-Asp-Thr-Leu-Pen-1-Nal-
(β-homoGlu)-(N-Me-Lys)-NH₂;

(SEQ ID NO: 19)
Ac-Pen-(N-Me-Arg)-Ser-Asp-Thr-Leu-Pen-Trp-
((β-homoGlu)-D-Lys)-NH₂;

(SEQ ID NO: 30)
Ac-Pen-(N-Me-Arg)-Ser-Asp-Thr-Leu-Pen-Trp-Glu-
(N-Me-D-Lys)-NH₂;
or (SEQ ID NO: 48)
Pen-(N-Me-Arg)-Ser-Asp-Thr-Leu-Pen-(Phe(4-
COOH))-(Glu);

(SEQ ID NO: 49)
Pen-(N-Me-Arg)-Ser-Asp-Thr-Leu-Pen-(Phe(4-
COOH))-(β-homo-Glu);

(SEQ ID NO: 50)
Pen-(N-Me-Arg)-Ser-Asp-Thr-Leu-Pen-(Phe(4-ᵗBu))-
Glu;

(SEQ ID NO: 51)
Pen-(N-Me-Arg)-Ser-Asp-Thr-Leu-Pen-(Phe(4-
ᵗBu))-(β-homo-Glu);

(SEQ ID NO: 52)
Pen-(N-Me-Arg)-Ser-Asp-Thr-Leu-Pen-(Phe(4-ᵗBu))-
Glu;

(SEQ ID NO: 53)
Pen-(N-Me-Arg)-Ser-Asp-Thr-Leu-Pen-Bip-Glu;

(SEQ ID NO: 54)
Pen-(N-Me-Arg)-Ser-Asp-Thr-Leu-Pen-Bip-
(β-homo-Glu);

(SEQ ID NO: 55)
Pen-(N-Me-Arg)-Ser-Asp-Thr-Leu-Pen-Trp-
(β-homoGlu);

(SEQ ID NO: 49)
Pen-(N-Me-Arg)-Ser-Asp-Thr-Leu-Pen-(Phe-(4-COOH)-
(β-homoGlu);

(SEQ ID NO: 56)
Pen-(N-Me-Arg)-Ser-Asp-Thr-Leu-Pen-Trp-Glu;

(SEQ ID NO: 57)
Pen-(N-Me-Arg)-Ser-Asp-Thr-Leu-Pen-2-Nal-
(β-homoGlu);

(SEQ ID NO: 58)
Pen-(N-Me-Arg)-Ser-Asp-Thr-Leu-Pen-1-Nal-
(β-homoGlu);

(SEQ ID NO: 59)
Pen-(N-Me-Arg)-Ser-Asp-Thr-Leu-Pen-2-Nal-Glu;

(SEQ ID NO: 51)
Pen-(N-Me-Arg)-Ser-Asp-Thr-Leu-Pen-Phe(4-ᵗBu)-
(β-homoGlu);

(SEQ ID NO: 51)
Pen-(N-Me-Arg)-Ser-Asp-Thr-Leu-Pen-Phe(4-ᵗBu)-
(β-homoGlu);

(SEQ ID NO: 55)
Pen-(N-Me-Arg)-Ser-Asp-Thr-Leu-Pen-Trp-
(β-homoGlu);

(SEQ ID NO: 57)
Pen-(N-Me-Arg)-Ser-Asp-Thr-Leu-Pen-2-Nal-
(β-homoGlu);

(SEQ ID NO: 58)
Pen-(N-Me-Arg)-Ser-Asp-Thr-Leu-Pen-1-Nal-
(β-homoGlu);

(SEQ ID NO: 58)
Pen-(N-Me-Arg)-Ser-Asp-Thr-Leu-Pen-1-Nal-
(β-homoGlu);

(SEQ ID NO: 55)
Pen-(N-Me-Arg)-Ser-Asp-Thr-Leu-Pen-Trp-
(β-homoGlu);

(SEQ ID NO: 56)
Pen-(N-Me-Arg)-Ser-Asp-Thr-Leu-Pen-Trp-Glu;

(SEQ ID NO: 55)
Ac-Pen-(N-Me-Arg)-Ser-Asp-Thr-Leu-Pen-Trp-
(β-homoGlu)-OH;

(SEQ ID NO: 49)
Ac-Pen-(N-Me-Arg)-Ser-Asp-Thr-Leu-Pen-(Phe-(4-
COOH)-(β-homoGlu)-OH;

-continued

Ac-Pen-(N-Me-Arg)-Ser-Asp-Thr-Leu-Pen-Trp-Glu-OH; (SEQ ID NO: 56)

Ac-Pen-(N-Me-Arg)-Ser-Asp-Thr-Leu-Pen-2-Nal-(β-homoGlu)-OH; (SEQ ID NO: 57)

Ac-Pen-(N-Me-Arg)-Ser-Asp-Thr-Leu-Pen-1-Nal-(β-homoGlu)-OH; (SEQ ID NO: 58)

Ac-Pen-(N-Me-Arg)-Ser-Asp-Thr-Leu-Pen-2-Nal-Glu-OH; (SEQ ID NO: 59)

Ac-Pen-(N-Me-Arg)-Ser-Asp-Thr-Leu-Pen-Phe(4-'Bu)-(β-homoGlu)-OH; (SEQ ID NO: 51)

Ac-Pen-(N-Me-Arg)-Ser-Asp-Thr-Leu-Pen-Phe(4-'Bu)-(β-homoGlu)-OH; (SEQ ID NO: 51)

Ac-Pen-(N-Me-Arg)-Ser-Asp-Thr-Leu-Pen-Trp-(β-homoGlu)-OH; (SEQ ID NO: 55)

Ac-Pen-(N-Me-Arg)-Ser-Asp-Thr-Leu-Pen-2-Nal-(β-homoGlu)-OH; (SEQ ID NO: 57)

Ac-Pen-(N-Me-Arg)-Ser-Asp-Thr-Leu-Pen-1-Nal-(β-homoGlu)-OH; (SEQ ID NO: 58)

Ac-Pen-(N-Me-Arg)-Ser-Asp-Thr-Leu-Pen-1-Nal-(β-homoGlu)-OH; (SEQ ID NO: 58)

Ac-Pen-(N-Me-Arg)-Ser-Asp-Thr-Leu-Pen-Trp-(β-homoGlu)-OH; (SEQ ID NO: 55)

Ac-Pen-(N-Me-Arg)-Ser-Asp-Thr-Leu-Pen-Trp-Glu-OH; (SEQ ID NO: 56)

Ac-Pen-(N-Me-Arg)-Ser-Asp-Thr-Leu-Pen-Trp-(β-homoGlu)-NH$_2$; (SEQ ID NO: 55)

Ac-Pen-(N-Me-Arg)-Ser-Asp-Thr-Leu-Pen-(Phe-(4-COOH)-(β-homoGlu)-NH$_2$; (SEQ ID NO: 49)

Ac-Pen-(N-Me-Arg)-Ser-Asp-Thr-Leu-Pen-Trp-Glu-NH$_2$; (SEQ ID NO: 56)

Ac-Pen-(N-Me-Arg)-Ser-Asp-Thr-Leu-Pen-2-Nal-(β-homoGlu)-NH$_2$; (SEQ ID NO: 57)

Ac-Pen-(N-Me-Arg)-Ser-Asp-Thr-Leu-Pen-1-Nal-(β-homoGlu)-NH$_2$; (SEQ ID NO: 58)

Ac-Pen-(N-Me-Arg)-Ser-Asp-Thr-Leu-Pen-2-Nal-Glu-NH$_2$; (SEQ ID NO: 59)

Ac-Pen-(N-Me-Arg)-Ser-Asp-Thr-Leu-Pen-Phe(4-'Bu)-(β-homoGlu)-NH$_2$; (SEQ ID NO: 51)

Ac-Pen-(N-Me-Arg)-Ser-Asp-Thr-Leu-Pen-Phe(4-'Bu)-(β-homoGlu)-NH$_2$; (SEQ ID NO: 51)

Ac-Pen-(N-Me-Arg)-Ser-Asp-Thr-Leu-Pen-Trp-(β-homoGlu)-NH$_2$; (SEQ ID NO: 55)

Ac-Pen-(N-Me-Arg)-Ser-Asp-Thr-Leu-Pen-2-Nal-(β-homoGlu)-NH$_2$; (SEQ ID NO: 57)

Ac-Pen-(N-Me-Arg)-Ser-Asp-Thr-Leu-Pen-1-Nal-(β-homoGlu)-NH$_2$; (SEQ ID NO: 58)

Ac-Pen-(N-Me-Arg)-Ser-Asp-Thr-Leu-Pen-1-Nal-(β-homoGlu)-NH$_2$; (SEQ ID NO: 58)

Ac-Pen-(N-Me-Arg)-Ser-Asp-Thr-Leu-Pen-Trp-(β-homoGlu)-NH$_2$; or (SEQ ID NO: 55)

Ac-Pen-(N-Me-Arg)-Ser-Asp-Thr-Leu-Pen-Trp-Glu-NH$_2$, (SEQ ID NO: 56)

wherein in certain embodiments, there is a disulfide bond between the two Pen residues of the peptide or peptide monomer compound.

The linker moieties of the present invention may include any structure, length, and/or size that is compatible with the teachings herein. In certain embodiments, a linker moiety is selected from the non-limiting group consisting of DIG, PEG13, PEG25, PEG1K, PEG2K, PEG3.4K, PEG4K, PEG5K, IDA, IDA-Palm, IDA-Boc, IDA-Ac, IDA-Isovaleric acid, ADA Triazine, Triazine-Boc, Isophthalic acid, 1,3-phenylenediacetic acid, Glu, Asp, D-Glu, D-Asp, 1,4-phenylenediacetic acid, Biphenyl diacetic acid, cyclopropylacetic acid, succinic acid, glutaric acid, Dodecanedioic acid, suitable aliphatic diacids, suitable aromatic diacids, heteroaromatics, and polyethylene glycols having a molecular weight from approximately 400 Da to approximately 40,000 Da. When the linker is IDA, ADA or any linker with free amine it can be acylated with acylating organic compound selected from the group consisting of 2-Me-Trifluorobutyl, Trifluoropentyl, Acetyl, Octonyl, Butyl, Pentyl, Hexyl, Palmityl, Lauryl, Oleoyl, Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances, small PEG (PEG4-PEG13), Glu, IsoGlu or Asp is used as spacer before acylations.

In certain embodiments, the linker connects two monomer subunits by connecting two sulfur containing C- or N-terminal amino acids. In some embodiments, the two sulfur containing amino acids are connected by a linker comprising a di-halide, an aliphatic chain, or a PEG. In certain embodiments, the linker connects two monomeric subunits by connecting sulfur containing C-terminal amino acids at the C-terminus of each monomer subunit. In certain embodiments, the linker connects two monomeric subunits by connecting sulfur containing N-terminal amino acids at the N-terminus of each monomer subunit. In certain embodiments, the linker connects two monomeric subunits by connecting a sulfur containing C-terminal amino acid of one monomer subunit to a sulfur-containing N-terminal amino acid of the other monomer subunit. In some embodiments, the two sulfur containing amino acids are connected by a linker comprising Homobifunctional maleimide cross-linkers, di-halide, 1,2-Bis(bromomomethyl)benzene, 1,2-Bis(chloromomethyl)benzene, 1,3-Bis(bromomomethyl) benzene, 1,3-Bis(chloromomethyl)benzene, 1,4-Bis (bromomomethyl)benzene, 1,4-Bis(chloromomethyl) benzene, 3,3'-bis-bromomethyl-biphenyl, or 2,2'-bis-bromomethyl-biphenyl. Particular haloacetyl crosslinkers contain an iodoacetyl or a bromoacetyl group. These homo bifunctional linkers may contain spacers comprising PEG or an aliphatic chain. In particular embodiments, the linker is a bifunctional linker (e.g., di-acid, di-amine, dihalide, N-Hydroxy succinimide (NHS)-activated diesters, bis-maleimides, which may be capable of linking two monomer subunits through amine, ester, thioether, di-thio, or ether bonds. In particular embodiments, wherein the monomer subunits are connected through the sidechain of an amino acid with an amine-containing sidechain, the linker is a di-acid. In particular embodiments, wherein the monomer subunits are connected through the sidechain of an amino acid with an acid-containing sidechain, the linker is a di-amine.

In certain embodiments, the linker is selected from the group consisting of DIG, PEG4, PEG4-biotin, PEG13, PEG25, PEG1K, PEG2K, PEG3.4K, PEG4K, PEG5K, IDA, ADA, Boc-IDA, Glutaric acid, Isophthalic acid, 1,3-phenylenediacetic acid, 1,4-phenylenediacetic acid, 1,2-phenylenediacetic acid, Triazine, Boc-Triazine, IDA-biotin, PEG4-Biotin, AADA, aliphatics, aromatics, heteroaromatics, and polyethylene glycol based linkers having a molecular weight from approximately 400 Da to approximately 40,000 Da. In particular embodiments, the linker is a bifunctional linker (e.g., di-acid, di-amine, dihalide, N-Hydroxy succinimide (NHS)-activated diesters, bis-maleimides, which may be capable of linking two monomer subunits through amine, ester, thioether, di-thio, or ether bonds. Non-limiting examples of suitable linker moieties are provided in Table 4.

TABLE 4

ILLUSTRATIVE LINKER MOIETIES

| Abbreviation | Description | Structure |
| --- | --- | --- |
| DIG | DIGlycolic acid, | 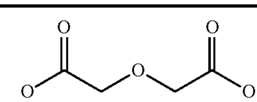 |
| PEG4 | Bifunctional PEG linker with 4 PolyEthylene Glycol units | 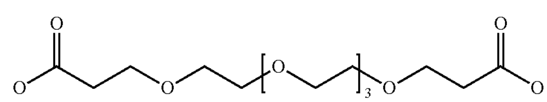 |
| PEG13 | Bifunctional PEG linker with 13 PolyEthylene Glycol units | 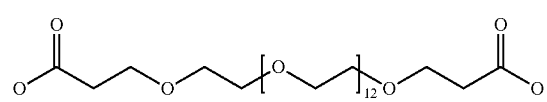 |
| PEG25 | Bifunctional PEG linker with 25 PolyEthylene Glycol units | 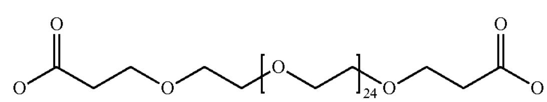 |
| PEG1K | Bifunctional PEG linker with PolyEthylene Glycol Mol wt of 1000 Da | |
| PEG2K | Bifunctional PEG linker with PolyEthylene Glycol Mol wt of 2000 Da | |
| PEG3.4K | Bifunctional PEG linker with PolyEthylene Glycol Mol wt of 3400 Da | |
| PEG5K | Bifunctional PEG linker with PolyEthylene Glycol Mol wt of 5000 Da | |
| IDA | β-Ala-Iminodiacetic acid | 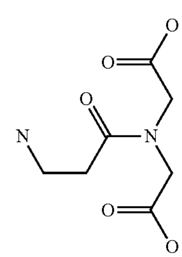 [SMILES: NCCC(=O)N(CC(=O)O)CC(=O)O] |

TABLE 4-continued

| ILLUSTRATIVE LINKER MOIETIES | | |
|---|---|---|
| Abbreviation | Description | Structure |
| Boc-IDA | Boc-β-Ala-Iminodiacetic acid | |
| Ac-IDA | Ac-β-Ala-Iminodiacetic acid | |
| IDA-Palm | Palmityl-β-Ala-Iminodiacetic acid | |
| GTA | Glutaric acid | |
| PMA | Pemilic acid | |
| AZA | Azelaic acid | |
| DDA | Dodecanedioic acid | |
| IPA | Isopthalic aicd | |

TABLE 4-continued

ILLUSTRATIVE LINKER MOIETIES

| Abbreviation | Description | Structure |
|---|---|---|
| 1,3-PDA | 1,3-Phenylenediacetic acid | 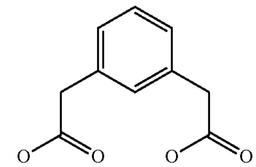 [SMILES: O=C(O)Cc1cccc(CC(=O)O)c1] |
| 1,4-PDA | 1,4-Phenylenediacetic acid | 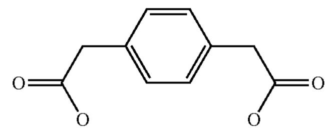 [SMILES: O=C(O)Cc1ccc(CC(=O)O)cc1] |
| 1,2-PDA | 1,2-Phenylenediacetic acid | 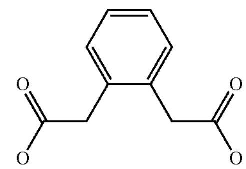 [SMILES: O=C(O)Cc1ccccc1CC(=O)O] |
| Triazine | Amino propyl Triazine di-acid | 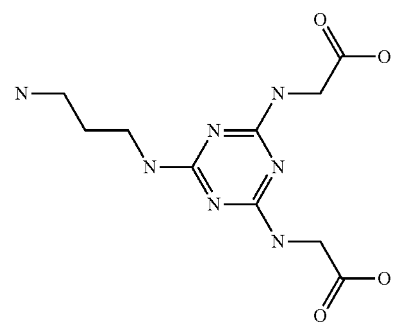 [SMILES: NCCCNc1nc(NCC(=O)O)nc(NCC(=O)O)n1] |
| Boc-Triazine | Boc-Triazine di-acid | 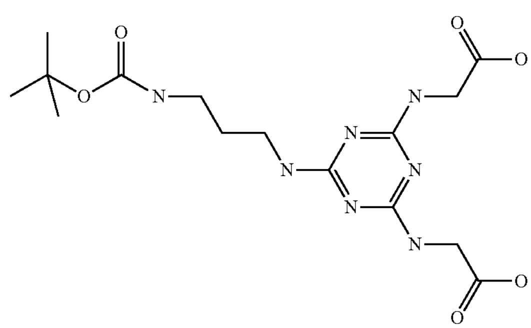 [SMILES: CC(C)(C)OC(=O)NCCCNc1nc(NCC(=O)O)nc(NCC(=O)O)n1] |
| ADA | Amino diacetic acid | 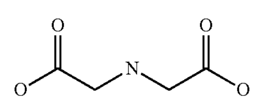 |
| AADA | n-Acetyl amino acetic acid | 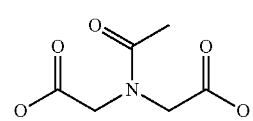 |
| PEG4-Biotin | PEG4-Biotin (Product number 10199, QuantaBioDesign) | 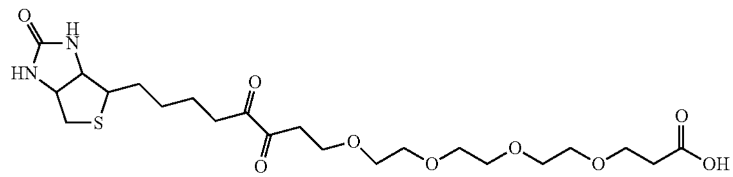 [SMILES: O=C(O)CCOCCOCCOCCOCCC(=O)C(=O)CCCCC1SCC2NC(=O)NC21] |

TABLE 4-continued
ILLUSTRATIVE LINKER MOIETIES
| Abbreviation | Description | Structure |
|---|---|---|
| 1,4 BMB | 1,4-Bis(halo-momethyl)benzene | 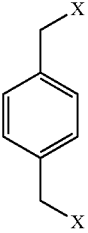<br>X = Cl, Br |
| 1,2 BMB | 1,2-Bis(halo-momethyl)benzene | 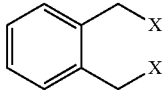<br>X-Cl, Br |
| 1,3 BMB | 1,3 -Bis(halo-momethyl)benzene, | 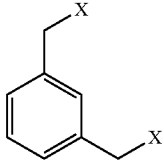<br>X = Cl, Br |
| 1,3 BMBip | 3,3'-Bis-Halomethyl-Biphenyl | 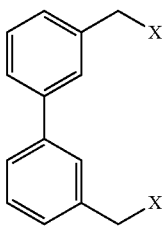<br>X = Cl, Br |
| IDA-Biotin | N-Biotin-β-Ala-Iminodiacetic acid | 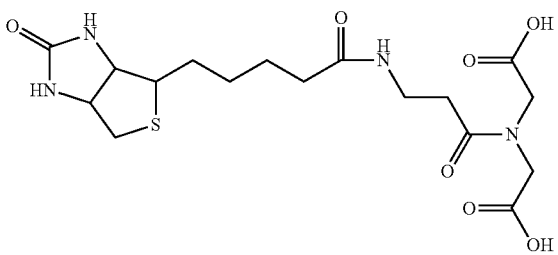 [SMILES: O=C(O)CN(CC(=O)O)C(=O)CCNC(=O)CCCCC1SCC2NC(=O)NC21] |
| 2,2 BMBip | 2,2'-Bis-Halomethyl-Biphenyl | 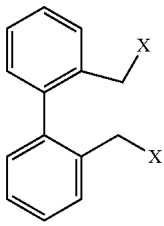<br>X = Cl, Br |

TABLE 4-continued

ILLUSTRATIVE LINKER MOIETIES

| Abbreviation | Description | Structure |
|---|---|---|
| BMal | Bis-Mal-dPEG | 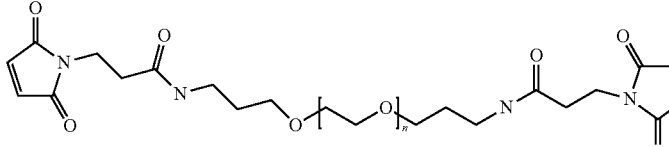 n = 1 to 20 |

When the linker is IDA, ADA or any linker with a free amine, it can be acylated, e.g. with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances, small PEG (PEG4-PEG13), Glu, IsoGlu or Asp is used as spacer before acylations. It is understood that once bound to a linker or another amino acid, an amino acid residue of the peptide compound may undergo structural changes, e.g., an acid may become an amide. Reference to a particular amino acid residue encompasses the amino acid residue in any altered structural form upon binding to a linker or forming an intramolecular bond with another amino acid of the peptide compound.

In certain embodiments, the compound is a peptide monomer comprising a monomer subunit of Formula (II) or a peptide dimer compound comprising two linked monomer subunits of Formula (II) (SEQ ID NO:60):

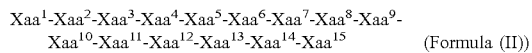

or a pharmaceutically acceptable salt, solvate, or hydrate thereof,
wherein:
$Xaa^1$ is absent, hydrogen, Ac, a suitable linker moiety, or an amino acid selected from the group consisting of Gln, Asn, Asp, Pro, Gly, His, Ala, Ile, Phe, Lys, Arg, Asn, Glu, Leu, Val, Tye, Trp, Met, Thr, and suitable isosteres and corresponding D-amino acids thereof;
$Xaa^2$ is absent, Ac, NH.2, a suitable linker moiety, or an amino acid selected from the group consisting of Gln, Asn, Asp, Pro, Gly, His, Ala, Ile, Phe, Lys, Arg, Asn, Glu, Leu, Val, Tye, Trp, Met, Thr, and suitable isosteres and corresponding D-amino acids thereof;
$Xaa^3$ is absent, Ac, NH2, a suitable linker moiety, or an amino acid selected from the group consisting of Gln, Asn, Asp, Pro, Gly, His, Ala, Ile, Phe, Lys, Arg, Asn, Glu, Leu, Val, Tye, Trp, Met and Thr, and suitable isosteres and corresponding D-amino acids thereof;
$Xaa^4$ is selected from the group consisting of Cys, Pen, Asp, Glu, hGlu, b-Asp, b-Glu, Lys, homo-Lys, Orn, Dap, Dab, and suitable isosteres and corresponding D-amino acids thereof;
$Xaa^5$ is selected from the group consisting of Gln, Asn, Asp, Pro, Gly, His, Ala, Ile, Phe, Lys, Arg, Asn, Glu, Leu, Val, Tye, Trp, Met, Thr, homo-Arg, Dap, Dab, N-Me-Arg, Arg-(Me)sym, Arg-(Me)asym, 4-Guan, Cit, Cav, and suitable isosteres thereof;
$Xaa^6$ is selected from the group consisting of Ser, Gln, Asn, Asp, Pro, Gly, His, Ala, Ile, Phe, Lys, Arg, Asn, Glu, Leu, Val, Tye, Trp, Met, and suitable isosteres thereof;
$Xaa^7$ is selected from the group consisting of Asp, N-Me-Asp and a suitable isostere replacement for Asp;
$Xaa^8$ is selected from the group consisting of Thr, Gln, Ser, Asn, Asp, Pro, Gly, His, Ala, Ile, Phe, Lys, Arg, Asn, Glu, Val, Tye, Trp, Met, and N-Methyl amino acids including N-Me-Thr;
$Xaa^9$ is selected from the group consisting of Gln, Asn, Asp, Pro, Gly, Ala, Phe, Leu, Asn, Glu, Val, homo-Leu, n-Butyl Ala, n-Pentyl Ala, n-Hexyl Ala, N-Me-Leu, and suitable isosteres thereof;
$Xaa^{10}$ is selected from the group consisting of Cys, Asp, Pen, Lys, homo-Lys, Orn, Glu, b-Asp, b-Glu, Dap, and Dab;
$Xaa^{11}$ is selected from the group consisting of Gly, Gln, Asn, Asp, Ala, Ile, Leu, Val, Met, Thr, Lys, Trp, Tyr, CONH.sub.2, COOH, His, Glu, Ser, Arg, Pro, Phe, Sar, 1Nal, 2Nal, hPhe, Phe(4-F), Phe (4-'Bu), O-Me-Tyr, dihydro-Trp, Dap, Dab, Dab(Ac), Orn, D-Orn, N-Me-Orn, N-Me-Dap, D-Dap, D-Dab Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, and corresponding D-amino acids and suitable isostere replacements;
$Xaa^{12}$ is absent, a suitable linker moiety, Amide, Lys, COOH, $CONH_2$, or an amino acid selected from the group consisting of Glu, Lys, Gln, Pro, Gly, His, Ala, Ile, Phe, Lys, Arg, Leu, Val, Tye, Trp, Met, Gla, Ser, Asn, Dap, Dab, Orn, D-Orn, N-Me-Orn, N-Me-Dap, N-Me-Dab, N-Me Lys, D-Dap, D-Dab, and suitable isosteres and corresponding D-amino acids thereof;
$Xaa^{13}$ is absent, Ac, a suitable linker moiety, or an amino acid selected from the group consisting of Gln, Pro, Gly, His, Ala, Ile, Phe, Lys, Arg, Leu, Val, Tye, Trp, Met, Glu, Gla, Ser, Asn, Dap, Dab, Orn, D-Orn, N-Me-Orn, N-Me-Dap, N-Me-Dab, N-Me Lys, D-Dap, D-Dab, COOH, $CONH_2$, and suitable isosteres and corresponding D-amino acids thereof;
$Xaa^{14}$ is absent, a suitable linker moiety, COOH, $CONH_2$, or an amino acid selected from the group consisting of natural amino acids, and suitable isosteres, corresponding D-amino acids and corresponding N-Methyl amino acids thereof; and
$Xaa^{15}$ is absent or a suitable linker moiety.

In certain embodiments, $Xaa^{15}$ is selected from the group consisting of DIG, DIG-OH, PEG13, PEG25, PEG1K, PEG2K, PEG3.4K, PEG4K, PEG5K, IDA, IDA-Palm, IDA-Boc, IDA-Isovaleric acid, Triazine, Triazine-Boc, Trifluorobutyric acid, 2-Me-trifluorobutyric acid, Trifluoropentanoic acid, Isophthalic acid, 1,3-phenylenediacetic acid, 1,4-phenylenediacetic acid, glutaric acid, Azelaic acid, Pimelic acid, and Dodecanedioic acid.

In certain embodiments, the compound is a dimer formed from two subunits of Formula (II) joined by a suitable C- or N-terminal linker selected from the group consisting of DIG, DIG-OH, PEG13, PEG25, PEG1K, PEG2K, PEG3.4K, PEG4K, PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, suitable aromatics, heteroaromatics, and polyethylene glycols having a molecular weight from approximately 400 Da to approximately 40,000 Da.

In certain embodiments, wherein one or both monomer subunits of the compound comprises a bond between $Xaa^4$ and $Xaa^{10}$. In one embodiment, $Xaa^4$ is Cys or Pen, $Xaa^{10}$ is Pen or Cys, and $Xaa^4$ and $Xaa^{10}$ are linked by a disulfide bond. In certain embodiments, both $Xaa^4$ and $Xaa^{10}$ are Pen. In other embodiments, both $Xaa^4$ and $Xaa^{10}$ are L-Pen. In yet other embodiments, both $Xaa^4$ and $Xaa^{10}$ are D-Pen.

In other embodiments of Formula (II), $Xaa^1$ is Ac, three of $Xaa^2$, $Xaa^3$, $Xaa^{11}$, $Xaa^{12}$, $Xaa^{13}$ are absent, and $Xaa^{15}$ is a linker.

In yet other embodiments of Formula (II), $Xaa^1$ is Ac, four of $Xaa^2$, $Xaa^3$, $Xaa^{11}$, $Xaa^{12}$, $Xaa^{13}$, $Xaa^{15}$ are absent.

In still other embodiments of Formula (II), five of $Xaa^1$, $Xaa^2$, $Xaa^3$, $Xaa^{11}$, $Xaa^{12}$, $Xaa^{13}$, $Xaa^{15}$ are absent.

In further embodiments of Formula (II), four of $Xaa^1$, $Xaa^2$, $Xaa^3$, $Xaa^{11}$, $Xaa^{12}$, $Xaa^{13}$, are absent and $Xaa^{15}$ is a linker.

In yet further embodiments, Formula (II) is a ten amino acid peptide.

In certain embodiments, the compound is a peptide monomer comprising a monomer subunit of Formula (III) or a peptide dimer compound comprising two linked monomer subunits of Formula (III) (SEQ ID NO:61):

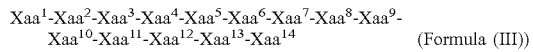
$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$ (Formula (III))

or a pharmaceutically acceptable salt, solvate, or hydrate thereof,
wherein each subunit optionally comprises a disulfide or lactam bond between $Xaa^4$ and $Xaa^{10}$,
$Xaa^1$ is absent, hydrogen, or an amino acid selected from the group consisting of Gln, Asp, Pro, Gly, His, Ala, Ile, Phe, Lys, Arg, Asn, Glu, Leu, Val, Tyr, Ser, Trp, Met, Thr, suitable isosteres and corresponding D-amino acids thereof;
$Xaa^2$ is absent or an amino acid selected from the group consisting of Gln, Asp, Pro, Gly, His, Ala, Ile, Phe, Lys, Arg, Asn, Glu, Leu, Val, Tyr, Trp, Met, Thr, and suitable isosteres and corresponding D-amino acids thereof;
$Xaa^3$ is absent an amino acid selected from the group consisting of Gln, Asp, Pro, Gly, His, Ala, Ile, Phe, Lys, Arg, Asn, Glu, Leu, Val, Tyr, Trp, Met, Ser and Thr, and suitable isosteres and corresponding D-amino acids thereof;
$Xaa^4$ is selected from the group consisting of Cys, Pen, Asp, Glu, HGlu, bAsp, b-Glu, Lys, HLys, Orn, Dap, Dab, and suitable isosteres and corresponding D-amino acids thereof;
$Xaa^5$ is selected from the group consisting of Gln, Asp, Pro, Gly, His, Ala, Ile, Phe, Lys, Arg, Asn, Glu, Leu, Val, Tyr, Trp, Met, Thr, HArg, Dap, Dab, N(alpha)Me-Arg, Arg-Me-sym, Arg-Me-asym, 4-Guan, Cit, Cav, and suitable isosteres thereof;

$Xaa^6$ is selected from the group consisting of Ser, Gln, Asn, Asp, Pro, Gly, His, Ala, Ile, Phe, Lys, Arg, Glu, Leu, Val, Tyr, Trp, Met, and suitable isosteres thereof;
$Xaa^7$ is selected from the group consisting of Asp, N-Me-Asp and a suitable isostere replacements for Asp;
$Xaa^8$ is selected from the group consisting of Thr, Gln, Ser, Asp, Pro, Gly, His, Ala, Ile, Phe, Lys, Arg, Asn, Glu, Val, Tyr, Trp, Leu, Met, and N-Methyl amino acids including N-Me-Thr;
$Xaa^9$ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, HCha, N-Me-Leu, and suitable isosteres thereof;
$Xaa^{10}$ is selected from the group consisting of Cys, Asp, Lys, Glu, Pen, HAsp, HGlu, HLys, Orn, b-Asp, b-Glu, Dap, and Dab;
$Xaa^{11}$ is selected from the group consisting of Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, HPhe, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, and corresponding D-amino acids and suitable isosteres thereof;
$Xaa^{12}$ is absent, or an amino acid selected from the group consisting of Glu, Amide, Lys, COOH, CONH2, Gln, Pro, Gly, His, Ala, Ile, Phe, Lys, Arg, Leu, Val, Tyr, Trp, Met, Gla, Ser, Asn, D-Glu, β-HGlu, 2-Nal, 1-Nal, D-Asp, Bip, β-HPhe, b-Glu, D-Tyr, D-Lys, Dap, Dab, Orn, D-Orn, N-Me-Orn, N-Me-Dap, N-Me-Dab, N-Me Lys, D-Dap, D-Dab, and suitable isosteres and corresponding D-amino acids thereof;
$Xaa^{13}$ may be absent, or $Xaa^{13}$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-Dap, D-Dab, COOH, CONH2, and suitable isosteres, and corresponding D-amino acids thereof; and
$Xaa^{14}$ is absent or an amino acid selected from the group consisting of natural amino acids, suitable isostere replacements, corresponding D-amino acids, and corresponding N-Methyl amino acids thereof.

In certain embodiments, the compound is a dimer formed from two subunits of Formula (III) joined by a suitable C- or N-terminal linker selected from the group consisting of DIG, DIG-OH, PEG13, PEG25, PEG1K, PEG2K, PEG3.4K, PEG4K, PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, suitable aromatics, heteroaromatics, and polyethylene glycols having a molecular weight from approximately 400 Da to approximately 40,000 Da.

In certain embodiments, wherein one or both monomer subunits of the compound comprises a bond between $Xaa^4$ and $Xaa^{10}$. In one embodiment, $Xaa^4$ is Cys or Pen, $Xaa^{10}$ is Pen or Cys, and $Xaa^4$ and $Xaa^{10}$ are linked by a disulfide bond. In certain embodiments, both $Xaa^4$ and $Xaa^{10}$ are Pen. In other embodiments, both $Xaa^4$ and $Xaa^{10}$ are L-Pen. In yet other embodiments, both $Xaa^4$ and $Xaa^{10}$ are D-Pen.

In other embodiments of Formula (III), $Xaa^1$ is Ac and three of $Xaa^2$, $Xaa^3$, $Xaa^{12}$, $Xaa^{13}$ $Xaa^{14}$ are absent.

In still other embodiments of Formula (III), four of $Xaa^1$, $Xaa^2$, $Xaa^3$, $Xaa^{12}$, $Xaa^{13}$, $Xaa^{14}$ are absent.

In yet other embodiments, Formula (III) is a ten amino acid peptide.

In certain embodiments of any of the compounds of any of Formulas (I)-(III), the compound comprises 8 to 20 amino acid residues, or about 9 to about 15 amino acid residues, or about 9-12 amino acid residues. In particular embodiments of any of the compounds of any of Formulas (I)-(III), the compound comprises ten amino acid residues.

For some embodiments of any of the compounds of any of Formulas (I)-(III), $Xaa^1$-$Xaa^5$, $Xaa^7$-$Xaa^9$, and $Xaa^{11}$-$Xaa^{13}$ are N(alpha)Methylated. $Xaa^5$ may further be Arg-Me-sym or Arg-Me-asym, and $Xaa^{11}$ may be O-Me-Tyr, N-Me-Lys(Ac), or 4-Me-Phe. In some instances, $Xaa^1$-$Xaa^4$, and $Xaa^{11}$-$Xaa^{14}$ are acylated. For example, in some instances one or more residues at positions $Xaa^1$-$Xaa^4$, and $Xaa^{11}$-$Xaa^{14}$ are acylated with an acylating organic compound selected from the group consisting of 2-Methyl-4,4,4,-Trifluorobutyl, Trifluoropentyl, Acetyl, Octonyl, Butyl, Pentyl, Hexyl, Palmityl, Trifluoromethyl butyl, cyclopentane carboxylic, cyclopropylacetic, 4-fluorobenzoic, 4-fluorophenyl acetic, and 3-Phenylpropionic acid. In some instances, one or more residues at positions $Xaa^1$-$Xaa^4$, and $Xaa^{11}$-$Xaa^{14}$ are acylated with an acylating organic compound selected from the group consisting of 2-Methyl-4,4,4,-Trifluorobutyl, Trifluoropentyl, Acetyl, Octonyl, Butyl, Pentyl, Hexyl, Palmityl, Lauryl, Oleoyl, Trifluoromethyl butyl, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations.

For some embodiments of any of the compounds of any of Formulas (I)-(III), the compound comprises N(alpha) methylation at one or more positions selected from the group consisting of $Xaa^3$, $Xaa^5$, $Xaa^7$-$Xaa^9$, and $Xaa^{11}$-$Xaa^{13}$. For some embodiments of any of the compounds of any of Formulas (I)-(III), $Xaa^5$ is N-Me-Arg.

For some embodiments of any of the compounds of any of Formulas (I)-(III), the compound comprises acylation at one or more position selected from the group consisting of $Xaa^1$-$Xaa^3$ and $Xaa^{11}$-$Xaa^{14}$.

In certain embodiments, the compound is a peptide monomer comprising a monomer subunit, or a peptide dimer comprising two monomer subunits, each subunit comprising the amino acid sequence:

```
                                     (SEQ ID NO: 62)
Pen-N(Me)Arg-Ser-Asp-Thr-Leu-Pen-Xaa¹-Xaa²-Xaa³
``` wherein $Xaa^1$ is any amino acid (natural or unnatural); in certain embodiments, $Xaa^1$ is Phe(4-'Bu) or Trp;
wherein $Xaa^2$ is absent or any amino acid (natural or unnatural); in certain embodiments, $Xaa^2$ is β-homoGlu, Glu, or D-Glu; and
wherein $Xaa^3$ can be any amino acid (natural or unnatural); in certain embodiments, $Xaa^3$ is Lys, D-Lys, N-Me-Lys or N-Me-D-Lys.

In particular embodiments, the two Pen residues are joined by an intramolecule disulfide bond.

In particular embodiments, the N-terminus and/or C-terminus of one or more monomer subunit is modified. In particular embodiments, the N-terminus comprises an Ac group. In particular embodiments, the C-terminus comprises a NH₂ group.

In particular embodiments of any of the compounds described herein, the subunits of any of the compound comprise any of the following amino acid sequences:

```
                                       (SEQ ID NO: 63)
Pen-(N-Me-Arg)-Ser-Asp-Thr-Leu-Pen-Trp-(D-Lys)

(SEQ ID NO: 19)
Pen-(N-Me-Arg)-Ser-Asp-Thr-Leu-Pen-Trp-bHomoGlu-
(D-Lys)

(SEQ ID NO: 25)
Pen-(N-Me-Arg)-Ser-Asp-Thr-Leu-Pen-Phe(4-'Bu)-
βHomoGlu-(D-Lys)

(SEQ ID NO: 30)
Pen-(N-Me-Arg)-Ser-Asp-Thr-Leu-Pen-Trp-Glu-(N-
Me-D-Lys)

(SEQ ID NO: 21)
Pen-(N-Me-Arg)-Ser-Asp-Thr-Leu-Pen-Trp-Glu-(N-
Me-Lys)

(SEQ ID NO: 64)
Pen-(N-Me-Arg)-Ser-Asp-Thr-Leu-Pen-Trp-(D-Glu)-
(D-Lys)

(SEQ ID NO: 65)
Pen-(N-Me-Arg)-Ser-Asp-Thr-Leu-Pen-Trp-Glu-(D-Lys)

(SEQ ID NO: 64)
Pen-(N-Me-Arg)-Ser-Asp-Thr-Leu-Pen-Trp-(D-Glu)-
(D-Lys)

(SEQ ID NO: 65)
Pen-(N-Me-Arg)-Ser-Asp-Thr-Leu-Pen-Trp-Glu-(D-Lys)
```

In particular embodiments, the two Pen residues are joined by an intramolecule disulfide bond.

In particular embodiments, the compound is a dimer comprising the following amino acid sequences of two monomer subunits joined by a DIG linker:

```
                                       (SEQ ID NO: 66)
[Ac-Pen-(N-Me-Arg)-Ser-Asp-Thr-Leu-Pen-Trp-(D-
Lys)-NH₂]₂-DIG (SEQ ID NO: 31)
[Ac-Pen-(N-Me-Arg)-Ser-Asp-Thr-Leu-Pen-Trp-
bHomoGlu-(D-Lys)-NH₂]₂-DIG (SEQ ID NO: 37)
[Ac-Pen-(N-Me-Arg)-Ser-Asp-Thr-Leu-Pen-Phe(4-'Bu)-
βHomoGlu-(D-Lys)-NH₂]₂-DIG (SEQ ID NO: 42)
[Ac-Pen-(N-Me-Arg)-Ser-Asp-Thr-Leu-Pen-Trp-Glu-(N-
Me-D-Lys)-NH₂]₂-DIG (SEQ ID NO: 33)
[Ac-Pen-(N-Me-Arg)-Ser-Asp-Thr-Leu-Pen-Trp-Glu-
(N-Me-Lys)-NH₂]₂-DIG (SEQ ID NO: 67)
[Ac-Pen-(N-Me-Arg)-Ser-Asp-Thr-Leu-Pen-Trp-(D-
Glu)-(D-Lys)-OH]₂-DIG
```

-continued

```
                                       (SEQ ID NO: 68)
[Ac-Pen-(N-Me-Arg)-Ser-Asp-Thr-Leu-Pen-Trp-Glu-
(D-Lys)-NH₂]₂-DIG (SEQ ID NO: 67)
[Ac-Pen-(N-Me-Arg)-Ser-Asp-Thr-Leu-Pen-Trp-(D-
Glu)-(D-Lys)-NH₂]₂-DIG (SEQ ID NO: 68)
[Ac-Pen-(N-Me-Arg)-Ser-Asp-Thr-Leu-Pen-Trp-Glu-
(D-Lys)-OH]₂-DIG
```

In particular embodiments, the two Pen residues of each subunit are joined by an intramolecule disulfide bond.

Solid Phase Peptide Synthesis

In particular embodiments, the methods of the present invention provide a process for the synthesis of a penicillamine containing peptide in commercial scale quantities by solid phase methods using inexpensive starting materials, mild reagents to yield high purity peptide.

In certain embodiments, the present invention provides methods of synthesizing the peptides of Compound B, Table 2, those disclosed in PCT Applications PCT/US2013/064439; PCT/US2014/032391; PCT/US2014/032392; PCT/US2015/053558; PCT/US2015/053603; U.S. Pat. No. 9,518,091B2, and other peptides disclosed herein, including but not limited to those of Formulas (I)-(III), and pharmaceutically acceptable salts, solvates, or hydrates thereof, via solid phase peptide synthesis. In further embodiments of the invention, solid phase peptide synthesis is performed on any suitable resin, such as, but not limited to Rink Amide (RAM) resin, Wang resin, tricyclic amide linker resin (Ramage Resin), Diphenyldiazomethane resin (PDDM-resin), DHPP Resin, and 4,4'-Dialkoxybenzhydrylamine resin.

In particular embodiments of the invention, the peptides of Compound B, Table 2, those disclosed in PCT Applications PCT/US2013/064439; PCT/US2014/032391; PCT/US2014/032392; PCT/US2015/053558; PCT/US2015/053603; U.S. Pat. No. 9,518,091B2, and other peptides disclosed herein, including but not limited to those of Formulas (I)-(III), are synthesized via solid phase peptide synthesis on a tricyclic amide linker resin (Ramage Resin).

In further embodiments of the invention, the peptides of Compound B and Table 2 are synthesized via solid phase peptide synthesis from protected amino acids selected from the group consisting of: Fmoc-D-Lys(Boc)-OH, Fmoc-β-homoGlu(O$^t$Bu)-OH, Fmoc-L-(4-$^t$Bu)Phe-OH, Fmoc-L-Pen(Acm)-OH, Fmoc-L-Pen(Trt)-OH, Fmoc-Pen($^{\psi Me,Me}$Pro)-OH, Bpoc-Pen($^{\psi Me,Me}$Pro)-OH, Cbz-Pen($^{\psi Me,Me}$Pro)-OH, Fmoc-Pen($^{\psi H,H}$ProPro)-OH, Bpoc-Pen($^{\psi H,H}$ProPro)-OH, Cbz-Pen($^{\psi H,H}$ProPro)-OH, Fmoc-Leu-Pen($^{\psi Me,Me}$Pro)-OH, Bpoc-Leu-Pen($^{\psi Me,Me}$Pro)-OH, Cbz-Leu-Pen($^{\psi Me,Me}$Pro)-OH, Fmoc-Leu-Pen($^{\psi H,H}$ProPro)-OH, Bpoc-Leu-Pen($^{\psi H,H}$ProPro)-OH, or Cbz-Leu-Pen($^{\psi H,H}$ProPro)-OH, Fmoc-L-Leu-OH, Fmoc-L-Thr($^t$Bu)OH, Fmoc-L-Asp($^t$Bu)-OH, Fmoc-L-Asp($^t$Bu)-Thr($^{\psi Me,Me}$Pro-OH, Fmoc-L-Ser($^t$Bu)-OH, Fmoc-L-NMe-Arg(Pbf)-OH, Fmoc-L-Trp(Boc)-OH, Fmoc-L-Glu(O$^t$Bu)-OH, Fmoc-D-Glu(O$^t$Bu)-OH, Fmoc-N-Me-D-Lys(Boc)-OH, and Fmoc-N-Me-D-Lys(Boc)-NH₂.

In yet further embodiments of the invention, the peptide of Compound B is synthesized via solid phase peptide synthesis from the following protected amino acids: Fmoc-D-Lys(Boc)-OH, Fmoc-β-homoGlu(O$^t$Bu)-OH, Fmoc-L-(4-$^t$Bu)Phe-OH, Fmoc-L-Pen(Acm)-OH, Fmoc-L-Leu-OH, Fmoc-L-Thr($^t$Bu)OH, Fmoc-L-Asp($^t$Bu)-OH, Fmoc-L-Ser($^t$Bu)-OH, and Fmoc-L-NMe-Arg(Pbf)-OH.

In still further embodiments of the invention, the peptide of Compound B is synthesized via solid phase peptide synthesis from the following protected amino acids: Fmoc-D-Lys(Boc)-OH, Fmoc-β-homoGlu(O$^t$Bu)-OH, Fmoc-L-(4-$^t$Bu)Phe-OH, Fmoc-L-Pen(Trt)-OH, Fmoc-L-Leu-OH, Fmoc-L-Asp($^t$Bu)-Thr($^{\psi Me,Me}$Pro)-OH, Fmoc-L-Ser($^t$Bu)-OH, and Fmoc-L-NMe-Arg(Pbf)-OH.

In still further embodiments, the methods of the present invention provide a solid phase synthesis method for synthesizing a peptide having the sequence:

```
                                       (SEQ ID NO: 62)
Ac-Pen-N(Me)Arg-Ser-Asp-Thr-Leu-Pen-Xaa¹-Xaa²-Xaa³
or
                                       (SEQ ID NO: 62)
Ac-Pen-N(Me)Arg-Ser-Asp-Thr-Leu-Pen-Xaa¹-Xaa²-
Xaa³-NH₂,
``` wherein:

Xaa¹ can be any natural or unnatural amino acid;

Xaa² can be absent or any natural or unnatural amino acid; and

Xaa³ can be any natural or unnatural amino acid.

In certain embodiments, Xaa¹ is Phe(4-$^t$Bu) or Trp.

In particular embodiments, Xaa² is β-homoGlu, Glu, or D-Glu.

In further embodiments, Xaa³ is Lys, D-Lys, N-Me-Lys or N-Me-D-Lys.

In yet further embodiments, Xaa¹ is Phe(4-$^t$Bu) or Trp; Xaa² is β-homoGlu, Glu, or D-Glu; and Xaa³ is Lys, D-Lys, N-Me-Lys or N-Me-D-Lys.

In certain embodiments, the present invention provides methods of synthesizing the peptide dimers of Compound A, Table 3, those disclosed in PCT Applications PCT/US2013/064439; PCT/US2014/032391; PCT/US2014/032392; PCT/US2015/053558; PCT/US2015/053603; U.S. Pat. No. 9,518,091B2, and other peptides disclosed herein, including but not limited to those of Formulas (I)-(III), and pharmaceutically acceptable salts, solvates, or hydrates, thereof wherein the appropriate peptide monomer is synthesized via solid phase peptide synthesis, followed by cyclization of the Pen residues and dimerization of the cyclized peptide with a suitable linker. In certain embodiments of the invention, the linker is diglycolic acid.

In particular embodiments, the present invention provides a method of synthesizing by solid phase peptide synthesis the peptide monomers and dimers of Formula I as illustrated in Scheme IA.

Scheme IA

 + Xaa$^{1-14}$

Suitable Resin for        Suitably protected AAs
Solid Phase Peptide

-continued

Step 1 | Repeat couplings, deprotections, and washes
↓

Xaa¹—Xaa²—Xaa³—Xaa⁴—Xaa⁵—Xaa⁶—Xaa⁷—Xaa⁸—Xaa⁹—Xaa¹⁰—Xaa¹¹—Xaa¹²—Xaa¹³—Xaa¹⁴—●

Step 2 | TFA, EDT, TIS, H₂O
↓

Xaa¹—Xaa²—Xaa³—Xaa⁴—Xaa⁵—Xaa⁶—Xaa⁷—Xaa⁸—Xaa⁹—Xaa¹⁰—Xaa¹¹—Xaa¹²—Xaa¹³—Xaa¹⁴

Steps 3 & 4 | ACN/H₂O, HOAc, I₂ Purification via RP-HPLC
↓

Xaa¹—Xaa²—Xaa³—Xaa⁴—Xaa⁵—Xaa⁶—Xaa⁷—Xaa⁸—Xaa⁹—Xaa¹⁰—Xaa¹¹—Xaa¹²—Xaa¹³—Xaa¹⁴

Xaa¹—Xaa²—Xaa³—Xaa⁴—Xaa⁵—Xaa⁶—Xaa⁷—Xaa⁸—Xaa⁹—Xaa¹⁰—Xaa¹¹—Xaa¹²—Xaa¹³—Xaa¹⁴

Step 5 | Suitable Linker NHS, DCC, NMP
↓

Steps 6 & 7 | DIEA, DMF, NMP Purification & Salt excahnge via RP-HPLC
↓

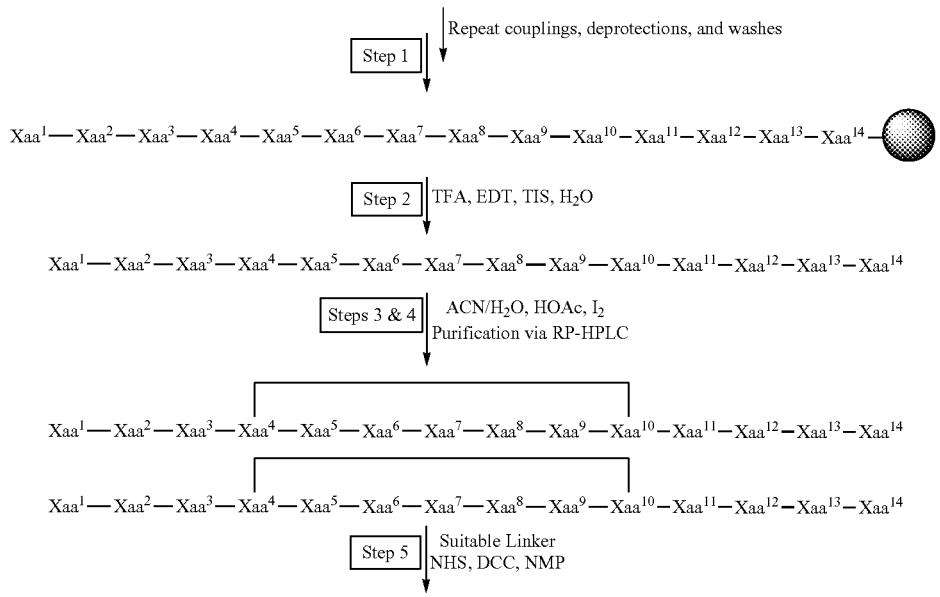

OR

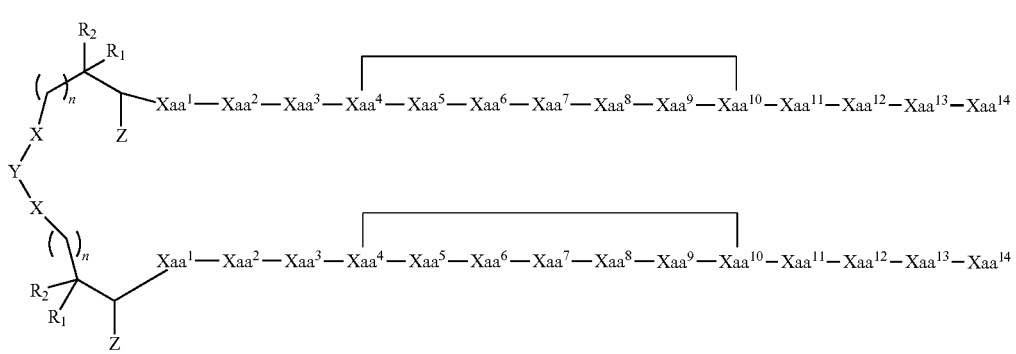

In certain embodiments,
Xaa$^1$ to Xaa$^{14}$ are defined as in Formula I (SEQ ID NO:18);
R$_1$ and R$_2$ are H, C$_1$-C$_6$ alkyl (branched or linear), or C$_3$-C$_6$ aryl;
n is any integer from 2 to 20
X is CR'R', NHCO, CONH, S—S, C=O, CHOH, S, S=O, N, NH, or O;
Y is a linker moiety;
Z is H, C$_1$-C$_6$ alkyl (branched or linear), C$_3$-C$_6$ aryl, heteroaryl, N, S, O, NHAc, or absent; and
each R' is, independently, H or C$_1$-C$_4$ alkyl.
In certain embodiments,
Xaa$^1$ to Xaa$^{14}$ are defined as in Formula I (SEQ ID NO:18)
R$_1$ and R$_2$ are H, C$_1$-C$_6$ alkyl (branched or linear), or C$_1$-C$_6$ aryl
n is any integer from 2 to 20
X is CR'R', C=O, S, N, or O;
Y is a linker moiety;
Z is H, C$_1$-C$_6$ alkyl (branched or linear), C$_3$-C$_6$ aryl, heteroaryl, N, S, or O; and
each R' is, independently, H or C$_1$-C$_4$ alkyl.
In yet further embodiments,
Xaa$^1$ to Xaa$^{14}$ are defined as in Formula I (SEQ ID NO:18)
R$_1$ and R$_2$ are H or Me
n is any integer from 2 to 20
X is CH$_2$, NHCO, CONH, S—S, C=O, CHOH, S, S=O, NH, or O;
Y is a linker moiety; and
Z is NHAc, absent or H.
In still further embodiments,
Xaa$^1$ to Xaa$^{14}$ are defined as in Formula I (SEQ ID NO:18)
R$_1$ and R$_2$ are H or Me
n is any integer from 2 to 10
X is CH$_2$, NHCO, CONH, S—S, C=O, CHOH, S, S=O, NH, or O;
Y is a linker moiety; and
Z is NHAc, absent or H.
In certain embodiments of the invention, in any of the above embodiments of Scheme IA, Y may be selected from the group consisting of DIG, PEG13, PEG25, PEG1K, PEG2K, PEG34K, PEG4K, PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, cyclopropylacetic acid, 4-fluoorobenzoic acid, 4-fluorophenylacetic acid, 3-phenylpropionic acid, succinic acid, biotin, glutaric acid, Azelaic acid, Pimelic acid, Dodecanedioic acid, aliphatic amino acids, aromatic amino acids, heteroaromatics, polyethylene glycols having a molecular weight from approximately 400 Da to approximately 40,000 Da, bifunctional linkers, N-Hydroxy succinimide (NHS)-activated diesters, and bis-maleimides.
In further embodiments of the invention, in any of the above embodiments of Scheme IA, Y may be selected from the linkers of Table 4.
In yet further embodiments,
Xaa$^1$ to Xaa$^{14}$ are defined as in Formula I (SEQ ID NO:18)
R$_1$ and R$_2$ are H or Me
n is any integer from 2 to 20
X is CH$_2$, NHCO, CONH, S—S, C=O, CHOH, S, S=O, NH, or O;
Y is a linker moiety as shown in Table C; and
Z is NHAc, absent or H.

In yet further embodiments,
Xaa$^1$ to Xaa$^{14}$ are defined as in Formula I (SEQ ID NO:18)
R$_1$ and R$_2$ are H or Me
n is any integer from 2 to 10
X is CH$_2$, NHCO, CONH, S—S, C=O, CHOH, S, S=O, NH, or O;
Y is a linker moiety as shown in Table C; and
Z is NHAc, absent or H.

TABLE C

POSSIBLE LINKERS

[Structures shown: para-, ortho-, and meta-substituted benzene linkers; bis-maleimide linkers with Spacer]

Spacer: PEG, aliphatic chain,

In any of the above embodiments of Scheme IA, Xaa$^4$ is Cys or Pen, Xaa$^{10}$ is Pen or Cys, and Xaa$^4$ and Xaa$^{10}$ are linked by a disulfide bond. In certain embodiments of Scheme IA, both Xaa$^4$ and Xaa$^{10}$ are Pen. In other embodiments of Scheme IA, both Xaa$^4$ and Xaa$^{10}$ are L-Pen. In yet other embodiments of Scheme IA, both Xaa$^4$ and Xaa$^{10}$ are D-Pen.

Scheme IB illustrates particular embodiments of the invention providing a method of synthesizing by solid phase peptide synthesis peptide dimers comprising a peptide having the following structure Ac-Pen-N(Me)Arg-Ser-Asp-Thr-Leu-Pen-Xaa$^1$-Xaa$^2$-Xaa$^3$-NH$_2$ (SEQ ID NO:62), wherein:
Xaa$^1$ can be any natural or unnatural amino acid;
Xaa$^2$ can be absent or any natural or unnatural amino acid; and
Xaa$^3$ can be any natural or unnatural amino acid.
In certain embodiments, Xaa$^1$ is Phe(4-$^t$Bu) or Trp.
In particular embodiments, Xaa$^2$ is β-homoGlu, Glu, or D-Glu.
In further embodiments, Xaa$^3$ is Lys, D-Lys, N-Me-Lys or N-Me-D-Lys.
In yet further embodiments, Xaa$^1$ is Phe(4-$^t$Bu) or Trp; Xaa$^2$ is β-homoGlu, Glu, or D-Glu; and Xaa$^3$ is Lys, D-Lys, N-Me-Lys or N-Me-D-Lys.

Scheme 1B
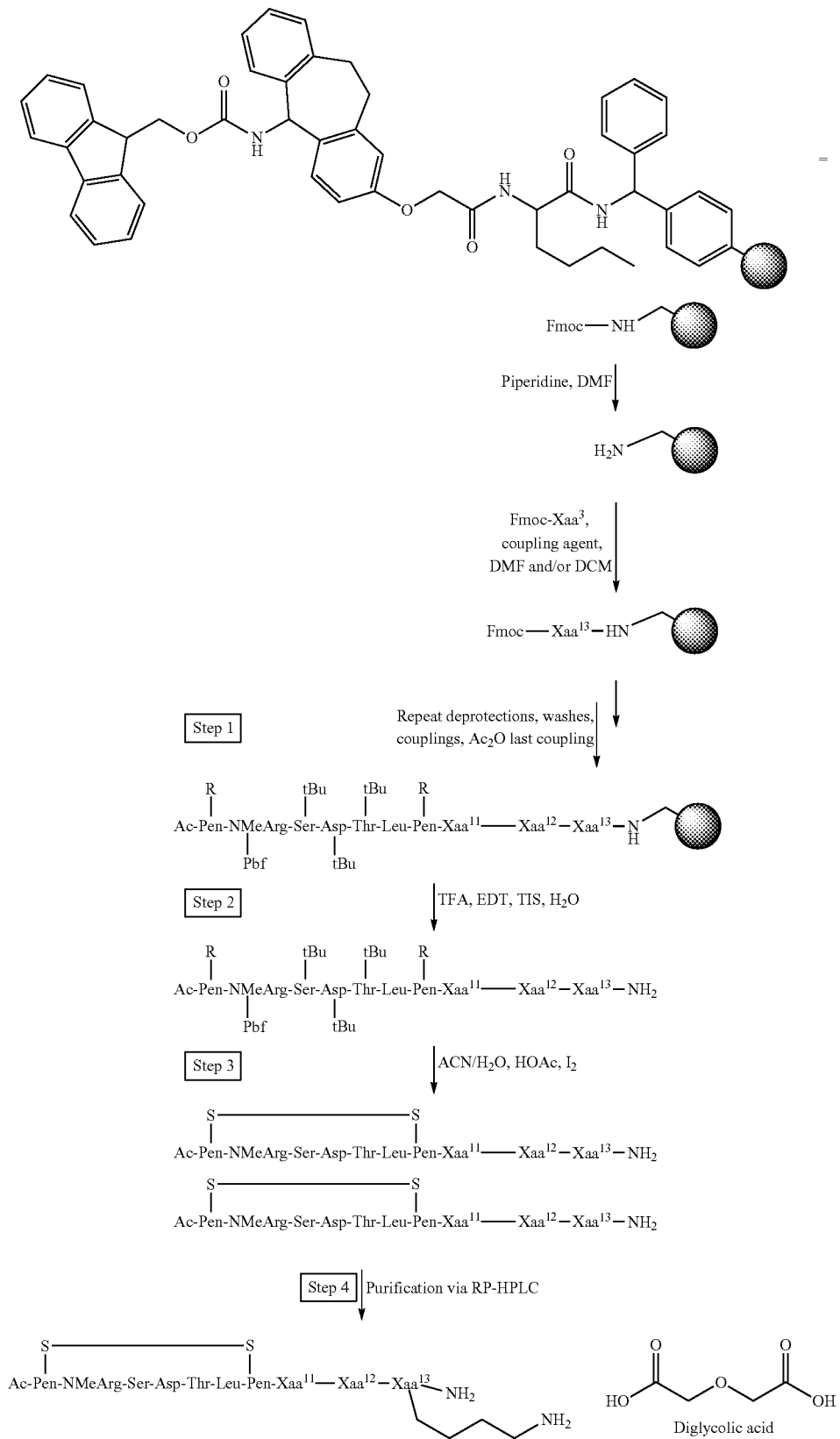

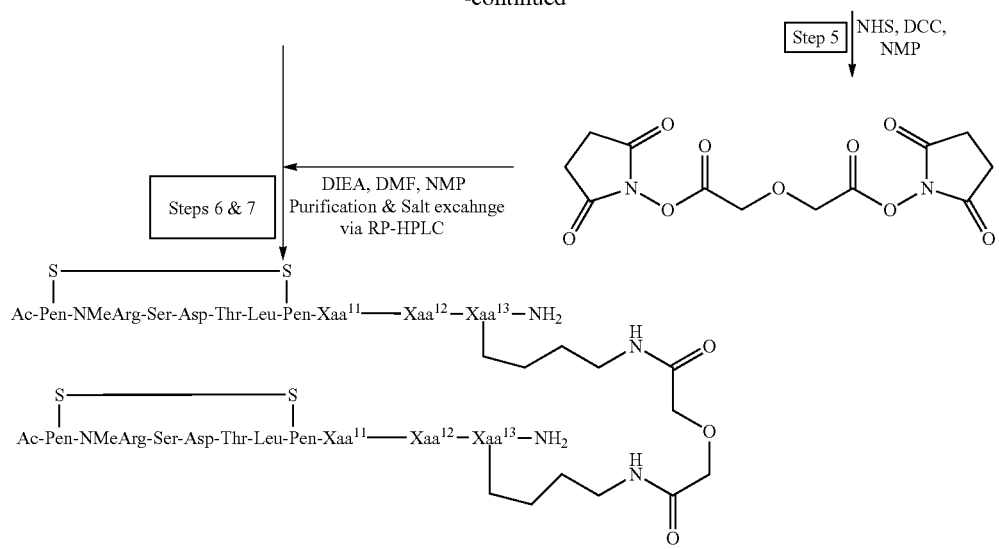

Where Xaa[11] can be any amino acid (natural or unnatural); in certain embodiments, Xaa[11] is Phe(4-$^t$Bu) or Trp Where Xaa[12] can be absent or any amino acid (natural or unnatural); in certain embodiments, Xaa[12] is beta-homoGlu, Glu, or D-Glu Where Xaa[13] can be any amino acid (natural or unnatural); in certain embodiments, Xaa[13] is Lys, D-Lys, N-Me-Lys or N-Me-D-Lys Where each R is independently Trt or Acm, and if R is Trt, R is absent after Step 2 (treatment with TFA)

In particular embodiments of Scheme IB, Xaa[11] is selected from the group consisting of: aromatic amino acids, substituted aromatic amino acids, Glu, D-Glu, homoGlu, Asp, D-Asp, D-homoGlu, Gla, β-homoGlu, Tic, Aic, Gln, Cit, Glu(OMe), Asn, D-His, Tic, Phe(3-COOH), Phe(4-$^t$Bu), D-Arg, Bip, Trp, D-Trp, Phe, D-Phe, D-Val, D-Thr, D-Tyr, D-Lys, D-Ile, D-His, N-Me-Glu, N-Me-Asp, alpha-homo-Glu, Biphenyl-Gly, Biphenyl-Ala, homo-Phe, D-1-Nal, D-2-Nal, Thr, and Val, Pro, and corresponding D-amino acids and isosteres In further embodiments of Scheme IB, Xaa[11] is Phe(4-$^t$Bu) or Trp In certain embodiments of Scheme IB, Xaa[12] is absent or selected from the group consisting of: aromatic amino acids, substituted aromatic amino acids, Glu, D-Glu, homoGlu, Asp, D-Asp, D-homoGlu, Gla, β-homoGlu, Tic, Aic, Gln, Cit, Glu(OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, homo-Phe, D-1-Nal, D-2-Nal, Thr, and Val, Pro, and corresponding D-amino acids and isosteres;

In particular embodiments of Scheme IB, Xaa[12] is absent'

In yet other embodiments of Scheme IB, Xaa[12] is β-homoGlu, Glu, or D-Glu

In further embodiments of Scheme IB, Xaa[13] is selected from the group consisting of: any amino acid with an amine side chain, Lys, D-Lys, N-Me-Lys, D-N-Me-Lys, N-Me-D-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, HomoGlu, D-homoGlu, N-Me-Glu, N-Me-Asp, N-Me-D-Glu, and N-Me-D-Asp.

In still further embodiments of Scheme IB, Xaa[13] is Lys, D-Lys, N-Me-Lys or N-Me-D-Lys In some embodiments of the invention, the peptide monomers can also be conjugated, or dimerized, at the N-terminus, in order to yield an N-terminal dimer peptide. In certain embodiments, conjugation is through a free N-terminal amine of Pen (Xaa$_4$) or through an amino acid with free amine side chain shown below in Scheme IC.

Scheme IC

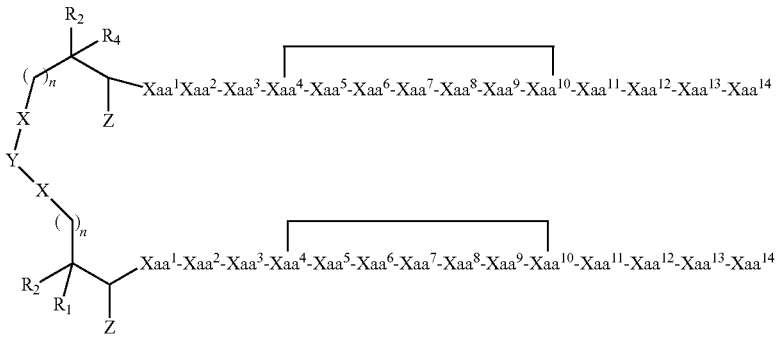

In certain embodiments of Scheme IC, $Xaa^1$ to $Xaa^{14}$, $R_1$, $R_2$, n, X, Y, and Z are defined as in the various embodiments of Scheme IA. In other embodiments, $Xaa^1$, $Xaa^2$ and $Xaa^3$ are absent, $Xaa^4$ to $Xaa^{14}$ are defined as in Formula I, and the peptide monomers are conjugated through the free amine of $Xaa^4$ using any suitable linker as described herein.

In yet other embodiments, $Xaa^1$ and $Xaa^2$ are absent, $Xaa^3$ is any amino acid with a side chain capable of forming a bond with any linker to form a dimer as described herein, and $Xaa^4$ to $Xaa^{14}$ are defined as in Formula I.

In yet further embodiments of the invention, peptide dimers dimerized at the at the N-terminus may be made by any of the peptide monomer or dimer synthesis methods disclosed herein, including, but not limited to, solid phase peptide synthesis and solution phase peptide synthesis, including the various fragment approaches described herein, particularly in Schemes V, VI, VII, VIII, and IX.

In particular embodiments of the invention, Compound A is synthesized by preparing Compound B via solid phase peptide synthesis as discussed, followed by cyclization of the Pen residues and dimerization of Compound B with diglycolic acid. The general scheme for synthesis of the peptide dimer Compound A is shown below in Scheme II.

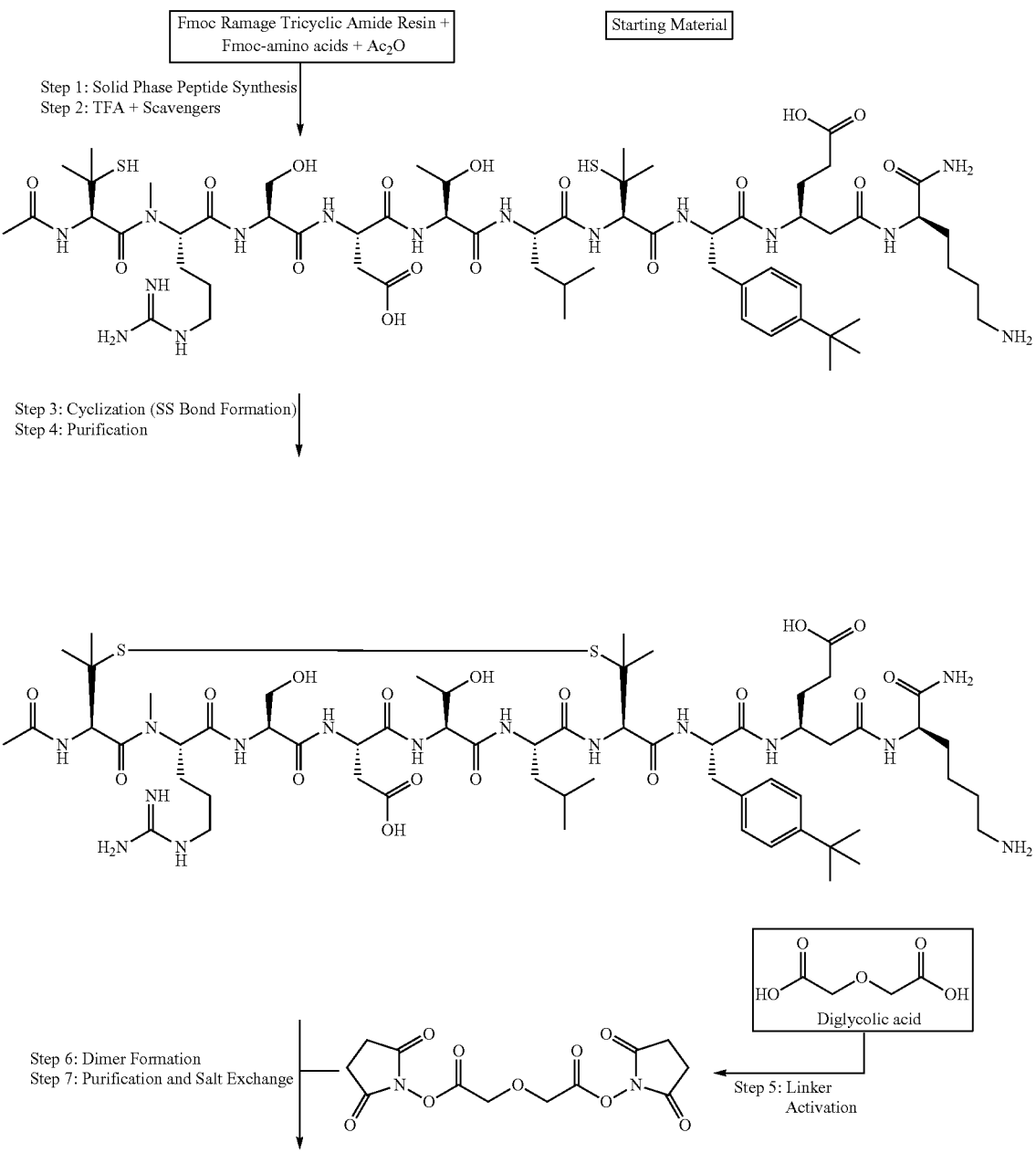

-continued

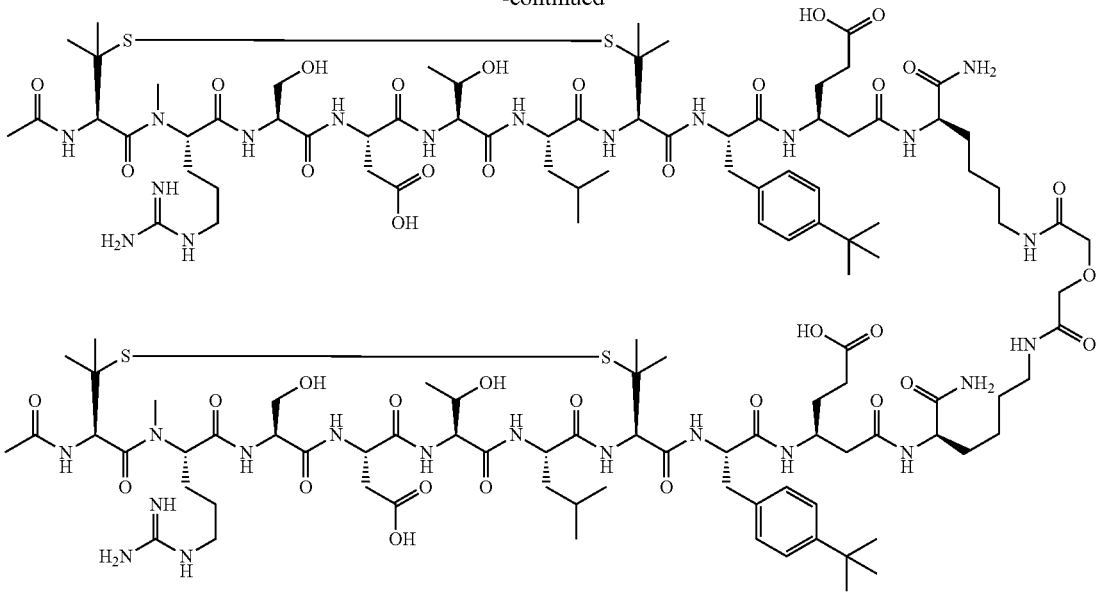

In particular embodiments, the present invention provides methods of synthesizing the cyclized peptide monomer Compound B.

In further embodiments of the invention, Compound B is prepared using solid phase peptide synthesis followed by cyclization of the Pen residues. In still further embodiments of the invention, Compound B is prepared using Fmoc solid phase peptide synthesis.

In particular embodiments of the invention, Compound B is synthesized on a suitable resin and with amino acids selected from the group consisting of Fmoc-D-Lys(Boc)-OH, Fmoc-β-homoGlu(O$^t$Bu)-OH, Fmoc-L-(4-$^t$Bu)Phe-OH, Fmoc-L-Pen(Acm)-OH, Fmoc-L-Pen(Trt)-OH, Fmoc-Pen($^{\psi Me,Me}$Pro)-OH, Bpoc-Pen($^{\psi Me,Me}$Pro)-OH, Cbz-Pen($^{\psi Me,Me}$Pro)-OH, Fmoc-Pen(Pro)-OH, Bpoc-Pen(Pro)-OH, Cbz-Pen(Pro)-OH, Fmoc-Leu-Pen($^{\psi Me,Me}$Pro)-OH, Bpoc-Leu-Pen($^{\psi Me,Me}$Pro)-OH, Cbz-Leu-Pen($^{\psi Me,Me}$Pro)-OH, Fmoc-Leu-Pen(Pro)-OH, Bpoc-Leu-Pen(Pro)-OH, Cbz-Leu-Pen(Pro)-OH, Fmoc-L-Leu-OH, Fmoc-L-Thr($^t$Bu)OH, Fmoc-L-Asp($^t$Bu)-OH, Fmoc-L-Asp($^t$Bu)-Thr($^{\psi Me,Me}$Pro)-OH, Fmoc-L-Ser($^t$Bu)-OH, Fmoc-L-NMe-Arg(Pbf)-OH, Fmoc-L-Trp(Boc)-OH, Fmoc-L-Glu(O$^t$Bu)-OH, Fmoc-D-Glu(O$^t$Bu)-OH, and Fmoc-N-Me-D-Lys(Boc)-OH.

In yet further embodiments of the invention, Compound B is prepared on tricyclic amide linker resin (Ramage Resin) with the following protected amino acids: Fmoc-D-Lys(Boc)-OH, Fmoc-β-homoGlu(O$^t$Bu)-OH, Fmoc-L-(4-$^t$Bu)Phe-OH, Fmoc-L-Pen(Acm)-OH, Fmoc-L-Leu-OH, Fmoc-L-Thr($^t$Bu)OH, Fmoc-L-Asp($^t$Bu)-OH, Fmoc-L-Ser($^t$Bu)-OH, Fmoc-L-NMe-Arg(Pbf)-OH. In other embodiments of the invention, Compound B is prepared on tricyclic amide linker resin (Ramage Resin) with the following protected amino acids: Fmoc-D-Lys(Boc)-OH, Fmoc-β-homoGlu(O$^t$Bu)-OH, Fmoc-L-(4-$^t$Bu)Phe-OH, Fmoc-L-Pen(Trt)-OH, Fmoc-L-Leu-OH, Fmoc-L-Asp($^t$Bu)-Thr($^{\psi Me,Me}$Pro)-OH, Fmoc-L-Ser($^t$Bu)-OH, Fmoc-L-NMe-Arg(Pbf)-OH.

In certain embodiments of the invention, the terminal Pen residue is acylated after coupling of the protected Pen residue and prior to deprotection, cleavage, cyclization and purification. In certain embodiments, deprotection and cleavage occur in the same step. In particular embodiments, the terminal Pen residue is acylated with acetic anhydride.

Representative methods of the invention for the preparation of Compound B are shown in Schemes IIIA and IIIB.

Scheme IIIA

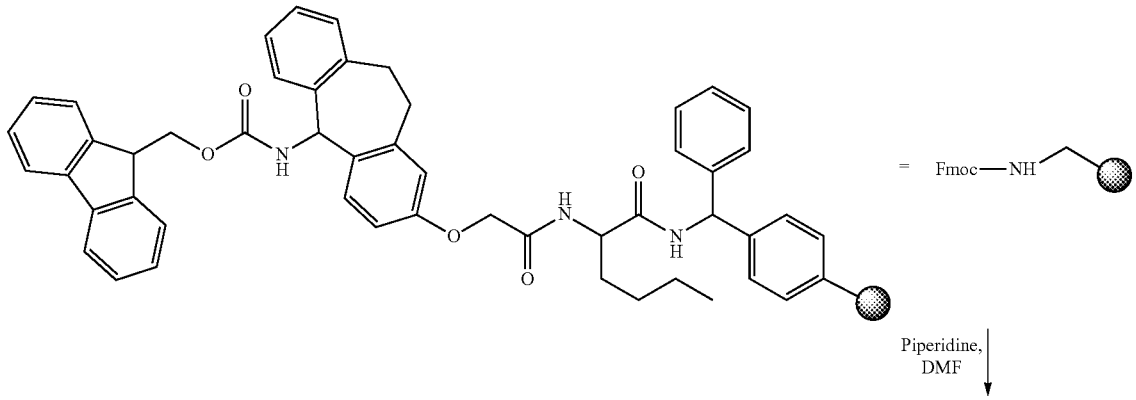

-continued
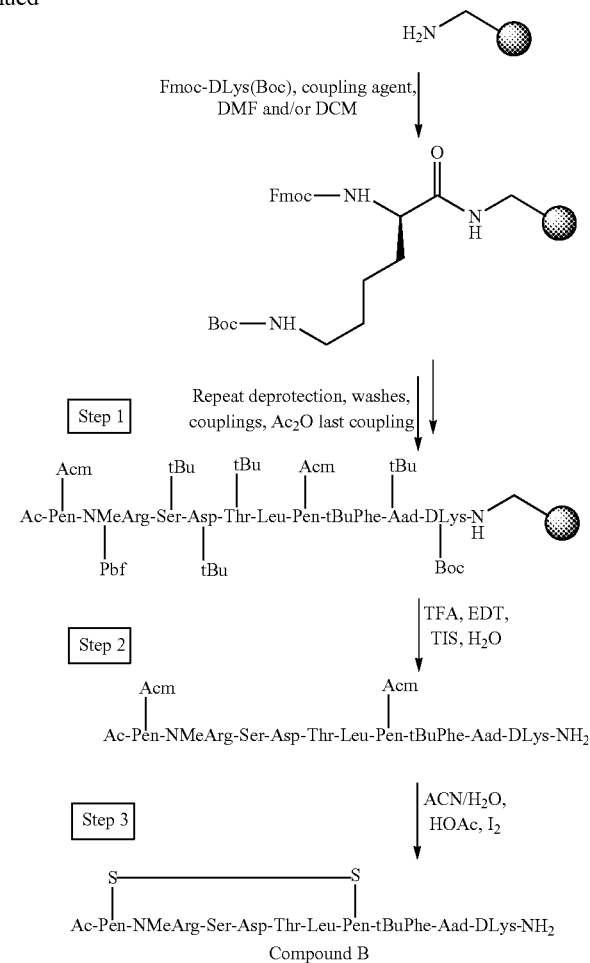
Aad = beta-homoGlu
Scheme IIIB
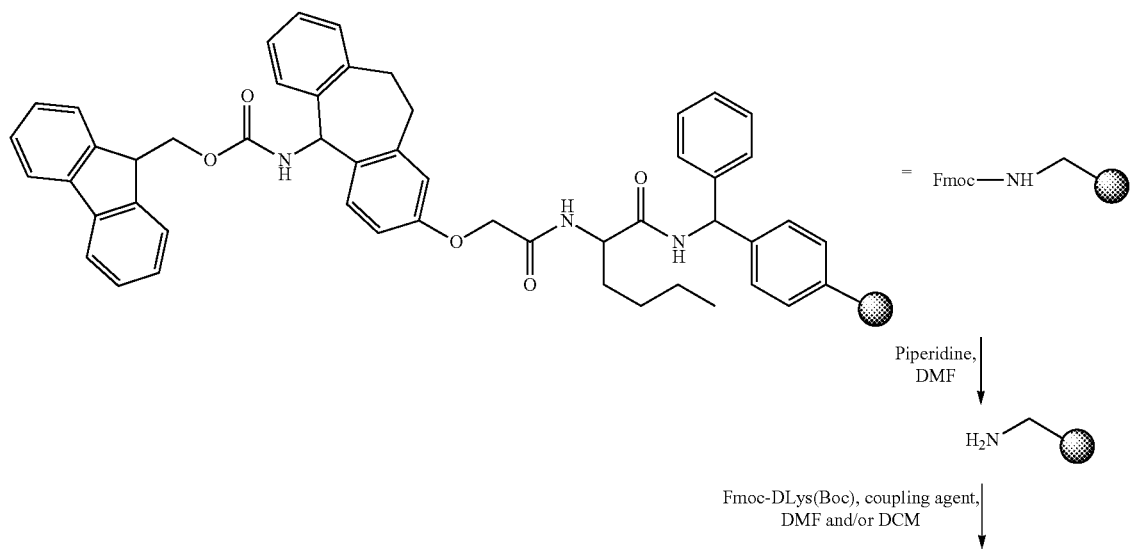

-continued
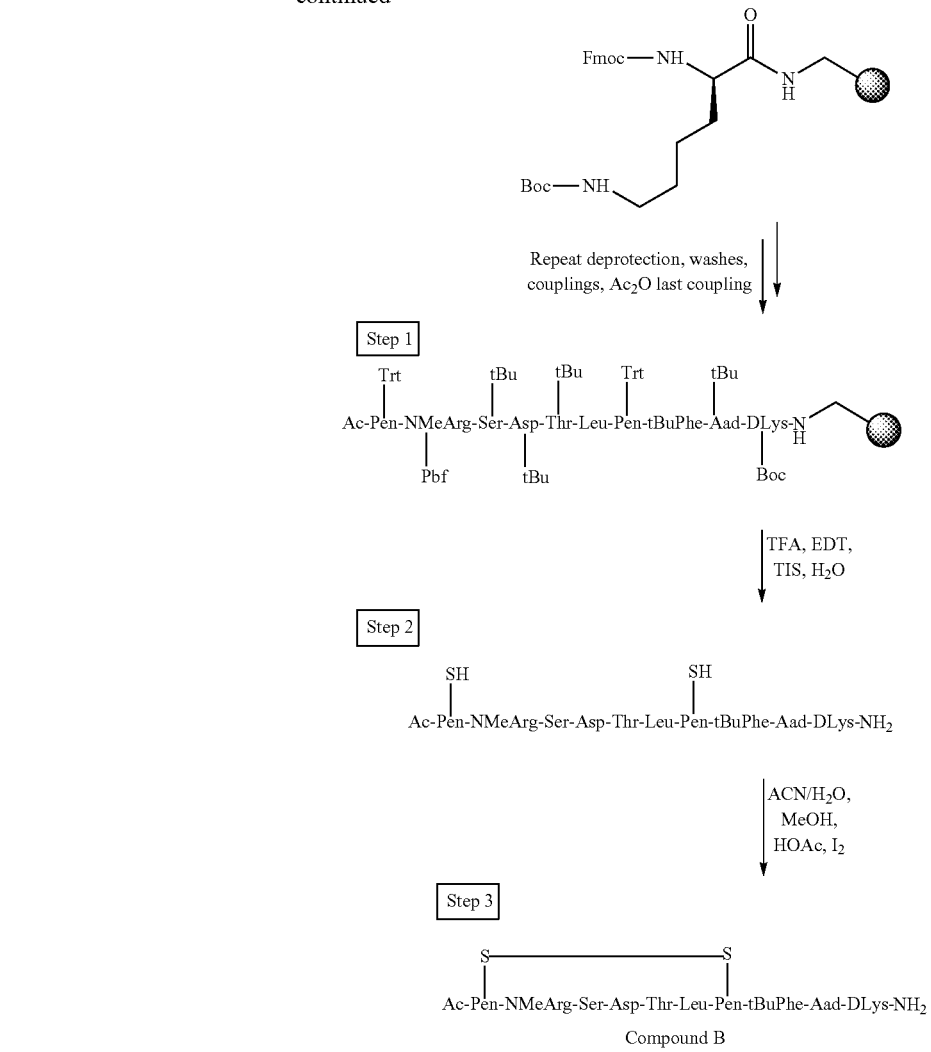
Aad is beta-homoGlu
A representative method of the invention for the preparation of Compound A from Compound B is shown in Scheme IV.
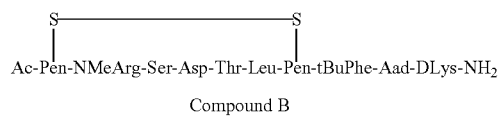

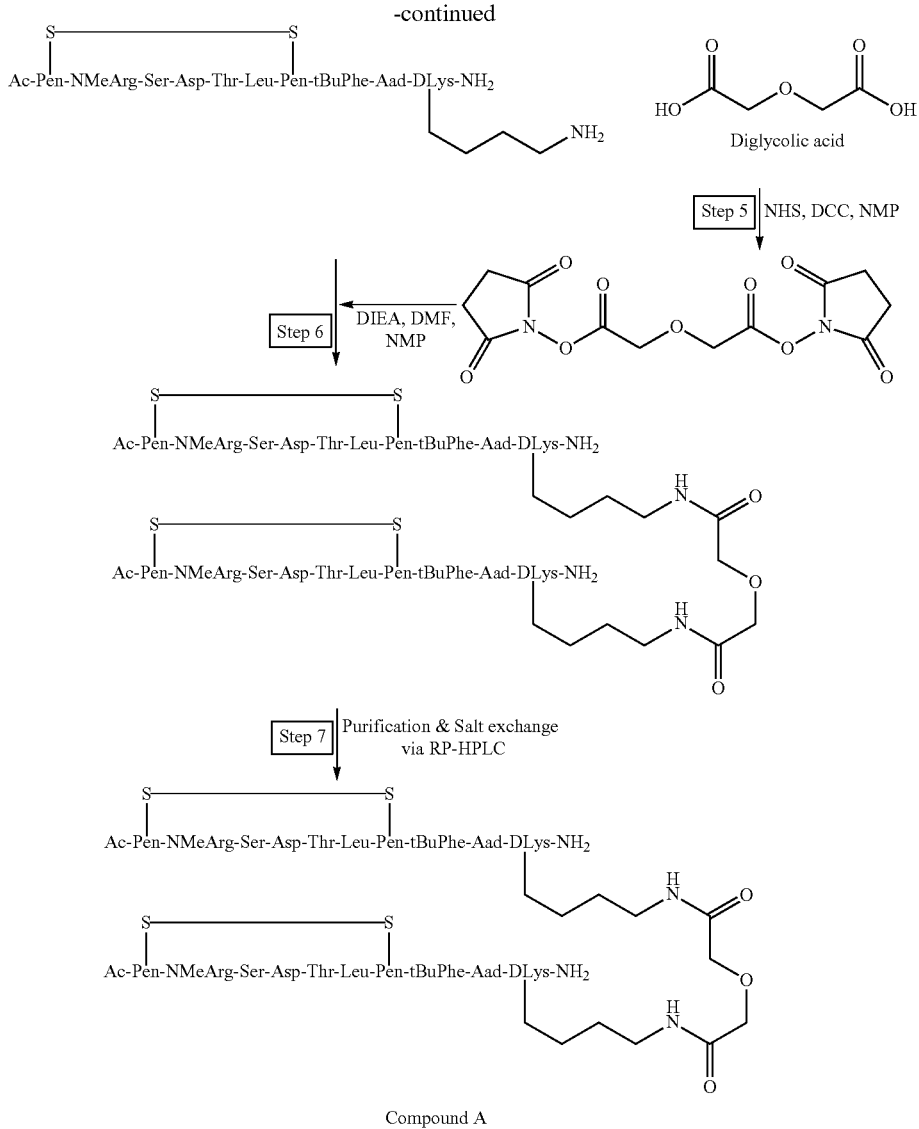

Compound A

In further embodiments of the invention, the peptide dimers Table 3, those disclosed in PCT Applications PCT/US2013/064439; PCT/US2014/032391; PCT/US2014/032392; PCT/US2015/053558; PCT/US2015/053603; U.S. Pat. No. 9,518,091B2, and other peptides disclosed herein, including but not limited to those of Formulas (I)-(III), and pharmaceutically acceptable salts, solvates, or hydrates thereof are synthesized through solid phase peptide synthesis as described above in Schemes IA and IB.

In certain embodiments of the invention, the two linked monomer subunits of the peptide dimer are linked together through their C-termini via a linking moiety. In other embodiments of the invention, the two linked monomer subunits of the peptide dimer are linked together through their N-termini via a linking moiety.

In certain embodiments of the invention, a penicillamine containing peptide such as $(Xaa^z)_n$-Pen-$(Xaa^z)_m$, or HPen-$(Xaa^z)_m$ wherein each $Xaa^z$ is independently selected from the group consisting of natural amino acids, unnatural amino acids, suitable isostere replacements, corresponding D-amino acids, and corresponding N-Methyl amino acids, and each of n and m are independently integers from 1-20 is synthesized as follows: the peptide fragment $(Xaa^z)_m$ linked to a suitable solid support is prepared using solid phase peptide synthesis techniques known to the practitioners in the art and condensed with an N-terminal protected pseudoproline penicillamine derivative such as, but not limited to: Fmoc-Pen($^{\psi Me,Me}$Pro)-OH, Bpoc-Pen($^{\psi Me,Me}$Pro)-OH, Cbz-Pen($^{\psi Me,Me\psi}$Pro)-OH, Fmoc-Pen(Pro)-OH, Bpoc-Pen(Pro)-OH, Cbz-Pen(Pro)-OH, Fmoc-Leu-Pen($^{\psi Me,Me}$)-OH, Bpoc-Leu-Pen($^{\psi Me,Me}$)-OH, Cbz-Leu-Pen($^{\psi Me,Me}$Pro)-OH, Fmoc-Leu-Pen(Pro)-OH, Bpoc-Leu-Pen(Pro)-OH, or Cbz-Leu-Pen(Pro)-OH. The N-terminus of the resulting peptide is deprotected under suitable conditions to yield the peptide fragment H-Pen($^{\psi Me,Me}$Pro)-$(Xaa^z)_m$ or H-Pen(Pro)-$(Xaa^z)_m$ linked to the solid support. Additional residues are coupled to the H-Pen($^{\psi Me,Me}$Pro)-$(Xaa^z)_m$ or H-Pen(Pro)-$(Xaa^z)_m$ peptide fragment using solid phase peptide synthesis techniques known to the practitioners in the art, followed by treatment with a TFA/water/TIS (9.0:0.5:0.25) solution in order to remove the pseudoproline (Pro or $^{\psi Me,Me}$Pro) group as well as any side-chain protecting groups. In certain embodiments, the peptide can undergo further deprotection to remove any remaining side-chain protecting groups and/or be cleaved from the solid support using techniques known to the practitioners in the art.

In certain embodiments of the invention, a penicillamine containing peptide such as H-Pen-(Xaa$^z$)$_m$ wherein each Xaa$^z$ is independently selected from the group consisting of natural amino acids, unnatural amino acids, suitable isostere replacements, corresponding D-amino acids, and corresponding N-Methyl amino acids, and m is an integer from 1-20 is synthesized as follows: the peptide fragment (Xaa$^z$)$_m$ linked to a suitable solid support is prepared using solid phase peptide synthesis techniques known to the practitioners in the art and condensed with an N-terminal protected pseudoproline penicillamine derivative such as, but not limited to: Fmoc-Pen($^{\psi Me,Me}$Pro)-OH, Bpoc-Pen($^{\psi Me,Me}$Pro)-OH, Cbz-Pen($^{\psi Me,Me}$Pro)-OH, Fmoc-Pen(Pro)-OH, Bpoc-Pen(Pro)-OH, Cbz-Pen(Pro)-OH, Fmoc-Leu-Pen($^{\psi Me,Me}$Pro)-OH, Bpoc-Leu-Pen($^{\psi Me,Me}$Pro)-OH, Cbz-Leu-Pen($^{\psi Me,Me}$Pro)-OH, Fmoc-Leu-Pen(Pro)-OH, Bpoc-Leu-Pen(Pro)-OH, or Cbz-Leu-Pen(Pro)-OH. The resulting peptide fragment is treated with a TFA/water/TIS (9.0:0.5:0.25) solution in order to remove the pseudoproline (Pro or ($^{\psi Me,Me}$Pro)) group as well as any side-chain protecting groups. In certain embodiments, the peptide can undergo further deprotection to remove any remaining side-chain protecting groups and/or be cleaved from the solid support using techniques known to the practitioners in the art.

In further embodiments of the invention, a penicillamine containing peptide such as Ac-Pen-(Xaa$^z$)$_m$, wherein each Xaa$^z$ is independently selected from the group consisting of natural amino acids, unnatural amino acids, suitable isostere replacements, corresponding D-amino acids, and corresponding N-Methyl amino acids, and m is an integer from 1-20 is synthesized as follows: the peptide fragment (Xaa$^z$)$_m$ linked to a suitable solid support is prepared using solid phase peptide synthesis techniques known to the practitioners in the art and condensed with an N-terminal protected pseudoproline penicillamine derivative selected from Ac-Pen($^{\psi Me,Me}$Pro)-OH and Ac-Pen(Pro)-OH. The resulting peptide fragment is treated with a TFA/water/TIS (9.0:0.5:0.25) solution in order to remove the pseudoproline (Pro or $^{\psi Me,Me}$Pro) group as well as any side-chain protecting groups. In certain embodiments, the peptide can undergo further deprotection to remove any remaining side-chain protecting groups and/or be cleaved from the solid support using techniques known to the practitioners in the art.

In still further embodiments, the solid phase peptide synthesis techniques described above can be used to incorporate one or more penicillamine residues in to a peptide chain, e.g., (Xaa$^z$)$_p$-Pen-(Xaa$^z$)$_n$-Pen-(Xaa$^z$)$_m$, HPen-(Xaa$^z$)$_n$-Pen-(Xaa$^z$)$_m$, and Ac-Pen-(Xaa$^z$)$_n$-Pen-(Xaa$^z$)$_m$, wherein each Xaa$^z$ is independently selected from the group consisting of natural amino acids, suitable isostere replacements, corresponding D-amino acids, and corresponding N-Methyl amino acids, and each of p, n, and m are independently integers from 1-20.

In certain embodiments, the C-terminus of the peptide comprises an NH$_2$ or an OH.

In certain embodiments, a free amine in the C-terminal amino acid is capped, e.g., with an acetyl group.

In further embodiments, a free amine in the N-terminal amino acid is capped, e.g., with an acetyl group.

In still further embodiments, the α-amino group of the N-terminal amino acid is capped, e.g., with an acetyl group.

Solution Phase Peptide Synthesis

In particular embodiments, the methods of the present invention provide a cost-effective process for the synthesis of a penicillamine containing peptide in commercial quantities by solution phase methods using inexpensive starting materials, mild reagents to yield high purity peptide.

In certain embodiments, the present invention provides methods of synthesizing the peptides of Compound B, Table 2, those disclosed in PCT Applications PCT/US2013/064439; PCT/US2014/032391; PCT/US2014/032392; PCT/US2015/053558; PCT/US2015/053603. U.S. Pat. No. 9,518,091B2, and other peptides disclosed herein, including but not limited to those of Formulas (I)-(III), and pharmaceutically acceptable salts, solvates, or hydrates thereof, via solution phase peptide synthesis.

In particular embodiments, the present invention provides methods of synthesizing the peptides of Compound B, Table 2, those disclosed in PCT Applications PCT/US2013/064439; PCT/US2014/032391; PCT/US2014/032392; PCT/US2015/053558, PCT/US2015/053603; U.S. Pat. No. 9,518,091B2, and other peptides disclosed herein, including but not limited to those of Formulas (I)-(III), and pharmaceutically acceptable salts, solvates, and hydrates thereof, via solution phase peptide synthesis using Cbz and Fmoc-protected amino acids.

In further embodiments, the present invention provides methods of synthesizing the peptides of Compound B, Table 2, those disclosed in PCT Applications PCT/US2013/064439; PCT/US2014/032391; PCT/US2014/032392; PCT/US2015/053558, PCT/US2015/053603; U.S. Pat. No. 9,518,091B2, and other peptides disclosed herein, including but not limited to those of Formulas (I)-(III), and pharmaceutically acceptable salts, solvates, and hydrates thereof, via solution phase peptide synthesis using Fmoc-protected amino acids.

In yet further embodiments, the present invention provides methods of synthesizing the peptides of Compound B, Table 2, those disclosed in PCT Applications PCT/US2013/064439; PCT/US2014/032391; PCT/US2014/032392; PCT/US2015/053558, PCT/US2015/053603; U.S. Pat. No. 9,518,091B2, and other peptides disclosed herein, including but not limited to those of Formulas (I)-(III), and pharmaceutically acceptable salts, solvates, and hydrates thereof, via solution phase peptide synthesis using Bpoc-protected amino acids.

In still further embodiments, the methods of the present invention provide a solution phase synthesis method for synthesizing a peptide having the sequence: Ac-Pen-N(Me)Arg-Ser-Asp-Thr-Leu-Pen-Xaa$^{11}$-Xaa$^{12}$-Xaa$^{13}$ (SEQ ID NO:62) or Ac-Pen-N(Me)Arg-Ser-Asp-Thr-Leu-Pen-Xaa$^{11}$-Xaa$^{12}$-Xaa$^{13}$-NH$_2$(SEQ ID NO:62), wherein:

Xaa$^{11}$ can be any natural or unnatural amino acid;

Xaa$^{12}$ can be absent or any natural or unnatural amino acid; and

Xaa$^{13}$ can be any natural or unnatural amino acid.

In certain embodiments, Xaa$^{11}$ is Phe(4-$^t$Bu) or Trp.

In particular embodiments, Xaa$^{12}$ is β-homoGlu, Glu, or D-Glu.

In further embodiments, Xaa$^{13}$ is Lys, D-Lys, N-Me-Lys or N-Me-D-Lys.

In yet further embodiments, Xaa$^{11}$ is Phe(4-$^t$Bu) or Trp; Xaa$^{12}$ is β-homoGlu, Glu, or D-Glu; and Xaa$^{13}$ is Lys, D-Lys, N-Me-Lys or N-Me-D-Lys.

In particular embodiments of the invention, the peptide sequences of Ac-Pen-N(Me)Arg-Ser-Asp-Thr-Leu-Pen-Xaa$^{11}$-Xaa$^{12}$-Xaa$^{13}$ (SEQ ID NO:62) or Ac-Pen-N(Me)Arg-Ser-Asp-Thr-Leu-Pen-Xaa$^{11}$-Xaa$^{12}$-Xaa$^{13}$-NH$_2$ (SEQ ID NO:62), wherein Xaa¹¹, Xaa¹², and Xaa¹³ are defined as above, can be synthesized by condensation of two protected peptide fragments.

For example, Ac-Pen-N(Me)Arg-Ser-Asp-Thr-Leu-Pen-Xaa¹¹-Xaa¹²-Xaa¹³-OH (SEQ ID NO:62) could be synthesized by condensation, followed by deprotection, of the following groups of peptide fragments (fragments are shown without protecting groups, but any suitable protecting groups can be used):

```
                                         (SEQ ID NO: 87)
Ac-Pen-OH and HN(Me)Arg-Ser-Asp-Thr-Leu-Pen-Xaa¹¹-

Xaa¹²-Xaa¹³-OH
                                         (SEQ ID NO: 69)
Ac-Pen N(Me)Arg-OH and HSer-Asp-Thr-Leu-Pen-Xaa¹¹-

Xaa¹²-Xaa¹³-OH
                                         (SEQ ID NO: 70)
Ac-Pen-N(Me)Arg-Ser-OH and HAsp-Thr-Leu-Pen-Xaa¹¹-

Xaa¹²-Xaa¹³-OH
                                      (SEQ ID NOs: 71 and 72)
Ac-Pen-N(Me)Arg-Ser-Asp-OH and HThr-Leu-Pen-Xaa¹¹-

Xaa¹²-Xaa¹³-OH
                                      (SEQ ID NOs: 73 and 74)
Ac-Pen-N(Me)Arg-Ser-Asp-Thr-OH and HLeu-Pen-Xaa¹¹-

Xaa¹²-Xaa¹³-OH
                                      (SEQ ID NOs: 75 and 76)
Ac-Pen-N(Me)Arg-Ser-Asp-Thr-Leu-OH and HPen-Xaa¹¹-

Xaa¹²-Xaa¹³-OH
                                      (SEQ ID NOs: 77 and 76)
Ac-Pen N(Me)Arg and Ser-Asp-Thr-Leu-OH and HPen- Xaa¹¹-Xaa¹²-Xaa¹³-OH
                                         (SEQ ID NO: 78)
Ac-Pen N(Me)Arg and Ser-Asp-Thr-Leu-Pen-OH and HXaa¹¹-Xaa¹²-Xaa¹³-OH
                                         (SEQ ID NO: 79)
Ac-Pen N(Me)Arg and Ser-Asp-Thr-Leu-Pen-Xaa¹¹and HXaa¹²-Xaa¹³-OH.
```

As a further example, Ac-Pen-N(Me)Arg-Ser-Asp-Thr-Leu-Pen-Xaa¹-Xaa²-Xaa³-NH₂ (SEQ ID NO:62) could be synthesized by condensation, followed by deprotection, of the following groups of peptide fragments (fragments are shown without protecting groups, but any suitable protecting groups can be used):

```
                                         (SEQ ID NO: 87)
Ac-Pen-OH and HN(Me)Arg-Ser-Asp-Thr-Leu-Pen-Xaa¹¹-

Xaa¹²-Xaa¹³-NH₂.
                                         (SEQ ID NO: 69)
Ac-Pen N(Me)Arg-OH and HSer-Asp-Thr-Leu-Pen-Xaa¹¹-

Xaa¹²-Xaa¹³-NH₂
                                         (SEQ ID NO: 70)
Ac-Pen-N(Me)Arg-Ser-OH and HAsp-Thr-Leu-Pen-Xaa¹¹-

Xaa¹²-Xaa¹³-NH₂
                                      (SEQ ID NOs: 71 and 72)
Ac-Pen-N(Me)Arg-Ser-Asp-OH and HThr-Leu-Pen-Xaa¹¹-

Xaa¹²-Xaa¹³-NH₂
                                      (SEQ ID NOs: 73 and 74)
Ac-Pen-N(Me)Arg-Ser-Asp-Thr-OH and HLeu-Pen-Xaa¹¹-

Xaa¹²-Xaa¹³-NH₂
                                      (SEQ ID NOs: 75 and 76)
Ac-Pen-N(Me)Arg-Ser-Asp-Thr-Leu-OH and HXaa¹¹-

Xaa¹²-Xaa¹³-NH₂
                                      (SEQ ID NOs: 77 and 76)
Ac-Pen N(Me)Arg and Ser-Asp-Thr-Leu-OH and HPen- Xaa¹¹-Xaa¹²-Xaa¹³-NH₂
                                         (SEQ ID NO: 78)
Ac-Pen N(Me)Arg and Ser-Asp-Thr-Leu-Pen-OH and HXaa¹¹-Xaa¹²-Xaa¹³-NH₂
                                         (SEQ ID NO: 79)
Ac-Pen N(Me)Arg and Ser-Asp-Thr-Leu-Pen-Xaa¹¹-OH and HXaa¹²-Xaa¹³-NH₂.
```

In particular embodiments, the present invention provides methods of synthesizing Ac-Pen-N(Me)Arg-Ser-Asp-Thr-Leu-Pen-Xaa¹¹-Xaa¹²-Xaa¹³-OH (SEQ ID NO:62) or Ac-Pen-N(Me)Arg-Ser-Asp-Thr-Leu-Pen-Xaa¹¹-Xaa¹²-Xaa¹³-NH₂ (SEQ ID NO:62), wherein Xaa¹¹, Xaa¹², and Xaa¹³ are defined as above, using solution phase peptide synthesis techniques with protected Pen amino acids selected from the group consisting of: Fmoc-Pen(Trt), Fmoc-Pen(Acm), Cbz-Pen(Trt), Cbz-Pen(Acm), Fmoc-Pen($^{\psi Me,Me}$Pro)-OH, Bpoc-Pen($^{\psi Me,Me}$Pro)-OH, Cbz-Pen($^{\psi Me,Me}$Pro)-OH, Fmoc-Pen(Pro)-OH, Bpoc-Pen(Pro)-OH, Cbz-Pen(Pro)-OH, Fmoc-Leu-Pen($^{\psi Me,Me}$Pro)-OH, Bpoc-Leu-Pen($^{\psi Me,Me}$Pro)-OH, Cbz-Leu-Pen($^{\psi Me,Me}$Pro)-OH, Fmoc-Leu-Pen(Pro)-OH, Bpoc-Leu-Pen(Pro)-OH, or Cbz-Leu-Pen(Pro)-OH.

In certain embodiments, the present invention provides methods of synthesizing the peptide dimers of Compound A, Table 3, those disclosed in PCT Applications PCT/US2013/064439; PC T/US2014/032391; PCT/US2014/032392; PC T/US2015/053558 PCT/US2015/053603; U.S. Pat. No. 9,518,091B2, and other peptides disclosed herein, including but not limited to those of Formulas (I)-(III), and pharmaceutically acceptable salts, solvates, and hydrates thereof: synthesis of the appropriate peptide monomer via solution phase peptide synthesis, cyclization of the monomer, and dimerization of the cyclized peptide with a suitable linker. In certain embodiments of the invention, the linker is diglycolic acid. In particular embodiments the peptide monomer comprises two Pen residues.

In certain embodiments of the invention, the peptides of the peptide dimers of Table 2 can be synthesized by solution phase peptide synthesis. In particular embodiments, the peptides are synthesized by condensation of the appropriate 8-mer and 2-mer fragments, 7-mer and 3-mer fragments, 6-mer and 4-mer fragments, 5-mer and 5-mer fragments, 4-mer and 6-mer fragments, 3-mer and 7-mer fragments, 2-mer and 8-mer fragments or, and 9 mer and a protected and/or acetyl-amino acid, followed by deprotection and cyclization.

As shown in Scheme V, in certain embodiments of the invention, Compound B can be synthesized by condensation of the appropriate protected 8-mer and 2-mer fragments, 7-mer and 3-mer fragments, 6-mer and 4-mer fragments, 5-mer and 5-mer fragments, 4-mer and 6-mer fragments, 3-mer and 7-mer fragments, 2-mer and 8-mer fragments, or and 9 mer and protected and/or acetylamino acid, followed by deprotection and cyclization.
Scheme V
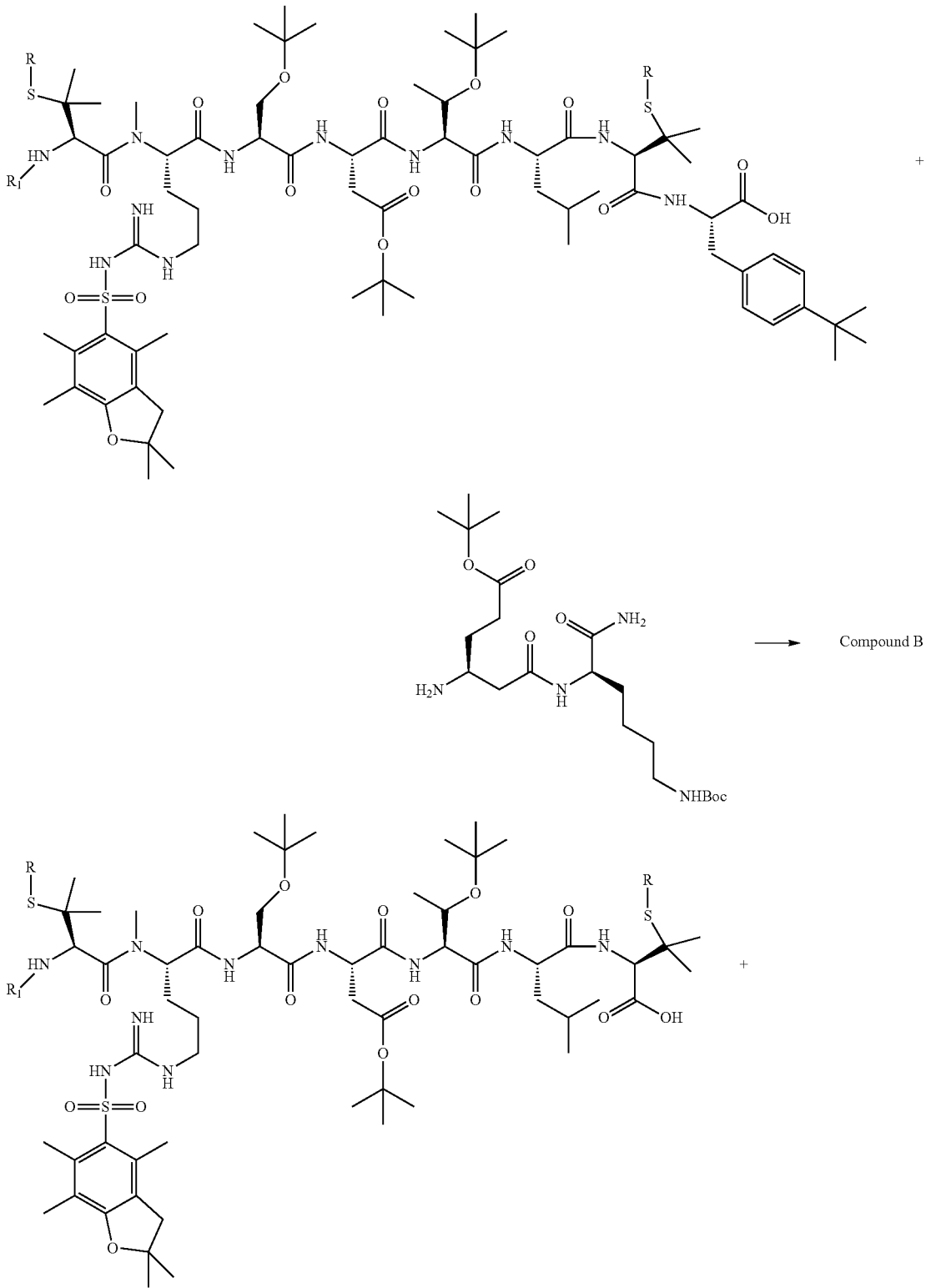

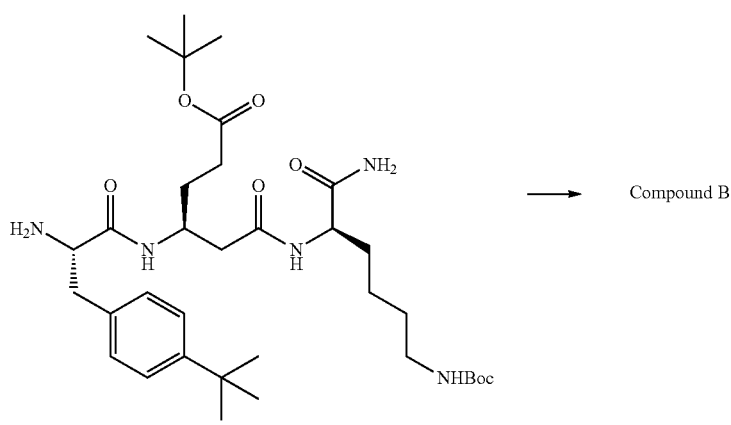
→ Compound B
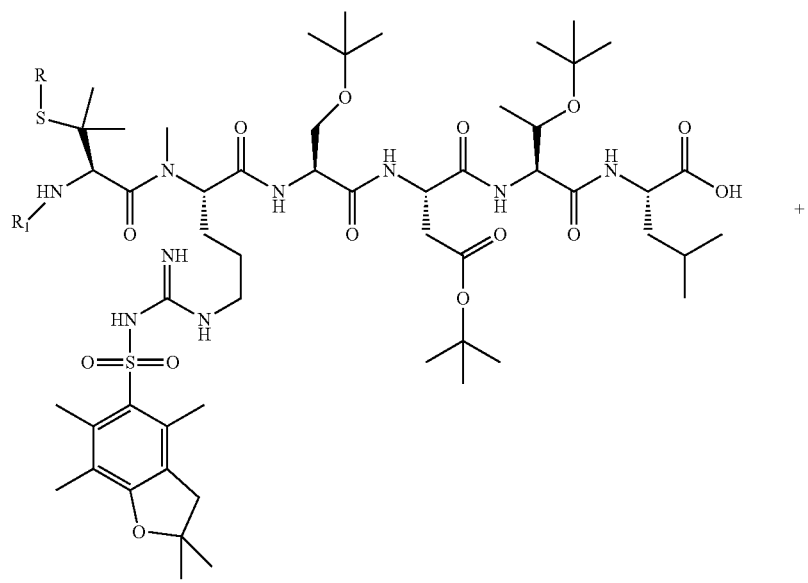
+
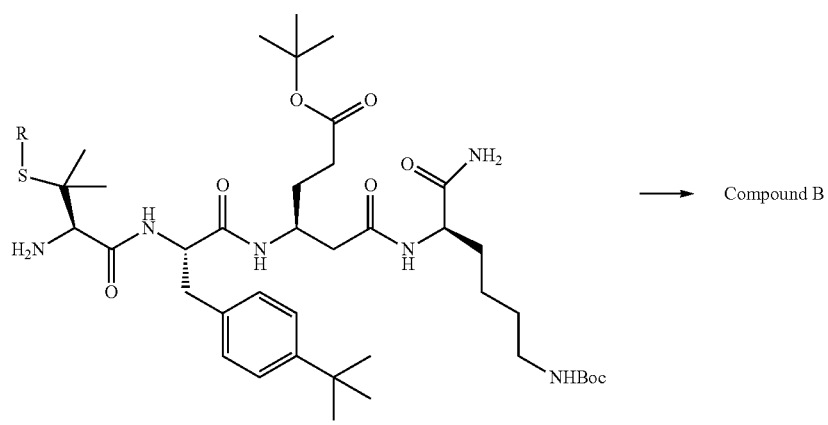
→ Compound B

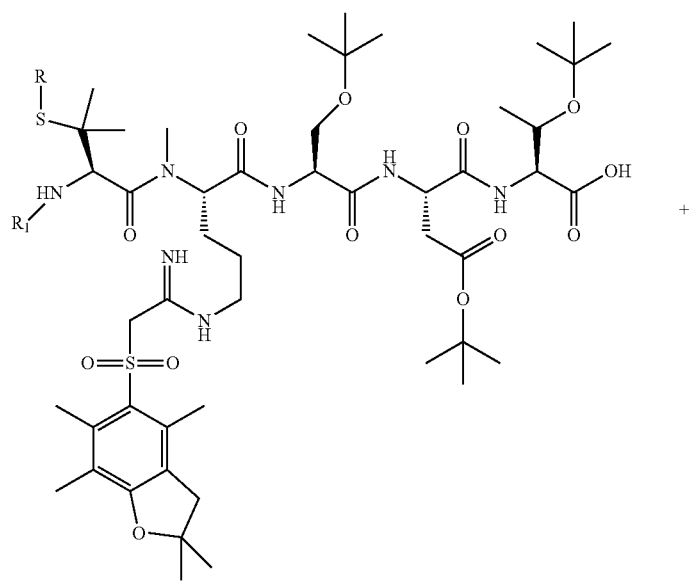
+
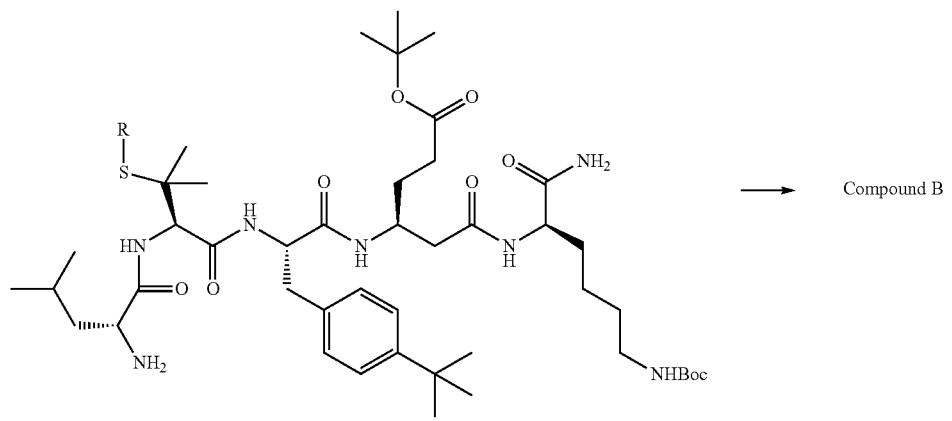
→ Compound B
R = Trt or Acm
R₁ = Fmoc, Cbz, or Ac
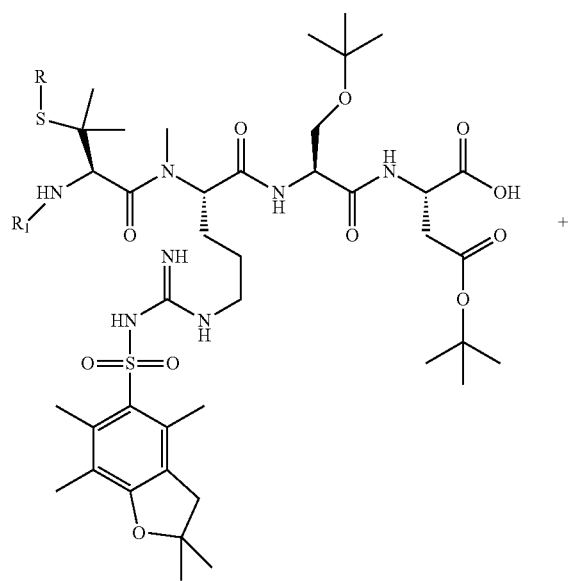
+

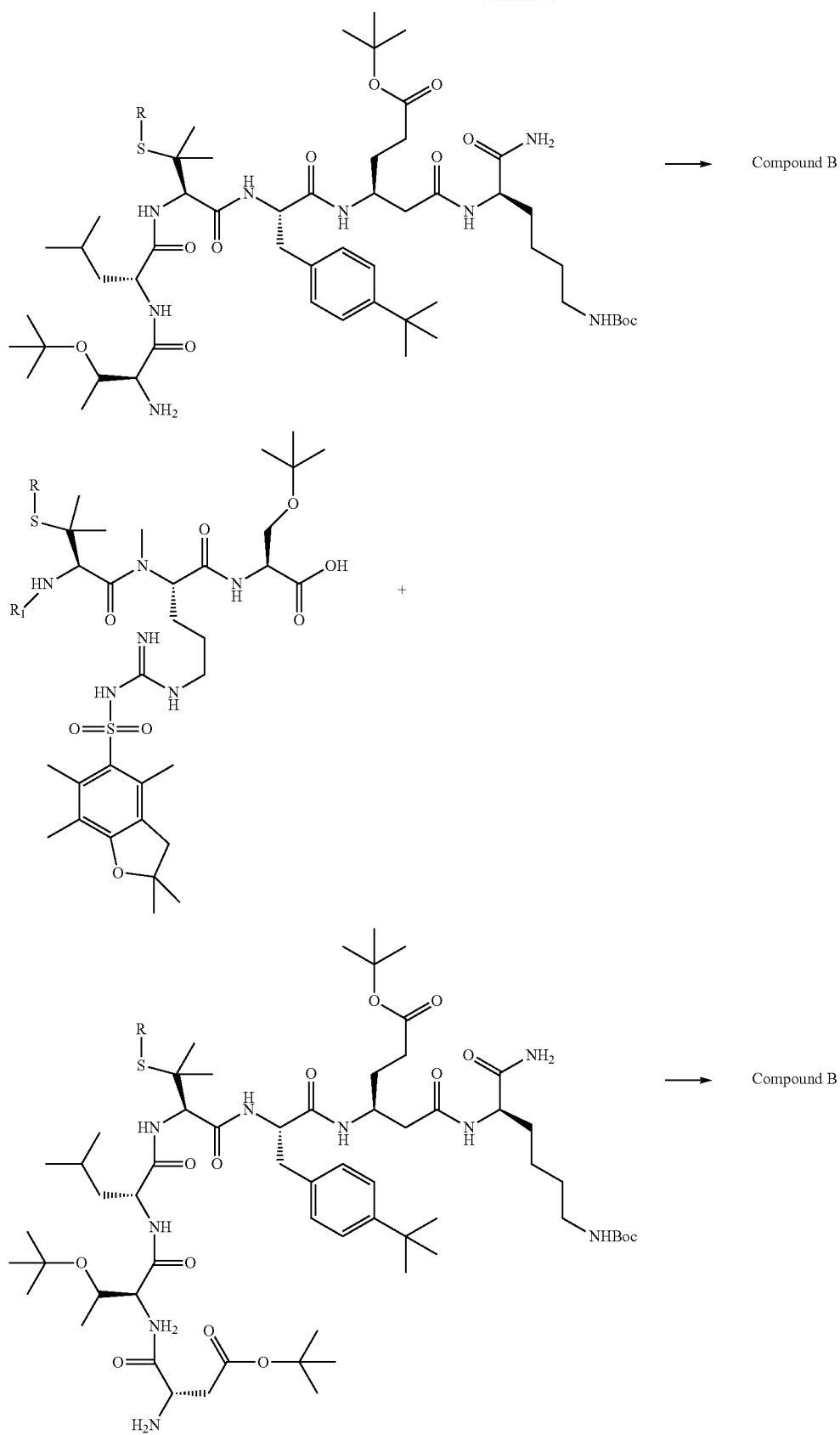

-continued
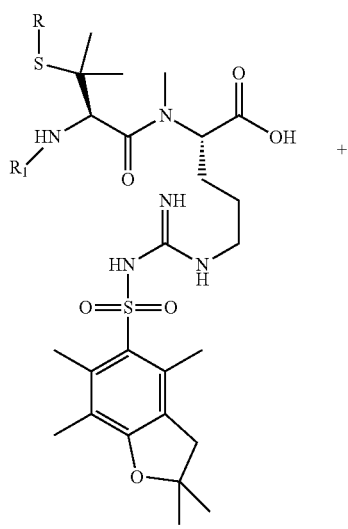
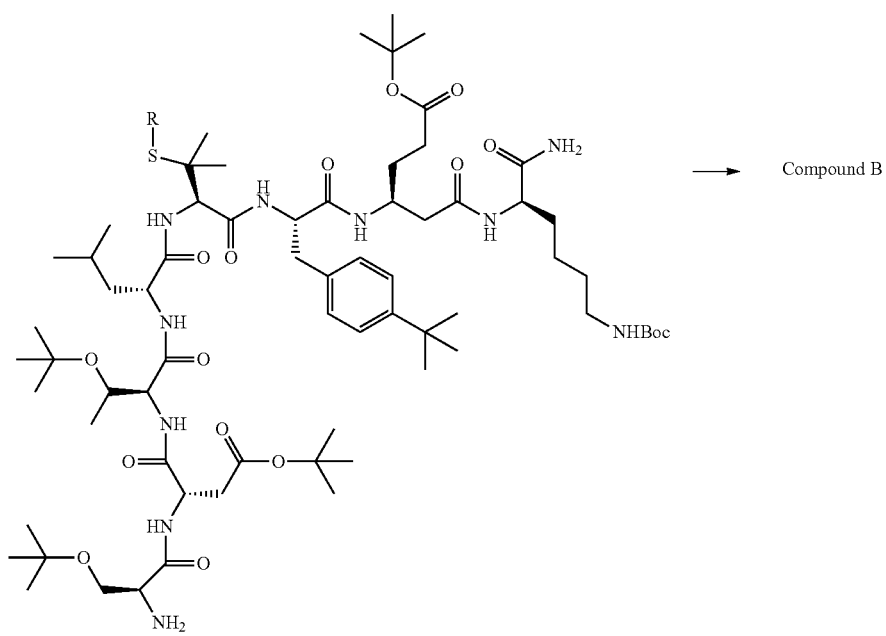
→ Compound B
R = Trt or Acm
R₁ = Fmoc, Cbz, or Ac
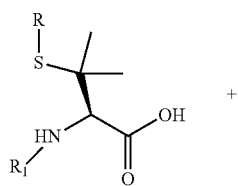
+

-continued

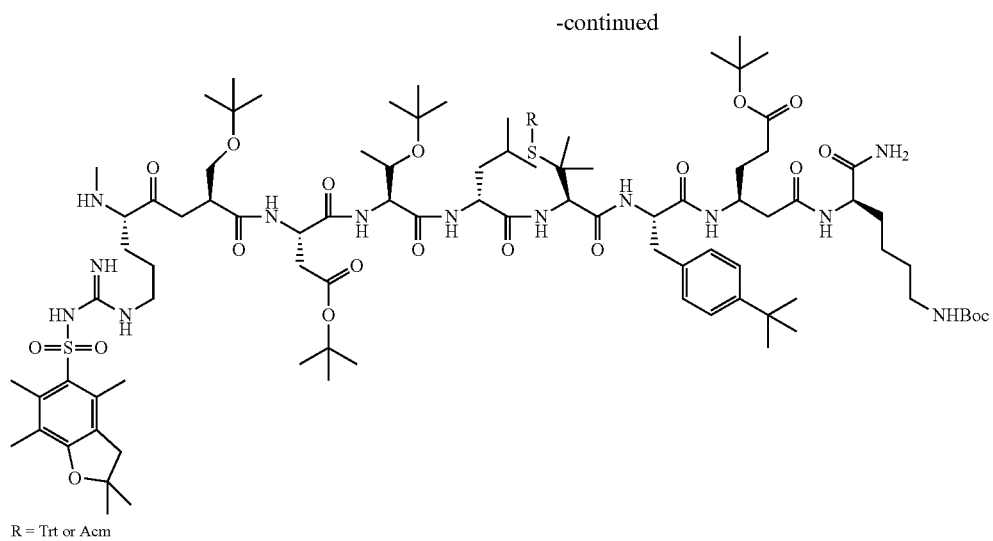

→ Compound B

R = Trt or Acm
R₁ = Fmoc, Cbz, or Ac

In further embodiments of the invention, the protected fragment Ac-Pen(R)-N(Me)Arg(pbf)-Ser(ᵗBu)-Asp(OᵗBu)-Thr(ᵗBu)-Leu-Pen(R)-Phe(4-ᵗBu)-β-homoGlu(OᵗBu)-D-Lys(Boc)-NH₂ (SEQ ID NO:25) is prepared by condensation of the octapeptide, Ac-Pen(R)-N(Me)Arg(pbf)-Ser(ᵗBu)-Asp(OᵗBu)-Thr(ᵗBu)-Leu-Pen(R)-Phe(4-ᵗBu)-OH (SEQ ID NO:80), with the dipeptide, Hβ-homoGlu(OᵗBu)-D-Lys(Boc)-NH₂; wherein each R is independently, Trt or Acm.

In still further embodiments of the invention, the protected fragment Ac-Pen(R)-N(Me)Arg(pbf)-Ser(ᵗBu)-Asp(OᵗBu)-Thr(ᵗBu)-Leu-Pen(R)-Phe(4-ᵗBu)-β-homoGlu(OᵗBu)-D-Lys(Boc)-NH₂ (SEQ ID NO:25) is prepared by condensation of the heptapeptide, Ac-Pen(R)-N(Me)Arg(pbf)-Ser(ᵗBu)-Asp(OᵗBu)-Thr(ᵗBu)-Leu-Pen(R)-OH (SEQ ID NO:81), with the tripeptide, HPhe(4-ᵗBu)-β-homoGlu(OᵗBu)-D-Lys(Boc)-NH₂; wherein each R is independently, Trt or Acm.

In yet further embodiments of the invention, the protected fragment Ac-Pen(R)-N(Me)Arg(pbf)-Ser(ᵗBu)-Asp(OᵗBu)-Thr(ᵗBu)-Leu-Pen(R)-Phe(4-ᵗBu)-β-homoGlu(OᵗBu)-D-Lys(Boc)-NH₂ (SEQ ID NO:25) is prepared by condensation of the hexapeptide, Ac-Pen(R)-N(Me)Arg(pbf)-Ser(ᵗBu)-Asp(OᵗBu)-Thr(ᵗBu)-Leu-OH (SEQ ID NO:3), with the tetrapeptide, H-Pen(R)-Phe(4-ᵗBu)-β-homoGlu(OᵗBu)-D-Lys(Boc)-NH₂ (SEQ ID NO:4); wherein each R is independently, Trt or Acm.

In certain embodiments of the invention, the protected fragment Ac-Pen(R)-N(Me)Arg(pbf)-Ser(ᵗBu)-Asp(OᵗBu)-Thr(ᵗBu)-Leu-Pen(R)-Phe(4-ᵗBu)-β-homoGlu(OᵗBu)-D-Lys(Boc)-NH₂ (SEQ ID NO:25) is prepared by condensation of the pentapeptide, Ac-Pen(R)-N(Me)Arg(pbf)-Ser(ᵗBu)-Asp(OᵗBu)-Thr(ᵗBu)-OH (SEQ ID NO:73), with the pentapeptide, H-Leu-Pen(R)-Phe(4-ᵗBu)-β-homoGlu(OᵗBu)-D-Lys(Boc)-NH₂ (SEQ ID NO:83); wherein each R is independently, Trt or Acm.

In other embodiments of the invention, the protected fragment Ac-Pen(R)-N(Me)Arg(pbf)-Ser(ᵗBu)-Asp(OᵗBu)-Thr(ᵗBu)-Leu-Pen(R)-Phe(4-ᵗBu)-β-homoGlu(OᵗBu)-D-Lys(Boc)-NH₂ (SEQ ID NO:25) is prepared by condensation of the tetrapeptide, Ac-Pen(R)-N(Me)Arg(pbf)-Ser(ᵗBu)-Asp(OᵗBu)-OH (SEQ ID NO:71), with the hexapeptide, HThr(ᵗBu)-Leu-Pen(R)-Phe(4-ᵗBu)-β-homoGlu(OᵗBu)-D-Lys(Boc)-NH₂ (SEQ ID NO:84); wherein each R is independently, Trt or Acm.

In particular embodiments of the invention, the protected fragment Ac-Pen(R)-N(Me)Arg(pbf)-Ser(ᵗBu)-Asp(OᵗBu)-Thr(ᵗBu)-Leu-Pen(R)-Phe(4-ᵗBu)-β-homoGlu(OᵗBu)-D-Lys(Boc)-NH₂ (SEQ ID NO:25) is prepared by condensation of the tripeptide, Ac-Pen(R)-N(Me)Arg(pbf)-Ser(ᵗBu)-OH, with heptapeptide, H-Asp(OᵗBu)-Thr(ᵗBu)-Leu-Pen(R)-Phe(4-ᵗBu)-β-homoGlu(OᵗBu)-D-Lys(Boc)-NH₂ (SEQ ID NO:85); wherein each R is independently, Trt or Acm.

In further embodiments of the invention, the protected fragment Ac-Pen(R)-N(Me)Arg(pbf)-Ser(ᵗBu)-Asp(OᵗBu)-Thr(ᵗBu)-Leu-Pen(R)-Phe(4-ᵗBu)-β-homoGlu(OᵗBu)-D-Lys(Boc)-NH₂ (SEQ ID NO:25) is prepared by condensation of the dipeptide, Ac-Pen(R)-N(Me)Arg(pbf)-OH, with the octapeptide, H-Ser(ᵗBu)-Asp(OᵗBu)-Thr(ᵗBu)-Leu-Pen(R)-Phe(4-ᵗBu)-β-homoGlu(OᵗBu)-D-Lys(Boc)-NH₂ (SEQ ID NO:86); wherein each R is independently, Trt or Acm.

In further embodiments of the invention, the protected fragment Ac-Pen(R)-N(Me)Arg(pbf)-Ser(ᵗBu)-Asp(OᵗBu)-Thr(ᵗBu)-Leu-Pen(R)-Phe(4-ᵗBu)-β-homoGlu(OᵗBu)-D-Lys(Boc)-NH₂ (SEQ ID NO:25) is prepared by condensation of the N-protected amino acid or N-acetylated amino acid, Y-Pen(R)-OH, with the nonopeptide, HN(Me)-Arg(pbf)-Ser(ᵗBu)-Asp(OᵗBu)-Thr(ᵗBu)-Leu-Pen(R)-Phe(4-ᵗBu)-β-homoGlu(OᵗBu)-D-Lys(Boc)-NH₂ (SEQ ID NO:87); wherein each R is independently, Trt or Acm.Y is Fmoc, Cbz or Ac In still further embodiments of the invention, the hexapeptide, Ac-Pen(Acm)-N(Me)Arg(pbf)-Ser(ᵗBu)-Asp(OᵗBu)-Thr(ᵗBu)-Leu-OH (SEQ ID NO:3), is prepared by condensation of Y-Pen(Acm) with the pentapeptide, HN(Me)Arg(pbf)-Ser(ᵗBu)-Asp(OᵗBu)-Thr(ᵗBu)-Leu-OMe (SEQ ID NO:5). Y is Fmoc, Cbz or Ac In still further embodiments of the invention, the hexapeptide, Ac-Pen(Trt)-N(Me)Arg(pbf)-Ser(ᵗBu)-Asp(OᵗBu)-Thr(ᵗBu)-Leu-OH (SEQ ID NO:3), is prepared by condensation of Y-Pen(Trt)-OH with the pentapeptide, HN(Me)Arg(pbf)-Ser(ᵗBu)-Asp(OᵗBu)-Thr(ᵗBu)-Leu-OMe (SEQ ID NO:5). Y is Fmoc, Cbz or Ac In yet further embodiments of the invention, the tetrapeptide, H-Pen($^{\psi Me,Me}$Pro)-Phe(4-ᵗBu)-β-homoGlu(OᵗBu)-D-Lys(Boc)-NH₂ (SEQ ID NO:4), is prepared by condensation of Fmoc-Pen($^{\psi Me,Me}$Pro), Bpoc-Pen($^{\psi Me,Me}$Pro), or Cbz-Pen($^{\psi Me,Me}$Pro) with the tripeptide H-Phe(4-ᵗBu)-β-homoGlu(OᵗBu)-D-Lys(Boc)-NH₂ followed by removal of the N-terminus protecting group.

In yet further embodiments of the invention, the octapeptide, H-Ser(tBu)-Asp(OtBu)-Thr(tBu)-Leu-Pen(Acm)-Phe(4-tBu)-β-homoGlu(OtBu)-D-Lys(Boc)-NH₂ (SEQ ID NO:86) is prepared by condensation of tetrapeptide Fmoc-Ser(tBu)-Asp(OtBu)-Thr(tBu)-Leu-OH (SEQ ID NO:77) and tetrapeptide H-Pen(Acm)-Phe(4-tBu)-β-homoGlu(OtBu)-D-Lys(Boc)-NH₂ (SEQ ID NO:4) followed by removal of the N-terminus protecting group.

In yet further embodiments of the invention, the nanopeptide, HN(Me)Arg-Ser(tBu)-Asp(OtBu)-Thr(tBu)-Leu-Pen(Acm)-Phe(4-tBu)-β-homoGlu(OtBu)-D-Lys(Boc)-NH₂ (SEQ ID NO:87) is prepared by condensation of the pentapeptide HN(Me)Arg-Ser(tBu)-Asp(OtBu)-Thr(tBu)-Leu-OH (SEQ ID NO:5) and tetrapeptide HPen(Acm)-Phe(4-tBu)-β-homoGlu(OtBu)-D-Lys(Boc)-NH₂ (SEQ ID NO:4).

Pseudoproline Penicillamine Derivatives in Solution Phase Peptide Synthesis

Pseudoproline Penicillamine Derivatives

In certain embodiments of the invention, the pseudoproline penicillamine derivative is:

Formula IVa

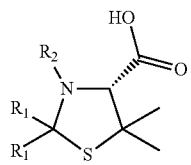

wherein each $R_1$ is independently selected from the group consisting of —H and $C_1$-$C_6$ alkyl, and $R_2$ is an amine-protecting group. In particular embodiments of the invention at least one $R_1$ is —$CH_3$. In further embodiments of the invention, both $R_1$s are —$CH_3$. In still further embodiments of the invention, at least one $R_1$ is H. In yet further embodiments of the invention, both $R_1$s are —H. In certain embodiments of the invention, $R_2$ is selected from the group consisting of Boc, Cbz, Fmoc, Bpoc and Ac.

In certain embodiments of the invention, the pseudoproline penicillamine derivative is (4R)-3-acetyl-2,2,5,5-tetramethyl-thiazolidine-4-carboxylic acid (Ac-Pen($^{\psi Me,Me}$Pro)-OH, Compound D-1):

Compound D-1

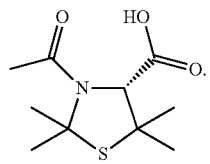

In further embodiments of the invention, the pseudoproline penicillamine derivative is (4R)-3-acetyl-5,5-dimethyl-thiazolidine-4-carboxylic acid (Ac-Pen(Pro)-OH, Compound I-1):

Compound I-1

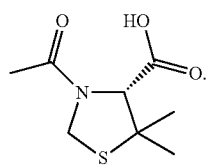

In other embodiments of the invention, the N-terminus of the pseudoproline penicillamine derivative is protected by any suitable, removable N-terminal protecting group, such as but not limited to t-Boc (tert-butyloxycarbonyl), Fmoc (9-fluorenylmethyloxycarbonyl), Bpoc (2-(4-Biphenyl)isopropoxycarbonyl), Cbz (Z, carboxybenzyl), or any other suitable protecting group known in the art such as those described in Isidro-Llobet, A. et al., "Amino Acid Protecting Groups" Chem. Rev. 109, 2455-2504, 2009.

In particular embodiments of the invention, the pseudoproline penicillamine derivative is (4R)-3-(9H-fluoren-9-ylmethoxycarbonyl)-2,2,5,5-tetramethyl-thiazolidine-4-carboxylic acid (Fmoc-Pen($^{\psi Me,Me}$Pro)-OH, Compound E-1):

Compound E-1

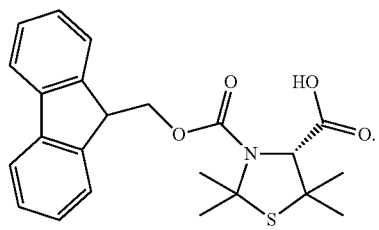

In further embodiments of the invention, the pseudoproline penicillamine derivative is (R)-3-(((2-([1,1'-biphenyl]-4-yl)propan-2-yl)oxy)carbonyl)-2,2,5,5-tetramethylthiazolidine-4-carboxylic acid (Bpoc-Pen($^{\psi Me,Me}$Pro)-OH Compound F-1)

Compound F-1

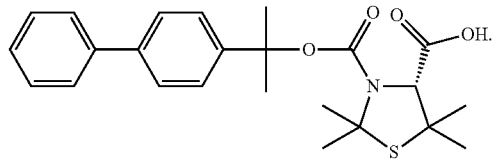

In further embodiments of the invention, the pseudoproline penicillamine derivative is (R)-3-((benzyloxy)carbonyl)-2,2,5,5-tetramethylthiazolidine-4-carboxylic acid (Cbz-Pen($^{\psi Me,Me}$Pro)-OH, Compound G-1).

Compound G-1

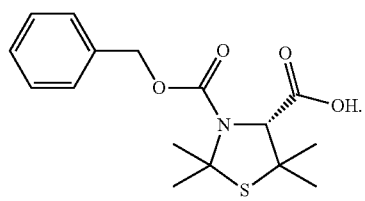

In other embodiments of the invention, the pseudoproline penicillamine derivative is (R)-3-(((9H-fluoren-9-yl)methoxy)carbonyl)-5,5-dimethylthiazolidine-4-carboxylic acid (Fmoc-Pen($^{\psi H,H}$ProPro)-OH, Compound J-1):

Compound J-1

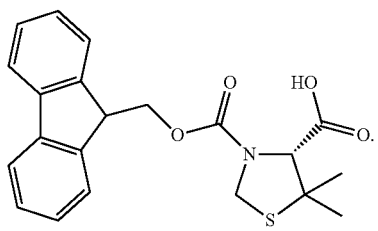

In further embodiments of the invention, the pseudoproline penicillamine derivative is (R)-3-(((2-([1,1'-biphenyl]-4-yl)propan-2-yl)oxy)carbonyl)-5,5-dimethylthiazolidine-4-carboxylic acid (Bpoc-Pen(Pro)-OH, Compound K-1)

Compound K-1

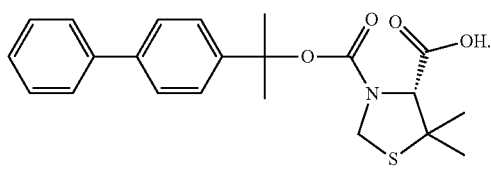

In further embodiments of the invention, the pseudoproline penicillamine derivative is (R)-3-((benzyloxy)carbonyl)-5,5-dimethylthiazolidine-4-carboxylic acid (Cbz-Pen($^{\psi H,H}$Pro)-OH, Compound L-1).

Compound L-1

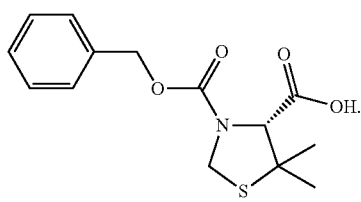

In addition to Pen($^{\psi H,H}$Pro)-OH derivatives having an R stereochemistry as described above, the invention also provides for the corresponding S stereoisomers of the above compounds as well as their use in peptide synthesis, specifically:
(4S)-3-acetyl-2,2,5,5-tetramethyl-thiazolidine-4-carboxylic acid
(4S)-3-acetyl-5,5-dimethyl-thiazolidine-4-carboxylic acid
(4S)-3-(9H-fluoren-9-ylmethoxycarbonyl)-2,2,5,5-tetramethyl-thiazolidine-4-carboxylic acid
(S)-3-(((2-([1,1'-biphenyl]-4-yl)propan-2-yl)oxy)carbonyl)-2,2,5,5-tetramethylthiazolidine-4-carboxylic acid
(S)-3-((benzyloxy)carbonyl)-2,2,5,5-tetramethylthiazolidine-4-carboxylic acid
(S)-3-(((9H-fluoren-9-yl)methoxy)carbonyl)-5,5-dimethylthiazolidine-4-carboxylic acid
(S)-3-(((2-([1,1'-biphenyl]-4-yl)propan-2-yl)oxy)carbonyl)-5,5-dimethylthiazolidine-4-carboxylic acid
(S)-3-((benzyloxy)carbonyl)-5,5-dimethylthiazolidine-4-carboxylic acid In certain embodiments of the invention, penicillamine and another amino acid are incorporated into the peptide as a pseudoproline dipeptide.

Pseudoproline dipeptides are known to minimize aggregation during peptide synthesis, particularly during solid phase peptide synthesis. In addition to protecting the penicillamine side chain, the pseudoproline dipeptide aids in solubilization of the peptide, thereby increasing solvation and coupling rates during peptide synthesis and in subsequent chain assembly.

In certain embodiments, the invention is directed to the pseudoproline dipeptides of Formula V, Formula Va and Formula Vb and their use in the synthesis of penicillamine containing peptides:

Formula V

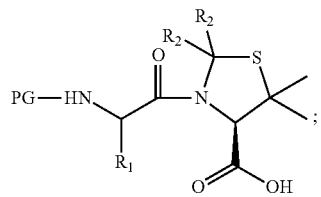

Formula Va

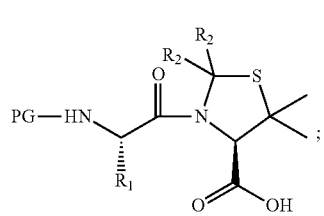

and

Formula Vb

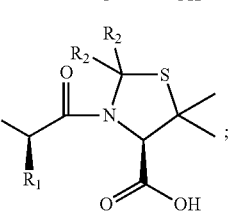

wherein $R_1$ is any suitable amino-acid side chain, each $R_2$ is independently selected from the group consisting of —H and $C_1$-$C_6$ alkyl, and PG is any suitable protecting group.

In certain embodiments, the amino-acid side chain is further protected by a suitable protecting group (PG).

In particular embodiments, PG is selected from the group consisting of Fmoc, Boc, and Cbz.

In particular embodiments of the invention, $R_1$ is an amino acid side chain corresponding to the side chain of an amino acid selected from natural amino acids, unnatural amino acids, suitable isostere replacements, corresponding D-amino acids, and corresponding N-Methyl amino acids.

In certain embodiments of the invention, each $R_2$ is independently —H or —$CH_3$ In certain embodiments, the invention is directed to the pseudoproline dipeptides of Formula VI, Formula VIa and Formula VIb and their use in the synthesis of penicillamine containing peptides:

Formula VI

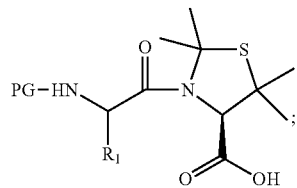

Formula VIa

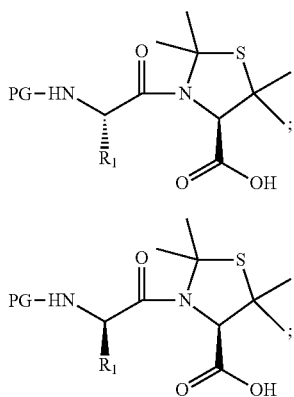

Formula VIb wherein R₁ is any suitable amino-acid side chain and PG is any suitable protecting group.

In certain embodiments, the amino-acid side chain is further protected by a suitable protecting group.

In particular embodiments, PG is selected from the group consisting of Fmoc, Boc, and Cbz.

In particular embodiments of the invention, R is an amino acid side chain corresponding to the side chain of an amino acid selected from natural amino acids, unnatural amino acids, suitable isostere replacements, corresponding D-amino acids, and corresponding N-Methyl amino acids.

In particular embodiments of the invention, the pseudoproline dipeptide is the dipeptide of Formula VII Formula VII

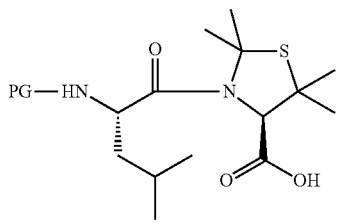

wherein PG is any suitable protecting group.

In particular embodiments, PG is selected from the group consisting of Fmoc, Boc, and Cbz.

Further embodiments of the invention are directed to the following pseudoproline dipeptides and their use in solid state and solution phase peptide synthesis.

Fmoc-Leu-Pen($^{\psi Me,Me}$Pro)-OH (Compound M):

Compound M

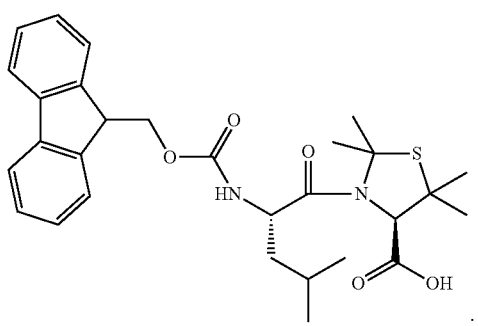

Bpoc-Leu-Pen($^{\psi Me,Me}$Pro)-OH (Compound N):

Compound N

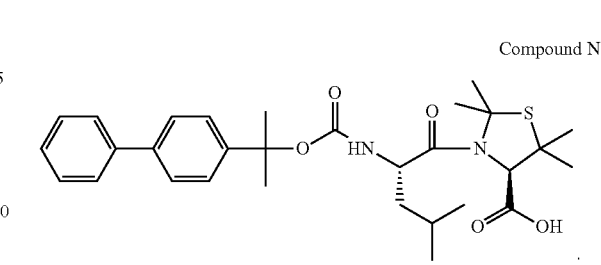

Cbz-Leu-Pen($^{\psi Me,Me}$Pro)-OH (Compound O):

Compound O

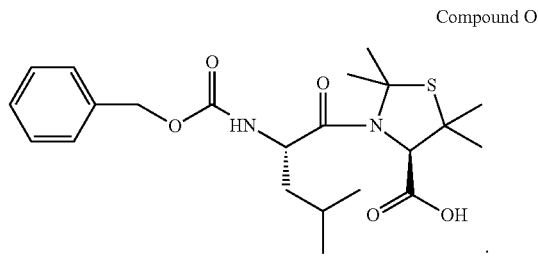 [SMILES: CC(C)C[C@H](NC(=O)OCc1ccccc1)C(=O)N1[C@H](C(=O)O)C(C)(C)SC1(C)C]

In certain embodiments, the invention is directed to the pseudoproline dipeptides of Formula VII, Formula VIIa and Formula VIIb and their use in the synthesis of penicillamine containing peptides:

Formula VII

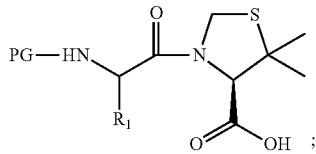

Formula VIIa

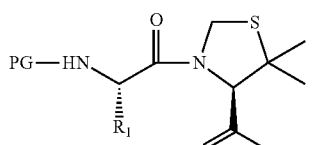

Formula VIIb

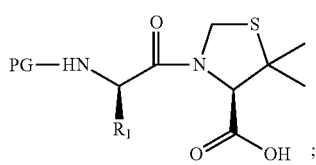

wherein R₁ is any suitable amino-acid side chain and PG is any suitable protecting group.

In certain embodiments, the amino-acid side chain is further protected by a suitable protecting group. In particular embodiments, PG is selected from the group consisting of Fmoc, Boc, and Cbz.

In particular embodiments of the invention, R₁ is an amino acid side chain corresponding to the side chain of an amino acid selected from natural amino acids, unnatural amino acids, suitable isostere replacements, corresponding D-amino acids, and corresponding N-Methyl amino acids.

In particular embodiments of the invention, the pseudoproline dipeptide is the dipeptide of Formula VIII:

Formula VIII

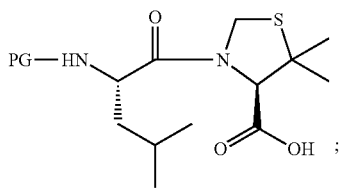

wherein PG is any suitable protecting group.

In particular embodiments, PG is selected from the group consisting of Fmoc, Boc, and Cbz.

Further embodiments of the invention are directed to the following pseudoproline dipeptides and their use in solid state and solution phase peptide synthesis.

Fmoc-Leu-Pen($^{\psi H,H}$Pro)-OH (Compound P):

Compound P

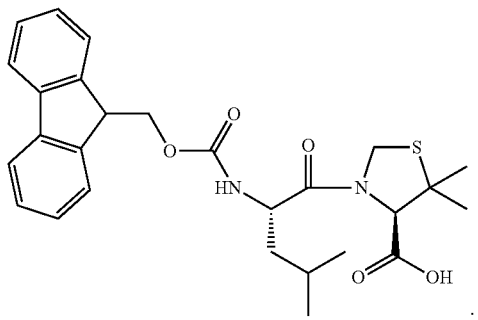

Bpoc-Leu-Pen($^{\psi H,H}$Pro)-OH (Compound Q):

Compound Q

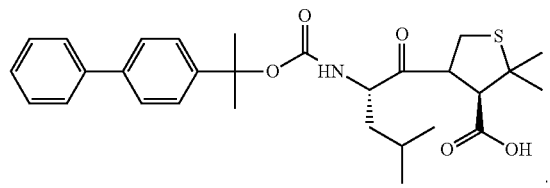

Cbz-Leu-Pen($^{\psi H,H}$Pro)-OH (Compound R):

Compound R

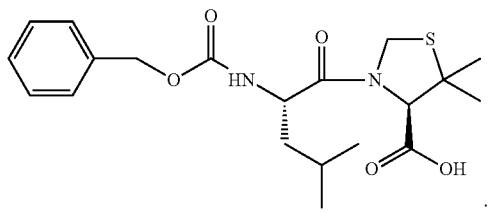

In certain embodiments of the invention directed to the synthesis of a peptide monomer comprising two or more penicillamine residues, the penicillamine residues are incorporated into the peptide as pseudoproline penicillamines.

In further embodiments of the invention directed to the synthesis of a peptide monomer comprising two or more penicillamine residues, the penicillamine residues are incorporated into the peptide as trityl-protected penicillamines.

In yet further embodiments of the invention directed to the synthesis of a peptide monomer comprising two or more penicillamine residues, the penicillamine residues are incorporated into the peptide as acetamidomethyl (Acm)-protected penicillamines.

In still further embodiments of the invention directed to the synthesis of a peptide monomer comprising two or more penicillamine residues, at least one penicillamine residue is incorporated into the peptide as a pseudoproline penicillamine and at least one penicillamine residue is incorporated into the peptide as a trityl-protected penicillamine.

In even further embodiments of the invention directed to the synthesis of a peptide monomer comprising two or more penicillamine residues, at least one penicillamine residue is incorporated into the peptide as a pseudoproline penicillamine and at least one penicillamine residue is incorporated into the peptide as an acetamidomethyl-protected penicillamine.

In particular embodiments of the invention directed to the synthesis of a peptide monomer comprising two or more penicillamine residues, at least one penicillamine residue is incorporated into the peptide as a trityl-protected penicillamine. and at least one penicillamine residue is incorporated into the peptide as an acetamidomethyl-protected penicillamine.

In particular embodiments of the invention, the methods described herein can be used to prepare peptides and peptide dimers on a commercial and/or industrial scale. In particular embodiments of the invention, the methods of the invention can be used to synthesize about 10 to 150 kg of peptide or peptide dimer. In certain embodiments of the invention, the methods described herein can be used to synthesize about 10 to 125 kg, 10 to 100 kg, 10 to 75 kg, 10 to 50 kg, 10 to 25 kg, 25 to 150 kg, 25 to 125 kg, 25 to 100 kg, 25 to 75 kg, 25 to 50 kg, 50 to 150 kg, 50 to 125 kg, 50 to 100 kg, 50 to 75 kg, 75 to 150 kg, 75 to 125 kg, 75 to 100 kg, 100 to 125 kg, 100 to 150 kg, or 125 to 150 kg, 100 to 500 kg, 500-1,000 kg, 1,000 to 10,000 kg, and all subranges there between.

Embodiments of the methods of synthesis disclosed herein can be used to synthesize Compound A, and/or Compound B, and other monomers and dimers. Certain embodiments of this invention provide feasibility to synthesize on commercial quantities up to multi metric ton scale. Certain embodiments of this invention provide significant advantages; such as simple operations, minimal side reactions, amenable to large scale production. Certain embodiments of this invention product Compound A and/or Compound B can be produced on large quantity using inexpensive starting materials. Certain embodiments of this invention provide significant advantages in terms of product purity. Certain embodiments of this invention provide scalable process cost-effective synthesis. Certain embodiments of this invention provide the process produces pharmaceutical grade compound A and/or Compound B.

In certain embodiments of the invention, the thiol group of a penicillamine is protected by pseudoproline derivative during solid phase peptide synthesis.

In certain embodiments of the invention, penicillamine is incorporated into a penicillamine containing peptide, such as, but not limited to, Compound B, the peptides of the peptide dimers of Table 2, as well as those disclosed in PCT Applications PCT/US2013/064439; PCT/US2014/032391; PCT/US2014/032392; PCT/US2015/05355; PCT/US2015/053603; U.S. Pat. No. 9,518,091B2, and other peptides disclosed herein, including but not limited to those of Formulas (I)-(III), and pharmaceutically acceptable salts, solvates, and hydrates thereof as a pseudoproline penicillamine derivative. In particular embodiments of the invention, the pseudoproline penicillamine derivative selected from the group consisting of Fmoc-Pen($^{\psi Me,Me}$Pro)-OH, Bpoc-Pen($^{\psi Me,Me}$Pro)-OH, Cbz-Pen($^{\psi Me,Me}$Pro)-OH, Fmoc-Pen(Pro)-OH, Bpoc-Pen(Pro)-OH, Cbz-Pen(Pro)-OH, and compounds of Formula IV. In further embodiments, the pseudoproline penicillamine derivative is a pseudoproline dipeptide selected from the group consisting of Fmoc-Leu-Pen($^{\psi Me,Me}$Pro)-OH, Bpoc-Leu-Pen($^{\psi Me,Me}$Pro)-OH, Cbz-Leu-Pen($^{\psi Me,Me}$Pro)-OH, Fmoc-Leu-Pen(Pro)-OH, Bpoc-Leu-Pen(Pro)-OH, Cbz-Leu-Pen(Pro)-OH, and the compounds of Formula V, Formula Va, Formula Vb, Formula VI, Formula VIa, Formula VIb, Formula VII, Formula VII, Formula VIIa, Formula VIIb, and Formula VIII.

In yet further embodiments of the invention, the penicillamine containing peptide Pen-(Xaa$^z$)$_m$, wherein each Xaa$^z$ is independently selected from the group consisting of natural amino acids, suitable isostere replacements, corresponding D-amino acids, and corresponding N-Methyl amino acids, and m is an integer from 1-20 is synthesized as follows: the peptide (Xaa$^z$)$_m$ is prepared using solution phase peptide synthesis techniques known to the practitioners in the art and condensed with an N-terminal protected pseudoproline penicillamine derivative such as, but not limited to: Fmoc-Pen($^{\psi Me,Me}$Pro)-OH, Bpoc-Pen($^{\psi Me,Me}$Pro)-OH, Cbz-Pen($^{\psi Me,Me}$Pro)-OH, Fmoc-Pen(Pro)-OH, Bpoc-Pen(Pro)-OH, or Cbz-Pen(Pro)-OH. The N-terminus of the resulting peptide is deprotected under suitable conditions to yield H-Pen($^{\psi Me,Me}$Pro)-(Xaa$^z$)$_m$ or H-Pen(Pro)-(Xaa$^z$)$_m$. The pseudoproline group is subsequently removed with a TFA/water/TIS (9.0:0.5:0.25) mixture.

In still further embodiments of the invention, the penicillamine containing peptide Ac-Pen-(Xaa$^z$)$_m$, wherein each Xaa$^z$ is independently selected from the group consisting of natural amino acids, suitable isostere replacements, corresponding D-amino acids, and corresponding N-Methyl amino acids, and m is an integer from 1-20 is synthesized as follows: the peptide (Xaa$^z$)$_m$ is prepared using solution phase peptide synthesis techniques known to the practitioners in the art and condensed with Ac-Pen($^{\psi Me,Me}$Pro)-OH or Ac-Pen(Pro)-OH to yield Ac-Pen($^{\psi Me,Me}$Pro)-(Xaa$^z$)$_m$ or Ac-Pen(Pro)-(Xaa$^z$)$_m$. The pseudoproline group is subsequently removed with a TFA/water/TIS (9.0:0.5:0.25) mixture.

In further embodiments of the invention, more than one penicillamine residue can be incorporated as described above, e.g., (Xaa$^z$)$_p$-Pen-(Xaa$^z$)$_n$-Pen-(Xaa$^z$)$_m$, (Xaa$^z$)$_p$-Pen-(Xaa$^z$)$_n$-Pen-(Xaa$^z$)$_m$, HPen-(Xaa$^z$)$_n$-Pen-(Xaa$^z$)$_m$, and Ac-Pen-(Xaa$^z$)$_n$-Pen-(Xaa$^z$)$_m$, wherein each Xaa$^z$ is independently selected from the group consisting of natural amino acids, suitable isostere replacements, corresponding D-amino acids, and corresponding N-Methyl amino acids, and each of p, n, and m are independently integers from 1-20.

In certain embodiments of the invention, the peptide fragment to which the pseudoproline penicillamine is condensed with is prepared using standard peptide synthesis protocols known to practitioners in the art. For example, amino functions of amino acids are protected with protecting groups such as, but not limited to, Boc, Cbz (Z), Fmoc, Bpoc, Ac and the carboxyl functions of amino acids are protected with groups such as, but not limited to, alkyl (e.g., methyl), amide, N—OSu, or arylphenol (e.g., nitrophenol). The condensation of the carboxyl group of the amino protected amino acid is done by using active ester method. The ester could be N-hydroxysuccinimide or other activated esters. The reaction is carried out by dissolving the carboxyl protected amino acid in polar aprotic solvent like, dimethylformamide, tetrahydrofuran, acetonitrile, dichloromethane in presence of tertiary amines such triethylamine, diisopropylethylamine, N-methymorpholine, at temperature of 10 to 40° C. for 2-24 hours.

Alternately the condensation of the carboxyl group of the amino protected amino acid is typically carried out by dissolving the appropriately protected amino acids in equimolar quantities in a solvent like dimethylformamide, tetrahydrofuran, dichloromethane, acetonitrile and adding one or more activating and condensing agents such as NHS, HBTU, DIC, HOBt, Oxyma in equimolar quantity at temperature of 0-10° C. and stirring at 5 to 40° C. for 2 to 20 hours. The protected group of amino/carboxyl is removed by the use of appropriate reagent known in the art.

In particular embodiments of the invention, treatment of the pseudoproline penicillamine derivative containing peptide with a TFA/water/TIS (9.0:0.5:0.25) mixture removes the pseudoproline to provide the unprotected penicillamine side chain.

In certain embodiments of the invention, a penicillamine containing peptide such as (Xaa$^z$)$_n$-Pen-(Xaa$^z$)$_m$, wherein each Xaa$^z$ is independently selected from the group consisting of natural amino acids, unnatural amino acids, suitable isostere replacements, corresponding D-amino acids, and corresponding N-Methyl amino acids, and each of n and m are independently integers from 1-20 is synthesized as follows: the peptide (Xaa$^z$)$_m$ is prepared using solution phase peptide synthesis techniques known to the practitioners in the art and condensed with an N-terminal protected pseudoproline penicillamine derivative such as, but not limited to: Fmoc-Pen($^{\psi Me,Me}$Pro)-OH, Bpoc-Pen($^{\psi Me,Me}$Pro)-OH, Cbz-Pen($^{\psi Me,Me}$Pro)-OH, Fmoc-Pen(Pro)-OH, Bpoc-Pen(Pro)-OH, Cbz-Pen(Pro)-OH, Fmoc-Leu-Pen($^{\psi Me,Me}$Pro)-OH, Bpoc-Leu-Pen($^{\psi Me,Me}$Pro)-OH, Cbz-Leu-Pen($^{\psi Me,Me}$Pro)-OH, Fmoc-Leu-Pen(Pro)-OH, Bpoc-Leu-Pen(Pro)-OH, Cbz-Leu-Pen(Pro)-OH, or the compounds of Formula V, Formula Va, Formula Vb, Formula VI, Formula VIa, Formula VIb, Formula VII, Formula VIIa, Formula VIIb, or Formula VIII. The N-terminus of the resulting peptide is deprotected under suitable conditions to yield H-Pen($^{\psi Me,Me}$Pro)-(Xaa$^z$)$_m$ or H-Pen(Pro)-(Xaa$^z$)$_m$. The peptide (Xaa$^z$)$_n$ is prepared using solution phase peptide synthesis techniques known to the practitioners in the art. The peptide (Xaa$^z$)$_n$-Pen-(Xaa$^z$)$_m$ is then prepared by condensation of (Xaa$^z$)$_n$ with H-Pen($^{\psi Me,Me}$Pro)-(Xaa$^z$)$_m$ or H-Pen(Pro)-(Xaa$^z$)$_m$ followed by treatment with a TFA/water/TIS (9.0:0.5:0.25) solution in order to remove the pseudoproline (Pro or $^{\psi Me,Me}$Pro) group as well as any side-chain protecting groups. In certain embodiments, the peptide can undergo further deprotection to remove any remaining side-chain protecting groups.

In certain embodiments of the invention, the decapeptide (Xaa$^z$)$_8$-Pen-Xaa$^z$ can be synthesized by coupling an N-terminal protected pseudoproline penicillamine derivative to amino acid Xaa$^z$, removing the N-terminal protecting group and condensing the resulting H-Pen($^{\psi Me,Me}$Pro)-Xaa$^z$ or H-Pen(Pro)-Xaa$^z$ peptide with (Xaa$^z$)$_8$ and deprotecting as discussed above to remove the pseudoproline (Pro or $^{\psi Me,Me}$Pro) group as well as any side-chain protecting groups.

In certain embodiments of the invention, the decapeptide (Xaa$^z$)$_7$-Pen-(Xaa$^z$)$_2$ can be synthesized by coupling an N-terminal protected pseudoproline penicillamine derivative to peptide (Xaa$^z$)$_2$, removing the N-terminal protecting group and condensing the resulting H-Pen($^{\psi Me,Me}$Pro)-

(Xaa$^z$)$_2$ or H-Pen(Pro)-(Xaa$^z$)$_2$ peptide with (Xaa$^z$)$_7$ and deprotecting as discussed above to remove the pseudoproline (Pro or $^{\psi Me,Me}$Pro) group as well as any side-chain protecting groups.

In certain embodiments of the invention, the decapeptide (Xaa$^z$)$_6$-Pen-(Xaa$^z$)$_3$ can be synthesized by coupling an N-terminal protected pseudoproline penicillamine derivative to peptide (Xaa$^z$)$_3$, removing the N-terminal protecting group and condensing the resulting H-Pen($^{\psi Me,Me}$Pro)-(Xaa$^z$)$_3$ or H-Pen(Pro)-(Xaa$^z$)$_3$ peptide with (Xaa$^z$)$_6$ and deprotecting as discussed above to remove the Pseudoproline (Pro or $^{\psi Me,Me}$Pro) group as well as any side-chain protecting groups.

In certain embodiments of the invention, the decapeptide (Xaa$^z$)$_5$-Pen-(Xaa$^z$)$_4$ can be synthesized by coupling an N-terminal protected pseudoproline penicillamine derivative to peptide (Xaa$^z$)$_4$, removing the N-terminal protecting group and condensing the resulting H-Pen($^{\psi Me,Me}$Pro)-(Xaa$^z$)$_4$ or H-Pen(Pro)-(Xaa$^z$)$_4$ peptide with (Xaa$^z$)$_5$ and deprotecting as discussed above to remove the pseudoproline (Pro or $^{\psi Me,Me}$Pro) group as well as any side-chain protecting groups.

In certain embodiments of the invention, the decapeptide (Xaa$^z$)$_4$-Pen-(Xaa$^z$)$_5$ can be synthesized by coupling an N-terminal protected pseudoproline penicillamine derivative to peptide (Xaa$^z$)$_5$, removing the N-terminal protecting group and condensing the resulting H-Pen($^{\psi Me,Me}$Pro)-(Xaa$^z$)$_5$ or H-Pen(Pro)-(Xaa$^z$)$_5$ peptide with (Xaa$^z$)$_4$ and deprotecting as discussed above to remove the pseudoproline (Pro or $^{\psi Me,Me}$Pro) group as well as any side-chain protecting groups.

In certain embodiments of the invention, the decapeptide (Xaa$^z$)$_3$-Pen-(Xaa$^z$)$_6$ can be synthesized by coupling an N-terminal protected pseudoproline penicillamine derivative to peptide (Xaa$^z$)$_6$, removing the N-terminal protecting group and condensing the resulting H-Pen($^{\psi Me,Me}$Pro)-(Xaa$^z$)$_6$ or H-Pen(Pro)-(Xaa$^z$)$_6$ peptide with (Xaa$^z$)$_4$ and deprotecting as discussed above to remove the pseudoproline (Pro or $^{\psi Me,Me}$Pro) group as well as any side-chain protecting groups.$_3$ In certain embodiments of the invention, the decapeptide (Xaa$^z$)$_2$-Pen-(Xaa$^z$)$_7$ can be synthesized by coupling an N-terminal protected pseudoproline penicillamine derivative to peptide (Xaa$^z$)$_7$, removing the N-terminal protecting group and condensing the resulting H-Pen($^{\psi Me,Me}$Pro)-(Xaa$^z$)$_7$ or H-Pen(Pro)-(Xaa$^z$)$_7$ peptide with (Xaa$^z$)$_2$ and deprotecting as discussed above to remove the pseudoproline (Pro or $^{\psi Me,Me}$Pro) group as well as any side-chain protecting groups.

In certain embodiments of the invention, the decapeptide Xaa$^z$-Pen-(Xaa$^z$)$_8$ can be synthesized by coupling an N-terminal protected pseudoproline penicillamine derivative to peptide (Xaa$^z$)$_8$, removing the N-terminal protecting group and condensing the resulting H-Pen($^{\psi Me,Me}$Pro)-(Xaa$^z$)$_8$ or H-Pen(Pro)-(Xaa$^z$)$_8$ peptide with Xaa$^z$ and deprotecting as discussed above to remove the pseudoproline (Pro or $^{\psi Me,Me}$Pro) group as well as any side-chain protecting groups.

In certain embodiments, the C-terminus of the peptide comprises an NH$_2$ or an OH.

In certain embodiments, a free amine in the C-terminal amino acid is capped, e.g., with an acetyl group.

In further embodiments, a free amine in the N-terminal amino acid is capped, e.g., with an acetyl group.

In still further embodiments, the α-amino group of the N-terminal amino acid is capped, e.g., with an acetyl group.

As shown in Scheme VI, in particular embodiments of the invention, Compound B can be synthesized by condensation of the appropriate protected 8-mer and 2-mer fragments, 7-mer and 3-mer fragments, 6-mer and 4-mer fragments, 5-mer and 5-mer fragments, 4-mer and 6-mer fragments, 3-mer and 7-mer fragments, or 2-mer and 8-mer fragments, followed by deprotection and cyclization.

In particular embodiments of the invention, the method provides synthesis of the linear decapeptide, Ac-Pen-N(Me)Arg-Ser-Asp-Thr-Leu-Pen-Phe(4-$^t$Bu)-β-homoGlu-D-Lys-NH$_2$ (SEQ ID NO:25). In further embodiments of the invention, Ac-Pen-N(Me)Arg-Ser-Asp-Thr-Leu-Pen-Phe(4-$^t$Bu)-β-homoGlu-D-Lys-NH$_2$ (SEQ ID NO:25) is oxidized to form an intramolecularcyclic peptide through an intramolecular disulfide bridge between the two Pen residues. In yet further embodiments, the cyclic decapeptide is dimerized with a suitable linker to yield a peptide dimer (Compound A).

In certain embodiments of the invention, the protected fragment Ac-Pen(R)-N(Me)Arg(pbf)-Ser($^t$Bu)-Asp(O$^t$Bu)-Thr($^t$Bu)-Leu-Pen(R)-Phe(4-$^t$Bu)-β-homoGlu(O$^t$Bu)-D-Lys(Boc)-NH$_2$ (SEQ ID NO:25) is prepared by condensation of the hexapeptide, Ac-Pen(R)-N(Me)Arg(pbf)-Ser($^t$Bu)-Asp(O$^t$Bu)-Thr($^t$Bu)-Leu-OH (SEQ ID NO:3), with the tetrapeptide, H-Pen(R)-Phe(4-$^t$Bu)-β-homoGlu(O$^t$Bu)-D-Lys(Boc)-NH$_2$ (SEQ ID NO:4), wherein each R is independently Acm or Trt.

In further embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-β homoGlu(O$^t$Bu)-D-Lys(Boc)-NH$_2$ (SEQ ID NO:25) is prepared by condensation of the hexapeptide, Ac-Pen($^{\psi Me,Me}$Pro)-N(Me)Arg(pbf)-Ser($^t$Bu)-Asp(O$^t$Bu)-Thr($^t$Bu)-Leu-OH (SEQ ID NO:3), with the tetrapeptide, H-Pen($^{\psi Me,Me}$Pro)-Phe(4-$^t$Bu)-β-homoGlu(O$^t$Bu)-D-Lys(Boc)-NH$_2$ (SEQ ID NO:4).

In still further embodiments of the invention, the hexapeptide, Ac-Pen(Acm)-N(Me)Arg(pbf)-Ser($^t$Bu)-Asp(O$^t$Bu)-Thr($^t$Bu)-Leu-OH (SEQ ID NO:3), is prepared by condensation of Y-Pen(Acm)-OH with the pentapeptide, HN(Me)Arg(pbf)-Ser($^t$Bu)-Asp(O$^t$Bu)-Thr($^t$Bu)-Leu-OMe (SEQ ID NO:5). Where Y=Acm, Trt or Ac In still further embodiments of the invention, the hexapeptide, Ac-Pen(Trt)-N(Me)Arg(pbf)-Ser($^t$Bu)-Asp(O$^t$Bu)-Thr($^t$Bu)-Leu-OH (SEQ ID NO:3), is prepared by condensation of Y-Pen(Trt)-OH with the pentapeptide, HN(Me)Arg(pbf)-Ser($^t$Bu)-Asp(O$^t$Bu)-Thr($^t$Bu)-Leu-OMe (SEQ ID NO:5). Where Y=Acm, Trt or Ac In yet further embodiments of the invention, the tetrapeptide, H-Pen($^{\psi Me,Me}$Pro)-Phe(4-$^t$Bu)-β-homoGlu(O$^t$Bu)-D-Lys(Boc)-NH$_2$ (SEQ ID NO:4), is prepared by condensation of Fmoc-Pen($^{\psi Me,Me}$Pro), Bpoc-Pen($^{\psi Me,Me}$Pro), or Cbz-Pen($^{\psi Me,Me}$Pro) with the tripeptide H-Phe(4-$^t$Bu)-β-homoGlu(O$^t$Bu)-D-Lys(Boc)-NH$_2$ followed by removal of the N-terminus protecting group.

In yet further embodiments of the invention, the tetrapeptide, H-Pen(Acm)-Phe(4-$^t$Bu)-β-homoGlu(O$^t$Bu)-D-Lys(Boc)-NH$_2$ (SEQ ID NO:4), is prepared by condensation of Fmoc-Pen(Acm)-OH, with the tripeptide H-Phe(4-$^t$Bu)-β-homoGlu(O$^t$Bu)-D-Lys(Boc)-NH$_2$ followed by removal of the N-terminus protecting group.

In yet further embodiments of the invention, the tetrapeptide, H-Pen(Trt)-Phe(4-$^t$Bu)-β-homoGlu(O$^t$Bu)-D-Lys(Boc)-NH$_2$ (SEQ ID NO:4), is prepared by condensation of Fmoc-Pen(Trt)-OH, with the tripeptide H-Phe(4-$^t$Bu)-β-homoGlu(O$^t$Bu)-D-Lys(Boc)-NH$_2$ followed by removal of the N-terminus protecting group.

In yet further embodiments of the invention, the decapeptide, Ac-Pen(Trt)-N(Me)Arg(pbf)-Ser($^t$Bu)-Asp(O$^t$Bu)-Thr($^t$Bu)-Leu-Pen(Trt)-Phe(4-$^t$Bu)-β-homoGlu(O$^t$Bu)-D-

Lys(Boc)-NH$_2$ (SEQ ID NO:25) is prepared by condensation of HN(Me)Arg(pbf)-Ser($^t$Bu)-Asp(O$^t$Bu)-Thr($^t$Bu)-Leu-Pen(Trt)-Phe(4-$^t$Bu)-β-homoGlu(O$^t$Bu)-D-Lys(Boc)-NH$_2$ (SEQ ID NO:87) and Fmoc-Pen(Trt)-OH followed by removal of the N-terminus protecting group and acetylation with actetic anhydride.

In yet further embodiments of the invention, the decapeptide, Ac-Pen(Acm)-N(Me)Arg(pbf)-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:25) is prepared by condensation of HN(Me)Arg(pbf)-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:87) and Fmoc-Pen(Acm)-OH followed by removal of the N-terminus protecting group and acetylation with actetic anhydride.

In yet further embodiments of the invention, the decapeptide, Ac-Pen(Trt)-N(Me)Arg(pbf)-Ser($^t$Bu)-Asp(O$^t$Bu)-Thr($^t$Bu)-Leu-Pen(Trt)-Phe(4-$^t$Bu)-β-homoGlu(O$^t$Bu)-D-Lys(Boc)-NH$_2$ (SEQ ID NO:25) is prepared by condensation of dipeptide Fmoc-Pen(Trt)-N(Me)Arg(pbf)-OH and octapeptide HSer($^t$Bu)-Asp(O$^t$Bu)-Thr($^t$Bu)-Leu-Pen(Trt)-Phe(4-$^t$Bu)-β-homoGlu(O$^t$Bu)-D-Lys(Boc)-NH$_2$ (SEQ ID NO:86), followed by removal of the N-terminus protecting group and acetylation with actetic anhydride.

In yet further embodiments of the invention, the decapeptide, Ac-Pen(Acm)-N(Me)Arg(pbf)-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:25) is prepared by condensation of dipeptide with Fmoc-Pen(Acm)-N(Me)Arg(pbf)-OH and octapeptide, HSer($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:86) followed by removal of the N-terminus protecting group and acetylation with actetic anhydride.

In yet further embodiments of the invention, the octapeptide, H-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:86) is prepared by condensation of tetrapeptide Fmoc-Ser($^t$Bu)-Asp(O$^t$Bu)-Thr($^t$Bu)-Leu-OH (SEQ ID NO:77) and tetrapeptide HPen(Acm)-Phe(4-$^t$Bu)-β-homoGlu(O$^t$Bu)-D-Lys(Boc)-NH$_2$ (SEQ ID NO:4) followed by removal of the N-terminus protecting group.

In yet further embodiments of the invention, the nanopeptide, HN(Me)Arg-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:87) is prepared by condensation of Pentapeptide HN(Me)Arg-Ser($^t$Bu)-Asp(O$^t$Bu)-Thr($^t$Bu)-Leu-OH (SEQ ID NO:5) and tetrapeptide HPen(Acm)-Phe(4-$^t$Bu)-β-homoGlu(O$^t$Bu)-D-Lys(Boc)-NH$_2$ (SEQ ID NO:4).

Scheme VI

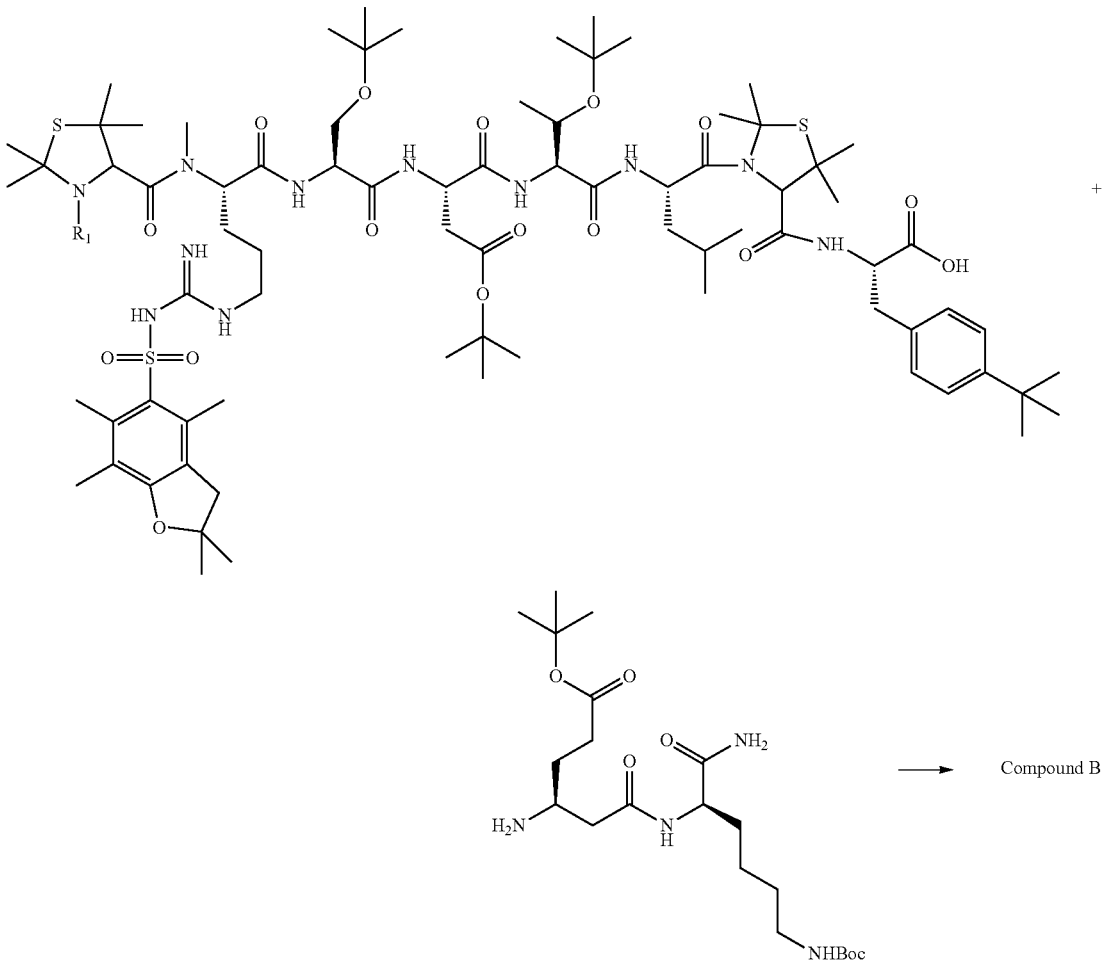

→ Compound B

-continued
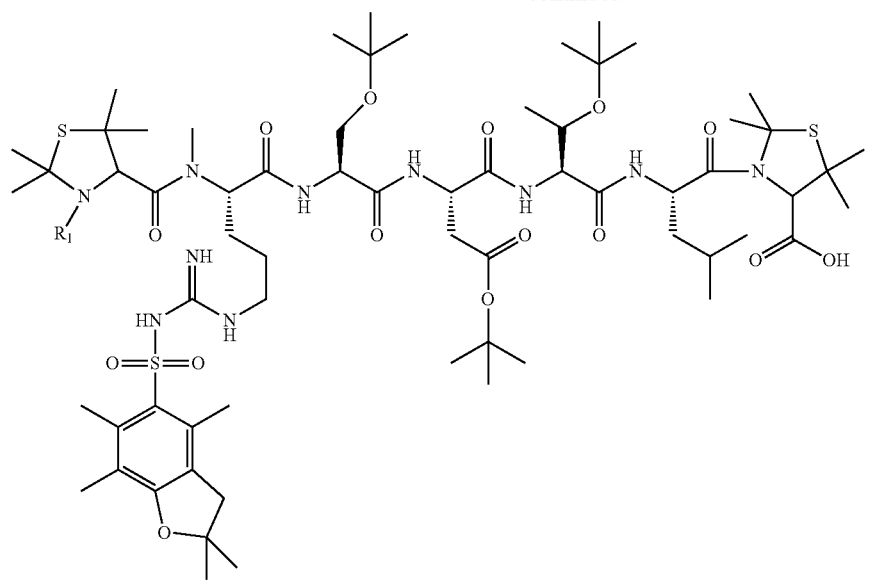
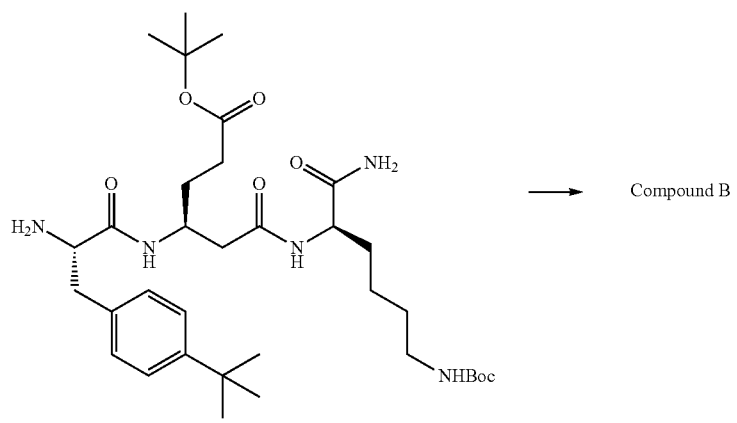
→ Compound B
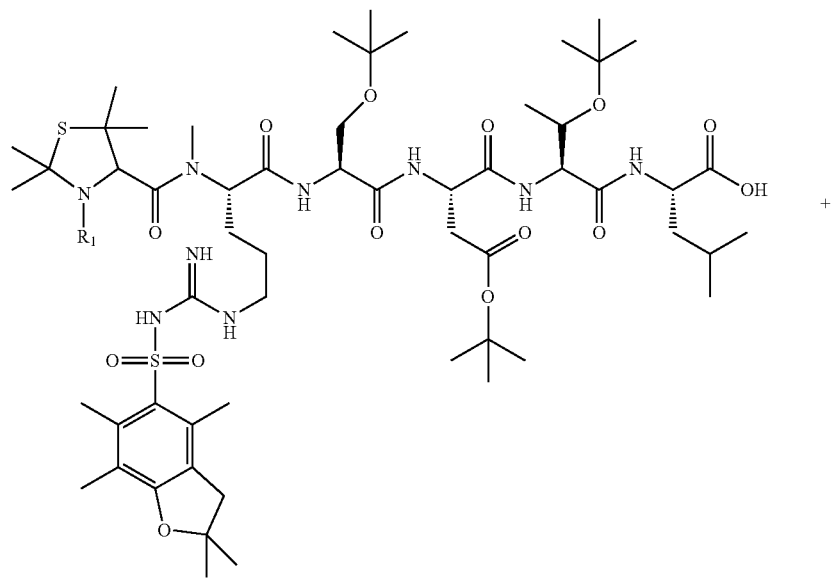

-continued
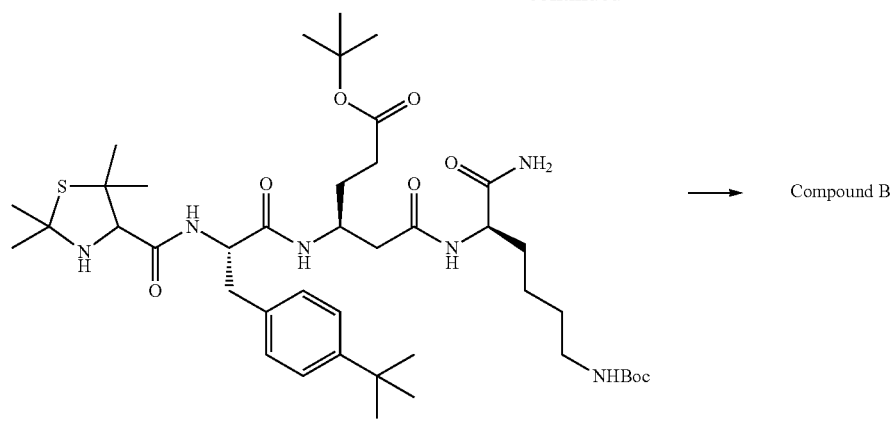
→ Compound B
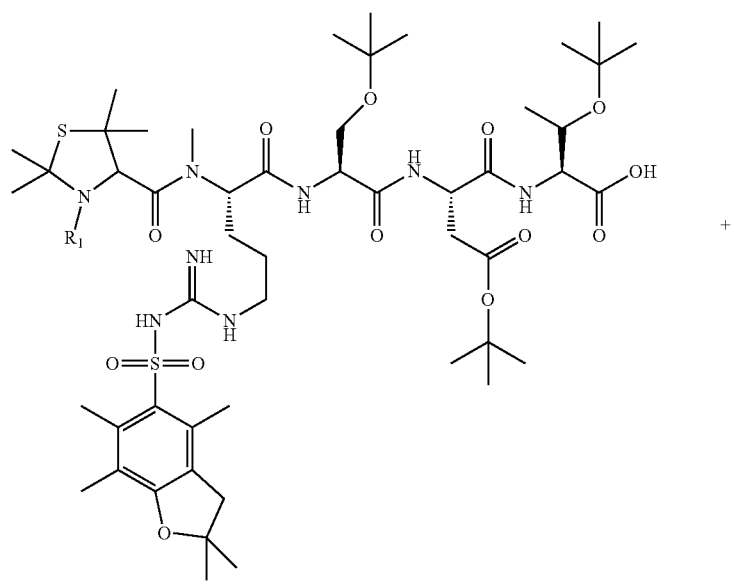
+
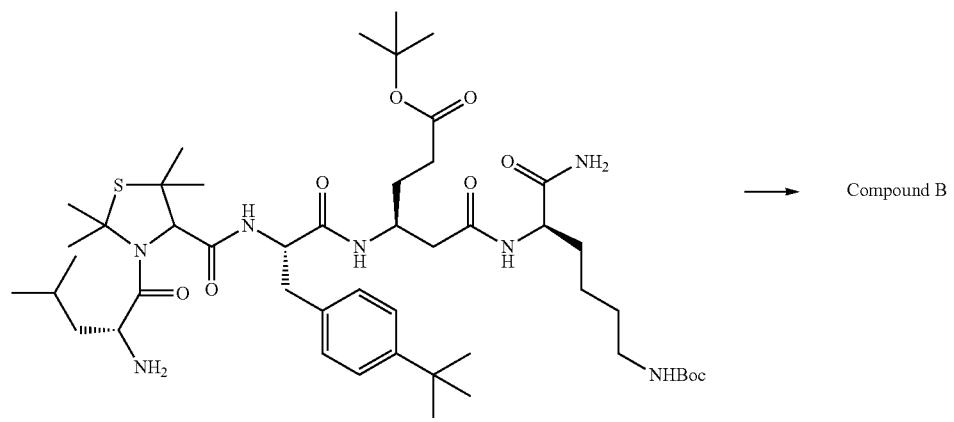
→ Compound B
$R_1$ = Ac, Fmoc, or Cbz

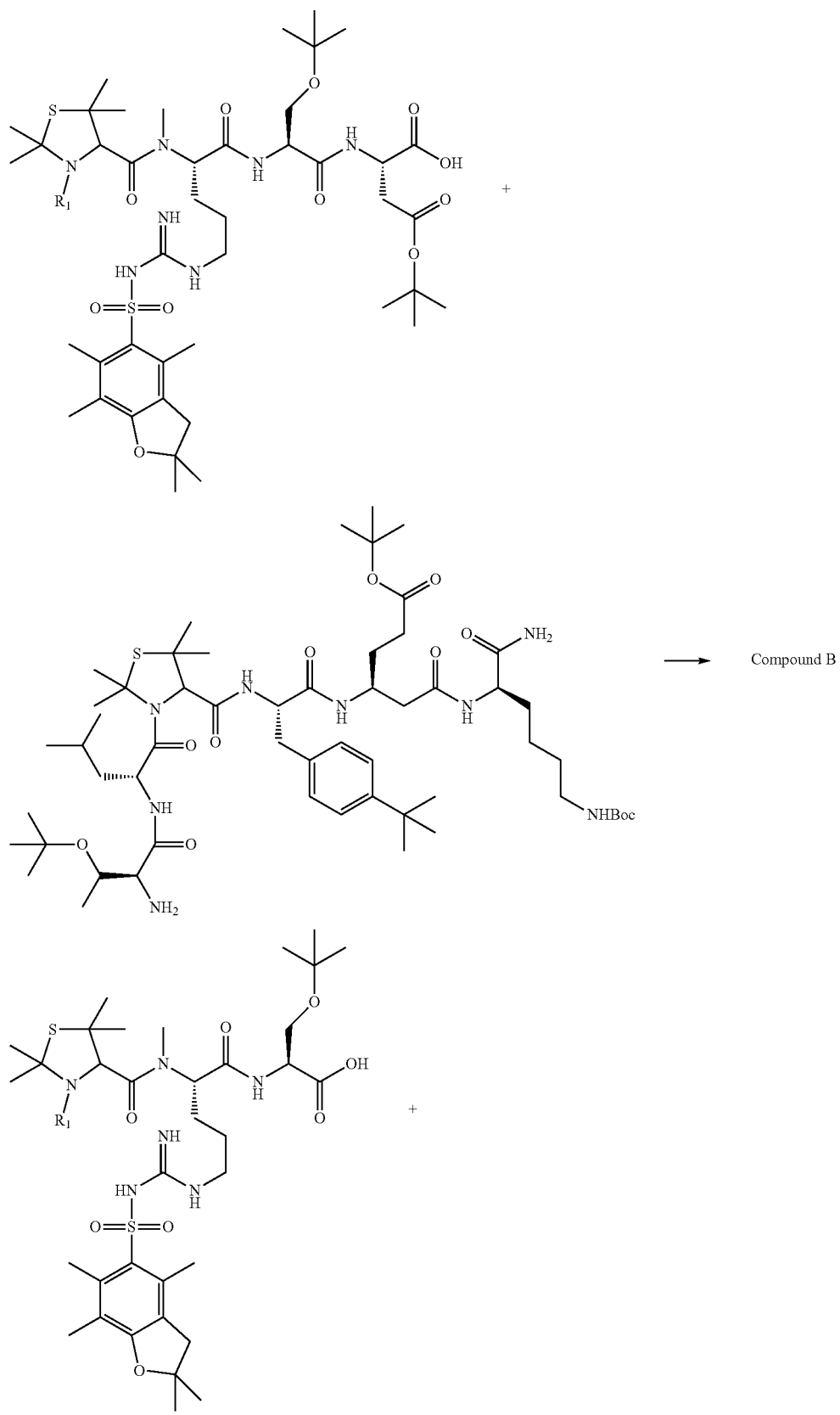

-continued
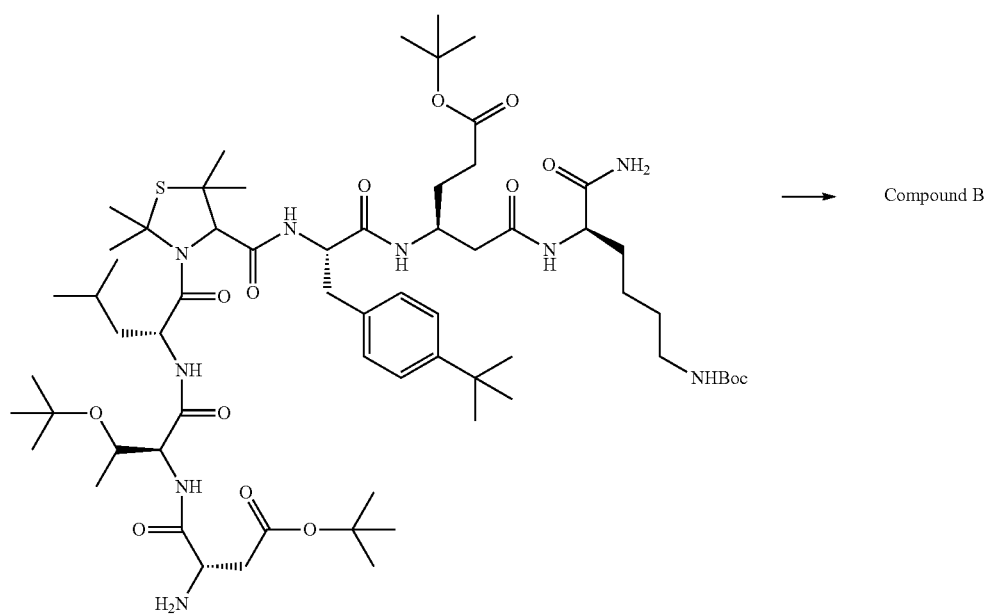
→ Compound B
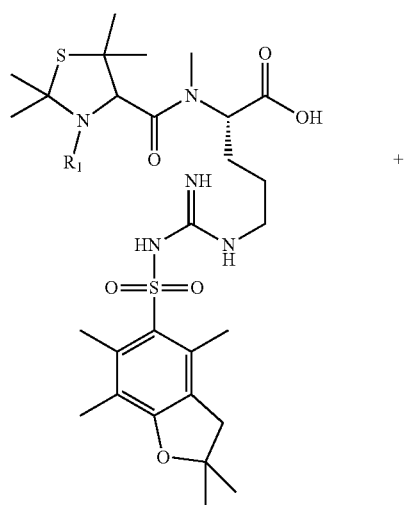
+

-continued

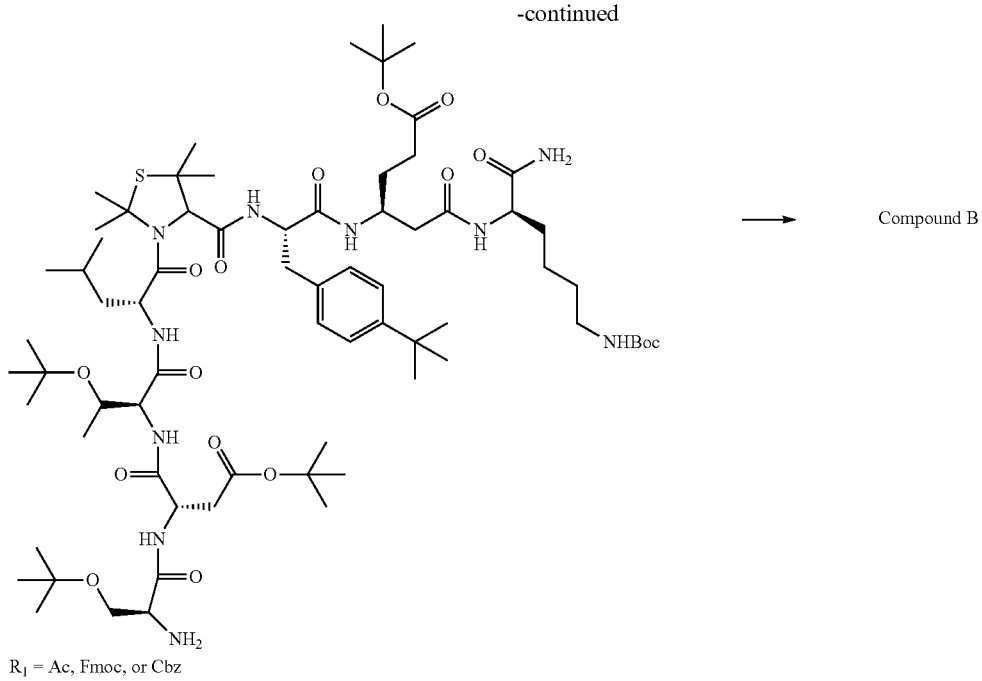

R₁ = Ac, Fmoc, or Cbz

→ Compound B

In further embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-β homoGlu(O$^t$Bu)-D-Lys(Boc)-NH$_2$ (SEQ ID NO:25) is prepared by condensation of the octapeptide, Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-OH (SEQ ID NO:80), with the dipeptide, 4β-homoGlu(O$^t$Bu)-D-Lys(Boc)-NH$_2$.

In still further embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-β-homoGlu(O$^t$Bu)-D-Lys(Boc)-NH$_2$ (SEQ ID NO:25) is prepared by condensation of the heptapeptide, Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-OH (SEQ ID NO:81), with the tripeptide, Phe(4-$^t$Bu)-β-homoGlu(O$^t$Bu)-D-Lys(Boc)-NH$_2$.

In yet further embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-β homoGlu(O$^t$Bu)-D-Lys(Boc)-NH$_2$ (SEQ ID NO:25) is prepared by condensation of the hexapeptide, Ac-Pen($^{\psi Me,Me}$Pro)-N(Me)Arg(pbf)-Ser($^t$Bu)-Asp(O$^t$Bu)-Thr($^t$Bu)-Leu-OH (SEQ ID NO:3), with the tetrapeptide, H-Pen($^{\psi Me,Me}$Pro)-Phe(4-$^t$Bu)-β-homoGlu(O$^t$Bu)-D-Lys(Boc)-NH$_2$ (SEQ ID NO:4).

In other embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-β homoGlu(O$^t$Bu)-D-Lys(Boc)-NH$_2$ (SEQ ID NO:25) is prepared by condensation of the pentapeptide, Ac-Pen($^{\psi Me,Me}$Pro)-N(Me)Arg(pbf)-Ser($^t$Bu)-Asp(O$^t$Bu)-Thr($^t$Bu)-OH (SEQ ID NO:73), with the pentapeptide, Leu-Pen($^{\psi Me,Me}$Pro)-Phe(4-$^t$Bu)-β-homoGlu(O$^t$Bu)-D-Lys(Boc)-NH$_2$ (SEQ ID NO:83).

In certain embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-βhomoGlu(O$^t$Bu)-D-Lys(Boc)-NH$_2$ (SEQ ID NO:25) is prepared by condensation of the tetrapeptide, Ac-Pen($^{\psi Me,Me}$Pro)-N(Me)Arg(pbf)-Ser($^t$Bu)-Asp(O$^t$Bu)-OH (SEQ ID NO:71), with the hexapeptide, Thr($^t$Bu)-Leu-Pen($^{\psi Me,Me}$Pro)-Phe(4-$^t$Bu)-β-homoGlu(O$^t$Bu)-D-Lys(Boc)-NH$_2$ (SEQ ID NO:84).

In particular embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-βhomoGlu(O$^t$Bu)-D-Lys(Boc)-NH$_2$ (SEQ ID NO:25) is prepared by condensation of the tripeptide, Ac-Pen($^{\psi Me,Me}$Pro)-N(Me)Arg(pbf)-Ser($^t$Bu)-OH, with the heptapeptide HAsp(O$^t$Bu)-Thr($^t$Bu)-Leu-Pen($^{\psi Me,Me}$Pro)-Phe(4-$^t$Bu)-β-homoGlu(O$^t$Bu)-D-Lys(Boc)-NH$_2$ (SEQ ID NO:85).

In further embodiments of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-βhomoGlu(O$^t$Bu)-D-Lys(Boc)-NH$_2$ (SEQ ID NO:25) is prepared by condensation of the dipeptide, Ac-Pen($^{\psi Me,Me}$Pro)-N(Me)Arg(pbf)-OH, with the octapeptide, HSer($^t$Bu)-Asp(O$^t$Bu)-Thr($^t$Bu)-Leu-Pen($^{\psi Me,Me}$Pro)-Phe(4-$^t$Bu)-β-homoGlu(O$^t$Bu)-D-Lys(Boc)-NH$_2$(SEQ ID NO:86).

In certain embodiments of the invention, Segment A, the protected hexapeptide Ac-Pen($^{\psi Me,Me}$Pro)-N(Me)Arg(pbf)-Ser($^t$Bu)-ASP(O$^t$Bu)-Thr($^t$Bu)-Leu-OH (SEQ ID NO:3) is prepared by condensation of the tetrapeptide HN(Me)Arg(pbf)-Ser($^t$Bu)-Asp(O$^t$Bu)-Thr($^t$Bu)-Leu-OMe (SEQ ID NO:5) with Ac-Pen($^{\psi Me,Me}$Pro) followed by saponification.

In other embodiments of the invention, Segment B is prepared by the condensation of Cbz-Pen($^{\psi Me,Me}$Pro), Fmoc-Pen($^{\psi Me,Me}$Pro) or Bpoc-Pen($^{\psi Me,Me}$Pro) with HPhe(4-$^t$Bu)-β-homoGlu(O$^t$Bu)-D-Lys(Boc)-NH$_2$ followed by removal of the Cbz, Fmoc or Bpoc protecting group.

In a particular embodiment of the invention, the protected fragment Ac-Pen($^{\psi Me,Me}$Pro)-N(Me)Arg(pbf)-Ser($^t$Bu)-Asp(O$^t$Bu)-Thr($^t$Bu)-Leu-Pen($^{\psi Me,Me}$Pro)-Phe(4-$^t$Bu)-βhomoGlu(O$^t$Bu)-D-Lys(Boc)-NH$_2$ (SEQ ID NO:25) is prepared by condensation of hexapetide, Ac-Pen($^{\psi Me,Me}$Pro)-N(Me)Arg(pbf)-Ser($^t$Bu)-Asp(O$^t$Bu)-Thr($^t$Bu)-Leu-OH (SEQ ID NO:3) with the tetrapeptide, H-Pen($^{\psi Me,Me}$Pro)-Phe(4-$^t$Bu)-β-homoGlu(O$^t$Bu)-D-Lys(Boc)-NH$_2$ (SEQ ID NO:4). The decapeptide is treated with cocktail mixture TFA/water/TIS (9.0:0.5:0.25), in one step removes the pseudoproline ($^{\psi Me,Me}$Pro) group, $^t$Bu, O$^t$Bu, pbf and Boc groups to provide Compound B, followed by oxidation with hydrogen peroxide to form disulfide bonds to provide the cyclized decapeptide, and dimerization with a diglycolate linker to provide Compound A.

In other embodiments of the invention, the protected fragment Ac-Pen(R)-N(Me)Arg(pbf)-Ser($^t$Bu)-Asp(O$^t$Bu)-Thr($^{\psi Me,Me}$Pro)-Leu-Pen(R)-Phe(4-$^t$Bu)-β-homoGlu(O$^t$Bu)-D-Lys(Boc)-NH$_2$ (SEQ ID NO:25) is prepared by condensation of the pentapeptide, Ac-Pen(R)-N(Me)Arg(pbf)-Ser($^t$Bu)-Asp(O$^t$Bu)-Thr($^{\psi Me,Me}$Pro)OH (SEQ ID NO:73), with the pentapeptide, HLeu-Pen(R)-Phe(4-$^t$Bu)-β-homoGlu(O$^t$Bu)-D-Lys(Boc)-NH$_2$ (SEQ ID NO:83). (R=Acm, Trt or $^{\psi Me,Me}$Pro)

In other embodiments of the invention, the protected fragment heptapeptide H-Asp(O$^t$Bu)-Thr($^{\psi Me,Me}$Pro)-Leu-Pen(R)-Phe(4-$^t$Bu)-β-homoGlu(O$^t$Bu)-D-Lys(Boc)-NH$_2$ (SEQ ID NO:85) is prepared by condensation of the dipeptide, Cbz-Asp(O$^t$Bu)-Thr($^{\psi Me,Me}$Pro)-OH, with the pentapeptide, H-Leu-Pen(R)-Phe(4-$^t$Bu)-β-homoGlu(O$^t$Bu)-D-Lys(Boc)-NH$_2$ (SEQ ID NO:83). (R=Acm, Trt or $^{\psi Me,Me}$Pro).

In other embodiments of the invention, the protected fragment decapeptide Ac-Pen(R)-N(Me)Arg(pbf)-Ser($^t$Bu)-Asp(O$^t$Bu)-Thr($^{\psi Me,Me}$Pro)-Leu-Pen(R)-Phe(4-$^t$Bu)-β-homoGlu(O$^t$Bu)-D-Lys(Boc)-NH$_2$ (SEQ ID NO:25) is prepared from tetrapeptide, R$_2$-Pen(R)-N(Me)Arg(pbf)-Ser($^t$Bu)-OH and hexapeptide, H-Asp(O$^t$Bu)-Thr($^{\psi Me,Me}$Pro)-Leu-Pen(R)-Phe(4-$^t$Bu)-β-homoGlu(O$^t$Bu)-D-Lys(Boc)-NH$_2$ (SEQ ID NO:85) (R=Acm, Trt or $^{\psi Me,Me}$Pro; R$_2$=Acetyl, Fmoc or Cbz).

In certain embodiments of the invention the peptides of Compound B, Table 2, those disclosed in PCT Applications PCT/US2013/064439; PCT/US2014/032391; PCT/US2014/032392; PCT/US2015/053558; PCT/US2015/053603, and U.S. Pat. No. 9,518,091B2, and other peptides disclosed herein, including but not limited to those of Formulas (I)-(III), and pharmaceutically acceptable salts, solvates, and hydrates thereof, can be synthesized by various fragment approaches. In particular, Compound B can be synthesized by various fragment approaches as shown in Schemes VII, VIII, IX, and X.

Synthesis Through 6+4 Fragments (Scheme-VII and VIII-A)

In one embodiment, a decapeptide can be synthesized through the stepwise synthesis of N-terminal hexapeptide and a stepwise synthesis of C-terminal tetrapeptide followed by the final coupling of these two fragments to give decapeptide monomer. The N-terminus can be acylated before the hexapeptide is coupled to the C-terminal tetrapeptide, or after coupling with the C-terminal tetrapeptide. In yet other embodiments, the N-terminal peptide can be acylated prior to coupling to the peptide chain.

In a certain embodiment of the invention, the N-terminal hexapeptide, Ac-Pen(Acm)-NMeArg(pbf)-Ser($^t$Bu)-Asp(O$^t$Bu)-Thr($^t$Bu)-Leu-OH (SEQ ID NO:3) (Ac-P$_6$-OH), is coupled with the C-terminal tetrapeptide, H-Pen(Acm)-Phe(4-$^t$Bu)-β-hGlu(O$^t$Bu)-(D)-Lys(Boc)-NH$_2$ (SEQ ID NO:4) (H-P$_4$-NH$_2$), to provide the decapeptide of Compound B (Ac-P$_{10}$-NH$_2$).

In a particular embodiment of the invention, the N-terminal hexapeptide, Fmoc-Pen(Acm)-NMeArg(pbf)-Ser($^t$Bu)-Asp(O$^t$Bu)-Thr($^t$Bu)-Leu-OH (SEQ ID NO:3) (Fmoc-P$_6$-OH), is coupled with the C-terminal tetrapeptide, H-Pen(Acm)-Phe(4-$^t$Bu)-β-hGlu(O$^t$Bu)-(D)-Lys(Boc)-NH$_2$ (SEQ ID NO:4) (H-P$_4$-NH$_2$), to provide the decapeptide Fmoc-P$_{10}$-NH$_2$, which can be deprotected and acylated to provide Compound B (Ac-P$_{10}$-NH$_2$).

In a further embodiment of the invention, the N-terminal hexapeptide, Ac-Pen(Trt)-NMeArg(pbf)-Ser($^t$Bu)-Asp(O$^t$Bu)-Thr($^t$Bu)-Leu-OH (SEQ ID NO:3) (Ac-P$_6$-OH), is coupled with the C-terminal tetrapeptide, H-Pen(Trt)-Phe(4-$^t$Bu)-β-hGlu(O$^t$Bu)-(D)-Lys(Boc)-NH$_2$ (SEQ ID NO:4) (H-P$_4$-NH$_2$), to provide the decapeptide of Compound B (Ac-P$_{10}$-NH$_2$).

In a still further embodiment of the invention, the N-terminal hexapeptide, Fmoc-Pen(Trt)-NMeArg(pbf)-Ser($^t$Bu)-Asp(O$^t$Bu)-Thr($^t$Bu)-Leu-OH (SEQ ID NO:3) (Fmoc-P$_6$-OH), is coupled with the C-terminal tetrapeptide, H-Pen(Trt)-Phe(4-$^t$Bu)-β-hGlu(O$^t$Bu)-(D)-Lys(Boc)-NH$_2$ (SEQ ID NO:4) (H-P$_4$-NH$_2$), to provide the decapeptide Fmoc-P$_{10}$-NH$_2$, which can be deprotected and acylated to provide Compound B (Ac-P$_{10}$-NH$_2$).

Synthesis Through 2+(4+4) Fragments (Scheme-VIII-B)

In another embodiment, a decapeptide can be synthesized through the synthesis of three intermediates, an N-terminal dipeptide, a middle tetrapeptide fragment and C-terminal tetrapeptide fragment. The middle tetrapeptide fragment and C-terminal tetrapeptide fragment can then be coupled to provide a C-terminal 8-mer peptide. The resulting 8-mer peptide can be coupled with the N-terminal dimer peptide to produce the decapeptide monomer. The N-terminus can be acylated before the dipeptide is coupled to the C-terminal 8-mer peptide or after coupling with the C-terminal 8-mer peptide. In yet other embodiments, the N-terminal peptide can be acylated prior to coupling to the peptide chain.

In yet another embodiment of the invention, the middle tetrapeptide fragment, Cbz-Ser($^t$Bu)-Asp(O$^t$Bu)-Thr($^t$Bu)-Leu-OMe (SEQ ID NO:77) (Cbz-P$_4$-OMe or Z-P$_4$-OMe) and C-terminal tetrapeptide fragment, H-Pen(Acm)-Phe(4-$^t$Bu)-β-hGlu(O$^t$Bu)-(D)-Lys(Boc)-NH$_2$ (SEQ ID NO:3) (N-P$_4$-NH$_2$), can be coupled to provide a C-terminal 8-mer peptide which can then be coupled with the N-terminal dimer peptide, Fmoc-Pen(Acm)-NMeArg(pbf)-OH (Fmoc-P$_2$-OH), to provide a decapeptide. The N-terminus of this resulting decapeptide can then be acylated to provide the decapeptide of Compound B (Ac-P$_{10}$-NH$_2$). In still other embodiments of the invention, the C-terminal 8-mer peptide can be coupled with the N-terminal dimer peptide, Ac-Pen(Acm)-NMeArg(pbf)-OH (Fmoc-P$_2$-OH), to provide a decapeptide of Compound B (Ac-P$_{10}$-NH$_2$).

In still another embodiment of the invention, the middle tetrapeptide fragment, Cbz-Ser($^t$Bu)-Asp(O$^t$Bu)-Thr($^t$Bu)-Leu-OMe (SEQ ID NO:77) (Cbz-P$_4$-OMe or Z-P$_4$-OMe) and C-terminal tetrapeptide fragment, H-Pen(Trt)-Phe(4-$^t$Bu)-β-hGlu(O$^t$Bu)-(D)-Lys(Boc)-NH$_2$ (SEQ ID NO:4) (N-P$_4$-NH$_2$), can be coupled to provide a C-terminal 8-mer peptide which can then be coupled with the N-terminal dimer peptide, Fmoc-Pen(Trt)-NMeArg(pbf)-OH (Fmoc-P$_2$-OH), to provide a decapeptide. The N-terminus of this resulting decapeptide can then be acylated to provide the decapeptide of Compound B (Ac-P$_{10}$-NH$_2$). In still other embodiments of the invention, the C-terminal 8-mer peptide can be coupled with the N-terminal dimer peptide, Ac-Pen(Trt)-NMeArg(pbf)-OH (Fmoc-P$_2$-OH), to provide a decapeptide of Compound B (Ac-P$_{10}$-NH$_2$).

Synthesis Through (2+4)+4 Fragments (Scheme-VIII-C)

In a further embodiment, a decapeptide can be synthesized through the three intermediates discussed above: an N-terminal dipeptide, a middle tetrapeptide fragment and C-terminal tetrapeptide fragment. First, the N-terminal dipeptide and middle tetrapeptide are coupled to provide the N-terminal hexapeptide. The resulting N-terminal hexapeptide is then coupled with the C-terminal tetrapeptide to provide the resulting decapeptide. The N-terminus can be acylated before the dipeptide is coupled to the middle tetrapeptide, after coupling with the middle tetrapeptide and before coupling with the C-terminal tetrapeptide, or after coupling with the C-terminal tetrapeptide. In yet other embodiments, the N-terminal peptide can be acylated prior to coupling to the peptide chain.

In a still further embodiment of the invention, the N-terminal dimer peptide, Fmoc-Pen(Acm)-NMeArg(pbf)-OH (Fmoc-P$_2$-OH) is coupled with the middle tetrapeptide fragment, -H-Ser($^t$Bu)-Asp(O$^t$Bu)-Thr($^t$Bu)-Leu-OMe (SEQ ID NO:77) (H-P$_4$-OMe) to provide an N-terminal hexapeptide, which is then coupled with the C-terminal tetrapeptide fragment, H-Pen(Acm)-Phe(4-$^t$Bu)-β-homoGlu(O$^t$Bu)-(D)-Lys(Boc)-NH$_2$ (SEQ ID NO:3) (N-P$_4$-NH$_2$), to provide a decapeptide. The N-terminus of this resulting decapeptide can then be acylated to provide the decapeptide of Compound B (Ac-P$_{10}$-NH$_2$). In still other embodiments of the invention, the N-terminal dimer Ac-Pen(Acm)-NMeArg(pbf)-OH (Ac-P$_2$-OH) is coupled with the middle tetrapeptide fragment, H-Ser($^t$Bu)-Asp(O$^t$Bu)-Thr($^t$Bu)-Leu-OMe (H-P$_4$-OMe) to provide an N-terminal hexapeptide, which is then coupled with the C-terminal tetrapeptide fragment, H-Pen(Acm)-Phe(4-$^t$Bu)-β-homoGlu(O$^t$Bu)-(D)-Lys(Boc)-NH$_2$ (H-P$_4$-NH$_2$), to provide the decapeptide of Compound B (Ac-P$_{10}$-NH$_2$).

In a still further embodiment of the invention, the N-terminal dimer peptide, Fmoc-Pen(Trt)-NMeArg(pbf)-OH (Fmoc-P$_2$-OH) is coupled with the middle tetrapeptide fragment, -H-Ser($^t$Bu)-Asp(O$^t$Bu)-Thr($^t$Bu)-Leu-OMe (SEQ ID NO:77) (H-P$_4$-OMe) to provide an N-terminal hexapeptide, which is then coupled with the C-terminal tetrapeptide fragment, H-Pen(Trt)-Phe(4-$^t$Bu)-β-hGlu(O$^t$Bu)-(D)-Lys(Boc)-NH$_2$ (SEQ ID NO:4) (N-P$_4$-NH$_2$), to provide a decapeptide. The N-terminus of this resulting decapeptide can then be acylated to provide the decapeptide of Compound B (Ac-P$_{10}$-NH$_2$). In still other embodiments of the invention, the N-terminal dimer Ac-Pen(Trt)-NMeArg(pbf)-OH (Ac-P$_2$-OH) is coupled with the middle tetrapeptide fragment, -H-Ser($^t$Bu)-Asp(O$^t$Bu)-Thr($^t$Bu)-Leu-OMe (SEQ ID NO:77) (H-P$_4$-OMe) to provide an N-terminal hexapeptide, which is then coupled with the C-terminal tetrapeptide fragment, H-Pen(Trt)-Phe(4-$^t$Bu)-β-hGlu(O$^t$Bu)-(D)-Lys(Boc)-NH$_2$ (SEQ ID NO:4) (H-P$_4$-NH$_2$), to provide the decapeptide of Compound B (Ac-P$_{10}$-NH$_2$).

Scheme VII

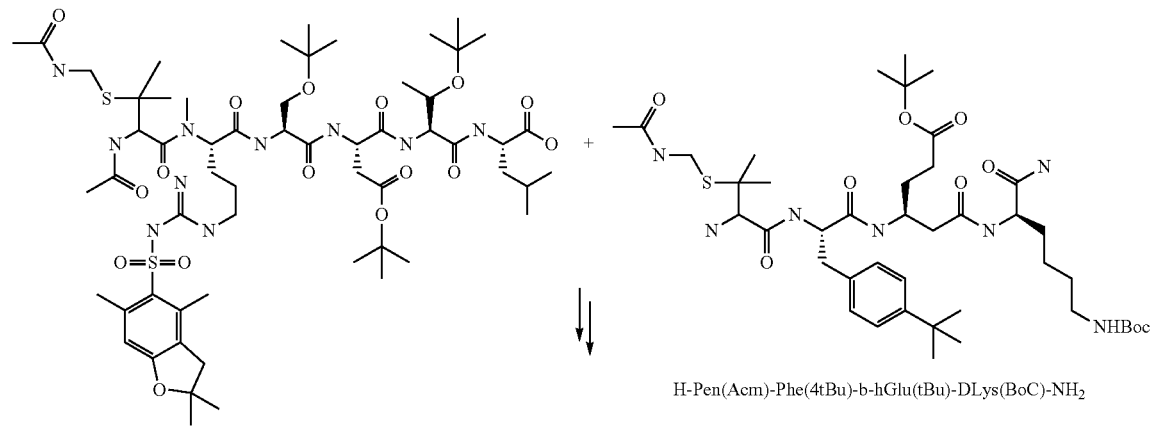

Ac-Pen(Acm)-NMeArg(Pfb)-Ser(OtBu)-Asp(tBu)-Thr(OtBu)-Leu-OH

H-Pen(Acm)-Phe(4tBu)-b-hGlu(tBu)-DLys(BoC)-NH$_2$

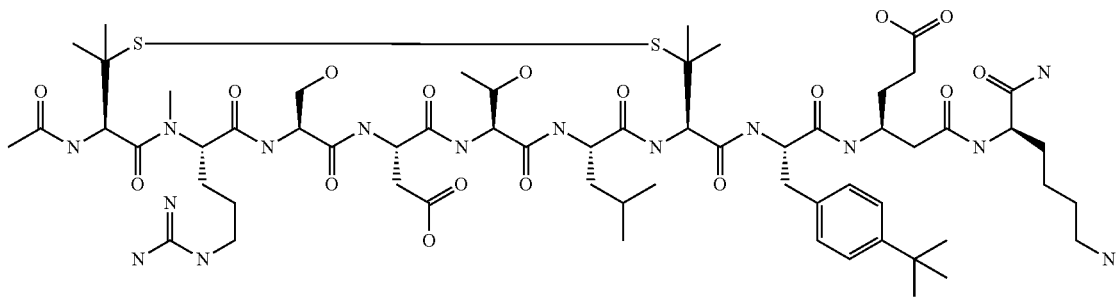

Ac-Pen-NMeArg-Ser-Asp-Thr-Leu-Pen-Phe(4tBu)-b-hGlu-DLys-NH$_2$

Compound B

-continued
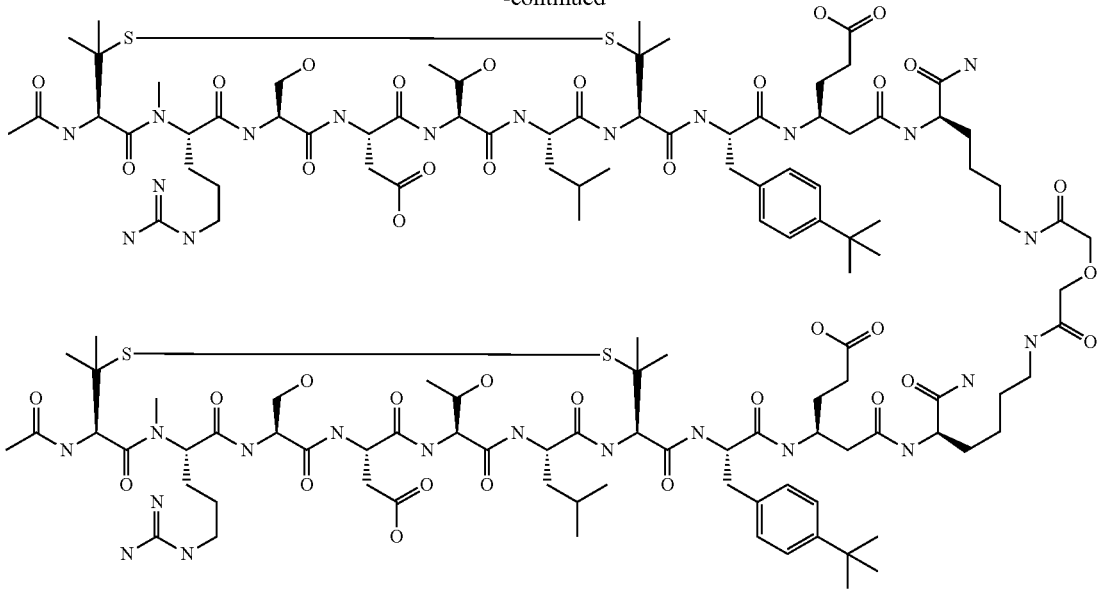
Compound A
Acetate Salt
M. WT: 2859.4 (free base)
M. F: $C_{126}H_{204}N_{30}O_{37}S_4 \cdot nC_2H_4O_2$
Scheme VIII
Synthesis of the Di, Tetra, and Hexa-Peptide Fragments:
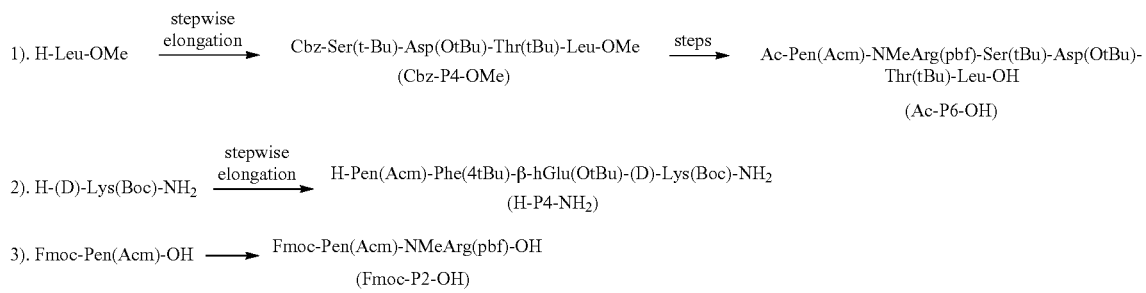
Coupling of the Peptide Fragments:
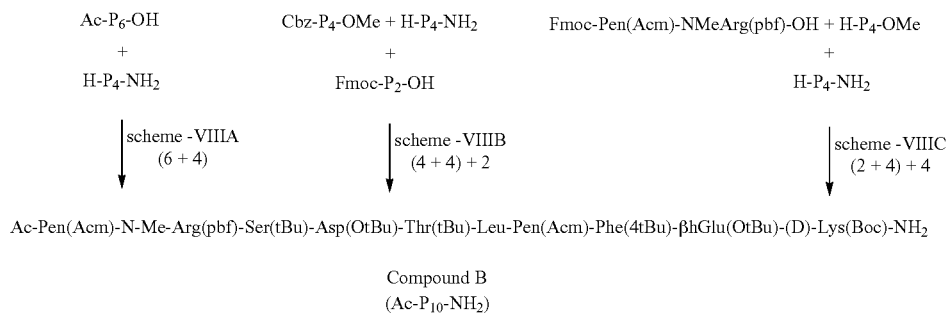
Ac-Pen(Acm)-N-Me-Arg(pbf)-Ser(tBu)-Asp(OtBu)-Thr(tBu)-Leu-Pen(Acm)-Phe(4tBu)-βhGlu(OtBu)-(D)-Lys(Boc)-NH₂
Compound B
(Ac-P₁₀-NH₂)

Scheme IX

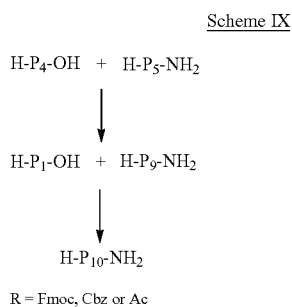

R = Fmoc, Cbz or Ac

Scheme IX illustrates yet another embodiment of the invention, wherein a decapeptide, such as Compound B, can be synthesized through solution phase peptide synthesis wherein a protected pentapeptide (H-P$_5$-NH$_2$) and a protected tetrapeptide (H-P$_5$-OH) are synthesized through solution phase peptide synthesis and condensed in solution to provide a nonopeptide (H-P$_9$-NH$_2$), which is then coupled with a protected amino acid (R-P$_1$-OH) to provide a decapeptide (R-P$_{10}$-OH), which is subsequently deprotected and purified.

EXAMPLES

Example 1: Solid Phase Synthesis of Compound A with Pen(Acm)

Peptide Sequence Assembly

The monomer peptide sequence Ac-Pen-N(Me)Arg-Ser-Asp-Thr-Leu-Pen-Phe(4-$^t$Bu)-β-homoGlu-D-Lys-NH$_2$ (SEQ ID NO:25) was assembled by standard solid phase peptide synthesis techniques as follows with the starting materials described in Table 5.

Solid phase synthesis was performed on a tricyclic amide linker resin (DL-form, 200-400 mesh, 0.6 mmol/g loading, 18.0 mmol scale). Approximately 2 equivalents of the Fmoc-protected amino acid was combined with 3.0 eq Oxyma (Ethyl (hydroxyimino)cyanoacetate) and 2.6 eq DIC (N,N'-Diisopropylcarbodiimide in DMF), and after 20 minutes of stirring the activated amino acid was added to the resin. After 20 minutes an extra 1.4 eq of DIC was added to the coupling solution in the reactor and the coupling reaction proceeded for approximately 1.3 hour to 2.0 hours. The coupling reaction was monitored by removing a sample of the resin from the reactor, washing it multiple times in a micro filtration syringe with DMF and IPA, and performing an appropriate calorimetric test for the specific amino acid. Fmoc-deprotection was performed using a solution of 20/80 piperidine/DMF.

Pen(Acm) was coupled as follows: 2.0 eq amino acid, 2.2 eq oxyma, and 2.0 eq DIC in 50:50 DCM:DMF were allowed to react for 20 minutes, after which the activated amino acid was transferred to the reactor and allowed to react for approximately 48 hrs at room temperature. The reaction was monitored by the Chloranil test.

Pen(Trt) was coupled as follows: 2.0 eq amino acid, 2.2 eq oxyma, and 2.0 eq DIC in 50:50 DCM:DMF were allowed to react for 20 minutes, after which the activated amino acid was transferred to the reactor and allowed to react for approximately 72 hrs at room temperature. The reaction was monitored by the Chloranil test.

After the final Pen(Acm) was coupled (coupling #10), Fmoc-deprotection was performed and the N-terminus of Pen(Acm) was capped with acetic anhydride. The resulting fully protected resin was washed with DMF and Isopropanol (IPA) and dried under vacuum.

After the final Pen(Trt) was coupled (coupling #10), Fmoc-deprotection was performed and the N-terminus of Pen(Trt) was capped with acetic anhydride. The resulting fully protected resin was washed with DMF and Isopropanol (IPA) and dried under vacuum.

TABLE 5

Starting Materials for Peptide Synthesis

| Starting Material | Structure | Process Step |
|---|---|---|
| Tricyclic Amide linker resin (Ramage Resin) | 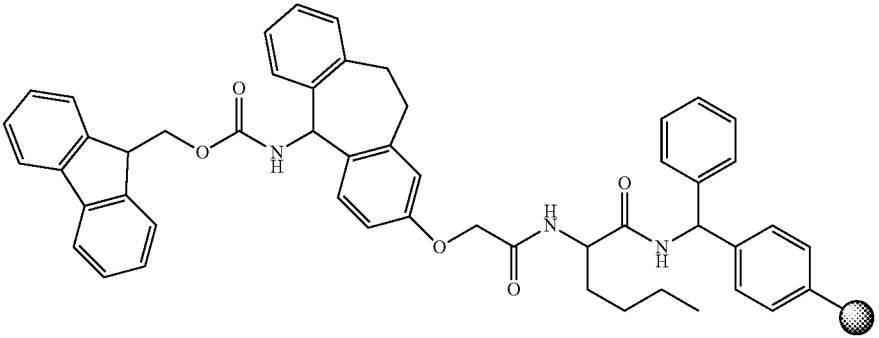 [SMILES: CCCCC(NC(=O)COc1ccc2c(c1)CCc1ccccc1C2NC(=O)OCC1c2ccccc2-c2ccccc21)C(=O)NC(c1ccccc1)c1ccc(C)cc1] | base resin |
| Fmoc-D-Lys(Boc)-OH | 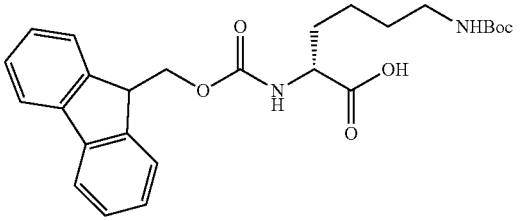 [SMILES: CC(C)(C)OC(=O)NCCCC[C@@H](NC(=O)OCC1c2ccccc2-c2ccccc21)C(=O)O] | coupling #1 |

TABLE 5-continued

Starting Materials for Peptide Synthesis

| Starting Material | Structure | Process Step |
|---|---|---|
| Fmoc-L-Aad(O$^t$Bu)-OH (also known as Fmoc-β-HomoGlu(O$^5$Bu)-OH) | 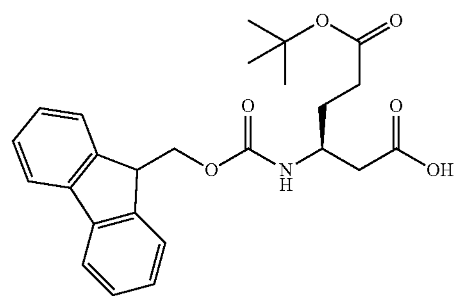 [SMILES: CC(C)(C)OC(=O)CC[C@@H](CC(=O)O)NC(=O)OCC1c2ccccc2-c2ccccc21] | coupling #2 |
| Fmoc-L-(4-$^t$Bu)Phe-OH | 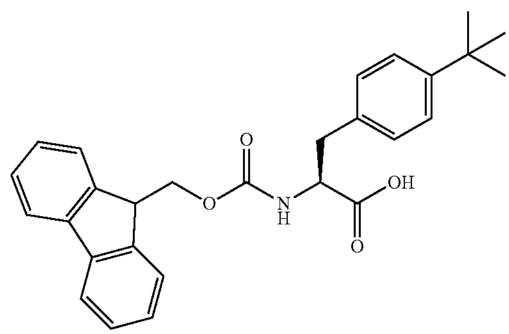 [SMILES: CC(C)(C)c1ccc(C[C@H](NC(=O)OCC2c3ccccc3-c3ccccc32)C(=O)O)cc1] | coupling #3 |
| Fmoc-L-Pen(Acm)-OH | 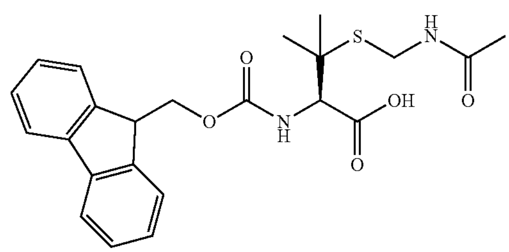 [SMILES: CC(=O)NCSC(C)(C)[C@H](NC(=O)OCC1c2ccccc2-c2ccccc21)C(=O)O] | couplings #4 and #10 |
| Fmoc-L-Pen(Trt)-OH | 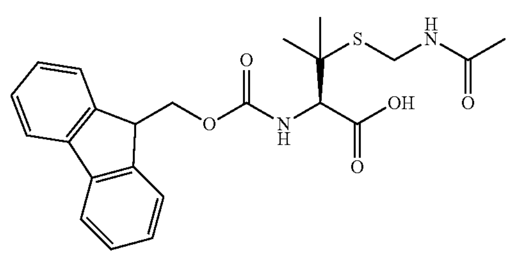 [SMILES: CC(=O)NCSC(C)(C)[C@H](NC(=O)OCC1c2ccccc2-c2ccccc21)C(=O)O] | couplings #4 and #10 |
| Fmoc-L-Leu-OH | 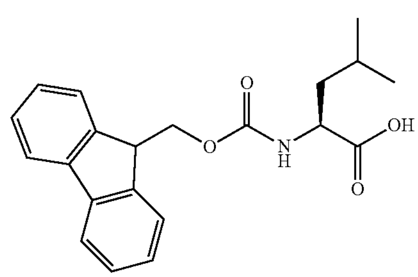 [SMILES: CC(C)C[C@H](NC(=O)OCC1c2ccccc2-c2ccccc21)C(=O)O] | coupling #5 |

TABLE 5-continued

Starting Materials for Peptide Synthesis

| Starting Material | Structure | Process Step |
|---|---|---|
| Fmoc-L-Thr(tBu)OH | | coupling # 6 |
| Fmoc-L-Asp(tBu)-OH | | coupling # 7 |
| Fmoc-L-Ser(tBu)-OH | | coupling # 8 |
| Fmoc-L-NMe-Arg(Pbf)-OH | | coupling # 9 |
| Acetic anhydride (Ac$_2$O) | | final capping |

Cleavage and Isolation of Monomer

To cleave the monomer peptide from the resin and to remove side chain protecting groups on the peptide, the protected peptide resin was treated with a cleavage solution containing TFA:water:EDT:TIPS (87.5v:3.5v:8v:1v). The cleavage solution was chilled in the ice bath and thawed to room temperature before use. The cleavage reaction mixture was stirred for about 2 hrs at room temperature. The spent resin was filtered off and washed with a 90:10 mixture of TFA:water. The combined filtrates and washes were then precipitated into cold ethyl ether and centrifuged to collect the peptide. The ethyl ether was decanted, and the solid precipitate was washed three times with cold ethyl ether. The unpurified linear monomer was dried to constant weight under vacuum. TFA cleavage of this peptide resin resulted in a peptide with an Acm-protected Pen residues.

The unpurified monomer was analyzed by RP-HPLC Method 20-40-20 min (Phenomenex Aeris PEPTIDE 3.6μ XB-C18 150×4.6 mm column), MPA: 0.1% TFA in water and MPB: 0.1% TFA in ACN). LC/MS was performed to verify the expected molecular weight of the linear monomer, and the observed MW of the main product was 1524.5±2 Da. The HPLC chromatogram of unpurified linear monomer is shown in FIG. 1.

Disulfide Bond Formation Pen(Acm)

The unpurified linear monomer was dissolved (3.0 gram scale) in 50:50 ACN:water, then diluted to 20:80 ACN:water at a concentration of 2 to 3 mg/mL. While stirring with a magnetic stirrer, a $I_2$/MeOH solution was added until the solution turned dark yellow. When the yellow color faded out, additional $I_2$/MeOH solution was added until the reaction mixture stayed a dark yellow to amber color. The reaction was monitored using LCMS and HPLC. When the reaction is completed (uncyclized monomer ≤5% (Area %), approximately 30 to 45 minutes), the reaction was quenched with ascorbic acid until a colorless solution was obtained. The reaction mixture was diluted with water (final solution ~10:90 ACN:water) and purified as discussed below.

Disulfide Bond Formation Pen(Trt)

Figure 2:
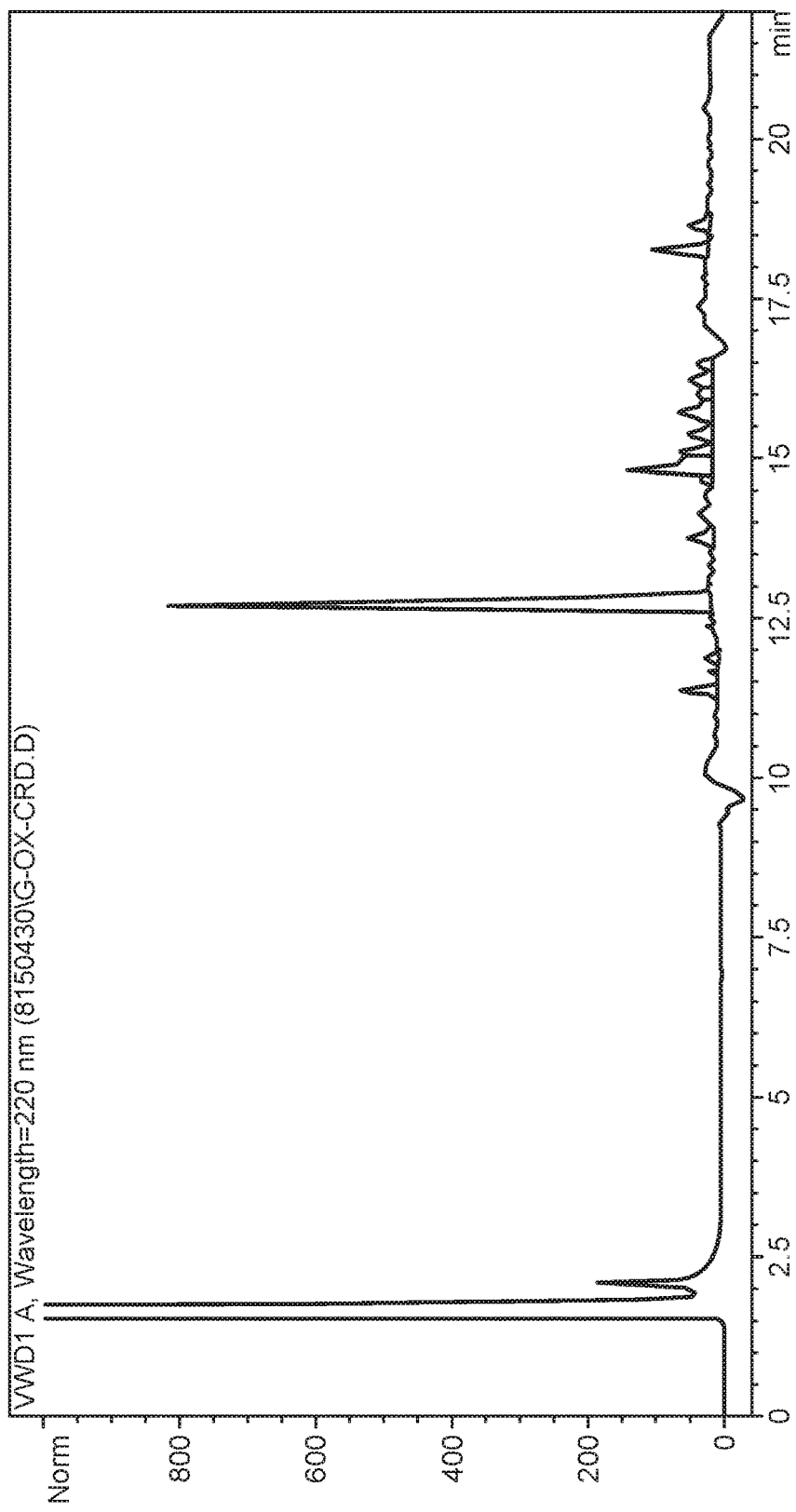
FIG. 2 represents the HPLC chromatogram of cyclized unpurified monomer. The cyclized monomer has a retention time of 12.714 min. Purity 59.92% (AUC)
Figure 3:
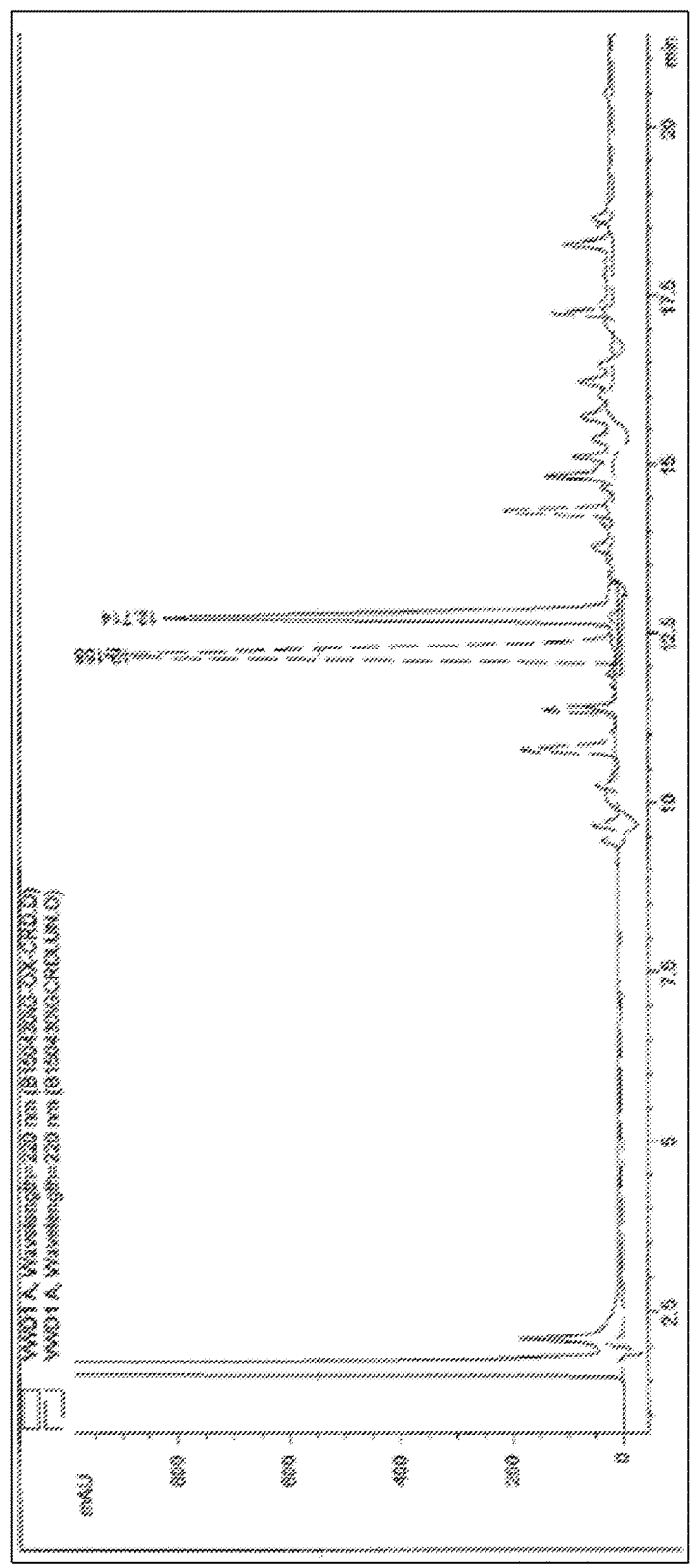
FIG. 3 represents the overlay of the HPLC chromatograms of uncyclized crude monomer (RT 12.158 min) and cyclized unpurified monomer (RT 12.714 min).

The unpurified linear monomer was dissolved (3.0 gram scale) in 50:50 ACN:water, then diluted to 20:80 ACN:water at a concentration of 2 to 3 mg/mL. While stirring with a magnetic stirrer, a $I_2$/MeOH solution was added until the solution turned light yellow. When the yellow color faded out, additional $I_2$/MeOH solution was added until the reaction mixture stayed a yellow to amber color. The reaction was monitored using LCMS and HPLC. When the reaction is completed (uncyclized monomer ≤5% (Area %), approximately 30 to 45 minutes), the reaction was quenched with ascorbic acid until a colorless solution was obtained. The reaction mixture was diluted with water (final solution 10:90 ACN:water) and purified as discussed below The unpurified cyclized monomer was analyzed by RP-HPLC Method 20-40-20 min (Phenomenex Luna 3.0μ XB-C18 150×4.6 mm column), MPA: 0.1% TFA in water and MPB: 0.1% TFA in ACN). LC/MS was performed to verify the expected molecular weight of the linear monomer, and the observed MW of the main product was 1381.2±2 Da. The HPLC chromatogram of cyclized unpurified monomer is shown in FIG. 2. And overlay HPLC of crude uncyclized and cyclized unpurified monomer is shown in FIG. 3.

Purification of Cyclized Monomer (Compound B)

The cyclized monomer (Compound B) was purified on a preparative RP-HPLC system using the following conditions: Buffer A: 0.1% TFA in water and Buffer B: 0.1% TFA in ACN, Phenomenex Luna 10μ C18 250×50 mm column with a flow rate of 80 mL/min. Approximately 3.0 g cyclized monomer was purified per run using a 23:35:60 min gradient (23% B to 35% B in 60 min). Fractions were collected (about 25 fractions per purification, ~40 mL per fraction) and analyzed by analytical HPLC Method 20-40-20 min and lyophilized. Fractions of purity ≥90% combined for dimerization, fraction with purity between 65 and 90 Area-% were combined for recycling, and fractions with purity <65 Area-% were discarded.

Figure 4:
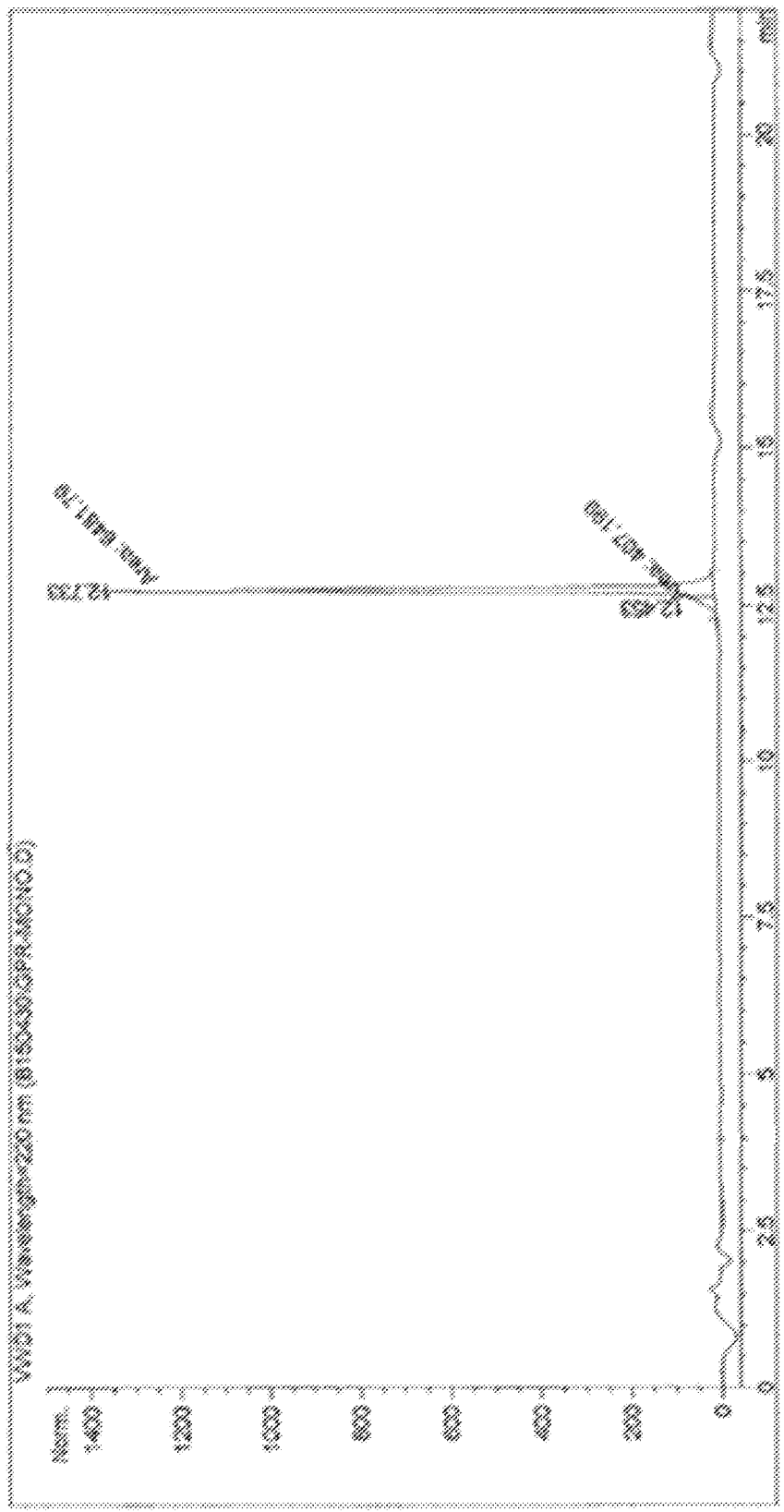
FIG. 4 represents the HPLC chromatogram of pure cyclized monomer (Compound B). The pure cyclized monomer has a retention time or 12.733 min. Purity 94.09% (AUC)

The purified monomer was analyzed by RP-HPLC Method 20-40-20 min (Phenomenex Luna 3.0μ XB-C18 150×4.6 mm column), MPA: 0.1% TFA in water and MPB: 0.1% TFA in ACN). LC/MS was performed to verify the expected molecular weight of the linear monomer, and the observed MW of the main product was 1381.8±2 Da. The HPLC chromatogram of purified linear monomer is shown in FIG. 4.

Linker Activation

Diglycolic acid-di-N-Hydroxysuccinimide ester (DIG-$OSu_2$) was prepared by reacting DIG (Diglycolic acid) (1.0 eq) with HO-Su (N-Hydroxysuccinimide) (2.2 eq) and DCC (N,N'-Dicyclohexylcarbodiimide) (2.2 eq) in NMP for 12 hours at a concentration of 0.1M. After 12 hrs reaction, the precipitated dicyclohexylurea was removed by filtration, and the DIG-$OSu_2$ solution (0.1M) was used for dimerization.

Monomer Dimerization

The cyclized pure monomer was converted to the corresponding dimer by coupling ~2 g monomer with 0.1M DIG linker solution (0.45 eq) and DIEA in DMF solution (5.0 eq). The dimerization reaction took approximately 15 to 30 min under ambient conditions. The reaction was monitored using LCMS and HPLC. When the reaction is completed (monomer ≤5% (Area %)), the reaction was quenched by adding acetic acid, diluted it with water and purified as discussed below.

Figure 5:
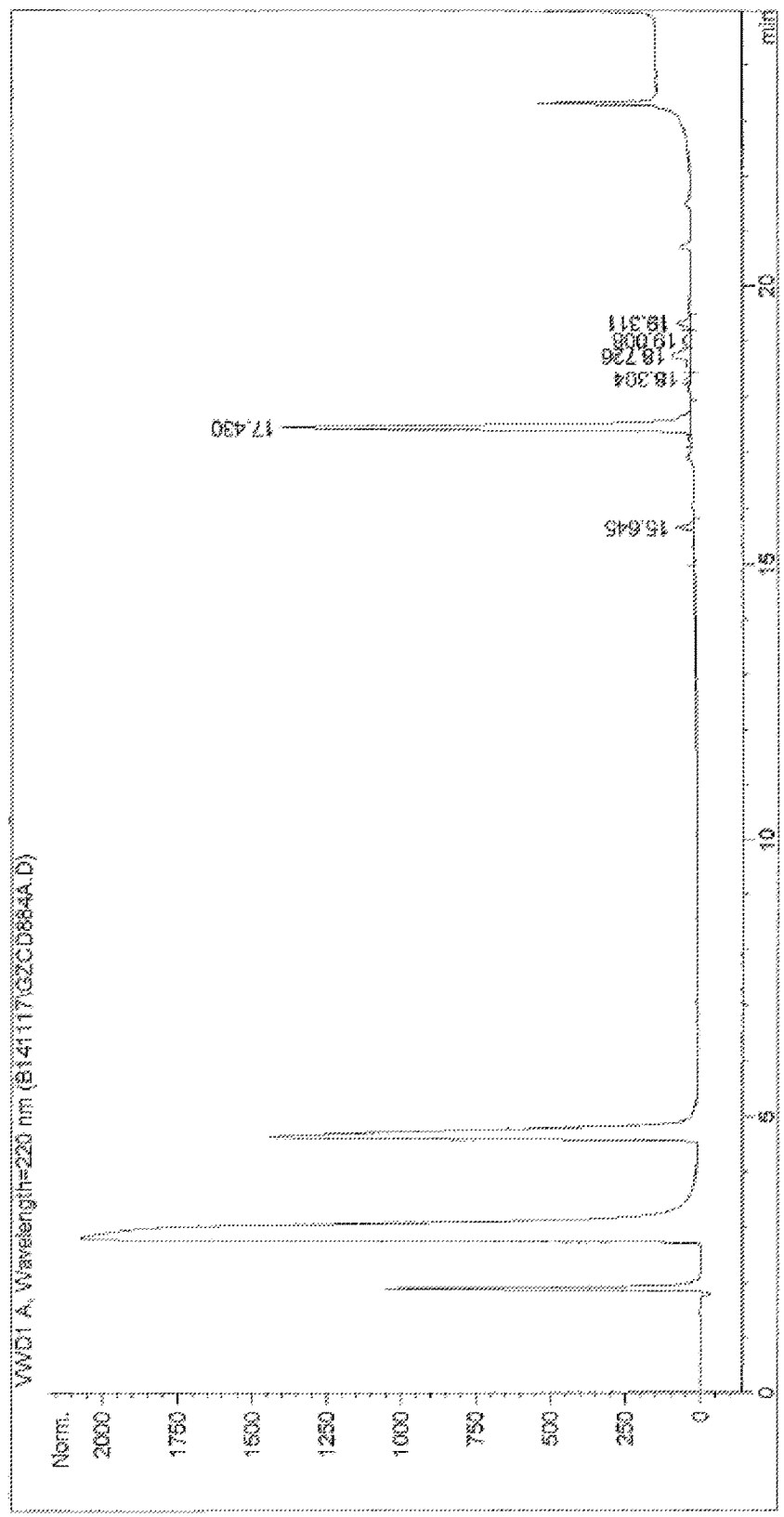
FIG. 5 represents the HPLC chromatogram of the crude dimer (Compound A). The crude dimer has a retention time of 17.43 min. Purity 83.59% (AUC). The peaks between 0 to 5 min are solvent front peaks.

The crude dimer (Compound A) was analyzed by the analytical HPLC Method 2-50-20 min (Phenomenex Luna 5μ C18 150×4.6 mm, 5 micron 100 A column), MPA: 0.1% TFA in water and MPB: 0.1% TFA in ACN). LC/MS was used to verify the expected molecular weight of the dimer, and the observed MW was 2859.3±2 Da. The HPLC chromatogram of crude dimer is shown in FIG. 5.

Purification of Compound a and Preparation of the Acetate Salt of Compound A.

The crude dimer was purified on a preparative RP-HPLC system using the following conditions: Buffer A: 0.1% TFA in water and Buffer B: 0.1% TFA in ACN, Phenomenex Luna 10μ C18 250×50 mm column with a flow rate of 80 mL/min. Approximately 2.0 g dimer was purified per run using a 33:40:60 min gradient (33% B to 40% B in 60 min). Fractions were collected (about 15 fractions per purification, ~20 mL per fraction) and analyzed by analytical HPLC Method 2-50-20 min. Fraction with purity ≥95.0 Area-% were combined as a final product and transferred to salt exchange step (Section 1.6), fractions between 70 and 94 Area-% were combined for recycling, and fractions with purity <60 Area-% were discarded.

The combined purified solution of Compound A from above was diluted with water (1:1) and loaded to a preparative RP-HPLC system using the following conditions: Buffer A: 0.2% AcOH in water and Buffer B: 0.2% AcOH in ACN, Phenomenex Luna 10μ C18 250×50 mm column with a flow rate of 80 mL/min. Approximately 2.0 g of dimer was loaded per run, after loading the salt exchange step was performed by passing through the column a solution of 0.1 M ammonium acetate, and the material eluted with 0.2% AcOH in ACN. The exchanged fractions were collected and analyzed by analytical HPLC Method 2-50-20 min. Fraction with purity ≥95.0 Area-% were combined as a final product, fractions with purity <95 Area-% were re-purified. Fractions were lyophilized using acetate only lyophilizer.

Figure 6:
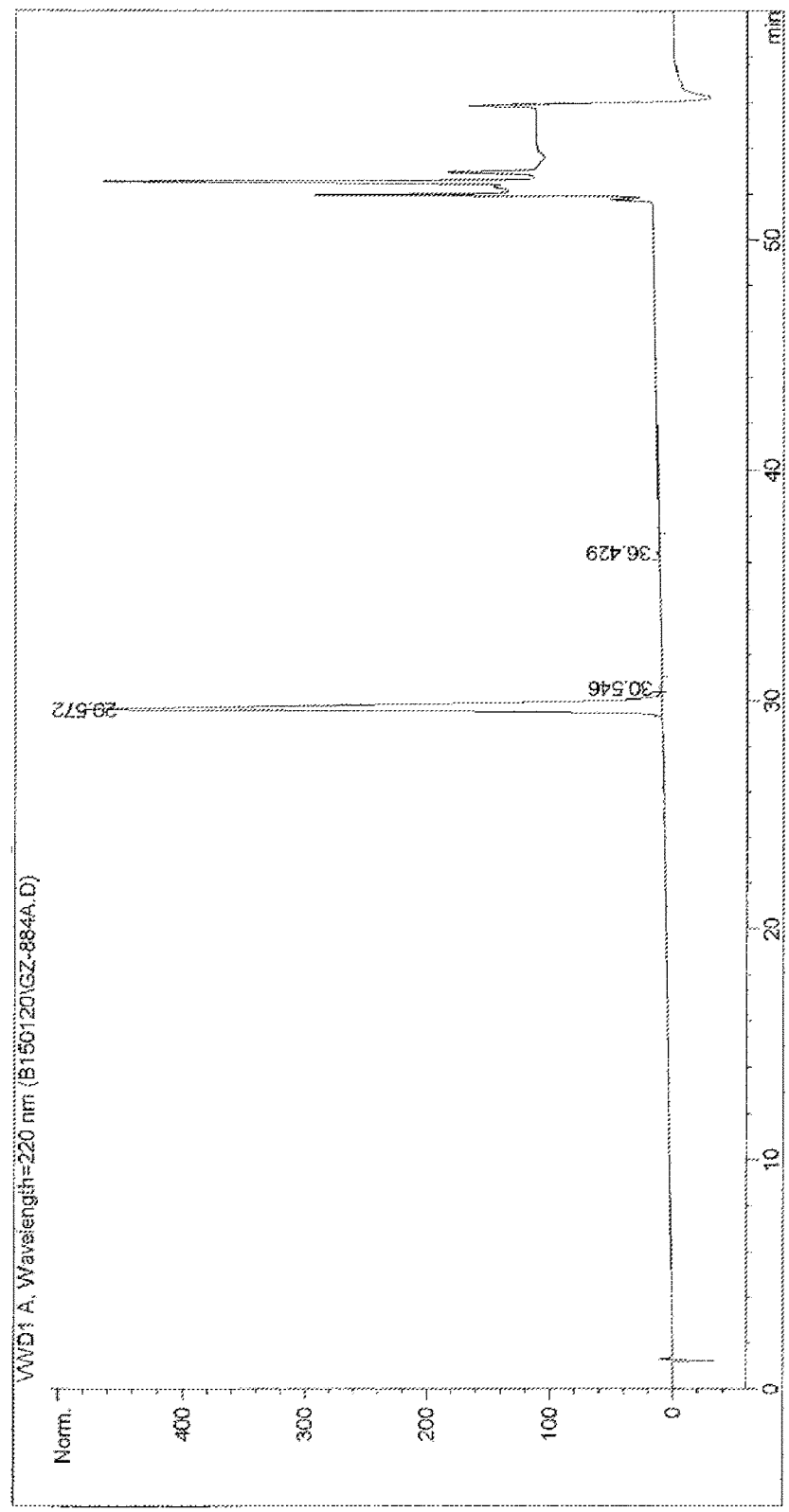
FIG. 6 represents the HPLC chromatogram of the pure dimer (Compound A). The purified dimer has a retention time of 29.57 min. Purity 99.25% (AUC). The peaks after 50 min are wash peaks.

The final purified dimer was analyzed by RP-HPLC Method 22-42-50 min (Phenomenex Aeris PEPTIDE 3.6μ XB-C18 150×4.6 mm column), MPA: 0.1% TFA in water and MPB: 0.1% TFA in ACN). LC/MS was performed to verify the expected molecular weight of the purified dimer, and the observed MW of the main product was 2859.3±2 Da. The HPLC chromatogram of pure dimer is shown in FIG. 6.

Example 2: Solid Phase Synthesis of Compound B with Fmoc-Pen(Trt)-OH and Fmoc-L-Asp(tBu)-Thr ($^{\psi Me,Me}$Pro)-OH Peptide Sequence Assembly The monomer peptide sequence Ac-Pen-N(Me)Arg-Ser-Asp-Thr-Leu-Pen-Phe(4-tBu)-β-homoGlu-D-Lys-NH$_2$ (SEQ ID NO:25) was assembled by standard solid phase peptide synthesis techniques as follows with the starting materials described in Table 6.

Solid phase synthesis was performed on a tricyclic amide linker resin (DL-form, 200-400 mesh, 0.6 mmol/g loading, 18.0 mmol scale). Approximately 2 equivalents of the Fmoc-protected amino acid was combined with 3.0 eq Oxyma (Ethyl (hydroxyimino)cyanoacetate) and 2.6 eq DIC (N,N'-Diisopropylcarbodiimide in DMF), and after 20 minutes of stirring the activated amino acid was added to the resin. After 20 minutes an extra 1.4 eq of DIC was added to the coupling solution in the reactor and the coupling reaction proceeded for approximately 1.3 hour to 2.0 hours. The coupling reaction was monitored by removing a sample of the resin from the reactor, washing it multiple times in a micro filtration syringe with DMF and IPA, and performing an appropriate calorimetric test for the specific amino acid. Fmoc-deprotection was performed using a solution of 20/80 piperidine/DMF.

Fmoc-Asp(OtBu)-Thr($^{\psi Me,Me}$Pro)-OH dipeptide was used for coupling Asp-Thr under the conditions described above.

Pen(Trt) was coupled as follows: 2.0 eq amino acid, 2.2 eq oxyma, and 2.0 eq DIC in 50:50 DCM:DMF were allowed to react for 20 minutes, after which the activated amino acid was transferred to the reactor and allowed to react for approximately 72 hrs at room temperature. The reaction was monitored by the Chloranil test.

After the final Pen(Trt) was coupled (coupling #9), Fmoc-deprotection was performed and the N-terminus of Pen(Trt) was capped with acetic anhydride. The resulting fully protected resin was washed with DMF and isopropanol (IPA) and dried under vacuum.

TABLE 6

STARTING MATERIALS FOR PEPTIDE SYNTHESIS

| Starting Material | Structure | Process Step |
|---|---|---|
| Tricyclic Amide linker resin (Ramage Resin) | 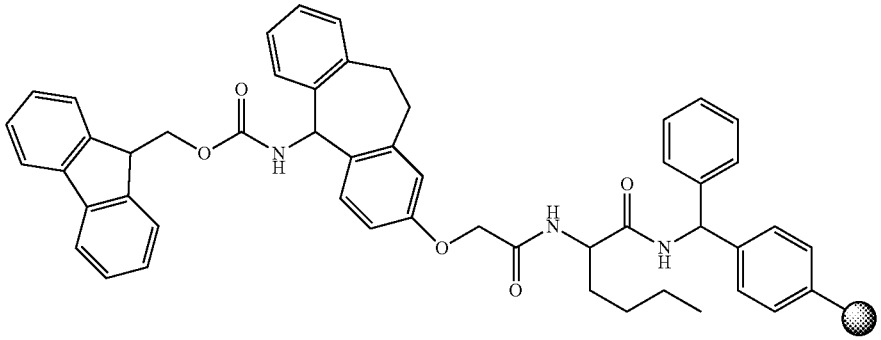 [SMILES: CCCCC(NC(=O)COc1ccc2c(c1)CCc1ccccc1C2NC(=O)OCC1c2ccccc2-c2ccccc21)C(=O)NC(c1ccccc1)c1ccc(C)cc1] | base resin |
| Fmoc-D-Lys(Boc)-OH | 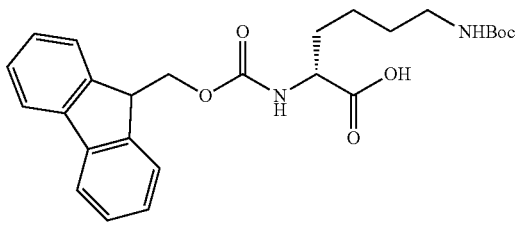 [SMILES: CC(C)(C)OC(=O)NCCCC[C@@H](NC(=O)OCC1c2ccccc2-c2ccccc21)C(=O)O] | coupling #1 |
| Fmoc-L-Aad(OtBu)-OH (also known as Fmoc-β-homoGlu(OtBu)-OH) | 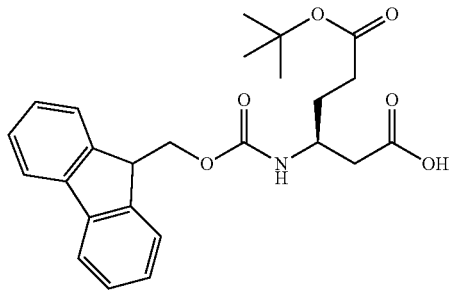 [SMILES: CC(C)(C)OC(=O)CC[C@@H](CC(=O)O)NC(=O)OCC1c2ccccc2-c2ccccc21] | coupling #2 |

TABLE 6-continued
STARTING MATERIALS FOR PEPTIDE SYNTHESIS
| Starting Material | Structure | Process Step |
| --- | --- | --- |
| Fmoc-L-(4-$^t$Bu)Phe-OH | 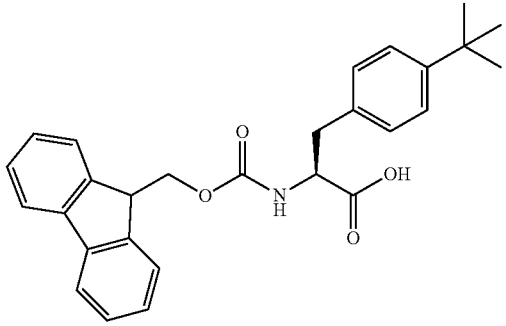 [SMILES: CC(C)(C)c1ccc(C[C@H](NC(=O)OCC2c3ccccc3-c3ccccc32)C(=O)O)cc1] | coupling # 3 |
| Fmoc-L-Pen(Trt)-OH | 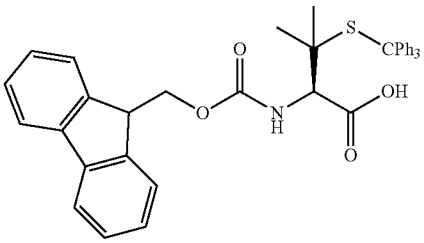 | couplings # 4 and # 9 |
| Fmoc-L-Leu-OH | 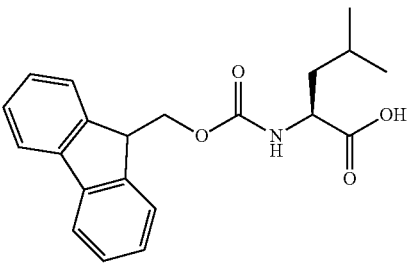 [SMILES: CC(C)C[C@H](NC(=O)OCC1c2ccccc2-c2ccccc21)C(=O)O] | coupling # 5 |
| Fmoc-L-Asp($^t$Bu)-Thr($^{\psi Me,Me}$Pro)-OH | 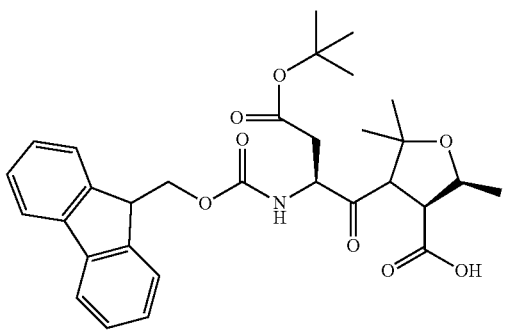 | coupling # 6 |
| Frnoc-L-Ser($^t$Bu)-OH | 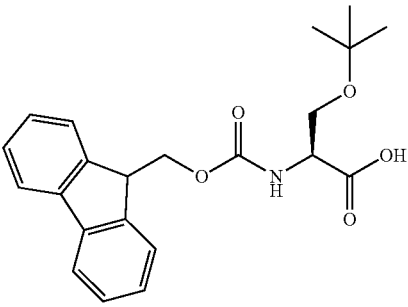 [SMILES: CC(C)(C)OC[C@H](NC(=O)OCC1c2ccccc2-c2ccccc21)C(=O)O] | coupling # 7 |

TABLE 6-continued

STARTING MATERIALS FOR PEPTIDE SYNTHESIS

| Starting Material | Structure | Process Step |
|---|---|---|
| Fmoc-L-NMe-Arg(Pbf)-OH | 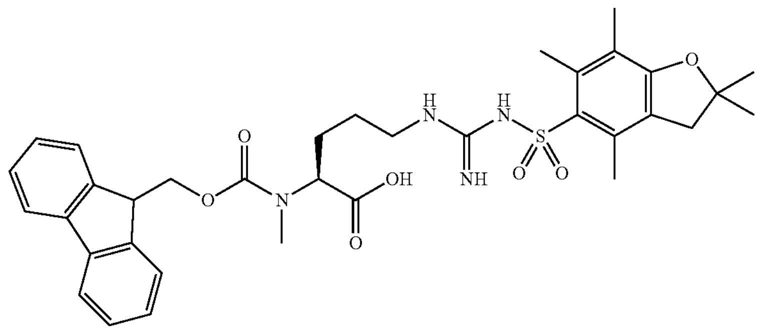 [SMILES: Cc1c(C)c(S(=O)(=O)NC(=N)NCCC[C@@H](C(=O)O)N(C)C(=O)OCC2c3ccccc3-c3ccccc32)c(C)c2c1OC(C)(C)C2] | coupling # 8 |
| Acetic anhydride (Ac$_2$O) | 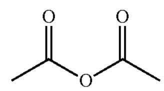 | final capping |

Cleavage and Isolation of Monomer

To cleave the monomer peptide from the resin and to remove side chain protecting groups on the peptide, the protected peptide resin was treated with a cleavage solution containing TFA:water:DODT:TIPS (90v:5v:2.5v:2.5v). Prior to use, the cleavage solution was chilled in the ice bath and thawed to room temperature. The cleavage reaction mixture was stirred for 1.5 h at room temperature. The spent resin was filtered off and washed with a 90:10 mixture of TFA:water. The combined filtrates and washes were then precipitated into cold ethyl ether and centrifuged to collect the peptide. The ethyl ether was decanted, and the solid precipitate was washed two times with cold ethyl ether. The unpurified linear monomer was dried to constant weight under vacuum.

Figure 7:
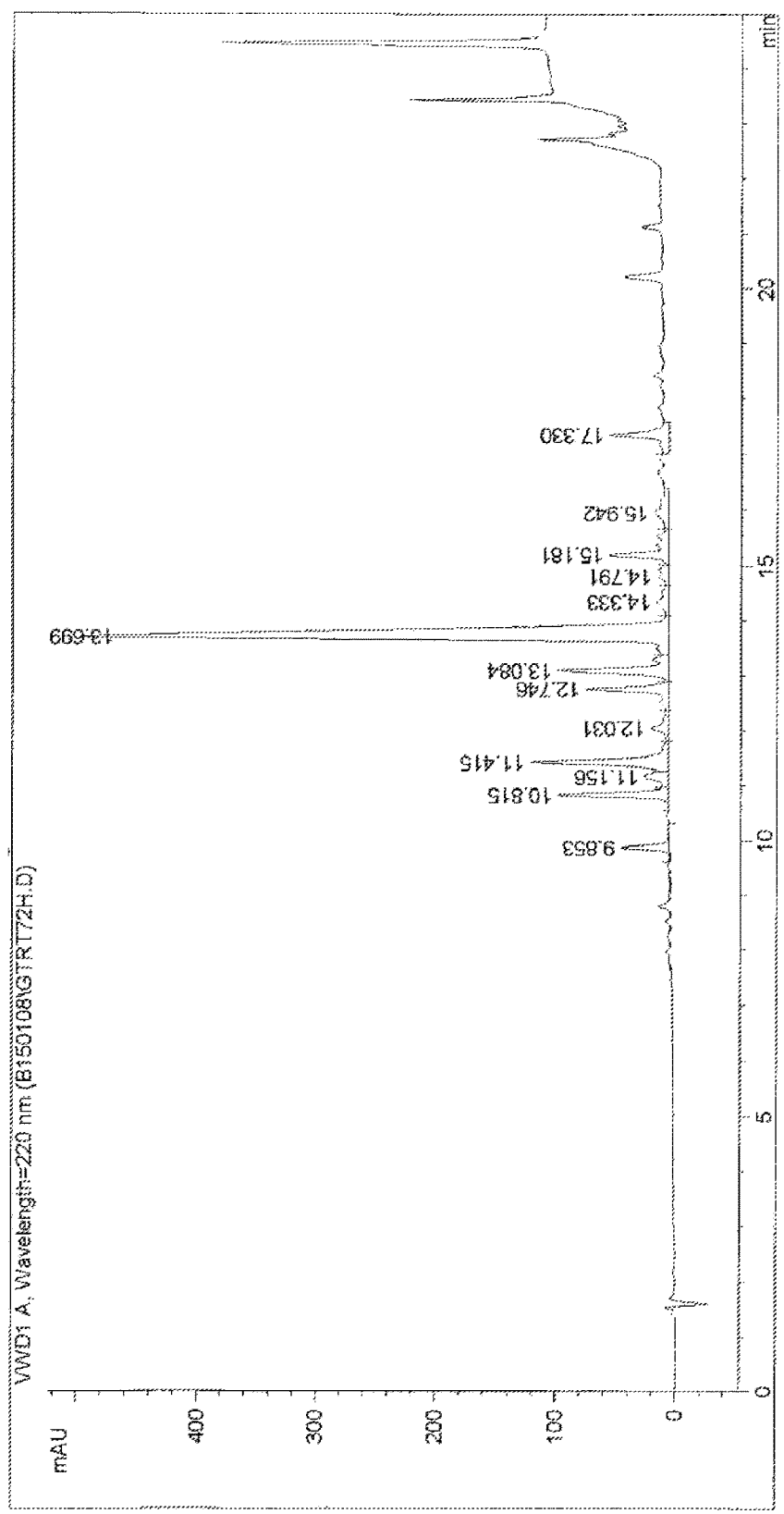
FIG. 7 represents the HPLC chromatogram of unpurified, unprotected, linear monomer. The monomer has a retention time of 13.699 min. Purity 51.23% (AUC).

The unpurified monomer was analyzed by RP-HPLC Method 20-40-20 min (Phenomenex Aeris PEPTIDE 3.6μ XB-C18 150×4.6 mm column), MPA: 0.1% TFA in water and MPB: 0.1% TFA in ACN). LC/MS was performed to verify the expected molecular weight of the linear monomer, and the observed MW of the main product was 1383.2±2 Da. The HPLC chromatogram of unpurified linear monomer is shown in FIG. 7.

Disulfide Bond Formation Pen(Trt)

The unpurified linear monomer was dissolved in 50:50 ACN:water then diluted to 2:18:80 AcOH:ACN:water to a concentration of 3 to 5 mg/mL. While stirring with a magnetic stirrer, a I$_2$/MeOH solution was added until the solution turned light yellow to yellow. When the yellow color faded out, additional I$_2$/MeOH solution was added until the reaction mixture stayed a yellow color. The reaction was monitored using LCMS and HPLC. When the reaction is completed (uncyclized monomer ≤5% (Area %), approximately 10 to 20 minutes), the reaction was quenched with ascorbic acid until a colorless solution was obtained. The reaction mixture was diluted with water (final solution ~10:90 ACN:water) and purified as discussed below.

Figure 8:
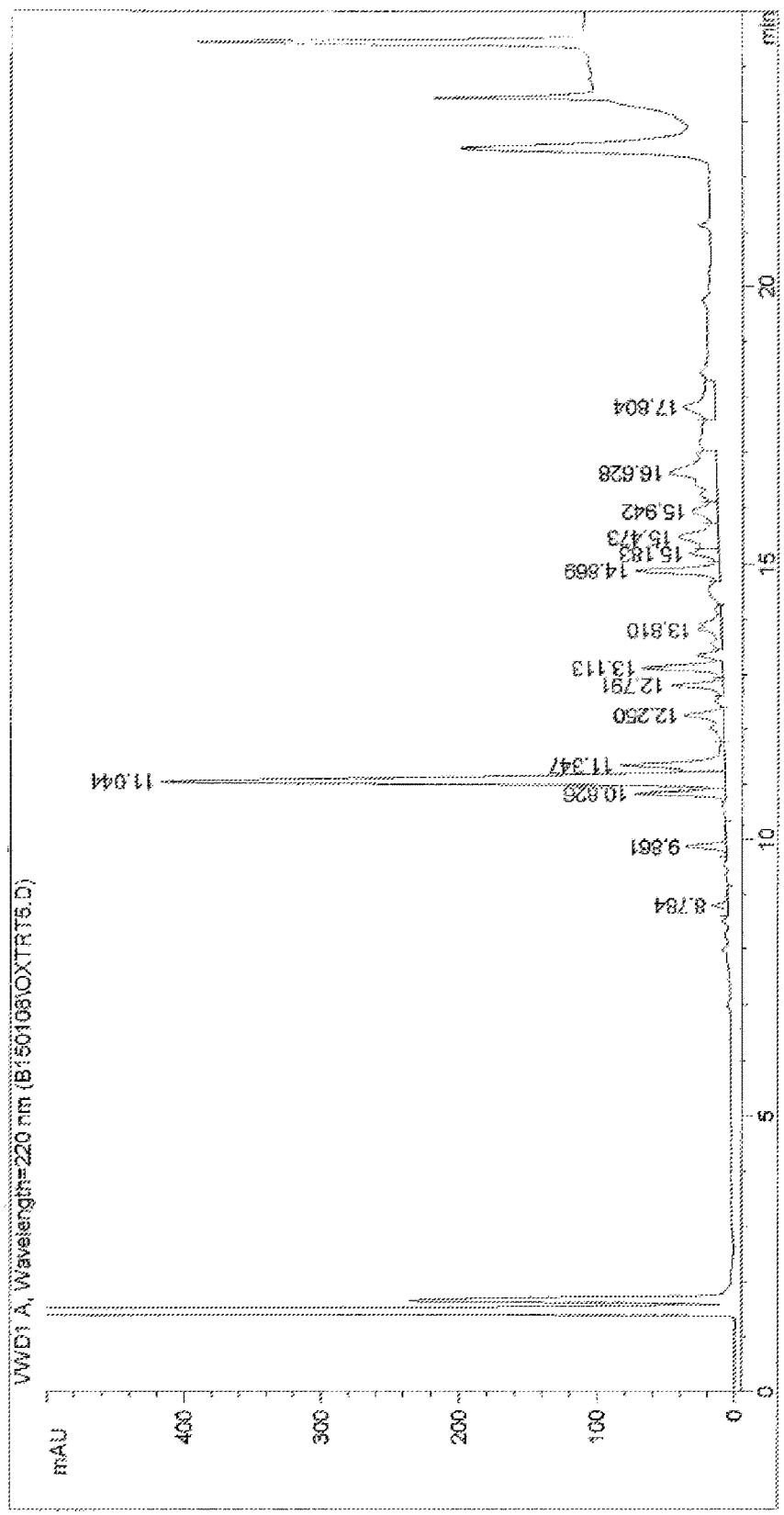
FIG. 8 represents the HPLC chromatogram of cyclized unpurified monomer. The cyclized monomer has a retention time of 11.04 min. Purity 40.10% (AUC)

The unpurified cyclized monomer was analyzed by RP-HPLC gradient Method 20-40% ACN20 min run-time (Phenomenex Aeris PEPTIDE 3.6μ XB-C18 150×4.6 mm column), MPA: 0.1% TFA in water and MPB: 0.1% TFA in ACN). LC/MS was performed to verify the expected molecular weight of the linear monomer, and the observed MW of the main product was 1381.2±2 Da. The HPLC chromatogram of cyclized unpurified monomer is shown in FIG. 8.

Purification of Cyclized Monomer

The cyclized monomer was purified on a preparative RP-HPLC system using the following conditions: Buffer A: 0.1% TFA in water and Buffer B: 0.1% TFA in ACN, Phenomenex Luna 10μ C18 250×50 mm column with a flow rate of 80 mL/min. Approximately 1.0 g cyclized monomer was purified per run using a 25:35; 60 min gradient (25% B to 35% B in 60 min). Fractions were collected (about 15 fractions per purification, ~20 mL per fraction) and analyzed by analytical HPLC Method 2-50; 20 min run-time and lyophilized. Fractions of purity >90% combined for dimerization, fraction with purity between 60 and 89 Area-% were combined for recycling, and fractions with purity <60 Area-% were discarded.

The purified monomer was analyzed by RP-HPLC gradient Method 2-50% ACN 20 min run-time (Phenomenex Aeris PEPTIDE 3.6μ XB-C18 150×4.6 mm column), MPA: 0.1% TFA in water and MPB: 0.1% TFA in ACN). LC/MS was performed to verify the expected molecular weight of the linear monomer, and the observed MW of the main product was 1381.8±2 Da.

Example 3: Synthesis of Pseudoproline Penicillamine Derivatives

Synthesis of (4R)-2,2,5,5-tetramethylthiazolidine-4-carboxylic acid (Compound C)

Compound C

A suspension of 25.0 g (167 mmol) of L(-)-penicillamine in 400 ml of acetone was heated under reflux until all the solid had dissolved (approximately 24 hours). The reaction mixture was filtered while hot and cooled to room temperature overnight. A small amount of crystals had formed overnight. The reaction mixture was kept at -20° C. overnight. The resulting solids were collected by suction filtration and washed with cold-acetone (100 mL). The thiazole product was dried in vacuo to provide Compound C as an off-white solid. (26.5 g, 83.5%) (See Preparation of N-terminal L(-)-penicillamine peptides as aldehyde sequestration agents: By Nagasawa, Herbert T. From PCT Int. Appl., 2001058928, 16 Aug. 2001)

Synthesis of (4R)-3-acetyl-2,2,5,5-tetramethyl-thiazolidine-4-carboxylic acid (Ac-Pen($^{\psi Me,Me}$Pro)-OH, Compound D-1)

Compound D-1

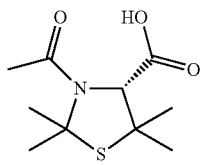

Compound C (7.56 g, 40 mmol) and acetyl N-hydroxysuccinimide ester (7.85 g, 50 mmol) were dissolved in acetonitrile (50 mL) and aqueous bicarbonate (50 mL). The resulting clear solution was stirred overnight at room temperature. Organic volatiles were removed under vacuum. The crude product was dissolved in water (50 mL). The organic phase was washed with methyl tert-butyl ether (2×50 mL). Aqueous phase was acidified with 1N. HCl solution, until pH is 3. The product was extracted into ethyl acetate (2×100 mL), combined organic layers were dried, filtered and evaporated to give the title compound (Ac-Pen($^{\psi Me,Me}$Pro)-OH, Compound D-1) as white solid (4.30 g, 50%). (See COOK, A. H., and I. M. HEILBRON. "THE CHEMISTRY OF N-amylpenicillin UP TO DECEMBER 1943". Chemistry of Penicillin. Ed. HANS T. CLARKE, JOHN R. JOHNSON, and ROBERT ROBINSON. Princeton University Press, 1949. 38-51.

Preparation of (4R)-3-(9H-fluoren-9-ylmethoxycarbonyl)-2,2,5,5-tetramethyl-thiazolidine-4-carboxylic acid (Fmoc-Pen($^{\psi Me,Me}$Pro)-OH, Compound E-1)

Compound E-1

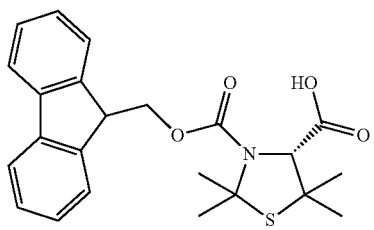

Compound C (1.89 g, 10 mmol) and Fmoc-Cl (3.09 g, 12 mmol) were dissolved in dichloromethane (50 mL). The reaction mixture was cooled to 0° C., then a solution of DiPEA in dichloromethane (2 mL) was added slowly over a period of 10 mins. The resulting clear solution was stirred at room temperature for 18 hrs. The reaction mixture was quenched with water (10 mL) and acidified using 1N HCl, until aqueous pH is ~2. The organic phase was separated, dried, filtered and evaporated to give Compound E-1 (Fmoc-Pen($^{\psi Me,Me}$Pro)-OH) as a sticky-solid (2.6 g, 64.5%).

Preparation of (4R)-5,5-dimethylthiazolidine-4-carboxylic acid (Compound H)

Compound H

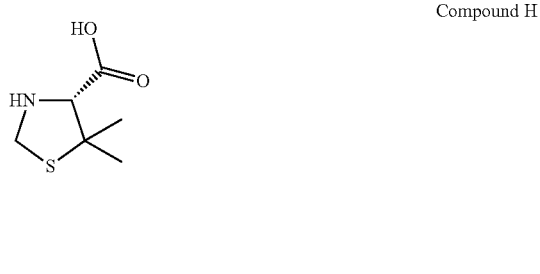

Compound H was prepared as described for Compound C, replacing acetone with paraformaldehyde.

Preparation of (4R)-3-acetyl-5,5-dimethyl-thiazolidine-4-carboxylic acid (Ac-Pen(Pro)-OH, Compound I)

Compound I-1

Compound I-1 was prepared starting with Compound H as described above for Compound D.

Synthesis of Penicillamine-Containing Peptides
TABLE 7
STARTING MATERIALS FOR PEPTIDE SYNTHESIS
| Starting Material | Structure |
|---|---|
| Cbz-D-Lys(Boc)-OH | 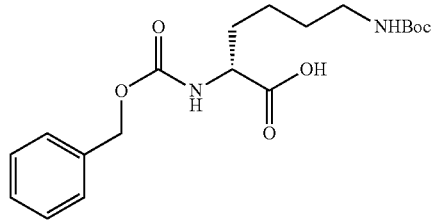 [SMILES: CC(C)(C)OC(=O)NCCCC[C@@H](NC(=O)OCc1ccccc1)C(=O)O] |
| D-Lys (Boc)-NH2 | 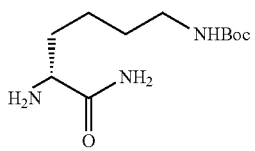 |
| Cbz-L-Aad(O'Bu)-OH (also known as Cbz-β-HomoGlu(O'Bu)-OH) | 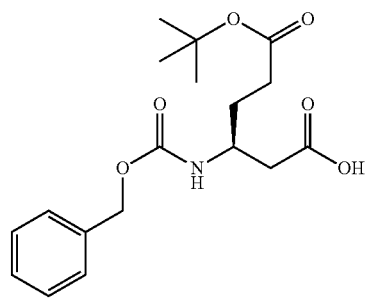 [SMILES: CC(C)(C)OC(=O)CC[C@@H](CC(=O)O)NC(=O)OCc1ccccc1] |
| Cbz-L-(4'Bu)Phe-OH | 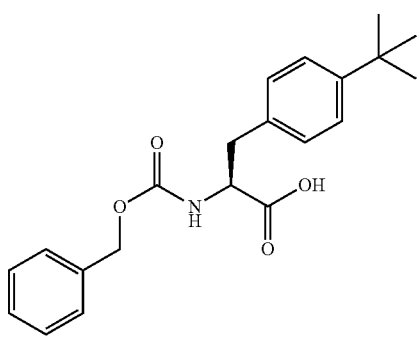 [SMILES: CC(C)(C)c1ccc(C[C@H](NC(=O)OCc2ccccc2)C(=O)O)cc1] |
| Fmoc-L-Pen(Acm)-OH | 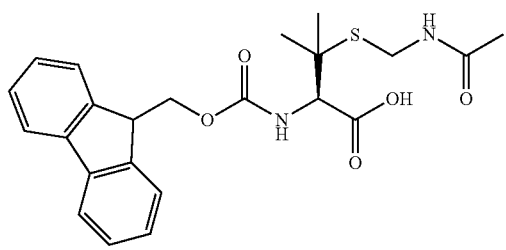 [SMILES: CC(=O)NCSC(C)(C)[C@H](NC(=O)OCC1c2ccccc2-c2ccccc21)C(=O)O] |
| Cbz-L-Pen(Acm)-OH | 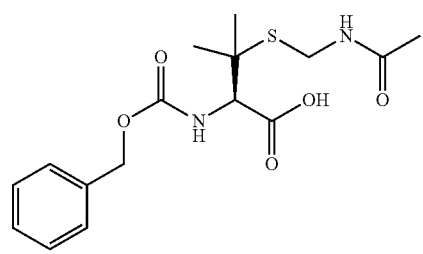 [SMILES: CC(=O)NCSC(C)(C)[C@H](NC(=O)OCc1ccccc1)C(=O)O] |

TABLE 7-continued

STARTING MATERIALS FOR PEPTIDE SYNTHESIS

| Starting Material | Structure |
| --- | --- |
| Cbz-L-Pen(Trt)-OH | 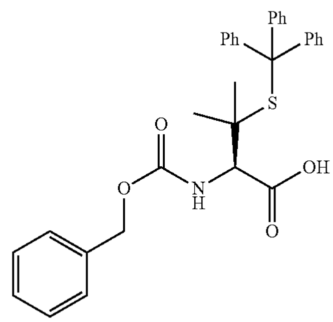 [SMILES: CC(C)(SC(c1ccccc1)(c1ccccc1)c1ccccc1)[C@H](NC(=O)OCc1ccccc1)C(=O)O] |
| Cbz-L-Leu-OH | 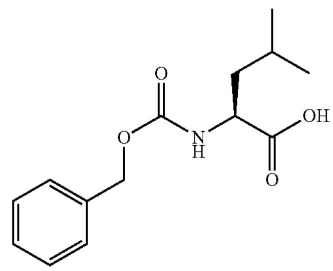 [SMILES: CC(C)C[C@H](NC(=O)OCc1ccccc1)C(=O)O] |
| Cbz-L-Leu-OMe | 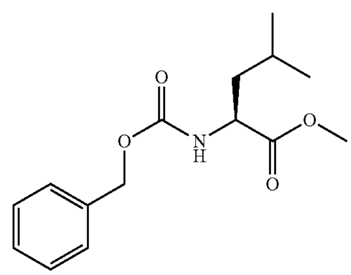 [SMILES: COC(=O)[C@H](CC(C)C)NC(=O)OCc1ccccc1] |
| Cbz-L-Thr(${}^{t}$Bu)OH | 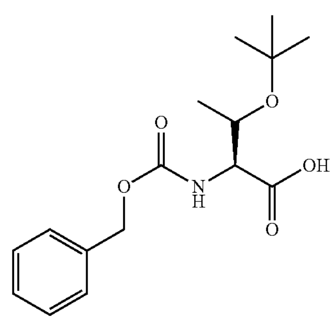 [SMILES: CC(OC(C)(C)C)[C@H](NC(=O)OCc1ccccc1)C(=O)O] |
| Cbz-L-Asp(${}^{t}$Bu)-OH | 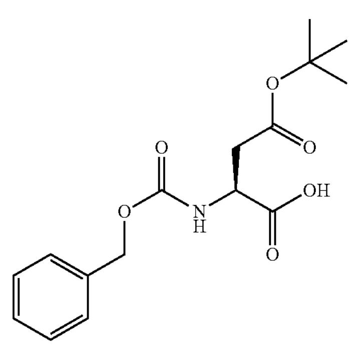 [SMILES: CC(C)(C)OC(=O)C[C@H](NC(=O)OCc1ccccc1)C(=O)O] |

TABLE 7-continued

STARTING MATERIALS FOR PEPTIDE SYNTHESIS

| Starting Material | Structure |
|---|---|
| Cbz-L-Ser(ᵗBu)-OH | |
| Cbz-L-NMe-Arg(Pbf)-OH | |
| Acetic anhydride (Ac₂O) | |

Synthesis of Ac-Pen($^{\Psi Me,Me}$Pro)-N-Me-Arg(PM-Ser(t-Bu)-Asp(OᵗBu)-Thr(ᵗBu)-Leu(-OH) (SEQ ID NO:3)

Cbz-Thr(ᵗBu)-Leu-OMe

To a suspension of Cbz-Thr(ᵗBu)-OH (0.05 mol) and NHS (0.075 mol) in DCM (250 mL), at 0° C., EDC.HCl (0.1 mol) was added over 10 minutes, and the mixture was stirred for 2 hours. A solution of H-Leu(OMe) in DCM was then added at 0° C., and the resulting mixture was stirred at room temperature for 18 h. The reaction mixture was diluted with water (100 mL) and the organic phase was washed with 1N HCl (100 mL), saturated NaHCO₃ (100 mL), and brine (100 mL). It was dried and concentrated to yield the title compound as a viscous oil, 15 g.

H-Thr(ᵗBu)-Leu-OMe

To a solution of Cbz-Thr(ᵗBu)-Leu-OMe (15 g) was added Pd/C (5%). The mixture was stirred under a hydrogen atmosphere (balloon) for 18 h. The mixture was filtered through a pad of celite and concentrated to yield the title compound as a viscous oil, 6.2 g (quantitative)

Cbz-Asp(OᵗBu)-Thr(ᵗBu)-Leu-OMe

To a suspension of Cbz-Asp(OᵗBu)-OH (1.2 equiv) and NHS (1.5 equiv) in DCM (50 mL), at 0° C., was added EDC.HCl (2.0 equiv), and the clear solution was stirred for 2 h. Then a solution of H-Thr(ᵗBu)-Leu-OMe (6.2 g) in DCM (50 mL) was added. The mixture was then stirred at room temperature for 18 h. The reaction mixture was diluted with water (100 mL) and the organic layer was separated out. The organic layer was washed with 1N HCl (100 mL), saturated NaHCO₃ (100 mL), brine (100 mL), dried, and concentrated to yield the title compound as a viscous oil. The crude product was purified by flash chromatography using Hexane/EtOAc (1:1). Yield of the pure compound 10 g (80.25%).

H-Asp(OᵗBu)-Thr(ᵗBu)-Leu-OMe

To a solution of Cbz-Asp(OᵗBu)-Thr(ᵗBu)-Leu-OMe (9.10 g) in methanol (80 mL) was added Pd/C. The mixture was stirred under a hydrogen atmosphere (balloon) for 24 h. Then it was filtered through a pad of celite and concentrated to yield the title compound as a viscous oil, 4.7 g (66.29%).

Cbz-Ser(ᵗBu)-Asp(OᵗBu)-Thr(ᵗBu)-Leu-OMe (SEQ ID NO: 77)

To a solution of Cbz-Ser(ᵗBu)-OH (1.2 equiv) and NHS (1.5 equiv) in DCM (50 mL), at 0° C., was added EDC.HCl (2.0 equiv) and the mixture was stirred at 0° C. for 2 h. Then a solution of H-Asp(OᵗBu)-Thr(ᵗBu)-Leu-OMe (4.7 g) in DCM (50 mL) was added, and the mixture was stirred at room temperature for 18 h. The mixture was diluted with water (100 mL) and the organic phase was separated. The organic phase was washed with 1N HCl (100 mL0, saturated. NaHCO$_3$ (100 mL), brine (100 mL), dried, and concentrated to yield the title compound as a viscous oil, 2.8 g (37.33%).

H-Ser($^t$Bu)-Asp(O$^t$Bu)-Thr($^t$Bu)-Leu-OMe (SEQ ID NO: 77)

To a solution of Cbz-Ser($^t$Bu)-Asp(O$^t$Bu)-Thr($^t$Bu)-Leu-OMe (SEQ ID NO:77) (2.8 g) in methanol (50 ml) was added Pd/C, and the mixture was stirred under a hydrogen atmosphere (balloon) for 24 h. Then it was filtered through a pad of celite and concentrated to yield the title compound as a viscous oil, 2.0 g (87.33%).

Cbz-N-Me-Arg(Pbf)-Ser($^t$Bu)-Asp(O$^t$Bu)-Thr($^t$Bu)-Leu-OMe (SEQ ID NO:5)

To a mixture of Cbz-N-Me-Arg(Pbf)-OH (2.0 g) and NHS (1.5 equiv) in DCM (25 mL) at 0° C. was added EDC.HCl, and the mixture was stirred at 0° C. for 2 h. Then a solution of H-Ser($^t$Bu)-Asp(O$^t$Bu)-Thr($^t$Bu)-Leu-OMe (2.0 g) in DCM (25 mL) was added, and the mixture was stirred at room temperature for 16 h. The mixture was diluted with water (100 mL), and the DCM layer was separated. The DCM-extract was washed with 1N HCl, saturated. NaHCO$_3$, brine, dried, and concentrated to yield the title compound as a sticky solid, 1.2 g (34.28%).

H-N-Me-Arg(Pbf)-Ser($^t$Bu)-Asp(O$^t$Bu)-Thr($^t$Bu)-Leu-OMe (SEQ ID NO:5)

To a solution of Cbz-N-Me-Arg(Pbf)-Ser($^t$Bu)-Asp(O$^t$Bu)-Thr($^t$Bu)-Leu-OMe (1.2 g) in methanol was added Pd/C. The mixture was stirred under a hydrogen atmosphere (balloon) for 24 h. The mixture was filtered through a pad of celite and concentrated to yield the title compound as a viscous oil, 1.0 g (94%).

Ac-Pen($^{\Psi Me,Me}$Pro)-N-Me-Arg(Pbf)-Ser($^t$Bu)-Asp(O$^t$Bu)-Thr($^t$Bu)-Leu-OMe (SEQ ID NO: 3)

To a mixture of Ac-Pen($^{\Psi Me,Me}$Pro)-OH (250 mg) and NHS (1.5 equiv), in DCM at 0° C., was added EDC.HCl (2.0 equiv), and the mixture was stirred at room temperature for 2 h. Then a solution of H-N-Me-Arg(Pbf)-Ser($^t$Bu)-Asp(O$^t$Bu)-Thr($^t$Bu)-Leu-OMe (1.0 g) in DCM was added, and the mixture was stirred at room temperature for 24 h. The reaction mixture was diluted with water and DCM layer was separated. DCM extract was washed with 1N HCl, saturated. NaHCO$_3$, brine, dried, and concentrated to yield the title compound as a sticky solid, 800 mg (66.6%).

Synthesis of H-Pen ($^{\Psi Me,Me}$Pro)-Phe(4-t-Bu)-β-homoGlu(O-t-Bu)-(D)-Lys(Boc)-NH$_2$ (SEQ ID NO:4)

Cbz-(D)-Lys(Boc)-NH$_2$

To a clear solution of Cbz-(D)-Lys(Boc)-OH (10.0 g, 26.288 mmol), in anhydrous CH$_2$Cl$_2$ (70 mL), at 0° C., was added NHS (4.54 g, 39.447 mmol, 1.5 equiv), followed by EDC.HCl (10.0 g, 52.164 mmol, 2.0 equiv). The mixture was stirred as it warmed to room temperature and then at room temperature for 2 hours. Then the mixture was again cooled to 0° C. and conc. NH$_4$OH (9.0 mL, 4.8 equiv) was added dropwise over 10 minutes. The resulting slurry was stirred at room temperature overnight. The reaction mixture was diluted with CH$_2$Cl$_2$/H$_2$O (200 mL/30 mL) when a clear biphasic mixture resulted. Transferred it to a separatory funnel, and collected the DCM layer. Then re-extracted the aqueous layer with DCM (2×40 mL). Washed the combined DCM-extract with brine, dried (MgSO4), and concentrated to yield the title compound as colorless solid.

H-(D)-Lys(Boc)-NH$_2$

To a clear solution of Cbz-(D)-Lys(Boc)-NH$_2$ in methanol was added 20% Pd(OH)$_2$/C (5 wt %). The reaction vessel was then evacuated/flushed with hydrogen gas and stirred under a hydrogen atmosphere (balloon) overnight. The reaction mixture was filtered through a pad of celite and concentrated to dryness to yield the title compound as a colorless sticky solid.

Cbz-β-homoGlu(O-t-Bu)-(D)-Lys(Boc)-NH$_2$

To a clear solution of Cbz-Glu(O-t-Bu)-OH (500 mg, 1.481 mmol) in anhydrous DMF (10 mL), at room temperature, was added NHS (215 mg, 1.868 mmol, 1.30 equiv), followed by EDC.HCl (405 mg, 2.107 mmol, 1.50 equiv). The clear, colorless solution was stirred at room temperature for 1.0 h. Then H-(D)-Lys(Boc)-NH$_2$ (345 mg, 1.408 mmol, 1.0 equiv) was added, and the clear, colorless reaction-mixture was stirred at room temperature overnight. Then the clear, colorless reaction-mixture was diluted with water (80 mL, 8 volumes) when the title compound precipitated out as a colorless solid. The product was collected it by suction filtration, rinsed with more water (3×10 mL), and air-dried. Weight of the colorless solid, 0.620 g (78%).

H-β-homoGlu(O-t-Bu)-(D)-Lys(Boc)-NH$_2$

To a clear solution of Cbz-β-homoGlu(O-t-Bu)-(D)-Lys(Boc)-NH$_2$ (600 mg) in methanol (20 mL) was added 20% Pd(OH)$_2$/C (100 mg). The reaction vessel was evacuated/flushed with hydrogen, and then stirred under a hydrogen atmosphere (balloon) overnight. Then the mixture was filtered through a pad of celite, and concentrated to yield the title compound as a sticky glue. Yield, quantitative.

Cbz-Phe(4-t-Bu)-β-homoGlu(O-t-Bu)-(D)-Lys(Boc)-NH$_2$

To a slurry of Cbz-Phe(4-t-Bu)-OH (390 mg, 1.097 mmol) and NHS (148 mg, 1.286 mmol, 1.3 equiv) in anhydrous CH$_2$Cl$_2$ (8.0 mL) was added EDC.HCl (247 mg, 1.288 mmol, 1.3 equiv), and the mixture was stirred at room temperature for 3 hours. Then a clear solution of H-β-homoGlu(O-t-Bu)-(D)-Lys(Boc)-NH$_2$ (425 mg, 0.990 mmol) in CH$_2$Cl$_2$ (10 mL) was added and the mixture was stirred at room temperature overnight. Then the mixture was diluted with DCM/saturated NaHCO3 (20 mL/10 mL), the layers were separated. The DCM extract was washed with 0.5 M KHSO4, brine, dried (MgSO4), and concentrated to yield the title compound as a colorless sticky solid.

H-Phe(4-t-Bu)-β-homoGlu(O-t-Bu)-(D)-Lys(Boc)-NH$_2$

To a solution of Cbz-Phe(4-t-Bu)-β-homoGlu(O-t-Bu)-(D)-Lys(Boc)-NH$_2$ in methanol was added 20% Pd(OH)$_2$/C. The reaction vessel was then evacuated/flushed with hydrogen, and the mixture was stirred under a hydrogen atmosphere (balloon) overnight. Then it was filtered through a pad of celite and concentrated to yield the title compound as a sticky solid. Yield, quantitative.

H-Pen($^{\Psi Me,Me}$Pro)-Phe(4-t-Bu)-β-homoGlu(O-t-Bu)-(D)-Lys(Boc)-NH$_2$ (SEQ ID NO: 4)

To a mixture of Cbz-Pen($^{\Psi Me,Me}$Pro)-OH (250 mg) and NHS (1.5 equiv), in DCM at 0° C., is added EDC.HCl (2.0 equiv), and the mixture is stirred at room temperature for 2 h. Then a solution of H-Phe(4-t-Bu)-β-homoGlu(O-t-Bu)-(D)-Lys(Boc)-NH$_2$ (1.0 g) in DCM is added, and the mixture is stirred at room temperature for 24 h. The reaction mixture is diluted with water and DCM layer is separated. DCM extract is washed with 1N HCl, saturated. NaHCO$_3$, brine, dried, and concentrated to yield the title compound.

Example 4: Synthesis of Compound B Via Di-, Tetra-, and Hexa-Peptide Fragments

Synthesis of the C-Terminal 4-AA Fragment: H-Pen(Acm)-Phe(4-$^t$Bu)-b-homoGlu(O$^t$Bu)-(D)-Lys(Boc)-NH$_2$ (SEQ ID NO:4)

Cbz-β-homoGlu(O$^t$Bu)-D-Lys(Boc)-NH$_2$ (Z-P$_2$-NH$_2$)

To a solution of Cbz-β-homoGlu(O$^t$Bu)-OH (50.25 g, 143 mmol, 1.0 eq) and H-D-Lys(Boc)-NH$_2$ (45.605 g, 185.9 mmol, 1.3 eq) in DMF (650 mL) under N$_2$ at 0° C. was added Cl-HOBt (24.253 g, 143 mmol, 1.0 eq). Then at −5° C., HBTU (59.664 g, 157.3 mmol, 1.1 eq) was added. Additional DMF (200 mL) was charged, and at the same time the inner temperature was maintained below −5° C. After the dissolution of the HBTU, DIPEA was added dropwise to adjust the pH of the reaction to about 6. During the addition of the DIPEA, the reaction temperature was kept at −3° C. or below. The progress of the reaction was monitored with TLC. A total of 1.8 equivalents of DIPEA was added After five hours from the initial addition of DIPEA, the reaction mixture was poured into 0.5N HCl (aq., 10 L, <10° C.), the resulting solid was collected and washed with 0.5 N HCl (aq. 3×), NaHCO$_3$ (sat., aq., 3×), H$_2$O (3×), and n-hexane (1×). After removing the volatile in vacuo, Z-P$_2$-NH$_2$ (79.1 g, 95.58%) was obtained with 84.6% HPLC purity.

H-β-homoGlu(O$^t$Bu)-D-Lys(Boc)-NH$_2$ (H-P$_2$-NH$_2$)

To a solution of Z-P$_2$-NH$_2$ (5.523 g, 9.545 mmol) in MeOH (110 mL) was added Pd/C (1.064 g, 10 wt. % loading, wet with 63.1 wt. % H$_2$O), after flushing with N$_2$, H$_2$ (in a balloon) was applied. The progress of the reaction was followed by TLC. After 1 hr, the Pd/C was removed, and the reaction was washed with MeOH (4×). The combined filtrate was concentrated in vacuo to give H-P$_2$-NH$_2$ (5.252 g).

Z-Phe(4-$^t$Bu)-β-homoGlu(O$^t$Bu)-D-Lys(Boc)-NH$_2$ (Z-P$_3$-NH$_2$)

To a solution of H-P$_2$-NH$_2$ (5.252 g, 9.545 mmol, 1.0 eq) and Z-Phe(4-$^t$Bu)-OH (3.291 g, 9.259 mmol, 0.97 eq) in DMF (70 mL) under N$_2$ at 0° C. was added Cl-HOBt (1.619 g, 9.545 mmol, 1.0 eq). Then at −5° C., HBTU (3.982 g, 10.5 mmol, 1.1 eq) was added. After the dissolution of the HBTU, DIPEA was added dropwise to adjust the pH of the reaction to about 6. During the addition of the DIPEA, the reaction temperature was kept at −2° C. or below. The progress of the reaction was monitored with TLC. A total of 1.8 eq of DIPEA was added. After 4.3 h, the reaction mixture was diluted with ethyl acetate (300 mL), and 0.5N HCl (aq., 70 mL, <10° C.). The aqueous layer was extracted by ethyl acetate (100 mL, 2×). The combined ethyl acetate layer was washed with 0.5 N HCl (aq. 4×), H$_2$O (1×), NaHCO$_3$ (sat., aq., 3×), H$_2$O (2×), and brine (1×). After drying on Na$_2$SO$_4$ (anhydrous), and removing the volatiles in vacuo, Z-P$_3$-NH$_2$ (7.08 g, 97.58%) was obtained with 87.5% HPLC purity.

H-Phe(4-$^t$Bu)-β-homoGlu(O$^t$Bu)-D-Lys(Boc)-NH$_2$ (H-P$_3$-NH$_2$)

To a solution of Z-P$_3$-NH$_2$ (7.062 g) in MeOH (140 mL) was added Pd/C (1.064 g, 10 wt. % loading, wet with 63.1 wt. % H$_2$O), after flushing with N$_2$, H$_2$ (in a balloon) was applied. The progress of the reaction was followed by TLC. After 1 hr, the Pd/C was removed, and the reaction washed with MeOH (4×). The combined filtrate was concentrated in vacuo to give H-P$_3$-NH$_2$ (5.784 g, 98.8%) with 89.0% HPLC purity.

Fmoc-Pen(Acm)-Phe(4-$^t$Bu)-β-hGlu(O$^t$Bu)-D-Lys(Boc)-NH$_2$ (SEQ ID NO:4) (Fmoc-P$_4$-NH$_2$)

To a solution of H-P$_3$-NH2 (5.766 g, 8.9 mmol, 1.0 eq) and Fmoc-Pen(Acm)-OH (3.82 g, 8.633 mmol, 0.97 eq) in DMF (72 mL) under N$_2$ at 0° C. was added Cl-HOBt (1.509 g, 8.9 mmol, 1.0 eq). Then at −5° C., HBTU (3.713 g, 9.79 mmol, 1.1 eq) was added. After the dissolution of the HBTU, DIPEA was added dropwise to adjust the pH of the reaction to about 6. During the addition of the DIPEA, the reaction temperature was kept at −2° C. or below. The progress of the reaction was followed by TLC. A total of 1.9 eq of DIPEA was added. After 3 hr, the reaction mixture was diluted with ethyl acetate (350 mL) and 0.5N HCl (aq., 100 mL, <10° C.). The aqueous layer was extracted with ethyl acetate (100 mL, 2×). The combined ethyl acetate layers were washed with 0.5 N HCl (aq. 4×), H$_2$O (1×), NaHCO$_3$ (sat., aq., 3×), H$_2$O (2×), and brine (1×). After drying over Na$_2$SO$_4$ (anhydrous), and removing the volatiles in vacuo, Fmoc-P$_4$-NH$_2$ (8.39 g, 90.6%) was obtained with 95.2% HPLC purity.

H-Pen(Acm)-Phe(4-$^t$Bu)-β-homoGlu(O$^t$Bu)-D-Lys(Boc)-NH$_2$ (SEQ ID NO:4) (H-P$_4$-NH$_2$)

To a solution of Fmoc-P$_4$-NH$_2$ (7.96 g, 7.417 mmol, 1.0 eq) in DMF (40 mL) was added piperidine (3.665 mL, 37.1 mmol, 5 eq). The progress of the reaction was followed by TLC. After 0.5 hr, petroleum ether was used to wash the reaction mixture. The resulting lower layer (DMF solution) was slowly poured into 0.5 N HCl (aq., 400 mL, <10° C.), and stirred for 10 min. The solid was collected and washed with 0.5 N HCl (aq. 3×), H$_2$O (2×), a mixture of NaHCO$_3$ (sat., aq.)/H$_2$O (½ by volume, 3×), and H$_2$O (3×). After removal of the volatiles, H-P$_4$-NH$_2$ (3.564 g) was obtained with 93.3% HPLC purity.

To the above solid, ethyl acetate (30 mL) was added and stirred for 10 min. The solid (solid A) was collected, and the filtrate was concentrated to 15 mL by volume. The concentrated ethyl acetate solution was slowly poured into petroleum ether (150 mL), and stirred for 10 mins. The resulting solid was collected (solid B). Both solid A and solid B were combined and dried in vacuo to give H-P$_4$-NH$_2$ (3.504 g, 55.5%) with 94.3% HPLC purity.

Synthesis of the N-Terminal 6-AA Fragment Via 4+2 Coupling: Fmoc-Pen(Acm)-N(Me)-Arg(pbf)-Ser($^t$Bu)-Asp(O$^t$Bu)-Thr($^t$Bu)-Leu-OMe (SEQ ID NO:3)

Fmoc-Pen(Acm)-N-Me-Arg(Pbf)-OH

To a solution of Fmoc-Pen(Acm)-OH (4 mmol, 1.0 eq) and HOAt (0.4 mmol, 0.1 eq) at −15° C. in DMF (16 mL, anhydrous) under N$_2$ was added HATU (4.2 mmol, 1.05 eq). DIPEA (4.4 mmol, 1.1 eq) was added in portions. The reaction mixture was stirred at −10-0° C. for ~1 hr. (Solution A) TLC was used to follow the progress of the reaction.

In another flask, a solution of H-N-Me-Arg(Pbf)-OH (4.4 mmol, 1.1 eq) in DMF (25 mL, anhydrous) under N$_2$ was added BSA (14.52 mmol, 3.3 eq). The mixture was warmed up to 45° C. and stirred for 4-5 hr. (Solution B)

To a cooled solution B (−15 to −10° C.), solution A was added and the combined mixture was stirred at 0° C. for 19 hr. The reaction progress was monitored by HPLC.

With the ice-cooled bath, the reaction mixture was diluted with ethyl acetate (50 mL), and 5% H$_3$PO$_4$ (aq., 150 mL), and stirred for 20 min. The mixture was diluted once more with ethyl acetate (100 mL). The organic layer was separated and washed with 5% H$_3$PO$_4$ (aq. 150 mL, 3×) H$_2$O (150 mL, 2×) and brine (100 mL, 2×). After drying and removal of the volatile, 3.485 g of solid product was obtained with 62.5% HPLC purity. Crude product was purified with prep-HPLC to give pure product (52.37%) with 97.7% purity.

Fmoc-Pen(Acm)-N(Me)-Arg(pbf)-Ser($^t$Bu)-Asp(O$^t$Bu)-Thr($^t$Bu)-Leu-OMe (SEQ ID NO: 3)

To a solution of Fmoc-Pen(Acm)-N-Me-Arg(Pbf)-OH (3.55 g, 4.1 mmol), H-Ser($^t$Bu)-Asp(O$^t$Bu)-Thr($^t$Bu)-Leu-OMe (2.46 g, 3.9 mmol), HATU (1.56 g, 4.1 mmol), HOAt (0.53 g, 3.9 mmol) in THF (41 mL) was added DIEA (1.26 g, 9.75 mmol) at −5° C. The mixture was stirred for 5 hr at this temperature. HPLC showed the reaction was complete, and the mixture was charged with EtOAc (120 mL), washed by 5% H$_3$PO$_4$ (120 mL×3), 10% Na$_2$CO$_3$ (120 mL×3) and brine (120 mL×2). The resulting organic layer was then dried over MgSO$_4$, concentrated to give crude product (5.6 g, 94.6%) with 89.8% purity.

Synthesis of the N-Terminal 6-AA Fragment Via 5+1 Coupling: Ac-Pen(Acm)-N(Me)-Arg(pbf)-Ser($^t$Bu)-Asp(O$^t$Bu)-Thr($^t$Bu)-Leu-OMe (SEQ ID NO:3) (Ac-P$_6$-OH)

Cbz-Thr($^t$Bu)-Leu-OMe

To a clear, colorless solution of Cbz-Thr($^t$Bu)-OH (13.60 g, 44.013 mmol) and NHS (6.60 g, 57.391 mmol, 1.30 equiv), in DMF (90 mL), at 0° C., was added EDC.HCl (11.30 g, 58.946 mmol, 1.34 equiv), over 10 minutes, and the mixture was stirred at room temperature for 1 h. Then cooled the clear reaction mixture to 0° C. and added H-Leu (OMe).HCl (8.80 g, 48.431 mmol, 1.10 equiv), as a solid, followed by dropwise addition of DIEA (11.50 mL, 66 mmol, 1.50 equiv). The mixture was then stirred at room temperature overnight. The reaction mixture was diluted with water (100 mL) and extracted with EtOAc (3×75 mL). The combined ethyl acetate extract was washed with 1N HCl (100 mL), saturated NaHCO$_3$ (100 mL), and brine (100 mL). It was dried (MgSO$_4$), and concentrated to yield the title compound as a viscous oil/glue (17.66 g, 92%).

H-Thr($^t$Bu)-Leu-OMe

To a solution of Cbz-Thr($^t$Bu)-Leu-OMe (15.90 g), in methanol (200 mL), was added 20% Pd(OH)$_2$/C (3.0 g). The reaction vessel was evacuated/flushed with hydrogen (3×), and the mixture was stirred under a hydrogen atmosphere (balloon) overnight. The mixture was filtered through a pad of celite, and concentrated to yield the title compound as a viscous oil (10.47 g, 95%).

Cbz-Asp(O$^t$Bu)-Thr($^t$Bu)-Leu-OMe

To a suspension of Cbz-Asp(O$^t$Bu)-OH.H2O (6.60 g, 19.337 mmol) and NHS (3.34 g, 29.04 mmol, 1.50 equiv), in DMF (35 mL), at 0° C., was added EDC.HCl (9.26 g, 48.30 mmol, 2.5 equiv), and the mixture was stirred at room temperature for 1 h. Then added this mixture to a suspension of H-Thr($^t$Bu)-Leu-OMe (5.48 g, 18.145 mmol) in DMF (30 mL), at 0° C. The mixture was then stirred at room temperature overnight. The reaction mixture was diluted with water (100 mL) and the title compound separated out as a glue/oil. It was extracted with EtOAc (3×75 mL). The combined EtOAc extract was washed with 1N HCl (100 mL), saturated NaHCO3 (100 mL), brine (100 mL), dried (MgSO4), and concentrated to yield the title compound as a puffy solid (9.80 g, 89%).

H-Asp(O$^t$Bu)-Thr($^t$Bu)-Leu-OMe

To a solution of Cbz-Asp(O$^t$Bu)-Thr($^t$Bu)-Leu-OMe (8.80 g) in methanol (200 mL) was added 20% Pd(OH)$_2$/C (1.50 g). The reaction vessel was evacuated/flushed with hydrogen, and the mixture was stirred under a hydrogen atmosphere (balloon) overnight. Then it was filtered through a pad of celite and concentrated to yield the title compound as a colorless glue (6.65 g, 97%).

Cbz-Ser($^t$Bu)-Asp(O$^t$Bu)-Thr($^t$Bu)-Leu-OMe (SEQ ID NO: 77)

To a solution of Cbz-Ser($^t$Bu)-OH (4.53 g, 15.34 mmol) and NHS (2.47 g, 21.478 mmol, 1.40 equiv) in DMF (25 mL) at 0° C., was added EDC.HCl (5.90 g, 30.777 mmol, 2.0 equiv), and the mixture was stirred at room temperature for 1 h. Then added this mixture to a solution of H-Asp(O$^t$Bu)-Thr($^t$Bu)-Leu-OMe (6.60 g, 13.953 mmol) in DMF (35 mL), at 0° C., over 10 minutes. The reaction mixture was stirred at room temperature overnight. The mixture was diluted with water (100 mL) and the title compound separated out as a glue. It was extracted with EtOAc (3×75 mL). The combined EtOAc-extract was washed with 1N HCl (100 mL), saturated. NaHCO$_3$ (100 mL), brine (100 mL), dried (MgSO4), and concentrated to yield the title compound as a viscous oil (9.60 g, 92%).

H-Ser($^t$Bu)-Asp(O$^t$Bu)-Thr($^t$Bu)-Leu-OMe (SEQ ID NO: 77)

To a clear solution of Cbz-Ser($^t$Bu)-Asp(O$^t$Bu)-Thr($^t$Bu)-Leu-OMe (SEQ ID NO:77) (9.50 g), in methanol (250 ml), was added 20% Pd(OH)$_2$/C (1.50 g). The reaction vessel was evacuated/flushed with hydrogen, and the mixture was stirred under a hydrogen atmosphere (balloon) overnight.

Then it was filtered through a pad of celite, and concentrated to yield the title compound as a viscous oil (7.40 g, 95%).

Cbz-N(Me)-Arg(Pbf)-Ser(tBu)-Asp(OtBu)-Thr(tBu)-Leu-OMe (SEQ ID NO:5)

To a mixture of Cbz-N-Me-Arg(Pbf)-OH (4.40 g, 7.665 mmol) and NHS (1.33 g, 11.565 mmol, 1.5 equiv), in DMF (15 mL) at 0° C. was added EDC.HCl (2.94 g, 15.336 mmol, 2.0 equiv) and the mixture was stirred at room temperature for 1 h. Then to this mixture was added to a solution of H-Ser(tBu)-Asp(OtBu)-Thr(tBu)-Leu-OMe (4.90 g, 7.954 mmol) in DMF (30 mL) at 0° C. The reaction mixture was stirred at room temperature overnight. The reaction mixture was diluted with water (100 mL) and the title compound separated out as a glue. It was extracted with EtOAc (3×75 mL). The combined EtOAc-extract was washed with saturated NaHCO$_3$, brine, dried (MgSO$_4$) and concentrated to yield the title compound as a colorless glue (8.18 g, 91%).

H-(N)Me-Arg(Pbf)-Ser(tBu)-Asp(OtBu)-Thr(tBu)-Leu-OMe (SEQ ID NO:5) (H-P$_5$-OMe)

To a clear solution of Cbz-N(Me)Arg(pbf)-Ser(tBu)-Asp(OtBu)-Thr(tBu)-Leu-OMe (5.60 g, 4.778 mmol) in methanol (75 mL) was added 20% Pd(OH)$_2$/C (1.0 g). The reaction vessel was then evacuated/flushed with hydrogen, and the mixture was stirred under a hydrogen atmosphere (balloon) overnight. Then it was filtered through a pad of celite, and concentrated to yield the title compound as a glue (4.70 g, 95%).

Fmoc-Pen(Acm)-N(Me)-Arg(pbf)-Ser(tBu)-Asp(OtBu)-Thr(tBu)-Leu-OMe (SEQ ID NO:3) (Fmoc-P$_6$-OMe)

In a 100 mL RBF, weighed Fmoc-Pen(Acm)-OH (639 mg, 1.443 mmol, 1.5 equiv), H-P$_5$-OMe (1.0 g, 0.963 mmol, 1.0 equiv), and oxyma (220 mg, 1.548 mmol, 1.60 equiv). Then added DCM-DMF (1:1) (5.0 mL). To the resulting clear solution added DIC (195 mg, 1.545 mmol, 1.6 equiv) dropwise and stirred the mixture at room temperature for 19 h. LC/MS showed about 10% unreacted H-P$_5$-OMe. Additional DIC (90 mg, 0.713 mmol. 0.5 eq) was added. After 24 h, no more starting material (H-P$_5$-OMe) remained. Then worked up the reaction by partitioning between EtOAc and saturated NaHCO$_3$. Evaporation of the combined EtOAc extract yielded the crude product, which was purified by flash chromatography using 2-5% MeOH in EtOAc to obtain pure Fmoc-P$_6$-OMe (1.183 g, 84%).

H-Pen(Acm)-N(Me)-Arg(pbf)-Ser(tBu)-Asp(OtBu)-Thr(tBu)-Leu-OMe (SEQ ID NO: 3) (H-P$_6$-OMe)

To a solution of Fmoc-P$_6$-OMe (769 mg), in DMF (3.0 mL), was added 4-methyl piperidine (260 mg, 5.0 equiv), and the mixture was stirred at room temperature for 1.0 h. Extraction with EtOAc followed by concentration yielded the crude product, which was used as such in the next reaction.

Ac-Pen(Acm)-N(Me)-Arg(pbf)-Ser(tBu)-Asp(OtBu)-Thr(tBu)-Leu-OMe (SEQ ID NO: 3) (Ac-P$_6$-OMe)

H-P$_6$-OMe from the previous step was diluted with DCM (10 mL). To the clear solution was added capping agent A (THF/Ac$_2$O/Pyr, 80/10/10) (1.0 mL, 1.06 mmol), and the mixture was stirred at room temperature for 1.0 h. Then the mixture was concentrated to dryness and purified by flash chromatography using 5-10% MeOH in EtOAc to yield the pure compound, Ac-P$_6$-OMe (614 mg, 91%).

Ac-Pen(Acm)-N(Me)-Arg(pbf)-Ser(tBu)-Asp(OtBu)-Thr(tBu)-Leu-OH (SEQ ID NO: 3) (Ac-P$_6$-OH)

To a clear solution of Ac-P$_6$-OMe (500 mg, 0.390 mmol) in acetonitrile (5.0 mL), at 15° C., was added water (75 microliter). LiBr (340 mg, 3.90 mmol, 10.0 equiv) followed by DBU (178 mg, 1.169 mmol, 3.0 equiv) was added. The mixture was then stirred at 15° C. for 8.0 h. Then cooled it to 0° C., and acidified with 0.5 M KHSO$_4$ to pH 3. Then extracted the reaction mixture with EtOAc (3×), washed the combined extract with brine, dried over MgSO$_4$, and concentrated to obtain the crude product, Ac-P$_6$-OH (386 mg, 78%) as a colorless solid.

Ac-Pen(Acm)-N(Me)-Arg(pbf)-Ser(tBu)-Asp(OtBu)-Thr(tBu)-Leu-Pen(Acm)-Phe(4-tBu)-β-homoGlu (OtBu)-(D)-Lys(Boc)-NH$_2$ (SEQ ID NO:25)(Ac-P$_{10}$-NH$_2$)

To Ac-P$_6$-OH (300 mg, 0.236 mmol), H-P$_4$-NH$_2$ (220 mg, 0.259 mmol, 1.1 equiv), and HOAt (32 mg, 0.235 mmol, 1.0 equiv) in DMF (1.5 mL) at 0° C., HATU (135 mg, 0.355 mmol, 1.5 equiv), followed by DIEA (31 mg, 0.239 mmol, 1.0 equiv) was added. The reaction mixture was stirred at 0° C. After 4 h, some unreacted starting material was still present. Additional HATU, HOAt and DIEA (0.25 eq. each) was added and continued stirring at room temperature for 24 h. The reaction mixture was cooled to 0° C., diluted with water (15 mL, 10 volumes), and the title compound precipitated as a colorless solid. The solid was filtered, rinsed with water (75 mL) and air dried. The crude product was purified by flash chromatography using 5-20% MeOH in EtOAc to yield the title compound as a colorless solid (422 mg, 85%).

Cbz-N(Me)-Arg(Pbf)-Ser(tBu)-Asp(OtBu)-Thr(tBu)-Leu-OMe (SEQ ID NO:5) (Z-P$_5$-OMe)

To a mixture of Cbz-N-Me-Arg(Pbf)-OH (4.40 g, 7.665 mmol) and NHS (1.33 g, 11.565 mmol, 1.5 equiv), in DMF (15 mL) at 0° C. was added EDC.HCl (2.94 g, 15.336 mmol, 2.0 equiv) and the mixture was stirred at room temperature for 1 h. Then this mixture was added to a solution of H-Ser(tBu)-Asp(OtBu)-Thr(tBu)-Leu-OMe (4.90 g, 7.954 mmol) in DMF (30 mL) at 0° C. The reaction mixture was stirred at room temperature overnight. The reaction mixture was diluted with water (100 mL) and the title compound separated out as a glue. It was extracted with EtOAc (3×75 mL). The combined EtOAc-extract was washed with satd. NaHCO$_3$, brine, dried (MgSO$_4$) and concentrated to yield the title compound as a colorless glue (8.18 g, 91%).

H-N-Me-Arg(Pbf)-Ser(tBu)-Asp(OtBu)-Thr(tBu)-Leu-OH (SEQ ID NO:5) (H-P$_5$-OH)

To a solution of H-N-Me-Arg(Pbf)-Ser(tBu)-Asp(OtBu)-Thr(tBu)-Leu-OMe (SEQ ID NO:5) (58.43 g, 56.2 mmol), LiBr (48.78 g, 562 mmol, 10 eq), H$_2$O (15.2 g, 843 mmol) in ACN (480 mL) was added DBU (25.65 g, 168.6 mmol, 3 eq) under 0° C. The mixture was stirred for further 45 h. The slurry was acidified with 5% H$_3$PO$_4$ (200 mL) to adjust pH to 6, and then addition of water (850 mL) precipitated most of the product. The slurry was stirred for 2 hr., filtered and washed with ACN/H₂O (⅓, v/v, 120 mL), and water (120 mL×2). The solid was dried under vacuum to give H-P₅-OH (50.55 g) with 87.7% yield and 96.3% HPLC purity.

H-N-Me-Arg(Pbf)-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH₂ (SEQ ID NO:87) (H-P₉-NH₂)

To a solution of H-N-Me-Arg(Pbf)-Ser($^t$Bu)-Asp(O$^t$Bu)-Thr($^t$Bu)-Leu-OH (SEQ ID NO:5) (20 g, 19.5 mmol) and H-Pen(Acm)-Phe(4-$^t$Bu)-β-homoGlu(O$^t$Bu)-D-Lys(Boc)-NH₂ (20 g, 23.5 mmol) and HOBt (2.64 g, 19.5 mmol) in DMF/DMSO (320 mL/40 mL) were added HBTU (8.13 g, 21.4 mmol), and DIEA (6.32 g, 48.9 mmol) under −15° C.~−5° C. (inner). The mixture was kept for 20 h. To the mixture was added 5% NaHCO₃ (aq.) (1.2 L) to precipitate white solid which was collected and washed with water and dried under vacuum to get 37.06 g product with 90% HPLC purity.

Fmoc-Pen(Acm)-N-Me-Arg(Pbf)-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH₂ (SEQ ID NO:25) (Fmoc-P10-NH₂)

To a solution of H-P₉-NH₂ (45 g, 24.23 mmol, 1.0 eq) in ACN/DMF (1/1, v/v, 200/200 mL) were added Fmoc-Pen(Acm)-OH (12.86 g, 29.07 mmol, 1.2 eq), Oxyma (4.13 g, 29.07 mmol, 1.2 eq) and DIC (3.67 g, 29.07 mol, 1.2 eq) under 0° C. 72 hr later, DIEA (3.76 g, 29.07 mol, 1.2 eq.) was added to the mixture and the mixture was cooled to −10° C. to −5° C. and stirred for another 24 hr (solution A). Then to a solution of Fmoc-Pen(Acm)-OH (3.22 g, 7.27 mmol, 0.3 eq.), Oxyma (1.03 g, 7.27 mmol) in ACN/DMF (1/1, v/v, 25/25 mL) was added DIC (0.92 g, 7.27 mmol, 0.3 eq) under 0° C. for 1.0 h (solution B). Charge solution B into A directly, and then add DIEA (0.94 g, 7.27 mmol, 0.3 eq.), The mixture was stirred at 0° C. for another 24 hr (solution A'); Then to a solution of Fmoc-Pen(Acm)-OH (1.07 g, 0.1 eq.), Oxyma (0.344 g, 0.1 eq.) in ACN/DMF (1/1, v/v, 10/10 mL) was added DIC (0.31 g, 0.3 eq) under 0° C. for 1.0 h (solution C). Charge solution C into A' directly. The mixture was kept for another 24 hr. Then another portion of DIEA (0.313 g, 0.1 eq) was added. The reaction mixture was stirred for another 48 hr. The total reaction time is 192 hr. Then the mixture was charged with EtOAc (1.5 L), 5% H₃PO₄ (1.5 L). The organic phase was separated and washed with 5% H₃PO₄ (1.5 L×2), sat. NaHCO₃ (aq.) (1.5 L×3), 5% NaCl (aq.) (1.5 L), brine (1.5 L), dried over MgSO₄ (20 g), and concentrated to give 65.94 g crude product Ac-Pen(Acm)-N-Me-Arg(Pbf)-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH₂ (SEQ ID NO:25)

To a solution of Fmoc-P₁₀-NH₂ (65.094 g, 24.23 mmol according to the quantity of H-P9-NH2 used at Step 4 above), in DCM (700 mL) was added DBU (7.37 g, 48.46 mmol). The mixture was stirred for 2 h under 10° C. and then washed with NaH₂PO₄/Na₂HPO₄ buffer (pH 6.0) (700 mL), 5% NaHCO₃ (aq.) (700 mL), dried over MgSO₄ (30 g). After removal of MgSO₄, to the filtrate was added DIEA (6.26 g, 48.43 mmol) and Ac2O (4.95 g, 48.43 mmol) and kept for 0.5 h. The mixture was concentrated to about 400 mL and charged with hexane (2 L) to precipitate a light yellow solid. The solid was collected and washed with hexane (50 mL×3) and dried in vacuum to give a light yellow solid 49.35 g with 82.3% yield and 87.2% HPLC purity.

(Ac-Pen(Acm)-N-Me-Arg-Ser-Asp-Thr-Leu-Pen(Acm)-Phe(4-$^t$Bu)-β-homoGlu-D-Lys-NH₂.2TFA) (SEQ ID NO:25)

To a solution of TFA/TIS/H₂O (95/2.5/2.5, v/v/v, 500 mL) was added Ac-P10-NH₂ (45 g) slowly under 0° C. The mixture was then heated to 20° C. for 2 h. The reaction mixture was then added to cooled MTBE (under −20° C. for 1 h) slowly to precipitate a white solid, which was collected and washed with MTBE (200 mL×4), dried under vacuum to give 40.31 g product with 104% yield and 60.3% HPLC purity and two Acm-removed products (7.2% and 11.1% by peak area)

Acetate Salt of Compound A

Segments A and B

Segment A, Ac-Pen($^{\psi Me,Me}$Pro)-N(Me)Arg(pbf)-Ser($^t$Bu)-ASP(O$^t$Bu)-Thr($^t$Bu)-Leu-OH (SEQ ID NO:3), and Segment B, H-Pen($^{\psi Me,Me}$Pro)-Phe(4-$^t$Bu)-β-homoGlu(O$^t$Bu)-D-Lys(Boc)-NH2 (SEQ ID NO:4), are prepared with the appropriate protected amino acids as follows. The pentapeptide, HN(Me)Arg(pbf)-Ser($^t$Bu)-ASP(O$^t$Bu)-Thr($^t$Bu)-Leu-OMe (SEQ ID NO:5), is prepared with the appropriate amino acids. Segment A is prepared by condensation of HN(Me)Arg(pbf)-Ser($^t$Bu)-ASP(O$^t$Bu)-Thr($^t$Bu)-Leu-OMe (SEQ ID NO:5) with Ac-Pen($^{\psi Me,Me}$Pro)-OH followed by saponification. The tripeptide Phe(4-$^t$Bu)-β-homoGlu(O$^t$Bu)-D-Lys(Boc)-NH2, is prepared with the appropriate amino acids. Segment B is prepared by the condensation of Fmoc-, Bpoc-, or Cbz-Pen($^{\psi Me,Me}$Pro)-OH with Phe(4-$^t$Bu)-β-homoGlu(O$^t$Bu)-D-Lys(Boc)-NH2 followed by removal of the Fmoc, Bpoc, or Cbz protecting group.

N-terminal protection is through Cbz groups, and succinidimyl groups are used for carboxyl group activation. The Cbz-group is removed by hydrogenation over 10% Pd/C to provide the unprotected peptide.

Decapeptide

The decapeptide, Ac-Pen($^{\psi Me,Me}$Pro)-N(Me)Arg(pbf)-Ser($^t$Bu)-ASP(O$^t$Bu)-Thr($^t$Bu)-Leu-Pen($^{\psi Me,Me}$Pro)-Phe(4-$^t$Bu)-β-homoGlu(O$^t$Bu)-D-Lys(Boc)-NH₂ (SEQ ID NO:25), is prepared by coupling Segment A and Segment B, in the presence of HBTU in an aprotic solvent such as DMF, DMA, NMP, and THF. After completion of the reaction, the resulting mass is treated with 10% hydrochloric acid solution and the separated solid is filtered. The resulting solid material is dissolved in ethyl acetate and treated with n-hexane and filtered to get the desired decapeptide, Segment AB.

In order to removal the Boc and Trityl protecting groups, the protected linear decapeptide amide (segment AB) is dissolved in a cold solution of cocktail mixture (0-5° C.) TFA/H20/TIS (9.0:0.5:0.25) and stirred for two hours. The reaction mass is filtered to remove precipitated product, the solution is concentrated to ¾ volume under reduced pressure and the remaining solution was triturated with isopropyl ether or methyl tert-butyl ether. After completion of the reaction, the mixture is concentrated and the residue is treated with ether. The separated product is filtered and suspended in water followed by adjustment to pH 7-8 with bases selected from sodium hydroxide, potassium hydroxide, sodium bicarbonate, sodium carbonate and calcium carbonate. The resultant solution is oxidized with hydrogen peroxide to afford the desired decapeptide and further treated with ammonium acetate to obtain the crude acetate salt of Compound A. This crude peptide solution is further purified by crystallization or employing preparative HPLC process to get the product purity of more than 97.0%.

Disulfide Bond Formation:

The unpurified linear monomer (32.0 g) was dissolved (3.0 gram scale) in 50:50 ACN:water then diluted to 20:80 ACN:water (concentration 2 to 3 mg/mL) and oxidized with $I_2$/MeOH (Methanol) solution until the color was dark yellow, the solution was stirred with stirring bar. When the yellow color faded out, additional $I_2$/MeOH solution was added until the reaction mixture stayed a dark yellow to amber color (cyclization time takes from 30 to 45 min). The reaction was monitored using LCMS and HPLC. When complete (uncyclized monomer ≤5% (Area %)), the reaction was quenched with ascorbic acid until a colorless solution was obtained. The resulting reaction was diluted with water (final solution ~10:90 ACN:water) and analyzed and purified as follows.

The unpurified cyclized monomer was analyzed by RP-HPLC Method 20-40-20 min (Phenomenex Luna 3.0μ XB-C18 150×4.6 mm column), MPA: 0.1% TFA in water and MPB: 0.1% TFA in ACN). LC/MS was performed to verify the expected molecular weight of the linear monomer, and the observed MW of the main product was 1381.2±2 Da.

Purification of Cyclized Monomer

The cyclized monomer was purified on a preparative RP-HPLC system using the following conditions: Buffer A: 0.1% TFA in water and Buffer B: 0.1% TFA in ACN, Phenomenex Luna 10μ C18 250×50 mm column with a flow rate of 80 mL/min. Approximately 3.0 g cyclized monomer was purified per run using a 23:35:60 min gradient (23% B to 35% B in 60 min). Fractions were collected (about 25 fractions per purification, ~40 mL per fraction) and analyzed by analytical HPLC Method 20-40-20 min and lyophilized. Fractions of purity ≥90% combined for dimerization, fraction with purity between 65 and 90 Area-% were combined for recycling, and fractions with purity <65 Area-% were discarded.

The purified monomer was analyzed by RP-HPLC Method 20-40-20 min (Phenomenex Luna 3.0μ XB-C18 150×4.6 mm column), MPA: 0.1% TFA in water and MPB: 0.1% TFA in ACN). LC/MS was performed to verify the expected molecular weight of the linear monomer, and the observed MW of the main product was 1381.8±2 Da Monomer Dimerization DIG-OSu$_2$ (Diglycolic acid-di-N-Hydroxysuccinimide ester) was prepared by reacting DIG (Diglycolic acid) (1.0 eq) with HO-Su (N-Hydroxysuccinimide) (2.2 eq) and DCC (N,N'-Dicyclohexylcarbodiimide) (2.2 eq) in NMP for 12 hours at a concentration of 0.1M. The precipitated dicyclohexylurea was removed by filtration, and the DIG-OSu$_2$ solution (0.1M) was used for dimerization.

The pure monomer (12.0 g) was converted to the corresponding dimer by coupling with 0.45 eq 0.1M DIG linker solution (DIG-OSu$_2$) and 5.0 eq DIEA in DMF solution (~2.0 g monomer was dimerized and purified at one time). Dimerization reaction took approximately 15 to 30 min under ambient conditions. The reaction was monitored using LCMS and HPLC. When the reaction is completed (monomer ≤5% (AUC)), quench the reaction by adding acetic acid, dilute it with water and purify.

The crude dimer was analyzed by the analytical HPLC Method 2-50-20 min (Phenomenex Luna 5μ C18 150×4.6 mm, 5 micron 100 A column), MPA: 0.1% TFA in water and MPB: 0.1% TFA in ACN). LC/MS was used to verify the expected molecular weight of the dimer, and the observed MW was 2859.3±2 Da.

Dimer Purification in 0.1% TFA Buffer

The crude dimer was purified on a preparative RP-HPLC system using the following conditions: Buffer A: 0.1% TFA in water and Buffer B: 0.1% TFA in ACN, Phenomenex Luna 10μ C18 250×50 mm column with a flow rate of 80 mL/min. Approximately 2.0 g dimer was purified per run using a 33:40:60 min gradient (33% B to 40% B in 60 min). Fractions were collected (about 15 fractions per purification, ~20 mL per fraction) and analyzed by analytical HPLC Method 2-50-20 min. Fraction with purity ≥95.0 Area-% were combined as a final product and transferred to salt exchange step (Section 1.6), fractions between 70 and 94 Area-% were combined for recycling, and fractions with purity <60 Area-% were discarded.

Salt Exchange in 0.2% Acetic Acid (AcOH) Buffer

The combined purified solution from Section 1.5 was diluted with water (one to one) and loaded to a preparative RP-HPLC system using the following conditions: Buffer A: 0.2% AcOH in water and Buffer B: 0.2% AcOH in ACN, Phenomenex Luna 10μ C18 250×50 mm column with a flow rate of 80 mL/min. Approximately 2.0 g dimer was loaded per run, after loading the salt exchange step was performed by passing through the column a solution of 0.1 M ammonium acetate, and the material eluted with 0.2% AcOH in ACN. The exchanged fractions were collected and analyzed by analytical HPLC Method 2-50-20 min. Fraction with purity ≥95.0 Area-% were combined as a final product, fractions with purity <95 Area-% were re-purified. Fractions were lyophilized using acetate only lyophilizer.

The final purified dimer was analyzed by RP-HPLC Method 22-42-50 min (Phenomenex Aeris PEPTIDE 3.6μ XB-C18 150×4.6 mm column), MPA: 0.1% TFA in water and MPB: 0.1% TFA in ACN). LC/MS was performed to verify the expected molecular weight of the purified dimer, and the observed MW of the main product was 2859.3±2 Da. Compound B (final dimer) purity 99.25% (Area-%).

General Peptide Synthesis Protocols

General Procedure for Preparation of N-Cbz Protected Amino Acids:

The amino acid (10.0 g) was dissolved in $H_2O$ (300 ml) and $Na_2CO_3$ (2.0 equiv) and $NaHCO_3$ (1.0 equiv) were added at room temperature, with stirring, to give a clear solution. Acetone (4.0 vol, with respect to the amino acid) was added and the slightly turbid solution was cooled in an ice water bath to 15-20° C. Cbz-Cl (1.25 equiv) was added slowly, with stirring, and the reaction mixture allowed to warm to room temperature. After stirring for an additional three hours at room temperature the mixture was extracted with methyl tert-butyl ether (50 ml). To the aqueous phase was slowly added 1N aqueous HCl to give a pH of 2. The resulting oil was extracted into methyl tert-butyl ether (2×100 mL) and the organic phase was washed with $H_2O$ (100 ml), dried, filtered and then concentrated in vacuo to give the N-Cbz protected amino acid as a white solid of viscous-oil.

General Procedure for Condensation:

Cbz-AA-OH (1.2 equiv.), N-hydroxysuccinimide (NETS; 1.2-1.4 equiv.), were suspended in dichloromethane. The resulting slurry was cooled to below 5° C. Then, 1-ethyl-3-(3-dimethylaminopropyl) carbodiimide hydrochloride (EDAC) was added in portions over a period of 30 mins. The resulting clear solution was stirred for 4 hours at 0° C. A solution of HRN-AA-OP (1-1.2 equiv.) in dichloromethane was added over a period of five minutes. The resulting brown solution was stirred at room temperature for overnight. The reaction mixture was diluted with water, and the organic phase was separated. The organic phase was washed with dilute HCl solution, bicarbonate solution (2 times) and brine. The organic phase is separated, dried, filtered and concentrated to give the peptide.

General Procedure for Deprotection of Cbz:

In an appropriate size round bottom flask or hydrogenation apparatus Cbz-protected compound was dissolved in methanol. The resulting clear solution was purged with argon gas, and catalytic amounts of 10% Pd/C was added. The mixture was stirred under $H_2$ (1 atm) at 23° C. until no starting material could be detected by TLC analysis. The amine compound was confirmed by developing on TLC and stained by ninhydrin. The catalyst was removed by filtration through a pad of Celite and washed with methanol. The filtrate was concentrated under reduced pressure to give the corresponding amine, which was used in the amide-formation reaction without further purification.

Protected linear decapeptide amide (segment AB, 10) was dissolved in a cold solution of cocktail mixture (0-5° C.) TFA/H20/TIS (9.0:0.5:0.25) and stirred for two hours. The reaction mass was filtered to remove precipitated product, the solution was concentrated to ¾ volume under reduced pressure and the remaining solution was triturated with isopropyl ether.

Medium Size Scale Using 2(4+4) Approach

Cbz-β-homoGlu(O$^t$Bu)-D-Lys(Boc)-NH$_2$ (Z-P2-NH$_2$)

To a solution of Cbz-β-homoGlu(O$^t$Bu)-OH (164.84 g, 469.089 mmol, 1.0 eq) and H-D-Lys(Boc)-NH$_2$ (149.60 g, 609.816 mmol, 1.3 eq) in DMF (2750 mL) under $N_2$ at 0° C. was added Cl-HOBt (79.54 g, 469.089 mmol, 1.0 eq). Then at −5° C., HBTU (195.69 g, 516 mmol, 1.1 eq) was added. Additional DMF (200 mL) was charged, and at the same time the inner temperature was maintained below −5° C. After the dissolution of the HBTU, DIPEA was added dropwise to adjust the pH of the reaction to ~6. During the addition of the DIPEA, the reaction temperature was maintained not higher than −3° C. The reaction was followed with TLC. Total DIPEA (1.8 eq) was used. 4 hr later from the beginning of the addition of the DIPEA, the reaction mixture was poured into 0.5N HCl (aq., 30 L, 0~5° C.), the resulting solid was collected and washed with 0.5 N HCl (aq. 3×), $H_2O$ (3×), NaHCO$_3$ (sat., aq., 3×), $H_2O$ (3×), and n-hexane (1×). After removing the volatile in vacuo, Z-P2-NH$_2$ (260.41 g) was obtained with 95.9% yield and 92.6% HPLC purity.

H-β-homoGlu(O$^t$Bu)-D-Lys(Boc)-NH2 (H-P2-NH$_2$)

To a solution of Z-P2-NH$_2$ (260.4 g, 449.967 mmol) in MeOH (3100 mL) was added Pd/C (47.876 g, 10 wt. % loading, wet with 63.1 wt. % $H_2O$), after flushing with $N_2$, $H_2$ (in balloon) was applied. The reaction was followed by TLC. 3 hr later, the Pd/C was removed, and washed with MeOH (4×). The combined filtrate was concentrated in vacuo to give H-P2-NH$_2$, 197.18 g, 98.6% yield and 91.9% HPLC purity.

Z-Phe(4-$^t$Bu)-β-homoGlu(O$^t$Bu)-D-Lys(Boc)-NH$_2$ (Z-P3-NH$_2$)

To a solution of H-P2-NH$_2$ (197.18 g, 443.53 mmol, 1.0 eq) and Z-Phe(4-$^t$Bu)-OH (152.91 g, 430.224 mmol, 0.97 eq) in DMF (2800 mL) under $N_2$ at 0° C. was added Cl-HOBt (75.21 g, 443.53 mmol, 1.0 eq). Then at −5° C., HBTU (185.02 g, 487.883 mmol, 1.1 eq) was added. After the dissolution of the HBTU, DIPEA was added dropwise to adjust the pH of the reaction ~6. During the addition of the DIPEA, the reaction temperature was maintained not higher than −2° C. The reaction was followed with TLC. Total DIPEA (1.8 eq) was added. 5 h later from the beginning of the addition of the DIPEA, the reaction mixture was diluted with ethyl acetate (7500 mL), and 0.5N HCl (aq., 8000 mL, <10° C.). The aqueous layer was extracted with ethyl acetate (1700 mL, 2×). The combined ethyl acetate layer was washed with 0.5 N HCl (aq. 4×), $H_2O$ (1×), NaHCO$_3$ (sat., aq., 3×), $H_2O$ (2×), and brine (1×). After drying on Na$_2$SO$_4$ (anhydrous), and removing the volatile in vacuo to give Z-P3-NH$_2$ (327.63 g) was obtained with 94.5% yield and 95.8% HPLC purity.

H-Phe(4-$^t$Bu)-β-homoGlu(O$^t$Bu)-D-Lys(Boc)-NH$_2$ (H-P3-NH$_2$)

To a solution of Z-P3-NH$_2$ (327.60 g) in MeOH (3200 mL) was added Pd/C (44.70 g, 10 wt. % loading, wet with 63.1 wt. % $H_2O$), after flushing with $N_2$, $H_2$ (in balloon) was applied. The reaction was followed by TLC. 4 hr later, the Pd/C was removed, and washed with MeOH (4×). The combined filtrate was concentrated in vacuo to give H-P3-NH$_2$ (268.65 g, 99.0% yield, 96.6% HPLC purity.)

Fmoc-Pen(Acm)-Phe(4-$^t$Bu)-β-homoGlu(O$^t$Bu)-D-Lys(Boc)-NH$_2$ (SEQ ID NO:4) (Fmoc-P4-NH$_2$)

To a solution of H-P3-NH2 (268.21 g, 414 mmol, 1.0 eq) and Fmoc-Pen(Acm)-OH (177.71 g, 401.58 mmol, 0.97 eq) in DMF (3000 mL) under $N_2$ at 0° C. was added Cl-HOBt (69.37 g, 409.1 mmol, 1.0 eq). Then at −5° C., HBTU (172.71 g, 455.4 mmol, 1.1 eq) was added. After the dissolution of the HBTU, DIPEA was added dropwise to adjust the pH of the reaction to ~6. During the addition of the DIPEA, the reaction temperature was maintained not higher than −2° C. The reaction was followed by TLC. Total DIPEA (1.9 eq) was added. 5 hr later from the beginning of the addition of the DIPEA, the reaction mixture was diluted with ethyl acetate (7500 mL), and 0.5N HCl (aq., 7500 mL, <10° C.). The aqueous layer was extracted with ethyl acetate (1000 mL, 2×). The combined ethyl acetate layer was washed with 0.5 N HCl (aq. 4×), H2O (1×), NaHCO3 (sat., aq., 3×), H2O (2×), and brine (1×). After drying on Na2SO4 (anhydrous), and removing the volatile in vacuo, Fmoc-P4-NH2 (436.5 g) was obtained with 98.32% yield and 93.9% HPLC purity.

H-Pen(Acm)-Phe(4-$^t$Bu)-β-homoGlu(O$^t$Bu)-D-Lys(Boc)-NH$_2$ (SEQ ID NO:4) (H-P4-NH$_2$)

To a solution of Fmoc-P4-NH$_2$ (436.40 g, 406.95 mmol, 1.0 eq) in DMF (2200 mL) was added Piperidine (100.5 mL, 1017.37 mmol, 2.5 eq). The reaction was followed by TLC. 1 hr later, PE (Petroleum ether, 60-90° C., 24×2000 mL) was used to wash the reaction mixture. The 0.5 N HCl (aq., 9000 mL, 0-5° C.) was slowly poured into the resulting lower layer (DMF solution), and stirred for not less than 10 min at 2-8° C. and then stored at −20° C. for 1 h. The solid was ground and was filtered at 10° C. The Solid was washed with $H_2O$ (1×2000 ml), NaHCO$_3$ (sat., aq.) (2×), $H_2O$ (3×), PE (1×), MTBE/PE (1/1 by volume, 1×), and dried to give solid product. Total H-P4-NH$_2$ (267.3 g, 96.2% HPLC purity and 77.3% yield) was obtained.

Z-Ser($^t$Bu)-Asp(O$^t$Bu)-Thr($^t$Bu)-Leu-OH (SEQ ID NO: 77) (Z-P4-OH)

Z-Thr($^t$Bu)-Leu-OMe (Z-P2-OMe)

A suspension of Z-Thr($^t$Bu)-OH.DCHA (196.27 g, 400 mmol, 1.0 eq.) and H-Leu-OMe.HCl (80 g, 440 mmol, 1.1 eq.) in DMF (1000 mL) under N$_2$ at 25° C. was stirred for 30 min. Then the resulting mixture was cooled to 0° C., and Cl-HOBt (67.84 g, 400 mmol, 1.0 eq.) was added. Then at −15 to −10° C., HBTU (166.86 g, 440 mmol, 1.1 eq.) was added. After the dissolution of the HBTU, DIPEA (129.1 g, 1 mol, 2.5 eq) was added dropwise to adjust the pH of the reaction to ~6. During the addition of the DIPEA, the reaction temperature was maintained not higher than −5° C. The reaction was followed with HPLC. Total DIPEA (2.5 eq.) was used. 9.5 hr later, the reaction mixture was diluted with ethyl acetate (3000 mL) and 5% H$_3$PO$_4$ (3000 mL). The organic layer was washed with 5% H$_3$PO$_4$ (3000 mL×3), Sat.NaHCO$_3$ (3000 mL×4), Water (3000 mL×3), brine (3000 mL×3) and dried over MgSO4 (50 g). After removing the volatile in vacuo, Z-P2-OMe (180 g) was obtained with 103% yield and 97.4% HPLC purity.

H-Thr($^t$Bu)-Leu-OMe (H-P2-OMe)

To a solution of Z-P2-OMe (179.83 g, 400 mmol, 1.0 eq.) and TsOH.H$_2$O (91.3 g, 480 mmol, 1.2 eq.) in DMF (800 mL) at 25° C. was added Pd/C (20 g, 10 wt. 5% loading, wet with 63.1 wt. % H$_2$O). After being flushed with N$_2$, H$_2$ (in balloon) was applied. The reaction was followed by HPLC. 5 hr later, the Pd/C was removed. The solution of H-P2-OMe (120.94 g, 100% yield) in DMF (800 mL) was directly used in next step without further work-up. The H-P2-OMe in the solution was with 92.9% HPLC purity.

Z-Asp(O$^t$Bu)-Thr($^t$Bu)-Leu-OMe (Z-P3-OMe)

A solution of H-P2-OMe (120.94 g, 400 mmol, 1.0 eq.), Z-Asp (O$^t$Bu)-OH.H$_2$O (131.9 g, 408 mmol, 1.02 eq.) in DMF (1000 mL) at 0° C. was added Cl-HOBt (67.69 g, 400 mmol, 1.0 eq.). Then at −10° C., HBTU (159.28 g, 420 mmol, 1.05 eq.) was added. DIPEA (155.52 g, 1.2 mol, 3 eq) in 2 hr 15 min, was added dropwise to adjust the pH of the reaction to ~6. 3 hr 15 min later, additional DIPEA (12.96 g, 0.1 mol) was added. During the addition of the DIPEA, the reaction temperature was maintained not higher than −3° C. The reaction was followed with HPLC. 1 hr later, the reaction was diluted with ethyl acetate (3000 mL) and 5% H$_3$PO$_4$ (3000 mL). The organic layer was washed with 5% H$_3$PO$_4$ (3000 mL×3), Sat.NaHCO$_3$ (3000 mL×4), water (2000 mL×2), brine (2000 mL×2) and dried over MgSO$_4$ (50 g). After removing the volatile in vacuo, Z-P3-OMe (233.3 g, oil) was obtained with 96.6% yield and 90.9% HPLC purity.

H-Asp(O$^t$Bu)-Thr($^t$Bu)-Leu-OMe (H-P3-OMe)

To a solution of Z-P3-OMe (233.3 g, 384 mmol, 1.0 eq.) and TsOH.H2O (76.09 g, 400 mmol, 1.04 eq.) in MeOH (1000 mL) was added Pd/C (25.0 g, 10 wt. 10% loading, wet with 63.1 wt. % H$_2$O), after flushing with N$_2$, H$_2$ (in balloon) was applied. The reaction was followed by HPLC. 5 hrs later, the Pd/C was removed, and washed with MeOH (3×50 mL). The combined filtrate was diluted with ethyl acetate (3000 mL) and Sat. NaHCO3 (aq. 2000 mL). The organic layer was washed with a mixture of Sat.NaHCO$_3$/H$_2$O (2:1, v/v, 3000 mL×2), water (3000 mL×2), brine (3000 mL×2) and dried over MgSO$_4$. After removing the volatile in vacuo, H-P3-OMe (167.5 g, oil) was obtained with 92.1% yield and 93.2% HPLC purity.

Z-Ser($^t$Bu)-Asp(O$^t$Bu)-Thr($^t$Bu)-Leu-OMe (SEQ ID NO: 77) (Z-P4-OMe)

To a solution of H-P3-OMe (167.5 g, 353.8 mmol, 1.0 eq.) and Z-Ser($^t$Bu)-OH (105.53 g, 357.34 mmol, 1.01 eq.) in DMF (1000 mL) under N$_2$ at 0° C. was added Cl-HOBt (59.88 g, 353.8 mmol, 1.0 eq.). Then at −5° C., HBTU (140.94 g, 371.49 mmol, 1.05 eq.) was added. DIPEA (91.7 g, 707.6 mmol, 2.0 eq) in 1.5 hr was added dropwise to adjust the pH of the reaction to ~6. During the addition of the DIPEA, the reaction temperature was maintained not higher than −3° C. The reaction was followed with HPLC. 2 hr later, the reaction mixture was diluted with ethyl acetate (3000 mL) and 5% H$_3$PO$_4$ (3000 mL). The organic layer was washed with 5% H$_3$PO$_4$ (3000 mL×3), Sat.NaHCO$_3$ (3000 mL×4), water (3000 mL×2), brine (3000 mL×3) and dried over MgSO$_4$. After removing the volatile in vacuo, Z-P4-OMe (260 g, solid) was obtained with 97.9% yield and 92.6% HPLC purity.

Z-Ser($^t$Bu)-Asp(O$^t$Bu)-Thr($^t$Bu)-Leu-OMe (SEQ ID NO: 77) (Z-P4-OMe)

To a solution of Z-P4-OMe (260.0 g, 346.3 mmol) in MTBE (260 mL) was added PE (3900 mL), and then the white solid was formed. The mixture was stirred at 25° C. for 1.5 h. The resulting solid was collected and washed with PE/MTBE (30:1, v/v, 500 mL×3). After removing the volatile in vacuo, Z-P4-OMe (232.3 g) was obtained with 89.3% yield and 99.1% HPLC purity.

Z-Ser($^t$Bu)-Asp(O$^t$Bu)-Thr($^t$Bu)-Leu-OH (SEQ ID NO: 77) (Z-P4-OH)

To a solution of LiBr (200 g, 2663.4 mmol, 10.0 eq.) in ACN (3332.5 mL) and H$_2$O (71.91 g, 3995 mmol, 15 eq.) at 0° C. was added Z-P4-OMe (200 g, 266.34 mmol, 1.0 eq.). The mixture was cooled to −5° C. and DBU (121.55 g, 799.02 mmol, 3.0 eq.) was added dropwise. The mixture was stirred at 0° C. for 13 hrs. HPLC showed that the reaction was complete. The mixture was quenched with 30% Citric Acid (2000 mL) to PH=2 and diluted with ethyl acetate (10000 mL). The organic layer was washed with water (10 L×5) to PH=7, and Brine (10 L×2), dried over MgSO4 and concentrated under reduced pressure. Z-P4-OH (194.8 g) was obtained with 99.2% yield and 91.1% HPLC purity.

Z-Ser($^t$Bu)-Asp(O$^t$Bu)-Thr($^t$Bu)-Leu-Pen(Acm)-Phe (4-$^t$Bu)-β-homoGlu(O$^t$Bu)-D-Lys(Boc)-NH$_2$ (SEQ ID NO:86) (Z-P8-NH2)

To a solution of Z-P4-OH (189.9 g, 257.7 mmol, 1.0 eq.) and H-P4-NH$_2$ (230 g, 270.6 mmol, 1.05 eq.) in DMF (2000 mL) under N$_2$ at 0° C. was added HOAt (35.25 g, 257.7 mmol, 1.0 eq.). Then at −5° C., HATU (108.06 g, 283.5 mmol, 1.1 eq.) was added. After the dissolution of the HATU, DIPEA (66.8 g, 515.4 mmol, 2.0 eq) in 1 hr 10 min was added dropwise to adjust the pH of the reaction to ~6. During the addition of the DIPEA, the reaction temperature was maintained not higher than −3° C. HPLC was used to follow the reaction. 3 hr 20 min later, additional H-P4-NH$_2$ (4.6 g, 0.02 eq), and HATU (2.16 g) was added. The reaction mixture was stirred for another 1 hr 50 min. Then the reaction mixture was diluted with ethyl acetate (6000 mL) and 5% H$_3$PO$_4$ (6000 mL). The organic layer was washed with 5% H$_3$PO$_4$ (6000 mL×3), Sat.NaHCO$_3$/NaCl (sat. aq.) (3:1, 6000 mL×4), water (6000 mL×2), brine (6000 mL×2) and dried over MgSO$_4$. After removing the volatile in vacuo, Z-P8-NH$_2$ (403.12 g) was obtained with 99.7% yield and 89.5% HPLC purity.

H-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:86) (H-P8-NH2)

To a solution of Z-P8-NH2 (318 g, 202.69 mmol, 1.0 eq.) in MeOH (3180 mL) at 25° C. was added Pd/C (595.3 g, 10 wt. 10% loading, wet with 63.1 wt. % H$_2$O, 1.2 eq.), after flushing with N$_2$, H$_2$ (in balloon) was applied. The reaction was followed by HPLC. 14.5 hrs later, the Pd/C was removed, and washed with MeOH (6×500 mL). The combined filtrate was diluted with ethyl acetate (18 L) and washed with Water (18 L×3), brine (18 L×2) and dried over MgSO$_4$. After removing the volatile in vacuo, H-P8-NH2 (246 g, solid) was obtained with 87% yield and 82.7% HPLC purity Preparation of Pre-Formed Fmoc-Pen(Acm)-OAt To a solution of Fmoc-Pen(Acm)-OH (73.58 g, 166.3 mmol, 2.0 eq) and HOAt (2.275 g, 16.6 mmol, 0.2 eq) at −10° C. in DMF (800 mL, anhydrous) and under N$_2$ (gas) was added HATU (62.12 g, 163 mmol, 1.96 eq). At −10° C., DIPEA (23.668 g, 183 mmol, 2.2 eq) was added dropwise. The reaction mixture was stirred at −10-0° C. for ~1 hr. (Solution A) TLC was used to follow the reaction.

H-N-Me-Arg(Pbf)-OH Using N,O-Bis (Trimethylsilyl) Acetamide (BSA)

To a solution of H-N-Me-Arg(Pbf)-OH (36.6 g, 83.1 mmol, 1.0 eq) in DMF (400 mL, anhydrous) and under N$_2$ (gas) was added BSA (50.74 g, 249.4 mmol, 3 eq). The mixture was warmed up to 45° C. and stirred for 4 hr. (Solution B).

Combination of the Solutions A and B; Fmoc-Pen(Acm)-N-Me-Arg(Pbf)-OH (Fmoc-P2-OH)

The Solution B was cooled to −10° C. Then the Solution A was added to Solution B. And the combined mixture was stirred at 0° C. for 18.5 hr. HPLC was used to follow the reaction. With an ice-cooled bath, the reaction mixture was diluted with 5% H$_3$PO$_4$ (0.2 L. The mixture was diluted further with 5% H$_3$PO$_4$ (2.5 L) and ethyl acetate (3 L). The organic layer was separated and washed with 5% H$_3$PO$_4$ (aq. 2.5 L, 3×), H$_2$O (2 L, 2×), brine (2 L, 2×). After drying and removal of the volatile, 118.8 g of solid product was afforded and 57.4% HPLC purity.

Purification of the Crude Product (Fmoc-P$_2$-OH)

Crude product (118.8 g) above was purified with prep-HPLC to give 57.5 g Fmoc-P2-OH with 80% total yield and 89.7% HPLC purity.

Fmoc-Pen(Acm)-N-Me-Arg(Phf)-Ser($^t$Bu)-Asp(O$^t$Bu)-Thr($^t$Bu)-Leu-Pen(Acm)-Phe(4-$^t$Bu)-β-homoGlu(O$^t$Bu)-D-Lys(Boc)-NH$_2$ (SEQ ID NO:25) (Fmoc-P10-NH$_2$)

To a solution of Fmoc-P2-OH (157.43 g, 182.2 mmol, 1.0 eq) (Note: 45.601 g from Batch 1, 57.894 g from Batch 2, 53.935 g from Batch 3, see the report for Fmoc-P2-OH preparation.) and H-P8-NH$_2$ (288.00 g, 200.43 mmol, 1.1 eq) in THF (4 L) under N$_2$ at 0° C. was added HOAt (24.9 g, 182.2 mmol, 1.0 eq). Then at −10° C., HATU (72.9 g, 191.31 mmol, 1.05 eq) was added. After the dissolution of the HATU, DIPEA was added dropwise to adjust the pH of the reaction to ~6 in not less than 30 min. During the addition of the DIPEA, the reaction temperature was maintained not higher than −5° C. Total DIPEA (58.94 g, 455.5 mmol, 2.5 eq) was used. The reaction was followed with HPLC. The reaction mixture was stirred for ~10 hr at −11--5° C. Then reaction mixture was diluted 5% H$_3$PO$_4$ (4.5 L) and EA (10 L), The organic layer was separated and washed with 5% H$_3$PO$_4$ (aq. 4.5 L, 3×), NaHCO$_3$ (aq. 5 L, 3×), H$_2$O (5 L, 2×) and brine (5 L, 2×). After drying and removal of the volatile, 421.12 g of solid was afforded and 73.5% HPLC purity.

Ac-P$_{10}$-NH$_2$

To a solution of Fmoc-P10-NH$_2$ (400 g, 173.845 mmol, 1.0 eq) in DCM (4 L) at room temperature (16° C.), added DBU (26.45 g, 173.845 mmol, 1.0 eq). The reaction was followed with TLC. 1 hr later, after removal of the Fmoc protective group, Ac$_2$O (26.62 g, 260.77 mmol, 1.5 eq) was added to the resulting mixture. Another 1 hr later, water (100 mL) was added to the reaction mixture and stirred for 30 mins. Then the reaction mixture was diluted with 5% H$_3$PO$_4$ (5 L) and DCM (4 L), The organic layer was separated and washed with 5% H$_3$PO$_4$ (aq. 5 L), NaHCO$_3$ (aq. 5 L) and H$_2$O (5 L, 2×). After drying and concentrating the filtrate to volume ~3 L, n-heptane (15 L) was added the resulting mixture while being stirred. The formed solid was collected and dried to give 338.46 g of product with 92.6% yield and 77.2% HPLC purity.

Global Deprotection

Ac-P$_{10}$-NH$_2$ (350 g) was added to a mixture of TFA/TIS/H$_2$O (95/2.5/2.5, v/v/v, 3.5 L) at 0° C. The Ac-P10-NH$_2$ was dissolved in ~10 min. Then the reaction mixture was warmed to 20° in 20 min, and was stirred at 20 to 25° C. for ~1.5 hours. The resulting reaction mixture was added to MTBE (35 L, −3° C.). The resulting mixture was stored for 0.5 h. The solid was collected and washed with MTBE (5 L×3), and dried in vacuo to give 288 g crude linear peptide with 56.2% HPLC purity.

Preparation of the Purified Cyclic Monomer Peptide

Oxidative Cyclization

The linear, crude peptide (20 g) was dissolved in 10000 mL of 10% ACN/purified water at a concentration of 2 mg of crude peptide/mL. The pH of the solution was around 3.2. With stirring, a solution of 5.2% iodine in ACN is added dropwise to the crude peptide solution to simultaneously remove the Acm protecting groups while oxidizing the peptide and forming the disulfide bridge. Completion of the reaction was monitored by analytical reverse phase HPLC (C18) using a buffer system consisting of 0.1% trifluoroacetic acid and ACN (see the method in Table 8 below). A yellow color persists after the entire amount of linear peptide has been consumed. The reaction was continued around 2.5 hours. Upon completion of oxidation reaction, excess iodine is quenched using 0.1 M ascorbic acid aqueous.

TABLE 8

OXIDATIVE CYCLIZATION MONITORING HPLC METHOD (HPLC METHOD 1)

| | RP-HPLC Conditions |
|---|---|
| Column name/Part # | YMC Pack-Pro C18/AS12S03-1545WT |
| Pore/Particle/column size | 120 Å/3 μm/4.6 × 150 mm |
| Buffer A | 0.1% TFA in water |
| Buffer B | 0.1% TFA in CAN |
| Gradient | 15% B to 45% B in 20 minutes |
| Flow rate | 1.5 mL/minute |
| Absorbance | 220 nm |
| Temperature | 45° C. |

RP-HPLC Purification of the Crude Cyclic Monomer Peptide

The solution of the cyclized monomer peptide (containing 20 g crude peptide) was filtered through a 1 μm membrane and the filtrate is loaded directly onto the preparative HPLC for purification.

The purification was performed by preparative HPLC using reverse phase C18 material as the support.

Primary Purification (to Remove Residual Palladium)
Prep column: 150*250 mm DAC column packed with silicycle C18 100 Å, 10 um resin.
MPA: 0.1% TFA in water
MPB: 0.1% TFA in ACN
Flow rate: 400 ml/min
Detect at: 215 nm
Loading amount: oxidized solution containing 28 g of crude peptide
Gradient:

| Time | MPA | MPB |
|---|---|---|
| 0.0 | 90% | 10% |
| 60.0 | 30% | 70% |

The quality of each different fraction collected as the peptide elutes from the column is monitored by analytical reverse phase HPLC (C18) using a buffer system consisting of 0.1% trifluoroacetic acid and ACN (see the method in Table 9). The fractions eluting at 25.4 min through 43.5 min were collected and combined. The pool was analyzed using the analytical HPLC method below.

TABLE 9

CYCLIC MONOMER PURIFICATION MONITORING HPLC METHOD(HPLC METHOD 2)

| | RP-HPLC Conditions |
|---|---|
| Column name/Part # | YMC Pack-Pro C18/AS12S03-1545 WT |
| Pore/Particle/column size | 120 Å/3 μm/4.6 × 150 mm |
| Buffer A | 0.1% TFA in water |
| Buffer B | 0.1% TFA in ACN |
| Gradient | 20% B to 40% B in 20 minutes |
| Flow rate | 1.5 mL/minute |
| Absorbance | 220 nm |
| Temperature | 45° C. |

Totally, 268 g of linear crude peptide was processed and yielded 96.6 L of collected fractions with purity around 59-60%.

Secondary Purification
Total 96.6 L of collected fractions with purity around 60% were further purified respectively by the method below.

Prep column: 200*250 mm DAC column packed with silicycle C18 100 Å, 10 um resin.
MPA: 20 mM TEAP (pH 6.5)
MPB: ACN
Flow rate: 800 ml/min, Detect at: 215 nm
Loading amount: 10 L/run three times; 7 L/run six times; 8 L/run, two times 8.8 L/run once.
Gradient:

| Time | MPA | MPB |
|---|---|---|
| 0.0 | 95% | 5% |
| 5.0 | 79% | 21% |
| 85.0 | 59% | 41% |

The quality of each different fraction collected as the peptide elutes from the column is monitored by HPLC method 2.

Fractions with purity ≥95% and no single impurity >1% are pooled. Totally, 13 L of fractions were collected with purity around 98%.

Total 26 L of fractions with purity around 98% and 22.9 L of fraction with purity around 85% were collected.

Tertiary Purification
Total 22.9 L of collected fractions with purity around 85% were further purified respectively by the method below.
Prep column: 150*250 mm DAC column packed with silicycle C18 100 Å, 10 um resin.
MPA: 20 mM TEAP (pH 6.5)
MPB: ACN
Flow rate: 400 ml/min, Detect at: 215 nm
Loading amount: 3 L/run three times; 3.5 L/run one time; 2.6 L/run, one time; 3.8 L/run once; 4 L/run once.
Gradient:

| Time | MPA | MPB |
|---|---|---|
| 0.0 | 77% | 23% |
| 80.0 | 57% | 43% |

The quality of each different fraction collected as the peptide elutes from the column is monitored by HPLC method 2. Fractions with purity ≥95% and no single impurity >1% are pooled. Totally, 10 L of fractions were collected with purity around 99%.

Concentration of Pooled Fractions Using Column

The qualified pooled fractions (~36 L) with around 97% purity were loaded onto the 15-CM RP-HPLC column packed with C18 silica gel and eluted with a gradient of 10%-70% ACN aq. containing 0.1% TFA in 60 min in three runs. The collected fractions are analyzed using the HPLC method in the above purification section.

In total, 5600 mL of fraction was collected and analyzed using HPLC Method 2.

Lyophilization of the Purified Cyclic Monomer Peptide

The concentrated pooled fractions were transferred to the flasks of the manifold freezing dryer. The lyophilization was continued for three days to give the white powder of the purified cyclic Compound B. Total 75.7 g of purified cyclic monomer is obtained, representing for an overall processing yield of 28.3% (total weight of purified peptide obtained/total weight of crude peptide processed).

Preparation of the Crude Dimer Peptide Compound a
Dimerization of the Purified Cyclic Monomer Peptide
Compound A was synthesized by classic solution phase peptide synthesis approach. One molecule of bis-N-Succinimidyl diglycolic acid (DIG(NHS)$_2$), was conjugated with two Compound B cyclic monomers in anhydrous DMF in the presence of DIPEA.

75.2 g of Compound B purified monomer peptide TFA salt (46.73 mmol) was dissolved in 700 mL of anhydrous DMF, followed by addition of 2.0 eq (16.0 mL) of DIPEA. Then, 0.49 eq (7.52 g) of DIG(NHS)$_2$ was added and the reaction was stirred at 25° C. under a blanket of nitrogen for around 40 min, then a sample was taken and analyzed by HPLC method 3 below. The HPLC analysis showed there were 3.8% unreacted Compound B.

Then an extra 0.015 eq of DIG(NHS)$_2$ was added to compel the conversion of Compound B, 90 min after addition of the first 0.49 eq DIG-(NHS)$_2$. After 40 min, a sample was taken and analyzed with HPLC method 3. The unreacted Compound B monomer was around 0.4%. After another 40 min, the reaction was quenched by addition of 6.0 mL of acetic acid. The resulting mixture was poured into 7.0 L of precooled MTBE (3° C.) and the precipitate was isolated by filtration, washed and dried in vacuo for NLT 12 hours to yield 80.3 g of crude Compound Ae. Yield is around 92.9%.

TABLE 10

DIMERIZATION MONITORING HPLC METHOD (HPLC METHOD 3)

| RP-HPLC CONDITIONS | |
|---|---|
| Column name/Part # | YMC Pack-Pro C18/AS12S03-1545 WT |
| Pore/Particle/column size | 120 Å/3 μm/4.6 × 150 mm |
| Buffer A | 0.1% TFA in water |
| Buffer B | 0.1% TFA in ACN |
| Gradient | 2% B to 60% B in 25 minutes |
| Flow rate | 1.0 mL/minute |
| Absorbance | 220 nm |
| Temperature | 45° C. |
| HPLC-System | Agilent 1200 or equivalent |

Purification and Lyophilization of Compound A

Primary Purification of the Crude Dimer 75.1 g of crude Compound A was dissolved in 5000 mL of 20% ACN/purified water, filtered through a 1 μm glass fiber membrane, and then 20% volume of the solution was loaded onto a preparative RP-HPLC column packed with C18 reversed-phase resin dedicated to this product. In the first step of the purification process, the peptide was eluted in gradient fashion with a 0.1% TFA in purified water/ACN buffer system. Fractions are collected at timed intervals, analyzed for purity by an analytical RP-HPLC methods and then pooled according to the criteria below.

Primary Purification

Prep column: 80*250 mm DAC column packed with Galaksil UP C18H 120 Å, 7 um resin.

MPA: 0.1% TFA in water

MPB: 0.1% TFA in ACN

Flow rate: 200 ml/min

Detect at: 215 nm

Loading amount: peptide solution containing 5.75 g of crude dimer peptide

Gradient:

| Time | MPA | MPB |
|---|---|---|
| 0.0 | 95% | 5% |
| 5.0 | 67% | 33% |
| 65.0 | 60% | 40% |

The quality of each different fraction collected as the peptide elutes from the column is monitored by analytical reverse phase HPLC (C18) using a buffer system consisting of 0.1% trifluoroacetic acid and ACN (see the method in Table 11).

TABLE 11

DIMER PURIFICATION MONITORING HPLC METHOD (HPLC METHOD 4)

| RP-HPLC Conditions | |
|---|---|
| Column name/Part # | Phenomenex(Aeris PEPTIDE), XB-C18 |
| Pore/Particle/column size | 100 Å/3.6 μm/4.6 × 150 mm |
| Buffer A | 0.1% TFA in water |
| Buffer B | 0.1% TFA in ACN |
| Gradient | 22% B to 42% B in 50 minutes |
| Flow rate | 1.5 mL/minute |
| Absorbance | 220 nm |
| Temperature | 50° C. |

Totally, 2048 mL of fractions were collected from two purification runs and the purity was around 98% by HPLC Method 4.

Salt Exchange

The Main Pool (purity ≥98.0% total 7200 mL, loading 3600 mL in each salt-exchange run) was loaded onto the preparative RP-HPLC C18 column. After loading, the peptide was washed isocratically with multiple column volumes of a 0.2% AcOH in a purified water/ACN buffer system, followed by an isocratic wash with a 0.5M ammonium acetate in purified water buffer system to effect complete salt exchange to the desired acetate form. The peptide is then washed isocratically with a 0.2% AcOH in purified water/ACN buffer system, then eluted in gradient fashion with a 0.2% AcOH in purified water/ACN buffer system. Fractions are collected at timed intervals, analyzed for purity by in-process control analytical HPLC Method 4 and those fractions with purity ≥97.0% were combined (two salt-exchange runs, total 8640 mL) and concentrated at ≤35° C. to 5400 mL, then taken to the lyophilization step.

Final Lyophilization

The resulting solution from the salt exchange run was lyophilized on a manifold lyophilizer for three days to obtain 46.2 g of Compound A.

All publications and patent applications described herein are hereby incorporated by reference in their entireties.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A protected peptide selected from the group consisting of:

(SEQ ID NO: 25)
Ac-Pen(Trt)-N(Me)Arg(pbf)-Ser(tBu)-Asp(OtBu)-Thr(tBu)-Leu-Pen(Trt)-Phe(4-tBu)-β-homoGlu(O$^t$Bu)-D-Lys(Boc)-OH;

(SEQ ID NO: 25)
Fmoc-Pen(Trt)-N(Me)Arg(pbf)-Ser(tBu)-Asp(OtBu)-Thr(tBu)-Leu-Pen(Trt)-Phe(4-tBu)-β-homoGlu(O$^t$Bu)-D-Lys(Boc)-OH;

(SEQ ID NO: 87)
HN(Me)Arg(pbf)-Ser(tBu)-Asp(OtBu)-Thr(tBu)-Leu-Pen(Trt)-Phe(4-tBu)-β-homoGlu(O$^t$Bu)-D-Lys(Boc)-OH;

(SEQ ID NO: 25)
Fmoc-Pen(Acm)-N(Me)Arg(pbf)-Ser(tBu)-Asp(OtBu)-Thr(tBu)-Leu-Pen(Acm)-Phe(4-tBu)-β-homoGlu(OtBu)-D-Lys(Boc)-OH;

(SEQ ID NO: 87)
HN(Me)Arg(pbf)-Ser(tBu)-Asp(OtBu)-Thr(tBu)-Leu-Pen(Acm)-Phe(4-tBu)-β-homoGlu(OtBu)-D-Lys(Boc)-OH;

(SEQ ID NO: 80)
Ac-Pen(Trt)-N(Me)Arg(pbf)-Ser(tBu)-Asp(O$^t$Bu)-Thr($^t$Bu)-Leu-Pen(Trt)-Phe(4-$^t$Bu)-OH;

(SEQ ID NO: 80)
Ac-Pen(Trt)-N(Me)Arg(pbf)-Ser(tBu)-Asp(O$^t$Bu)-Thr($^t$Bu)-Leu-Pen(Acm)-Phe(4-$^t$Bu)-OH;

(SEQ ID NO: 80)
Ac-Pen(Acm)-N(Me)Arg(pbf)-Ser(tBu)-Asp(O$^t$Bu)-Thr($^t$Bu)-Leu-Pen(Acm)-Phe(4-$^t$Bu)-OH;

(SEQ ID NO: 80)
Ac-Pen(Acm)-N(Me)Arg(pbf)-Ser(tBu)-Asp(O$^t$Bu)-Thr($^t$Bu)-Leu-Pen(Trt)-Phe(4-$^t$Bu)-OH;

(SEQ ID NO: 81)
Ac-Pen(Trt)-N(Me)Arg(pbf)-Ser(tBu)-Asp(O$^t$Bu)-Thr($^t$Bu)-Leu-Pen(Trt)-OH;

-continued

Ac-Pen(Trt)-N(Me)Arg(pbf)-Ser(tBu)-Asp(OʹBu)- (SEQ ID NO: 81)
Thr(ʹBu)-Leu-Pen(Acm)-OH;

Ac-Pen(Acm)-N(Me)Arg(pbf)-Ser(tBu)-Asp(OʹBu)- (SEQ ID NO: 81)
Thr(ʹBu)-Leu-Pen(Acm)-OH;

Ac-Pen(Acm)-N(Me)Arg(pbf)-Ser(tBu)-Asp(OʹBu)- (SEQ ID NO: 81)
Thr(ʹBu)-Leu-Pen(Trt)-OH;

Ac-Pen(Trt)-N(Me)Arg(pbf)-Ser(tBu)-Asp(OʹBu)- (SEQ ID NO: 3)
Thr(ʹBu)-Leu-OH;

Ac-Pen(Acm)-N(Me)Arg(pbf)-Ser(tBu)-Asp(OʹBu)- (SEQ ID NO: 3)
Thr(ʹBu)-Leu-OH;

Ac-Pen(Trt)-N(Me)Arg(pbf)-Ser(tBu)-Asp(OʹBu)- (SEQ ID NO: 73)
Thr(ʹBu)-OH;

Ac-Pen(Acm)-N(Me)Arg(pbf)-Ser(tBu)-Asp(OʹBu)- (SEQ ID NO: 73)
Thr(ʹBu)-OH;

Ac-Pen(Trt)-N(Me)Arg(pbf)-Ser(tBu)-Asp(OʹBu)-OH; (SEQ ID NO: 71)

Ac-Pen(Acm)-N(Me)Arg(pbf)-Ser(tBu)-Asp(OʹBu)-OH; (SEQ ID NO: 71)

Ac-Pen(Trt)-N(Me)Arg(pbf)-Ser(tBu)-OH;

Ac-Pen(Acm)-N(Me)Arg(pbf)-Ser(tBu)-OH;

Ac-Pen(Trt)-N(Me)Arg(pbf)-OH;

Ac-Pen(Acm)-N(Me)Arg(pbf)-OH;

Phe(4-ʹBu)-β-homoGlu(OʹBu)-D-Lys(Boc)-NH$_2$;

H-Pen(Trt)-Phe(4-ʹBu)-β-homoGlu(OʹBu)-D- (SEQ ID NO: 4)
Lys(Boc)-NH$_2$;

H-Pen(Acm)-Phe(4-ʹBu)-β-homoGlu(OʹBu)-D- (SEQ ID NO: 4)
Lys(Boc)-NH$_2$;

Leu-Pen(Trt)-Phe(4-ʹBu)-β-homoGlu(OʹBu)-D- (SEQ ID NO: 83)
Lys(Boc)-NH$_2$;

Leu-Pen(Acm)-Phe(4-ʹBu)-β-homoGlu(OʹBu)-D- (SEQ ID NO: 83)
Lys(Boc)-NH$_2$;

Thr(ʹBu)-Leu-Pen(Trt)-Phe(4-ʹBu)-β-homoGlu(OʹBu)- (SEQ ID NO: 84)
D-Lys(Boc)-NH$_2$;

Thr(ʹBu)-Leu-Pen(Acm)-Phe(4-ʹBu)-β-homoGlu(OʹBu)- (SEQ ID NO: 84)
D-Lys(Boc)-NH$_2$;

Asp(OʹBu)-Thr(ʹBu)-Leu-Pen(Trt)-Phe(4-ʹBu)-β- (SEQ ID NO: 85)
homoGlu(OʹBu)-D-Lys(Boc)-NH$_2$;

Asp(OʹBu)-Thr(ʹBu)-Leu-Pen(Acm)-Phe(4-ʹBu)-β- (SEQ ID NO: 85)
homoGlu(OʹBu)-D-Lys(Boc)-NH$_2$;

Ser(tBu)-Asp(OʹBu)-Thr(ʹBu)-Leu-Pen(Trt)- (SEQ ID NO: 86)
Phe(4-ʹBu)-β-homoGlu(OʹBu)-D-Lys(Boc)-NH$_2$;

Ser(tBu)-Asp(OʹBu)-Thr(ʹBu)-Leu-Pen(Acm)- (SEQ ID NO: 86)
Phe(4-ʹBu)-β-homoGlu(OʹBu)-D-Lys(Boc)-NH$_2$;

Ac-Pen(Trt)-N(Me)Arg(pbf)-Ser(tBu)-Asp(OtBu)- (SEQ ID NO: 25)
Thr(tBu)-Leu-Pen(Trt)-Phe(4-tBu)-β-
homoGlu(OʹBu)-D-Lys(Boc)-NH$_2$;

Fmoc-Pen(Trt)-N(Me)Arg(pbf)-Ser(tBu)-Asp(OtBu)- (SEQ ID NO: 25)
Thr(tBu)-Leu-Pen(Trt)-Phe(4-tBu)-β-
homoGlu(OʹBu)-D-Lys(Boc)-NH$_2$;

HN(Me)Arg(pbf)-Ser(tBu)-Asp(OtBu)-Thr(tBu)-Leu- (SEQ ID NO: 87)
Pen(Trt)-Phe(4-tBu)-β-homoGlu(OtBu)-
D-Lys(Boc)-NH$_2$;

Ac-Pen(Acm)-N(Me)Arg(pbf)-Ser(tBu)-Asp(OtBu)- (SEQ ID NO: 25)
Thr(tBu)-Leu-Pen(Acm)-Phe(4-tBu)-β-
homoGlu(OʹBu)-D-Lys(Boc)-NH$_2$;

Fmoc-Pen(Acm)-N(Me)Arg(pbf)-Ser(tBu)-Asp(OtBu)- (SEQ ID NO: 25)
Thr(tBu)-Leu-Pen(Acm)-Phe(4-tBu)-β-
homoGlu(OʹBu)-D-Lys(Boc)-NH$_2$;

HN(Me)Arg(pbf)-Ser(tBu)-Asp(OtBu)-Thr(tBu)-Leu- (SEQ ID NO: 87)
Pen(Acm)-Phe(4-tBu)-β-homoGlu(OʹBu)-
D-Lys(Boc)-NH$_2$;

Ac-Pen($^{\psi Me,Me}$Pro)-N(Me)Arg(pbf)-Ser(tBu)-Asp(OtBu)- (SEQ ID NO: 25)
Thr($^{\psi Me,Me}$Pro)-Leu-Pen($^{\psi Me,Me}$Pro)-
Phe(4-tBu)-β-homoGlu(OʹBu)-D-Lys(Boc)-NH$_2$;

Ac-Pen(Acm)-N(Me)Arg(pbf)-Ser(tBu)-Asp(OtBu)- (SEQ ID NO: 25)
Thr($^{\psi Me,Me}$Pro)-Leu-Pen(Acm)-Phe(4-tBu)-β-
homoGlu(OʹBu)-D-Lys(Boc)-NH$_2$;

```
                                                   (SEQ ID NO: 25)
Ac-Pen(Trt)-N(Me)Arg(pbf)-Ser(tBu)-Asp(OtBu)-

Thr(ᵠMe,MePro)-Leu-Pen(Trt)-Phe(4-tBu)-β- homoGlu(OᵗBu)-D-Lys(Boc)-NH₂;

(SEQ ID NO: 80)
Ac-Pen(ᵠMe,MePro)-N(Me)Arg(pbf)-Ser(tBu)-Asp(OᵗBu)-

Thr(ᵗBu)-Leu-Pen(ᵠMe,MePro)-Phe(4-ᵗBu)-OH;

(SEQ ID NO: 80)
Ac-Pen(Pro)-N(Me)Arg(pbf)-Ser(tBu)-Asp(OᵗBu)-

Thr(ᵗBu)-Leu-Pen(ᵠMe,MePro)-Phe(4-ᵗBu)-OH;

(SEQ ID NO: 80)
Ac-Pen(ᵠMe,MePro)-N(Me)Arg(pbf)-Ser(tBu)-Asp(OᵗBu)-

Thr(ᵗBu)-Leu-Pen(Pro)-Phe(4-ᵗBu)-OH;

(SEQ ID NO: 80)
Ac-Pen(Pro)-N(Me)Arg(pbf)-Ser(tBu)-Asp(OᵗBu)-

Thr(ᵗBu)-Leu-Pen(Pro)-Phe(4-ᵗBu)-OH;

(SEQ ID NO: 81)
Ac-Pen(ᵠMe,MePro)-N(Me)Arg(pbf)-Ser(tBu)-Asp(OᵗBu)-

Thr(ᵗBu)-Leu-Pen(ᵠMe,MePro)-OH;

(SEQ ID NO: 81)
Ac-Pen(Pro)-N(Me)Arg(pbf)-Ser(tBu)-Asp(OᵗBu)-
Thr(ᵗBu)-Leu-Pen(ᵠMe,MePro)-OH;

(SEQ ID NO: 81)
Ac-Pen(ᵠMe,MePro)-N(Me)Arg(pbf)-Ser(tBu)-Asp(OᵗBu)-

Thr(ᵗBu)-Leu-Pen(Pro)-OH;

(SEQ ID NO: 81)
Ac-Pen(Pro)-N(Me)Arg(pbf)-Ser(tBu)-Asp(OᵗBu)-

Thr(ᵗBu)-Leu-Pen(Pro)-OH;

(SEQ ID NO: 75)
Ac-Pen(ᵠMe,MePro)-N(Me)Arg(pbf)-Ser(tBu)-Asp(OᵗBu)-

Thr(ᵗBu)-Leu-OH;

(SEQ ID NO: 75)
Ac-Pen(Pro)-N(Me)Arg(pbf)-Ser(tBu)-Asp(OᵗBu)-

Thr(ᵗBu)-Leu-OH;

(SEQ ID NO: 73)
Ac-Pen(ᵠMe,MePro)-N(Me)Arg(pbf)-Ser(tBu)-Asp(OᵗBu)-
Thr(ᵗBu)-OH;

(SEQ ID NO: 73)
Ac-Pen(Pro)-N(Me)Arg(pbf)-Ser(tBu)-Asp(OᵗBu)-

Thr(ᵗBu)-OH;

(SEQ ID NO: 71)
Ac-Pen(ᵠMe,MePro)-N(Me)Arg(pbf)-Ser(tBu)-Asp(OᵗBu)-
OH;

(SEQ ID NO: 71)
Ac-Pen(Pro)-N(Me)Arg(pbf)-Ser(tBu)-Asp(OᵗBu)-OH;

Ac-Pen(ᵠMe,MePro)-N(Me)Arg(pbf)-Ser(tBu)-OH;

Ac-Pen(Pro)-N(Me)Arg(pbf)-Ser(tBu)-OH;

Ac-Pen(ᵠMe,MePro)-N(Me)Arg(pbf)-OH;

Ac-Pen(Pro)-N(Me)Arg(pbf)-OH;

(SEQ ID NO: 86)
Ser(tBu)-Asp(OᵗBu)-Thr(ᵗBu)-Leu-Pen(ᵠMe,MePro)-

Phe(4-ᵗBu)-β-homoGlu(OᵗBu)-D-Lys(Boc)-NH₂;

(SEQ ID NO: 86)
Ser(ᵗBu)-Asp(OᵗBu)-Thr(ᵗBu)-Leu-Pen(Pro)-Phe(4-ᵗBu)-

β-homoGlu(OᵗBu)-D-Lys(Boc)-NH₂;

(SEQ ID NO: 85)
Asp(OᵗBu)-Thr(ᵗBu)-Leu-Pen(ᵠMe,MePro)-Phe(4-ᵗBu)-

β-homoGlu(OᵗBu)-D-Lys(Boc)-NH₂;

(SEQ ID NO: 85)
Asp(OᵗBu)-Thr(ᵗBu)-Leu-Pen(Pro)-Phe(4-ᵗBu)-β- homoGlu(OᵗBu)-D-Lys(Boc)-NH₂;

(SEQ ID NO: 84)
Thr(ᵗBu)-Leu-Pen(ᵠMe,MePro)-Phe(4-ᵗBu)-β- homoGlu(OᵗBu)-D-Lys(Boc)-NH₂;

(SEQ ID NO: 84)
Thr(ᵗBu)-Leu-Pen(Pro)-Phe(4-ᵗBu)-β-homoGlu(OᵗBu)-

D-Lys(Boc)-NH₂;

(SEQ ID NO: 83)
Leu-Pen(ᵠMe,MePro)-Phe(4-ᵗBu)-β-homoGlu(OᵗBu)-

D-Lys(Boc)-NH₂;

(SEQ ID NO: 83)
Leu-Pen(Pro)-Phe(4-ᵗBu)-β-homoGlu(OᵗBu)-D-

Lys(Boc)-NH₂;

(SEQ ID NO: 4)
H-Pen(ᵠMe,MePro)-Phe(4-ᵗBu)-β-homoGlu(OᵗBu)-

D-Lys(Boc)-NH₂;

(SEQ ID NO: 4)
H-Pen(Pro)-Phe(4-ᵗBu)-β-homoGlu(OᵗBu)-D-

Lys(Boc)-NH₂;

Phe(4-ᵗBu)-β-homoGlu(OᵗBu)-D-Lys(Boc)-NH₂;

β-homoGlu(OᵗBu)-D-Lys(Boc)-NH₂;

(SEQ ID NO: 3)
Ac-Pen(ᵠMe,MePro)-N(Me)Arg(pbf)-Ser(ᵗBu)-

AspP(OᵗBu)-Thr(ᵗBu)-Leu-OH;
and (SEQ ID NO: 25)
Ac-Pen(ᵠMe,MePro)-N(Me)Arg(pbf)-Ser(ᵗBu)-

Asp(OᵗBu)-Thr(ᵗBu)-Leu-Pen(ᵠMe,MePro)-Phe(4-ᵗBu)-

β-homoGlu(OᵗBu)-D-Lys(Boc)-NH₂.
```

2. The protected peptide according to claim 1, wherein the peptide is Ac-Pen(Acm)-N(Me)Arg(pbf)-OH.

3. The protected peptide according to claim 1, wherein the peptide is selected from the group consisting of:

```
                                                   (SEQ ID NO: 25)
Fmoc-Pen(Acm)-N(Me)Arg(pbf)-Ser(tBu)-Asp(OtBu)-

Thr(tBu)-Leu-Pen(Acm)-Phe(4-tBu)-β- homoGlu(OtBu)-D-Lys(Boc)-OH;
```

```
                                              (SEQ ID NO: 80)
Ac-Pen(Acm)-N(Me)Arg(pbf)-Ser(tBu)-Asp(OtBu)-

Thr(tBu)-Leu-Pen(Acm)-Phe(4-tBu)-OH;

(SEQ ID NO: 81)
Ac-Pen(Acm)-N(Me)Arg(pbf)-Ser(tBu)-Asp(OtBu)-

Thr(tBu)-Leu-Pen(Acm)-OH;

(SEQ ID NO: 3)
Ac-Pen(Acm)-N(Me)Arg(pbf)-Ser(tBu)-Asp(OtBu)-

Thr(tBu)-Leu-OH;

(SEQ ID NO: 73)
Ac-Pen(Acm)-N(Me)Arg(pbf)-Ser(tBu)-Asp(OtBu)-

Thr(tBu)-OH;

(SEQ ID NO: 71)
Ac-Pen(Acm)-N(Me)Arg(pbf)-Ser(tBu)-Asp(OtBu)-OH;
and

Ac-Pen(Acm)-N(Me)Arg(pbf)-Ser(tBu)-OH.
```

4. The protected peptide according to claim 1, wherein the peptide is β-homoGlu(OtBu)-D-Lys(Boc)-NH₂.

5. The protected peptide according to claim 1, wherein the peptide is Ac-Pen(Trt)-N(Me)Arg(pbf)-OH.

6. The protected peptide according to claim 1, wherein the peptide is selected from the group consisting of:

```
                                              (SEQ ID NO: 25)
Ac-Pen(Trt)-N(Me)Arg(pbf)-Ser(tBu)-Asp(OtBu)-

Thr(tBu)-Leu-Pen(Trt)-Phe(4-tBu)-β- homoGlu(OtBu)-D-Lys(Boc)-OH;

(SEQ ID NO: 25)
Fmoc-Pen(Trt)-N(Me)Arg(pbf)-Ser(tBu)-Asp(OtBu)-

Thr(tBu)-Leu-Pen(Trt)-Phe(4-tBu)-β- homoGlu(OtBu)-D-Lys(Boc)-OH;

(SEQ ID NO: 80)
Ac-Pen(Trt)-N(Me)Arg(pbf)-Ser(tBu)-Asp(OtBu)-

Thr(tBu)-Leu-Pen(Trt)-Phe(4-tBu)-OH;

(SEQ ID NO: 80)
Ac-Pen(Trt)-N(Me)Arg(pbf)-Ser(tBu)-Asp(OtBu)-

Thr(tBu)-Leu-Pen(Acm)-Phe(4-tBu)-OH;

(SEQ ID NO: 81)
Ac-Pen(Trt)-N(Me)Arg(pbf)-Ser(tBu)-Asp(OtBu)-

Thr(tBu)-Leu-Pen(Trt)-OH;

(SEQ ID NO: 81)
Ac-Pen(Trt)-N(Me)Arg(pbf)-Ser(tBu)-Asp(OtBu)-

Thr(tBu)-Leu-Pen(Acm)-OH;

(SEQ ID NO: 3)
Ac-Pen(Trt)-N(Me)Arg(pbf)-Ser(tBu)-Asp(OtBu)-

Thr(tBu)-Leu-OH;

(SEQ ID NO: 73)
Ac-Pen(Trt)-N(Me)Arg(pbf)-Ser(tBu)-Asp(OtBu)-

Thr(tBu)-OH;

(SEQ ID NO: 71)
Ac-Pen(Trt)-N(Me)Arg(pbf)-Ser(tBu)-Asp(OtBu)-OH;
and

Ac-Pen(Trt)-N(Me)Arg(pbf)-Ser(tBu)-OH.
```

7. The protected peptide according to claim 1, wherein the peptide is selected from the group consisting of:

```
                                              (SEQ ID NO: 87)
HN(Me)Arg(pbf)-Ser(tBu)-Asp(OtBu)-Thr(tBu)-Leu- Pen(Trt)-Phe(4-tBu)-β-homoGlu(OtBu)-D-Lys(Boc)-OH;
and (SEQ ID NO: 87)
HN(Me)Arg(pbf)-Ser(tBu)-Asp(OtBu)-Thr(tBu)-Leu- Pen(Acm)-Phe(4-tBu)-β-homoGlu(OtBu)-D-Lys(Boc)-OH.
```

8. The protected peptide according to claim 1, wherein the peptide is selected from the group consisting of:

```
                                              (SEQ ID NO: 4)
H-Pen(Acm)-Phe(4-tBu)-β-homoGlu(OtBu)-D-

Lys(Boc)-NH₂;

(SEQ ID NO: 83)
Leu-Pen(Acm)-Phe(4-tBu)-β-homoGlu(OtBu)-D-

Lys(Boc)-NH₂;

(SEQ ID NO: 25)
Ac-Pen(Acm)-N(Me)Arg(pbf)-Ser(tBu)-Asp(OtBu)-

Thr(tBu)-Leu-Pen(Acm)-Phe(4-tBu)-β- homoGlu(OtBu)-D-Lys(Boc)-NH₂;
and (SEQ ID NO: 25)
Fmoc-Pen(Acm)-N(Me)Arg(pbf)-Ser(tBu)-Asp(OtBu)-

Thr(tBu)-Leu-Pen(Acm)-Phe(4-tBu)-β- homoGlu(OtBu)-D-Lys(Boc)-NH₂.
```

9. The protected peptide according to claim 1, wherein the peptide is selected from the group consisting of:

```
                                              (SEQ ID NO: 4)
H-Pen(Trt)-Phe(4-tBu)-β-homoGlu(OtBu)-D-
Lys(Boc)-NH₂;

(SEQ ID NO: 83)
Leu-Pen(Trt)-Phe(4-tBu)-β-homoGlu(OtBu)-D-

Lys(Boc)-NH₂;

(SEQ ID NO: 25)
Ac-Pen(Trt)-N(Me)Arg(pbf)-Ser(tBu)-Asp(OtBu)-

Thr(tBu)-Leu-Pen(Trt)-Phe(4-tBu)-β- homoGlu(OtBu)-D-Lys(Boc)-NH₂;

(SEQ ID NO: 25)
Fmoc-Pen(Trt)-N(Me)Arg(pbf)-Ser(tBu)-Asp(OtBu)-

Thr(tBu)-Leu-Pen(Trt)-Phe(4-tBu)-β- homoGlu(OtBu)-D-Lys(Boc)-NH₂;
and
```

```
                                              (SEQ ID NO: 25)
Ac-Pen(Trt)-N(Me)Arg(pbf)-Ser(tBu)-Asp(OtBu)-

Thr(ψMe,MePro)-Leu-Pen(Trt)-Phe(4-tBu)-β- homoGlu(OtBu)-D-Lys(Boc)-NH2.
```

10. The protected peptide according to claim 1, wherein the peptide is

```
Phe(4-tBu)-β-homoGlu(OtBu)-D-Lys(Boc)-NH2;

(SEQ ID NO: 84)
Thr(tBu)-Leu-Pen(Acm)-Phe(4-tBu)-β- homoGlu(OtBu)-D-Lys(Boc)-NH2;

(SEQ ID NO: 85)
Asp(OtBu)-Thr(tBu)-Leu-Pen(Acm)-Phe(4-tBu)-β- homoGlu(OtBu)-D-Lys(Boc)-NH2;
or
                                              (SEQ ID NO: 86)
Ser(tBu)-Asp(OtBu)-Thr(tBu)-Leu-Pen(Acm)-Phe(4-tBu)-

β-homoGlu(OtBu)-D-Lys(Boc)-NH2.
```

11. The protected peptide according to claim 1, wherein the peptide is selected from the group consisting of:

```
                                              (SEQ ID NO: 87)
HN(Me)Arg(pbf)-Ser(tBu)-Asp(OtBu)-Thr(tBu)-Leu- Pen(Trt)-Phe(4-tBu)-β-homoGlu(OtBu)-D-Lys(Boc)-NH2;
and
                                              (SEQ ID NO: 87)
HN(Me)Arg(pbf)-Ser(tBu)-Asp(OtBu)-Thr(tBu)-Leu- Pen(Acm)-Phe(4-tBu)-β-homoGlu(OtBu)-

D-Lys(Boc)-NH2.
```

12. The protected peptide according to claim 1, wherein the peptide is selected from the group consisting of:

```
                                              (SEQ ID NO: 80)
Ac-Pen(Pro)-N(Me)Arg(pbf)-Ser(tBu)-Asp(OtBu)-

Thr(tBu)-Leu-Pen(Pro)-Phe(4-tBu)-OH;

(SEQ ID NO: 81)
Ac-Pen(Pro)-N(Me)Arg(pbf)-Ser(tBu)-Asp(OtBu)-

Thr(tBu)-Leu-Pen(Pro)-OH;

(SEQ ID NO: 75)
Ac-Pen(Pro)-N(Me)Arg(pbf)-Ser(tBu)-Asp(OtBu)-

Thr(tBu)-Leu-OH;

(SEQ ID NO: 73)
Ac-Pen(Pro)-N(Me)Arg(pbf)-Ser(tBu)-Asp(OtBu)-

Thr(tBu)-OH;

(SEQ ID NO: 71)
Ac-Pen(Pro)-N(Me)Arg(pbf)-Ser(tBu)-Asp(OtBu)-OH;

Ac-Pen(Pro)-N(Me)Arg(pbf)-Ser(tBu)-OH;

Ac-Pen(Pro)-N(Me)Arg(pbf)-OH;
```

```
                                              (SEQ ID NO: 86)
Ser(tBu)-Asp(OtBu)-Thr(tBu)-Leu-Pen(Pro)-

Phe(4-tBu)-β-homoGlu(OtBu)-D-Lys(Boc)-NH2;

(SEQ ID NO: 85)
Asp(OtBu)-Thr(tBu)-Leu-Pen(Pro)-Phe(4-tBu)-

β-homoGlu(OtBu)-D-Lys(Boc)-NH2;

(SEQ ID NO: 84)
Thr(tBu)-Leu-Pen(Pro)-Phe(4-tBu)-β- homoGlu(OtBu)-D-Lys(Boc)-NH2;

(SEQ ID NO: 83)
Leu-Pen(Pro)-Phe(4-tBu)-β-homoGlu(OtBu)-D-

Lys(Boc)-NH2;
and
                                              (SEQ ID NO: 4)
H-Pen(Pro)-Phe(4-tBu)-β-homoGlu(OtBu)-D-

Lys(Boc)-NH2.
```

13. The protected peptide according to claim 1, wherein the peptide is selected from the group consisting of:

```
                                              (SEQ ID NO: 25)
Ac-Pen(ψMe,MePro)-N(Me)Arg(pbf)-Ser(tBu)-

Asp(OtBu)-Thr(ψMe,MePro)-Leu-Pen(ψMe,MePro)-

Phe(4-tBu)-β-homoGlu(OtBu)-D-Lys(Boc)-NH2;

(SEQ ID NO: 80)
Ac-Pen(ψMe,MePro)-N(Me)Arg(pbf)-Ser(tBu)-

Asp(OtBu)-Thr(tBu)-Leu-Pen(ψMe,MePro)-Phe(4-tBu)-OH;

(SEQ ID NO: 80)
Ac-Pen(ψMe,MePro)-N(Me)Arg(pbf)-Ser(tBu)-

Asp(OtBu)-Thr(tBu)-Leu-Pen(Pro)-Phe(4-tBu)-OH;

(SEQ ID NO: 81)
Ac-Pen(ψMe,MePro)-N(Me)Arg(pbf)-Ser(tBu)-

Asp(OtBu)-Thr(tBu)-Leu-Pen(ψMe,MePro)-OH;

(SEQ ID NO: 81)
Ac-Pen(ψMe,MePro)-N(Me)Arg(pbf)-Ser(tBu)-

Asp(OtBu)-Thr(tBu)-Leu-Pen(Pro)-OH;

(SEQ ID NO: 75)
Ac-Pen(ψMe,MePro)-N(Me)Arg(pbf)-Ser(tBu)-

Asp(OtBu)-Thr(tBu)-Leu-OH;

(SEQ ID NO: 73)
Ac-Pen(ψMe,MePro)-N(Me)Arg(pbf)-Ser(tBu)-

Asp(OtBu)-Thr(tBu)-OH;

(SEQ ID NO: 71)
Ac-Pen(ψMe,MePro)-N(Me)Arg(pbf)-Ser(tBu)-

Asp(OtBu)-OH;

Ac-Pen(ψMe,MePro)-N(Me)Arg(pbf)-Ser(tBu)-OH;

Ac-Pen(ψMe,MePro)-N(Me)Arg(pbf)-OH;

(SEQ ID NO: 85)
Asp(OtBu)-Thr(tBu)-Leu-Pen(ψMe,MePro)-

Phe(4-tBu)-β-homoGlu(OtBu)-D-Lys(Boc)-NH2;
```

-continued

Thr(tBu)-Leu-Pen(ψMe,MePro)-Phe(4-tBu)-β- (SEQ ID NO: 84)
homoGlu(OtBu)-D-Lys(Boc)-NH₂;

Leu-Pen(ψMe,MePro)-Phe(4-tBu)-β-homoGlu(OtBu)- (SEQ ID NO: 83)
D-Lys(Boc)-NH₂;

H-Pen(ψMe,MePro)-Phe(4-tBu)-β-homoGlu(OtBu)-D- (SEQ ID NO: 4)
Lys(Boc)-NH₂;
and

Ser(tBu)-Asp(OtBu)-Thr(tBu)-Leu-Pen(ψMe,MePro)- (SEQ ID NO: 86)
Phe(4-tBu)-β-homoGlu(OtBu)-D-Lys(Boc)-NH₂.

14. The protected peptide according to claim 1, wherein the peptide is
Phe(4-tBu)-β-homoGlu(OtBu)-D-Lys(Boc)-NH₂;
Ac-Pen(Acm)-N(Me)Arg(pbf)-Ser(tBu)-Asp(OtBu)-Thr(tBu)-Leu-Pen(Trt)-Phe(4-tBu)-OH (SEQ ID NO:80); or
Ac-Pen(Acm)-N(Me)Arg(pbf)-Ser(tBu)-Asp(OtBu)-Thr(tBu)-Leu-Pen(Trt)-OH (SEQ ID NO:81).

15. The protected peptide according to claim 1, wherein the peptide is
Ac-Pen(Acm)-N(Me)Arg(pbf)-Ser(tBu)-Asp(OtBu)-Thr(ψMe,MePro)-Leu-Pen(Acm)-Phe(4-tBu)-β-homoGlu(OtBu)-D-Lys(Boc)-NH₂ (SEQ ID NO:25).

16. The protected peptide according to claim 1, wherein the peptide is
Thr(tBu)-Leu-Pen(Trt)-Phe(4-tBu)-β-homoGlu(OtBu)-D-Lys(Boc)-NH₂ (SEQ ID NO:84);
Asp(OtBu)-Thr(tBu)-Leu-Pen(Trt)-Phe(4-tBu)-β-homoGlu(OtBu)-D-Lys(Boc)-NH₂ (SEQ ID NO:85); or
Ser(tBu)-Asp(OtBu)-Thr(tBu)-Leu-Pen(Trt)-Phe(4-tBu)-β-homoGlu(OtBu)-D-Lys(Boc)-NH₂ (SEQ ID NO:86).

17. The protected peptide according to claim 1, wherein the peptide is
Ac-Pen(Pro)-N(Me)Arg(pbf)-Ser(tBu)-Asp(OtBu)-Thr(tBu)-Leu-Pen(ψMe,MePro)-Phe(4-tBu)-OH (SEQ ID NO:80); or
Ac-Pen(Pro)-N(Me)Arg(pbf)-Ser(tBu)-Asp(OtBu)-Thr(tBu)-Leu-Pen(ψMe,MePro)-OH (SEQ ID NO:81).

18. The protected peptide according to claim 1, wherein the peptide is Ac-Pen(Acm)-N(Me)Arg(pbf)-Ser(tBu)-Asp(OtBu)-Thr(tBu)-Leu-OH (SEQ ID NO:3).

19. The protected peptide according to claim 1, wherein the peptide is Ac-Pen(Acm)-N(Me)Arg(pbf)-Ser(tBu)-Asp(OtBu)-Thr(tBu)-Leu-Pen(Acm)-Phe(4-tBu)-β-homoGlu(OtBu)-D-Lys(Boc)-NH₂ (SEQ ID NO:25).

20. The protected peptide according to claim 1, wherein the peptide is H-Pen(Acm)-Phe(4-tBu)-β-homoGlu(OtBu)-D-Lys(Boc)-NH₂ (SEQ ID NO:4).

21. The protected peptide according to claim 1, wherein the peptide is Fmoc-Pen(Acm)-N(Me)Arg(pbf)-Ser(tBu)-Asp(OtBu)-Thr(tBu)-Leu-Pen(Acm)-Phe(4-tBu)-β-homoGlu(OtBu)-D-Lys(Boc)-NH₂ (SEQ ID NO:25).

22. The protected peptide according to claim 1, wherein the peptide is Ac-Pen(Trt)-N(Me)Arg(pbf)-Ser(tBu)-Asp(OtBu)-Thr(tBu)-Leu-OH (SEQ ID NO:3).

23. The protected peptide according to claim 1, wherein the peptide is H-Pen(Trt)-Phe(4-tBu)-β-homoGlu(OtBu)-D-Lys(Boc)-NH₂ (SEQ ID NO:4);
Ac-Pen(Trt)-N(Me)Arg(pbf)-Ser(tBu)-Asp(OtBu)-Thr(tBu)-Leu-Pen(Trt)-Phe(4-tBu)-β-homoGlu(OtBu)-D-Lys(Boc)-NH₂ (SEQ ID NO:25);
Ac-Pen(Trt)-N(Me)Arg(pbf)-Ser(tBu)-Asp(OtBu)-Thr(ψMe,MePro)-Leu-Pen(Trt)-Phe(4-tBu)-β-homoGlu(OtBu)-D-Lys(Boc)-NH₂ (SEQ ID NO:25); or
HN(Me)Arg(pbf)-Ser(tBu)-Asp(OtBu)-Thr(tBu)-Leu-Pen(Trt)-Phe(4-tBu)-β-homoGlu(OtBu)-D-Lys(Boc)-NH₂ (SEQ ID NO:87).

24. The protected peptide according to claim 1, wherein the peptide is HN(Me)Arg(pbf)-Ser(tBu)-Asp(OtBu)-Thr(tBu)-Leu-Pen(Acm)-Phe(4-tBu)-β-homoGlu(OtBu)-D-Lys(Boc)-NH₂ (SEQ ID NO:87).

* * * * *

UNITED STATES PATENT AND TRADEMARK OFFICE
CERTIFICATE OF CORRECTION

PATENT NO. : 10,407,468 B2
APPLICATION NO. : 15/467810
DATED : September 10, 2019
INVENTOR(S) : Ashok Bhandari et al.

It is certified that error appears in the above-identified patent and that said Letters Patent is hereby corrected as shown below:

In the Claims

At Column 252, Claim number 1, Line number 7:
"Ser($^t$Bu)-Asp(O$^t$Bu)-Thr(Bu)-Leu-Pen(Pro)-Phe(4-$^t$Bu)-"
Should read:
-- Ser($^t$Bu)-Asp(O$^t$Bu)-Thr($^t$Bu)-Leu-Pen(Pro)-Phe(4-$^t$Bu)- --

Signed and Sealed this
Fifteenth Day of September, 2020

Andrei Iancu
*Director of the United States Patent and Trademark Office*

SEQUENCE LISTING

<160> NUMBER OF SEQ ID NOS: 87

<210> SEQ ID NO 1
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)
<223> OTHER INFORMATION: N-Methyl-Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe(4-tBu), 2-amino-3-(4-tert-butyl-
      phenyl)propionic acid
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-N(Me)Arg-Ser-Asp-
      Thr-Leu-Pen-Phe(4-tBu)-BetahomoGlu-D-Lys forming a homodimer
      molecule

<400> SEQUENCE: 1

Xaa Arg Ser Asp Thr Leu Xaa Phe Xaa Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)

```
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe(4-tBu), 2-amino-3-(4-tert-butyl-
      phenyl)propionic acid
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form

<400> SEQUENCE: 2

Xaa Arg Ser Asp Thr Leu Xaa Phe Xaa Lys
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (2)..(2)
<223> OTHER INFORMATION: N-Methyl Arginine

<400> SEQUENCE: 3

Xaa Arg Ser Asp Thr Leu
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (2)..(2)
<223> OTHER INFORMATION: Phe(4-tBu), 2-amino-3-(4-tert-butyl-
      phenyl)propionic acid
<220> FEATURE:
<221> NAME/KEY: MOD_RES
<222> LOCATION: (3)..(3)
<223> OTHER INFORMATION: Beta-homoglutamic acid
<220> FEATURE:
<221> NAME/KEY: MOD_RES
<222> LOCATION: (4)..(4)
<223> OTHER INFORMATION: D-Lys form

<400> SEQUENCE: 4

Xaa Phe Xaa Lys
1

<210> SEQ ID NO 5
<211> LENGTH: 5
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-Methyl Arginine

<400> SEQUENCE: 5

Arg Ser Asp Thr Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (9)..(9)
<223> OTHER INFORMATION: D-Lys form

<400> SEQUENCE: 6

Xaa Arg Ser Asp Thr Leu Xaa Trp Lys
1               5

<210> SEQ ID NO 7
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
```

-continued

```
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form

<400> SEQUENCE: 7

Xaa Arg Ser Asp Thr Leu Xaa Trp Xaa Lys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (10)..(10)
<223> OTHER INFORMATION: D-form N-Methyl Lysine

<400> SEQUENCE: 8

Xaa Arg Ser Asp Thr Leu Xaa Trp Glu Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
```

```
<223> OTHER INFORMATION: Penicillamine
<220> FEATURE:
<221> NAME/KEY: MOD_RES
<222> LOCATION: (10)..(10)
<223> OTHER INFORMATION: N-Methyl Lysine

<400> SEQUENCE: 9

Xaa Arg Ser Asp Thr Leu Xaa Trp Glu Lys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (9)..(9)
<223> OTHER INFORMATION: D form Glu
<220> FEATURE:
<221> NAME/KEY: MOD_RES
<222> LOCATION: (10)..(10)
<223> OTHER INFORMATION: D form Lysine

<400> SEQUENCE: 10

Xaa Arg Ser Asp Thr Leu Xaa Trp Glu Lys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
```

```
<222> LOCATION: (7)..(7)
<223> OTHER INFORMATION: Penicillamine
<220> FEATURE:
<221> NAME/KEY: MOD_RES
<222> LOCATION: (10)..(10)
<223> OTHER INFORMATION: D form Lysine

<400> SEQUENCE: 11

Xaa Arg Ser Asp Thr Leu Xaa Trp Glu Lys
 1               5                  10

<210> SEQ ID NO 12
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (9)..(9)
<223> OTHER INFORMATION: D-Lys form
<220> FEATURE:
<221> NAME/KEY: MISC_FEATURE
<222> LOCATION: (9)..(9)
<223> OTHER INFORMATION: Sidechain amine linkage to diglycolic acid
      which is further linked to the peptide Ac-Pen-(N-Me-Arg)-Ser-Asp-
      Thr-Leu-Pen-Trp-(D-Lys)-NH2 forming a homodimer molecule

<400> SEQUENCE: 12

Xaa Arg Ser Asp Thr Leu Xaa Trp Lys
 1               5

<210> SEQ ID NO 13
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)
```

```
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-Trp-BetaHomoGlu-(D-Lys)-NH2 forming a homodimer
      molecule

<400> SEQUENCE: 13

Xaa Arg Ser Asp Thr Leu Xaa Trp Xaa Lys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (10)..(10)
<223> OTHER INFORMATION: D-form N-Methyl Lysine
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-Trp-Glu-(N-Me-D-Lys)-NH2 forming a homodimer molecule

<400> SEQUENCE: 14

Xaa Arg Ser Asp Thr Leu Xaa Trp Glu Lys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
```

```
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (10)..(10)
<223> OTHER INFORMATION: N-Methyl Lysine
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-Trp-Glu-(N-Me-Lys)-NH2 forming a homodimer molecule

<400> SEQUENCE: 15

Xaa Arg Ser Asp Thr Leu Xaa Trp Glu Lys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (9)..(9)
<223> OTHER INFORMATION: D form Glu
<220> FEATURE:
<221> NAME/KEY: MOD_RES
<222> LOCATION: (10)..(10)
<223> OTHER INFORMATION: D form Lysine
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-Trp-(D-Glu)-(D-Lys) forming a homodimer molecule

<400> SEQUENCE: 16
```

Xaa Arg Ser Asp Thr Leu Xaa Trp Glu Lys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(7)
<223> OTHER INFORMATION: Disulfide bridge between residues at position 1
      and position 7
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (10)..(10)
<223> OTHER INFORMATION: D form Lysine
<220> FEATURE:
<221> NAME/KEY: MOD_RES
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-Trp-Glu-(D-Lys) forming a homodimer molecule

<400> SEQUENCE: 17

Xaa Arg Ser Asp Thr Leu Xaa Trp Glu Lys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Any amino acid or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(3)
<223> OTHER INFORMATION: Any amino acid or absent
<220> FEATURE:
<221> NAME/KEY: MOD_RES
<222> LOCATION: (4)..(4)
<223> OTHER INFORMATION: Any amino acid capable of forming a bond with
      amino acid at position 10
<220> FEATURE:
<221> NAME/KEY: MOD_RES
<222> LOCATION: (5)..(5)
<223> OTHER INFORMATION: N-Me-Arg, Arg, N-Me-Lys, Phe(4-guanidino),
      Phe(4-carbomyl), Cit, Phe(4-NH2), N-Me-homoArg, homoArg, Tyr, Dap,
      Dab, Arg-Me-sym, Arg-Me-asym, Cav, and His
<220> FEATURE:

```
<221> NAME/KEY: MOD_RES
<222> LOCATION: (6)..(6)
<223> OTHER INFORMATION: Ser, Gly, Thr or Ile
<220> FEATURE:
<221> NAME/KEY: MOD_RES
<222> LOCATION: (7)..(7)
<223> OTHER INFORMATION: Asp, Asp(OMe) or N-Me-Asp
<220> FEATURE:
<221> NAME/KEY: MOD_RES
<222> LOCATION: (8)..(8)
<223> OTHER INFORMATION: Thr, Val, Ile, Leu, homoLeu, Gln, Ser, Asp,
      Pro, Gly, His, Ala, Phe, Lys, Arg, Asn, Glu, Tyr, Trp, Met, Nle,
      and N-methyl amino acids, including N-Me-Thr
<220> FEATURE:
<221> NAME/KEY: MOD_RES
<222> LOCATION: (9)..(9)
<223> OTHER INFORMATION: Gln, Ser, Asp, Pro, Gly, Ala, Phe, Glu, Ile,
      Val, N-butyl Ala, N-pental Ala, N-hexyl Ala, cyclobutyl Ala,
      cyclopentylAla, Leu, Nle, Cba, homoLeu, Cpa, Aoc, and N-Me-Leu
<220> FEATURE:
<221> NAME/KEY: MOD_RES
<222> LOCATION: (10)..(10)
<223> OTHER INFORMATION: any amino acid capable of forming a bond with
      amino acid at position 4
<220> FEATURE:
<221> NAME/KEY: MOD_RES
<222> LOCATION: (11)..(11)
<223> OTHER INFORMATION: absent or selected from the group consisting
      of: aromatic amino acids, substituted aromatic amino acids, and
      Tic
<220> FEATURE:
<221> NAME/KEY: MOD_RES
<222> LOCATION: (12)..(12)
<223> OTHER INFORMATION: absent or selected from the group consisting
      of: aromatic amino acids, substituted aromatic amino acids, Glu,
      D-Glu, homoGlu, Asp, D-Asp, D-homoGlu, Gla, beta-homoGlu, Tic,
      Aic, Gln, Cit, Glu(OMe), Asn, D-His, Tic, Phe(3-COOH), D-Arg, Bip,
      D-Trp, Phe,
<220> FEATURE:
<221> NAME/KEY: MOD_RES
<222> LOCATION: (12)..(12)
<223> OTHER INFORMATION: Continued from above: D-Val, D-Thr, D-Tyr,
      D-Lys, D-Ile, D-His, N-Me-Glu, N-Me-Asp, alpha-homoGlu, Biphenyl-
      Gly, Biphenyl-Ala, Homo-Phe, D-1-Nal, D-2-Nal, Thr, and Val, and
      corresponding D-amino acids and isosteres
<220> FEATURE:
<221> NAME/KEY: MOD_RES
<222> LOCATION: (13)..(13)
<223> OTHER INFORMATION: absent or Pro or any amino acid
<220> FEATURE:
<221> NAME/KEY: MOD_RES
<222> LOCATION: (14)..(14)
<223> OTHER INFORMATION: any amino acid with an amine side chain, Lys,
      D-Lys, N-Me-Lys, D-N-Me-Lys, Orn, Dab, Dap, HomoLys, D-Dap, D-Dab,
      D-Orn, Cys, HomoCys, Pen, D-HomoCys, D-Cys, D-Pen, Asp, Glu,
      D-Asp, D-Glu and HomoSer, HomoGlu, D-homoGlu, N-Me-Glu, N-Me-Asp,
      N-Me-D-Glu
<220> FEATURE:
<221> NAME/KEY: MOD_RES
<222> LOCATION: (14)..(14)
<223> OTHER INFORMATION: Continued from above: and N-Me-D-Asp

<400> SEQUENCE: 18

Xaa Xaa Xaa Xaa Xaa Xaa Xaa Xaa Xaa Xaa Xaa Xaa Xaa Xaa
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form

<400> SEQUENCE: 19

Xaa Arg Ser Asp Thr Leu Xaa Trp Xaa Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe-(4-COOH)
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form

<400> SEQUENCE: 20

Xaa Arg Ser Asp Thr Leu Xaa Phe Xaa Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (10)..(10)
<223> OTHER INFORMATION: N-Methyl Lysine

<400> SEQUENCE: 21

Xaa Arg Ser Asp Thr Leu Xaa Trp Glu Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: 2-Napthylalanine
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form

<400> SEQUENCE: 22

Xaa Arg Ser Asp Thr Leu Xaa Xaa Xaa Lys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
```

```
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: 1-Napthylalanine
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form

<400> SEQUENCE: 23

Xaa Arg Ser Asp Thr Leu Xaa Xaa Xaa Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: 2-Napthylalanine
<220> FEATURE:
<221> NAME/KEY: MOD_RES
<222> LOCATION: (10)..(10)
<223> OTHER INFORMATION: N-Methyl Lysine

<400> SEQUENCE: 24

Xaa Arg Ser Asp Thr Leu Xaa Xaa Glu Lys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
```

```
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe-(4-tert butyl)
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form

<400> SEQUENCE: 25

Xaa Arg Ser Asp Thr Leu Xaa Phe Xaa Lys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe-(4-tert butyl)
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: N-Methyl Lysine

<400> SEQUENCE: 26

Xaa Arg Ser Asp Thr Leu Xaa Phe Xaa Lys
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: N-Methyl Lysine

<400> SEQUENCE: 27

Xaa Arg Ser Asp Thr Leu Xaa Trp Xaa Lys
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: 2-Napthylalanine
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: N-Methyl-Lysine

<400> SEQUENCE: 28

Xaa Arg Ser Asp Thr Leu Xaa Xaa Xaa Lys
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
```

```
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: 1-Napthylalanine
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: N-Methyl-Lysine

<400> SEQUENCE: 29

Xaa Arg Ser Asp Thr Leu Xaa Xaa Xaa Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (10)..(10)
<223> OTHER INFORMATION: D form N-Methyl Lysine

<400> SEQUENCE: 30

Xaa Arg Ser Asp Thr Leu Xaa Trp Glu Lys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
```

<223> OTHER INFORMATION: Penicillamine
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-Trp-BetaHomoGlu-(D-Lys) forming a homodimer molecule

<400> SEQUENCE: 31

Xaa Arg Ser Asp Thr Leu Xaa Trp Xaa Lys
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe-(4-COOH)
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-(Phe-(4-COOH)-( -homoGlu)-(D-Lys) forming a homodimer
      molecule

<400> SEQUENCE: 32

Xaa Arg Ser Asp Thr Leu Xaa Phe Xaa Lys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)

```
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (10)..(10)
<223> OTHER INFORMATION: N-Methyl Lysine
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-Trp-Glu-(N-Me-Lys) forming a homodimer molecule

<400> SEQUENCE: 33

Xaa Arg Ser Asp Thr Leu Xaa Trp Glu Lys
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: 2-Napthylalanine
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-2-Nal-( -homoGlu)-(D-Lys) forming a homodimer molecule

<400> SEQUENCE: 34

Xaa Arg Ser Asp Thr Leu Xaa Xaa Xaa Lys
1               5                   10

<210> SEQ ID NO 35
<211> LENGTH: 10
```

```
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: 1-Napthylalanine
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-1-Nal-( -homoGlu)-(D-Lys) forming a homodimer molecule

<400> SEQUENCE: 35

Xaa Arg Ser Asp Thr Leu Xaa Xaa Xaa Lys
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: 2-Napthylalanine
<220> FEATURE:
<221> NAME/KEY: MOD_RES
<222> LOCATION: (10)..(10)
<223> OTHER INFORMATION: N-Methyl Lysine
<220> FEATURE:
<221> NAME/KEY: MISC_FEATURE
<222> LOCATION: (10)..(10)
<223> OTHER INFORMATION: Sidechain amine linkage to diglycolic acid
``` which is further linked to the peptide Ac-Pen-(N-Me-Arg)-Ser-Asp-
Thr-Leu-Pen-2-Nal-Glu-(N-Me-Lys) forming a homodimer molecule

<400> SEQUENCE: 36

Xaa Arg Ser Asp Thr Leu Xaa Xaa Glu Lys
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe-(4-tert butyl)
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form
<220> FEATURE:
<221> NAME/KEY: MISC_FEATURE
<222> LOCATION: (10)..(10)
<223> OTHER INFORMATION: Sidechain amine linkage to diglycolic acid
which is further linked to the peptide Ac-Pen-(N-Me-Arg)-Ser-Asp-
Thr-Leu-Pen-Phe(4-tBu)-( -homoGlu)-(D-Lys) forming a homodimer
molecule

<400> SEQUENCE: 37

Xaa Arg Ser Asp Thr Leu Xaa Phe Xaa Lys
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine

```
<220> FEATURE:
<221> NAME/KEY: MOD_RES
<222> LOCATION: (8)..(8)
<223> OTHER INFORMATION: Phe-(4-tert butyl)
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: N-Methyl Lysine
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-
      Asp-Thr-Leu-Pen-Phe(4-tBu)-(-homoGlu)-(N-Me-Lys) forming a
      homodimer molecule

<400> SEQUENCE: 38

Xaa Arg Ser Asp Thr Leu Xaa Phe Xaa Lys
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: N-Methyl Lysine
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-
      Asp-Thr-Leu-Pen-Trp-(-homoGlu)-(N-Me-Lys) forming a homodimer
      molecule

<400> SEQUENCE: 39

Xaa Arg Ser Asp Thr Leu Xaa Trp Xaa Lys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
```

```
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: 2-Napthylalanine
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: N-Methyl-Lysine
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-2-Nal-( -homoGlu)-(N-Me-Lys) forming a homodimer
      molecule

<400> SEQUENCE: 40

Xaa Arg Ser Asp Thr Leu Xaa Xaa Xaa Lys
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: 1-Napthylalanine
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: N-Methyl-Lysine
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-1-Nal-( -homoGlu)-(N-Me-Lys) forming a homodimer
``` molecule

<400> SEQUENCE: 41

Xaa Arg Ser Asp Thr Leu Xaa Xaa Xaa Lys
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (10)..(10)
<223> OTHER INFORMATION: D form N-Methyl Lysine
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-Trp-Glu-(N-Me-D-Lys) forming a homodimer molecule

<400> SEQUENCE: 42

Xaa Arg Ser Asp Thr Leu Xaa Trp Glu Lys
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe-(4-COOH)
<220> FEATURE:
<221> NAME/KEY: MOD_RES
<222> LOCATION: (10)..(10)
<223> OTHER INFORMATION: D form Lysine

<400> SEQUENCE: 43

```
Xaa Arg Ser Asp Thr Leu Xaa Phe Glu Lys
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe-(4-tert butyl)
<220> FEATURE:
<221> NAME/KEY: MOD_RES
<222> LOCATION: (10)..(10)
<223> OTHER INFORMATION: D-Lys form

<400> SEQUENCE: 44

Xaa Arg Ser Asp Thr Leu Xaa Phe Glu Lys
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe-(4-tert butyl)
<220> FEATURE:
<221> NAME/KEY: MOD_RES
<222> LOCATION: (10)..(10)
<223> OTHER INFORMATION: N-Methyl Lysine

<400> SEQUENCE: 45

Xaa Arg Ser Asp Thr Leu Xaa Phe Glu Lys
1               5                   10
```

```
<210> SEQ ID NO 46
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Biphenylalanine (Bip)
<220> FEATURE:
<221> NAME/KEY: MOD_RES
<222> LOCATION: (10)..(10)
<223> OTHER INFORMATION: D-Lys form

<400> SEQUENCE: 46

Xaa Arg Ser Asp Thr Leu Xaa Xaa Glu Lys
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Biphenylalanine (Bip)
<220> FEATURE:
<221> NAME/KEY: MOD_RES
<222> LOCATION: (9)..(9)
<223> OTHER INFORMATION: Beta-homoglutamic acid
<220> FEATURE:
<221> NAME/KEY: MOD_RES
<222> LOCATION: (10)..(10)
<223> OTHER INFORMATION: D-Lys form

<400> SEQUENCE: 47

Xaa Arg Ser Asp Thr Leu Xaa Xaa Xaa Lys
1               5                   10

<210> SEQ ID NO 48
```

```
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe-(4-COOH)

<400> SEQUENCE: 48

Xaa Arg Ser Asp Thr Leu Xaa Phe Glu
1               5

<210> SEQ ID NO 49
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe-(4-COOH)
<220> FEATURE:
<221> NAME/KEY: MOD_RES
<222> LOCATION: (9)..(9)
<223> OTHER INFORMATION: Beta-homoglutamic acid

<400> SEQUENCE: 49

Xaa Arg Ser Asp Thr Leu Xaa Phe Xaa
1               5

<210> SEQ ID NO 50
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe-(4-tert butyl)

<400> SEQUENCE: 50

Xaa Arg Ser Asp Thr Leu Xaa Phe Glu
1               5

<210> SEQ ID NO 51
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe-(4-tert butyl)
<220> FEATURE:
<221> NAME/KEY: MOD_RES
<222> LOCATION: (9)..(9)
<223> OTHER INFORMATION: Beta-homoglutamic acid

<400> SEQUENCE: 51

Xaa Arg Ser Asp Thr Leu Xaa Phe Xaa
1               5

<210> SEQ ID NO 52
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
```

```
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Phe-(4-tert butyl)

<400> SEQUENCE: 52

Xaa Arg Ser Asp Thr Leu Xaa Phe Glu
1               5

<210> SEQ ID NO 53
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Biphenylalanine (Bip)

<400> SEQUENCE: 53

Xaa Arg Ser Asp Thr Leu Xaa Xaa Glu
1               5

<210> SEQ ID NO 54
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: Biphenylalanine (Bip)
<220> FEATURE:
<221> NAME/KEY: MOD_RES
<222> LOCATION: (9)..(9)
<223> OTHER INFORMATION: Beta-homoglutamic acid

<400> SEQUENCE: 54
```

```
Xaa Arg Ser Asp Thr Leu Xaa Xaa Xaa
1               5
```

<210> SEQ ID NO 55
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (9)..(9)
<223> OTHER INFORMATION: Beta-homoglutamic acid

<400> SEQUENCE: 55

```
Xaa Arg Ser Asp Thr Leu Xaa Trp Xaa
1               5
```

<210> SEQ ID NO 56
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine

<400> SEQUENCE: 56

```
Xaa Arg Ser Asp Thr Leu Xaa Trp Glu
1               5
```

<210> SEQ ID NO 57
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES

```
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: 2-Napthylalanine
<220> FEATURE:
<221> NAME/KEY: MOD_RES
<222> LOCATION: (9)..(9)
<223> OTHER INFORMATION: Beta-homoglutamic acid

<400> SEQUENCE: 57

Xaa Arg Ser Asp Thr Leu Xaa Xaa Xaa
1               5

<210> SEQ ID NO 58
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: 1-Napthylalanine
<220> FEATURE:
<221> NAME/KEY: MOD_RES
<222> LOCATION: (9)..(9)
<223> OTHER INFORMATION: Beta-homoglutamic acid

<400> SEQUENCE: 58

Xaa Arg Ser Asp Thr Leu Xaa Xaa Xaa
1               5

<210> SEQ ID NO 59
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
```

```
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (8)..(8)
<223> OTHER INFORMATION: 2-Napthylalanine

<400> SEQUENCE: 59

Xaa Arg Ser Asp Thr Leu Xaa Xaa Glu
1               5

<210> SEQ ID NO 60
<211> LENGTH: 14
<212> TYPE: PRT
<213> ORGANISM: Artificial Sequence
<220> FEATURE:
<223> OTHER INFORMATION: Synthesized peptide formula
<220> FEATURE:
<221> NAME/KEY: MOD_RES
<222> LOCATION: (1)..(1)
<223> OTHER INFORMATION: is absent, or an amino acid selected from the
      group consisting of Gln, Asn, Asp, Pro, Gly, His, Ala, Ile, Phe,
      Lys, Arg, Asn, Glu, Leu, Val, Tye, Trp, Met, Thr, and suitable
      isosteres and corresponding D-amino acids thereof
<220> FEATURE:
<221> NAME/KEY: MOD_RES
<222> LOCATION: (2)..(2)
<223> OTHER INFORMATION: is absent, or an amino acid selected from the
      group consisting of Gln, Asn, Asp, Pro, Gly, His, Ala, Ile, Phe,
      Lys, Arg, Asn, Glu, Leu, Val, Tye, Trp, Met, Thr, and suitable
      isosteres and corresponding D-amino acids thereof
<220> FEATURE:
<221> NAME/KEY: MOD_RES
<222> LOCATION: (3)..(3)
<223> OTHER INFORMATION: is absent, or an amino acid selected from the
      group consisting of Gln, Asn, Asp, Pro, Gly, His, Ala, Ile, Phe,
      Lys, Arg, Asn, Glu, Leu, Val, Tye, Trp, Met and Thr, and suitable
      isosteres and corresponding D-amino acids thereof
<220> FEATURE:
<221> NAME/KEY: MOD_RES
<222> LOCATION: (4)..(4)
<223> OTHER INFORMATION: is selected from the group consisting of Cys,
      Pen, Asp, Glu, hGlu, b-Asp, b-Glu, Lys, homo-Lys, Orn, Dap, Dab,
      and suitable isosteres and corresponding D-amino acids thereof
<220> FEATURE:
<221> NAME/KEY: MOD_RES
<222> LOCATION: (5)..(5)
<223> OTHER INFORMATION: is selected from the group consisting of Gln,
      Asn, Asp, Pro, Gly, His, Ala, Ile, Phe, Lys, Arg, Asn, Glu, Leu,
      Val, Tye, Trp, Met, Thr, homo-Arg, Dap, Dab, N-Me-Arg,
      Arg-(Me)sym, Arg-(Me)asym, 4-Guan, Cit, Cav, and suitable
      isosteres thereof
<220> FEATURE:
<221> NAME/KEY: MOD_RES
<222> LOCATION: (6)..(6)
<223> OTHER INFORMATION: is selected from the group consisting of Ser,
      Gln, Asn, Asp, Pro, Gly, His, Ala, Ile, Phe, Lys, Arg, Asn, Glu,
      Leu, Val, Tye, Trp, Met, and suitable isosteres thereof
<220> FEATURE:
<221> NAME/KEY: MOD_RES
<222> LOCATION: (7)..(7)
<223> OTHER INFORMATION: is selected from the group consisting of Asp,
      N-Me-Asp and a suitable isostere replacement for Asp
<220> FEATURE:
<221> NAME/KEY: MOD_RES
<222> LOCATION: (8)..(8)
<223> OTHER INFORMATION: is selected from the group consisting of Thr,
      Gln, Ser, Asn, Asp, Pro, Gly, His, Ala, Ile, Phe, Lys, Arg, Asn,
      Glu, Val, Tye, Trp, Met, and N-Methyl amino acids including
      N-Me-Thr
<220> FEATURE:
<221> NAME/KEY: MOD_RES
<222> LOCATION: (9)..(9)
<223> OTHER INFORMATION: is selected from the group consisting of Gln,
```

```
         Asn, Asp, Pro, Gly, Ala, Phe, Leu, Asn, Glu, Val, homo-Leu,
         n-Butyl Ala, n-Pentyl Ala, n-Hexyl Ala, N-Me-Leu, and suitable
         isosteres thereof
<220> FEATURE:
<221> NAME/KEY: MOD_RES
<222> LOCATION: (10)..(10)
<223> OTHER INFORMATION: is selected from the group consisting of Cys,
         Asp, Pen, Lys, homo-Lys, Orn, Glu, b-Asp, b-Glu, Dap, and Dab
<220> FEATURE:
<221> NAME/KEY: MOD_RES
<222> LOCATION: (11)..(11)
<223> OTHER INFORMATION: is selected from the group consisting of Gly,
         Gln, Asn, Asp, Ala, Ile, Leu, Val, Met, Thr, Lys, Trp, Tyr,
         CONH.sub.2, COOH, His, Glu, Ser, Arg, Pro, Phe, Sar, 1Nal, 2Nal,
         hPhe, Phe(4-F), Phe (4-tBu), O-Me-Tyr, dihydro-Trp, Dap, Dab,
         Dab(Ac), Orn, D-Orn...
<220> FEATURE:
<221> NAME/KEY: MOD_RES
<222> LOCATION: (11)..(11)
<223> OTHER INFORMATION: Continued from above: N-Me-Orn, N-Me-Dap,
         D-Dap, D-Dab Bip, Ala(3,3diphenyl), Biphenyl-Ala, aromatic ring
         substituted Phe, aromatic ring substituted Trp, aromatic ring
         substituted His, hetero aromatic amino acids, N-Me-Lys,
         N-Me-Lys(Ac)...
<220> FEATURE:
<221> NAME/KEY: MOD_RES
<222> LOCATION: (11)..(11)
<223> OTHER INFORMATION: Continued from above: 4-Me-Phe, and
         corresponding D-amino acids and suitable isostere replacements
<220> FEATURE:
<221> NAME/KEY: MOD_RES
<222> LOCATION: (12)..(12)
<223> OTHER INFORMATION: is absent, Lys, or an amino acid selected
         from the group consisting of Glu, Lys, Gln, Pro, Gly, His, Ala,
         Ile, Phe, Lys, Arg, Leu, Val, Tye, Trp, Met, Gla, Ser, Asn, Dap,
         Dab, Orn, D-Orn, N-Me-Orn, N-Me-Dap, N-Me-Dab, N-Me Lys...
<220> FEATURE:
<221> NAME/KEY: MOD_RES
<222> LOCATION: (12)..(12)
<223> OTHER INFORMATION: Continued from above:  D-Dap, D-Dab, and
         suitable isosteres and corresponding D-amino acids thereof
<220> FEATURE:
<221> NAME/KEY: MOD_RES
<222> LOCATION: (13)..(13)
<223> OTHER INFORMATION: is absent, or an amino acid selected from Gln,
         Pro, Gly, His, Ala, Ile, Phe, Lys, Arg, Leu, Val, Tye, Trp, Met,
         Glu, Gla, Ser, Asn, Dap, Dab, Orn, D-Orn, N-Me-Orn, N-Me-Dap,
         N-Me-Dab, N-Me Lys, D-Dap, D-Dab and suitable isosteres and
         corresponding
<220> FEATURE:
<221> NAME/KEY: MOD_RES
<222> LOCATION: (14)..(14)
<223> OTHER INFORMATION: is absent, or an amino acid selected from the
         group consisting of natural amino acids,  and suitable isosteres,
         corresponding D-amino acids and corresponding N-Methyl amino acids
         thereof

<400> SEQUENCE: 60

Xaa Xaa Xaa Xaa Xaa Xaa Xaa Xaa Xaa Xaa Xaa Xaa Xaa Xaa
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Synthesized peptide formula
<220> FEATURE:
<221> NAME/KEY: MOD_RES
<222> LOCATION: (1)..(1)
<223> OTHER INFORMATION: is absent, or an amino acid selected from the
         group consisting of Gln, Asp, Pro, Gly, His, Ala, Ile, Phe, Lys,
         Arg, Asn, Glu, Leu, Val, Tyr, Ser, Trp, Met, Thr, suitable
         isosteres and corresponding D-amino acids thereof
<220> FEATURE:
<221> NAME/KEY: MOD_RES
<222> LOCATION: (2)..(2)
```

-continued

```
<223> OTHER INFORMATION: is absent, or an amino acid selected from the
      group consisting of Gln, Asp, Pro, Gly, His, Ala, Ile, Phe, Lys,
      Arg, Asn, Glu, Leu, Val, Tyr, Trp, Met, Thr, and suitable
      isosteres and corresponding D-amino acids thereof
<220> FEATURE:
<221> NAME/KEY: MOD_RES
<222> LOCATION: (3)..(3)
<223> OTHER INFORMATION: is absent, or an amino acid selected from the
      group consisting of Gln, Asp, Pro, Gly, His, Ala, Ile, Phe, Lys,
      Arg, Asn, Glu, Leu, Val, Tyr, Trp, Met, Ser and Thr, and suitable
      isosteres and corresponding D-amino acids thereof
<220> FEATURE:
<221> NAME/KEY: MOD_RES
<222> LOCATION: (4)..(4)
<223> OTHER INFORMATION: is selected from the group consisting of Cys,
      Pen, Asp, Glu, hGlu, b-Asp, b-Glu, Lys, homo-Lys, Orn, Dap, Dab,
      and suitable isosteres and corresponding D-amino acids thereof
<220> FEATURE:
<221> NAME/KEY: MOD_RES
<222> LOCATION: (5)..(5)
<223> OTHER INFORMATION: is selected from the group consisting of Gln,
      Asn, Asp, Pro, Gly, His, Ala, Ile, Phe, Lys, Arg, Asn, Glu, Leu,
      Val, Tye, Trp, Met, Thr, homo-Arg, Dap, Dab, N-Me-Arg,
      Arg-(Me)sym, Arg-(Me)asym, 4-Guan, Cit, Cav, and suitable '
      isosteres thereof
<220> FEATURE:
<221> NAME/KEY: MOD_RES
<222> LOCATION: (6)..(6)
<223> OTHER INFORMATION: is selected from the group consisting of Ser,
      Gln, Asn, Asp, Pro, Gly, His, Ala, Ile, Phe, Lys, Arg, Asn, Glu,
      Leu, Val, Tye, Trp, Met, and suitable isosteres thereof
<220> FEATURE:
<221> NAME/KEY: MOD_RES
<222> LOCATION: (7)..(7)
<223> OTHER INFORMATION: is selected from the group consisting of Asp,
      N-Me-Asp and a suitable isostere replacement for Asp
<220> FEATURE:
<221> NAME/KEY: MOD_RES
<222> LOCATION: (8)..(8)
<223> OTHER INFORMATION: is selected from the group consisting of Thr,
      Gln, Ser, Asn, Asp, Pro, Gly, His, Ala, Ile, Phe, Lys, Arg, Asn,
      Glu, Val, Tye, Trp, Met, and N-Methyl amino acids including
      N-Me-Thr
<220> FEATURE:
<221> NAME/KEY: MOD_RES
<222> LOCATION: (9)..(9)
<223> OTHER INFORMATION: is selected from the group consisting of Gln,
      Asn, Asp, Pro, Gly, Ala, Phe, Leu, Asn, Glu, Val, homo-Leu,
      n-Butyl Ala, n-Pentyl Ala, n-Hexyl Ala, N-Me-Leu, and suitable
      isosteres thereof
<220> FEATURE:
<221> NAME/KEY: MOD_RES
<222> LOCATION: (10)..(10)
<223> OTHER INFORMATION: is selected from the group consisting of Cys,
      Asp, Pen, Lys, homo-Lys, Orn, Glu, b-Asp, b-Glu, Dap, and Dab
<220> FEATURE:
<221> NAME/KEY: MOD_RES
<222> LOCATION: (11)..(11)
<223> OTHER INFORMATION: is selected from the group consisting of Gly,
      Gln, Asn, Asp, Ala, Ile, Leu, Val, Met, Thr, Lys, Trp, Tyr,
      CONH.sub.2, COOH, His, Glu, Ser, Arg, Pro, Phe, Sar, 1Nal, 2Nal,
      hPhe, Phe(4-F), Phe(4-tBu), O-Me-Tyr, dihydro-Trp, Dap, Dab,
      Dab(Ac), Orn, D-Orn...
<220> FEATURE:
<221> NAME/KEY: MOD_RES
<222> LOCATION: (11)..(11)
<223> OTHER INFORMATION: Continued from above: N-Me-Orn, N-Me-Dap,
      D-Dap, D-Dab Bip, Ala(3,3diphenyl), Biphenyl-Ala, aromatic ring
      substituted Phe, aromatic ring substituted Trp, aromatic ring
      substituted His, hetero aromatic amino acids, N-Me-Lys,
      N-Me-Lys(Ac)...
<220> FEATURE:
<221> NAME/KEY: MOD_RES
<222> LOCATION: (11)..(11)
<223> OTHER INFORMATION: Continued from above: 4-Me-Phe, and
      corresponding D-amino acids and suitable isostere replacements
<220> FEATURE:
<221> NAME/KEY: MOD_RES
<222> LOCATION: (12)..(12)
```

```
<223> OTHER INFORMATION: is absent, Lys, or an amino acid selected from
      the group consisting of Glu, Lys, Gln, Pro, Gly, His, Ala, Ile,
      Phe, Lys, Arg, Leu, Val, Tye, Trp, Met, Gla, Ser, Asn, Dap, Dab,
      Orn, D-Orn, N-Me-Orn, N-Me-Dap, N-Me-Dab, N-Me Lys...
<220> FEATURE:
<221> NAME/KEY: MOD_RES
<222> LOCATION: (12)..(12)
<223> OTHER INFORMATION: Continued from above: D-Dap, D-Dab, and
      suitable isosteres and corresponding D-amino acids thereof
<220> FEATURE:
<221> NAME/KEY: MOD_RES
<222> LOCATION: (13)..(13)
<223> OTHER INFORMATION: is absent, or an amino acid selected from Gln,
      Pro, Gly, His, Ala, Ile, Phe, Lys, Arg, Leu, Val, Tye, Trp, Met,
      Glu, Gla, Ser, Asn, Dap, Dab, Orn, D-Orn, N-Me-Orn, N-Me-Dap,
      N-Me-Dab, N-Me Lys, D-Dap, D-Dab and suitable isosteres and
      corresponding
<220> FEATURE:
<221> NAME/KEY: MOD_RES
<222> LOCATION: (14)..(14)
<223> OTHER INFORMATION: is absent, or an amino acid selected from the
      group consisting of natural amino acids, and suitable isosteres,
      corresponding D-amino acids and corresponding N-Methyl amino
      acids thereof

<400> SEQUENCE: 61

Xaa Xaa Xaa Xaa Xaa Xaa Xaa Xaa Xaa Xaa Xaa Xaa Xaa Xaa
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: penicillamine
<220> FEATURE:
<221> NAME/KEY: MOD_RES
<222> LOCATION: (2)..(2)
<223> OTHER INFORMATION: N-Me-Arginine
<220> FEATURE:
<221> NAME/KEY: MOD_RES
<222> LOCATION: (7)..(7)
<223> OTHER INFORMATION: penicillamine
<220> FEATURE:
<221> NAME/KEY: MOD_RES
<222> LOCATION: (8)..(8)
<223> OTHER INFORMATION: is any amino acid (natural or unnatural) or
      in certain embodiments is Phe(4-tBu) or Trp
<220> FEATURE:
<221> NAME/KEY: MOD_RES
<222> LOCATION: (9)..(9)
<223> OTHER INFORMATION: is absent or any amino acid (natural or
      unnatural); or in certain embodiments, beta-homoGlu, Glu, or
      D-Glu
<220> FEATURE:
<221> NAME/KEY: MOD_RES
<222> LOCATION: (10)..(10)
<223> OTHER INFORMATION: any amino acid (natural or unnatural); or in
      certain embodiments, is Lys, D-Lys, N-Me-Lys or N-Me-D-Lys.

<400> SEQUENCE: 62

Xaa Arg Ser Asp Thr Leu Xaa Xaa Xaa Xaa
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Synthesized peptide
<220> FEATURE:
```

```
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (9)..(9)
<223> OTHER INFORMATION: D-Lys form

<400> SEQUENCE: 63

Xaa Arg Ser Asp Thr Leu Xaa Trp Lys
1               5

<210> SEQ ID NO 64
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (9)..(9)
<223> OTHER INFORMATION: D-Glu form
<220> FEATURE:
<221> NAME/KEY: MOD_RES
<222> LOCATION: (10)..(10)
<223> OTHER INFORMATION: D-Lys form

<400> SEQUENCE: 64

Xaa Arg Ser Asp Thr Leu Xaa Trp Glu Lys
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (10)..(10)
<223> OTHER INFORMATION: D-Lys form

<400> SEQUENCE: 65
```

Xaa Arg Ser Asp Thr Leu Xaa Trp Glu Lys
1               5                   10

<210> SEQ ID NO 66
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (9)..(9)
<223> OTHER INFORMATION: D-Lys form
<220> FEATURE:
<221> NAME/KEY: MISC_FEATURE
<222> LOCATION: (9)..(9)
<223> OTHER INFORMATION: Sidechain amine linkage to diglycolic acid
      which is further linked to the peptide Ac-Pen-(N-Me-Arg)-Ser-Asp-
      Thr-Leu-Pen-Trp-BetaHomoGlu-(D-Lys) forming a homodimer molecule

<400> SEQUENCE: 66

Xaa Arg Ser Asp Thr Leu Xaa Trp Lys
1               5

<210> SEQ ID NO 67
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (9)..(9)
<223> OTHER INFORMATION: D-Glu form
<220> FEATURE:
<221> NAME/KEY: MOD_RES
<222> LOCATION: (10)..(10)
<223> OTHER INFORMATION: D-Lys form
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-Trp-BetaHomoGlu-(D-Lys) forming a homodimer molecule

<400> SEQUENCE: 67

Xaa Arg Ser Asp Thr Leu Xaa Trp Glu Lys
1               5                   10

```
<210> SEQ ID NO 68
<211> LENGTH: 10
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (2)..(2)
<223> OTHER INFORMATION: N-Methyl Arginine
<220> FEATURE:
<221> NAME/KEY: MOD_RES
<222> LOCATION: (7)..(7)
<223> OTHER INFORMATION: Penicillamine
<220> FEATURE:
<221> NAME/KEY: MOD_RES
<222> LOCATION: (10)..(10)
<223> OTHER INFORMATION: D-Lys form
<220> FEATURE:
<221> NAME/KEY: MISC_FEATURE
<222> LOCATION: (10)..(10)
<223> OTHER INFORMATION: Sidechain amine linkage to diglycolic acid
      which is further linked to the peptide Ac-Pen-(N-Me-Arg)-Ser-Asp-
      Thr-Leu-Pen-Trp-BetaHomoGlu-(D-Lys) forming a homodimer molecule

<400> SEQUENCE: 68

Xaa Arg Ser Asp Thr Leu Xaa Trp Glu Lys
1               5                   10

<210> SEQ ID NO 69
<211> LENGTH: 8
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (5)..(5)
<223> OTHER INFORMATION: penicillamine
<220> FEATURE:
<221> NAME/KEY: MOD_RES
<222> LOCATION: (6)..(6)
<223> OTHER INFORMATION: is any amino acid (natural or unnatural) or
      in certain embodiments is Phe(4-tBu) or Trp
<220> FEATURE:
<221> NAME/KEY: MOD_RES
<222> LOCATION: (7)..(7)
<223> OTHER INFORMATION: is absent or any amino acid (natural or
      unnatural); or in certain embodiments, beta-homoGlu, Glu, or D-Glu
<220> FEATURE:
<221> NAME/KEY: MOD_RES
<222> LOCATION: (8)..(8)
<223> OTHER INFORMATION: any amino acid (natural or unnatural); or in
      certain embodiments, is Lys, D-Lys, N-Me-Lys or N-Me-D-Lys.

<400> SEQUENCE: 69

Ser Asp Thr Leu Xaa Xaa Xaa Xaa
1               5

<210> SEQ ID NO 70
<211> LENGTH: 7
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (4)..(4)
<223> OTHER INFORMATION: penicillamine
<220> FEATURE:
<221> NAME/KEY: MOD_RES
```

```
<222> LOCATION: (5)..(5)
<223> OTHER INFORMATION: is any amino acid (natural or unnatural) or
      in certain embodiments is Phe(4-tBu) or Trp
<220> FEATURE:
<221> NAME/KEY: MOD_RES
<222> LOCATION: (6)..(6)
<223> OTHER INFORMATION: is absent or any amino acid (natural or
      unnatural); or in certain embodiments, beta-homoGlu, Glu, or D-Glu
<220> FEATURE:
<221> NAME/KEY: MOD_RES
<222> LOCATION: (7)..(7)
<223> OTHER INFORMATION: any amino acid (natural or unnatural); or in
      certain embodiments, is Lys, D-Lys, N-Me-Lys or N-Me-D-Lys.

<400> SEQUENCE: 70

Asp Thr Leu Xaa Xaa Xaa Xaa
1               5

<210> SEQ ID NO 71
<211> LENGTH: 4
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: penicillamine
<220> FEATURE:
<221> NAME/KEY: MOD_RES
<222> LOCATION: (2)..(2)
<223> OTHER INFORMATION: N-Me-Arginine

<400> SEQUENCE: 71

Xaa Arg Ser Asp
1

<210> SEQ ID NO 72
<211> LENGTH: 6
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (3)..(3)
<223> OTHER INFORMATION: penicillamine
<220> FEATURE:
<221> NAME/KEY: MOD_RES
<222> LOCATION: (4)..(4)
<223> OTHER INFORMATION: is any amino acid (natural or unnatural) or
      in certain embodiments is Phe(4-tBu) or Trp
<220> FEATURE:
<221> NAME/KEY: MOD_RES
<222> LOCATION: (5)..(5)
<223> OTHER INFORMATION: is absent or any amino acid (natural or
      unnatural); or in certain embodiments, beta-homoGlu, Glu, or D-Glu
<220> FEATURE:
<221> NAME/KEY: MOD_RES
<222> LOCATION: (6)..(6)
<223> OTHER INFORMATION: any amino acid (natural or unnatural); or in
      certain embodiments, is Lys, D-Lys, N-Me-Lys or N-Me-D-Lys.

<400> SEQUENCE: 72

Thr Leu Xaa Xaa Xaa Xaa
1               5

<210> SEQ ID NO 73
<211> LENGTH: 5
<212> TYPE: PRT
<213> ORGANISM: Artificial Sequence
<220> FEATURE:
<223> OTHER INFORMATION: Synthesized peptide
```

```
<220> FEATURE:
<221> NAME/KEY: MOD_RES
<222> LOCATION: (1)..(1)
<223> OTHER INFORMATION: penicillamine
<220> FEATURE:
<221> NAME/KEY: MOD_RES
<222> LOCATION: (2)..(2)
<223> OTHER INFORMATION: N-Me-Arginine

<400> SEQUENCE: 73

Xaa Arg Ser Asp Thr
1               5

<210> SEQ ID NO 74
<211> LENGTH: 5
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (2)..(2)
<223> OTHER INFORMATION: penicillamine
<220> FEATURE:
<221> NAME/KEY: MOD_RES
<222> LOCATION: (3)..(3)
<223> OTHER INFORMATION: is any amino acid (natural or unnatural) or
      in certain embodiments is Phe(4-tBu) or Trp
<220> FEATURE:
<221> NAME/KEY: MOD_RES
<222> LOCATION: (4)..(4)
<223> OTHER INFORMATION: is absent or any amino acid (natural or
      unnatural); or in certain embodiments, beta-homoGlu, Glu, or D-Glu
<220> FEATURE:
<221> NAME/KEY: MOD_RES
<222> LOCATION: (5)..(5)
<223> OTHER INFORMATION: any amino acid (natural or unnatural); or in
      certain embodiments, is Lys, D-Lys, N-Me-Lys or N-Me-D-Lys.

<400> SEQUENCE: 74

Leu Xaa Xaa Xaa Xaa
1               5

<210> SEQ ID NO 75
<211> LENGTH: 6
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: penicillamine
<220> FEATURE:
<221> NAME/KEY: MOD_RES
<222> LOCATION: (2)..(2)
<223> OTHER INFORMATION: N-Me-Arginine

<400> SEQUENCE: 75

Xaa Arg Ser Asp Thr Leu
1               5

<210> SEQ ID NO 76
<211> LENGTH: 4
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: penicillamine
<220> FEATURE:
```

<221> NAME/KEY: MOD_RES
<222> LOCATION: (2)..(2)
<223> OTHER INFORMATION: is any amino acid (natural or unnatural) or
      in certain embodiments is Phe(4-tBu) or Trp
<220> FEATURE:
<221> NAME/KEY: MOD_RES
<222> LOCATION: (3)..(3)
<223> OTHER INFORMATION: is absent or any amino acid (natural or
      unnatural); or in certain embodiments, beta-homoGlu, Glu, or D-Glu
<220> FEATURE:
<221> NAME/KEY: MOD_RES
<222> LOCATION: (4)..(4)
<223> OTHER INFORMATION: any amino acid (natural or unnatural); or in
      certain embodiments, is Lys, D-Lys, N-Me-Lys or N-Me-D-Lys.

<400> SEQUENCE: 76

Xaa Xaa Xaa Xaa
1

<210> SEQ ID NO 77
<211> LENGTH: 4
<212> TYPE: PRT
<213> ORGANISM: Artificial Sequence
<220> FEATURE:
<223> OTHER INFORMATION: Synthesized peptide

<400> SEQUENCE: 77

Ser Asp Thr Leu
1

<210> SEQ ID NO 78
<211> LENGTH: 5
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (5)..(5)
<223> OTHER INFORMATION: Penicillamine

<400> SEQUENCE: 78

Ser Asp Thr Leu Xaa
1               5

<210> SEQ ID NO 79
<211> LENGTH: 6
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (5)..(5)
<223> OTHER INFORMATION: Penicillamine
<220> FEATURE:
<221> NAME/KEY: MOD_RES
<222> LOCATION: (6)..(6)
<223> OTHER INFORMATION: is any amino acid (natural or unnatural) or
      in certain embodiments is Phe(4-tBu) or Trp

<400> SEQUENCE: 79

Ser Asp Thr Leu Xaa Xaa
1               5

<210> SEQ ID NO 80
<211> LENGTH: 8
<212> TYPE: PRT
<213> ORGANISM: Artificial Sequence
<220> FEATURE:
<223> OTHER INFORMATION: Synthesized peptide

```
<220> FEATURE:
<221> NAME/KEY: MOD_RES
<222> LOCATION: (1)..(1)
<223> OTHER INFORMATION: penicillamine
<220> FEATURE:
<221> NAME/KEY: MOD_RES
<222> LOCATION: (2)..(2)
<223> OTHER INFORMATION: N-Me-Arginine
<220> FEATURE:
<221> NAME/KEY: MOD_RES
<222> LOCATION: (7)..(7)
<223> OTHER INFORMATION: Penicillamine

<400> SEQUENCE: 80

Xaa Arg Ser Asp Thr Leu Xaa Phe
1               5

<210> SEQ ID NO 81
<211> LENGTH: 7
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: penicillamine
<220> FEATURE:
<221> NAME/KEY: MOD_RES
<222> LOCATION: (2)..(2)
<223> OTHER INFORMATION: N-Me-Arginine
<220> FEATURE:
<221> NAME/KEY: MOD_RES
<222> LOCATION: (7)..(7)
<223> OTHER INFORMATION: Penicillamine

<400> SEQUENCE: 81

Xaa Arg Ser Asp Thr Leu Xaa
1               5

<210> SEQ ID NO 82
<211> LENGTH: 4
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: Penicillamine
<220> FEATURE:
<221> NAME/KEY: MOD_RES
<222> LOCATION: (3)..(3)
<223> OTHER INFORMATION: beta-homoGlu
<220> FEATURE:
<221> NAME/KEY: MOD_RES
<222> LOCATION: (4)..(4)
<223> OTHER INFORMATION: D-Lys form

<400> SEQUENCE: 82

Xaa Phe Glu Lys
1

<210> SEQ ID NO 83
<211> LENGTH: 5
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (2)..(2)
<223> OTHER INFORMATION: Penicillamine
```

```
<220> FEATURE:
<221> NAME/KEY: MOD_RES
<222> LOCATION: (4)..(4)
<223> OTHER INFORMATION: beta-homoGlu
<220> FEATURE:
<221> NAME/KEY: MOD_RES
<222> LOCATION: (5)..(5)
<223> OTHER INFORMATION: D-Lys form

<400> SEQUENCE: 83

Leu Xaa Phe Glu Lys
1               5

<210> SEQ ID NO 84
<211> LENGTH: 6
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: beta-homoGlu
<220> FEATURE:
<221> NAME/KEY: MOD_RES
<222> LOCATION: (6)..(6)
<223> OTHER INFORMATION: D-Lys form

<400> SEQUENCE: 84

Thr Leu Xaa Phe Glu Lys
1               5

<210> SEQ ID NO 85
<211> LENGTH: 7
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (4)..(4)
<223> OTHER INFORMATION: Penicillamine
<220> FEATURE:
<221> NAME/KEY: MOD_RES
<222> LOCATION: (6)..(6)
<223> OTHER INFORMATION: beta-homoGlu
<220> FEATURE:
<221> NAME/KEY: MOD_RES
<222> LOCATION: (7)..(7)
<223> OTHER INFORMATION: D-Lys form

<400> SEQUENCE: 85

Asp Thr Leu Xaa Phe Glu Lys
1               5

<210> SEQ ID NO 86
<211> LENGTH: 8
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (5)..(5)
<223> OTHER INFORMATION: Penicillamine
<220> FEATURE:
<221> NAME/KEY: MOD_RES
<222> LOCATION: (7)..(7)
<223> OTHER INFORMATION: beta-homoGlu
```

```
<220> FEATURE:
<221> NAME/KEY: MOD_RES
<222> LOCATION: (8)..(8)
<223> OTHER INFORMATION: D-Lys form

<400> SEQUENCE: 86

Ser Asp Thr Leu Xaa Phe Glu Lys
1               5

<210> SEQ ID NO 87
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MOD_RES
<222> LOCATION: (1)..(1)
<223> OTHER INFORMATION: N-Methyl Arginine
<220> FEATURE:
<221> NAME/KEY: MOD_RES
<222> LOCATION: (6)..(6)
<223> OTHER INFORMATION: Penicillamine
<220> FEATURE:
<221> NAME/KEY: MOD_RES
<222> LOCATION: (7)..(7)
<223> OTHER INFORMATION: Phe-(4-tert butyl)
<220> FEATURE:
<221> NAME/KEY: MOD_RES
<222> LOCATION: (8)..(8)
<223> OTHER INFORMATION: Beta-homoglutamic acid
<220> FEATURE:
<221> NAME/KEY: MOD_RES
<222> LOCATION: (9)..(9)
<223> OTHER INFORMATION: D-Lys form

<400> SEQUENCE: 87

Arg Ser Asp Thr Leu Xaa Phe Xaa Lys
1               5
```